US012637497B2

(12) United States Patent
Keeler-Klunk et al.

(10) Patent No.: US 12,637,497 B2
(45) Date of Patent: May 26, 2026

(54) AAV CAPSID CHIMERIC ANTIGEN RECEPTORS AND USES THEREOF

(71) Applicant: University of Massachusetts, Westborough, MA (US)

(72) Inventors: Allison Keeler-Klunk, Worcester, MA (US); Terence Flotte, Worcester, MA (US); Motahareh Arjomandnejad, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 1249 days.

(21) Appl. No.: 17/605,615

(22) PCT Filed: Apr. 23, 2020

(86) PCT No.: PCT/US2020/029527
§ 371 (c)(1),
(2) Date: Oct. 22, 2021

(87) PCT Pub. No.: WO2020/219679
PCT Pub. Date: Oct. 29, 2020

(65) Prior Publication Data
US 2022/0220170 A1 Jul. 14, 2022

Related U.S. Application Data

(60) Provisional application No. 62/838,288, filed on Apr. 24, 2019.

(51) Int. Cl.
| | |
|---|---|
| *C07K 14/47* | (2006.01) |
| *A61K 40/11* | (2025.01) |
| *A61K 40/22* | (2025.01) |
| *A61K 40/31* | (2025.01) |
| *A61K 40/42* | (2025.01) |
| *A61K 40/46* | (2025.01) |
| *C07K 14/005* | (2006.01) |
| *C07K 14/705* | (2006.01) |
| *C07K 14/725* | (2006.01) |
| *C12N 15/62* | (2006.01) |
| *C12N 15/86* | (2006.01) |

(52) U.S. Cl.
CPC .......... *C07K 14/4702* (2013.01); *A61K 40/11* (2025.01); *A61K 40/22* (2025.01); *A61K 40/31* (2025.01); *A61K 40/42* (2025.01); *A61K 40/4221* (2025.01); *A61K 40/46* (2025.01); *C07K 14/005* (2013.01); *C07K 14/70503* (2013.01); *C07K 14/7051* (2013.01); *C07K 14/70517* (2013.01); *C07K 14/70521* (2013.01); *C07K 14/70578* (2013.01); *C12N 15/62* (2013.01); *C12N 15/86* (2013.01); *A61K 2239/31* (2023.05); *A61K 2239/38* (2023.05); *A61K 2239/48* (2023.05); *C07K 2317/622* (2013.01); *C07K 2319/02* (2013.01); *C07K 2319/03* (2013.01); *C07K 2319/33* (2013.01);

*C07K 2319/50* (2013.01); *C12N 2740/16043* (2013.01); *C12N 2750/14134* (2013.01)

(58) Field of Classification Search
None
See application file for complete search history.

(56) References Cited

U.S. PATENT DOCUMENTS

2017/0067908 A1 3/2017 Nakai et al.

FOREIGN PATENT DOCUMENTS

| CA | 3068639 A1 | 1/2019 |
|---|---|---|
| WO | WO 2007/140474 A2 | 12/2007 |
| WO | WO 2019/043081 A1 | 3/2019 |

OTHER PUBLICATIONS

Extended European Search Report for Application No. 20795297.9, mailed Dec. 19, 2022.
Arjomandnejad et al., Modulating immune responses to AAV by expanded polyclonal T-regs and capsid specific chimeric antigen receptor T-regulatory cells. Mol Ther Methods Clin Dev. Oct. 28, 2021;23:490-506. doi: 10.1016/j.omtm.2021.10.010. eCollection Dec. 10, 2021.
Arjomandnejad et al., CAR-T Regulatory (CAR-Treg) Cells: Engineering and Applications. Biomedicines. Jan. 26, 2022;10(2):287. doi: 10.3390/biomedicines10020287.
Finn et al., Proteasome inhibitors decrease AAV2 capsid derived peptide epitope presentation on MHC class I following transduction. Mol Ther. Jan. 2010;18(1):135-42. doi: 10.1038/mt.2009.257. Epub Nov. 10, 2009.
Harris et al., Adoptive T Cell Therapies: A Comparison of T Cell Receptors and Chimeric Antigen Receptors. Trends Pharmacol Sci. Author manuscript; available in PMC: Mar. 1, 2017. Published in final edited form as: Trends Pharmacol Sci. Dec. 17, 2015;37(3):220-230. doi: 10.1016/j.tips.2015.11.004.
International Search Report and Written Opinion for Application No. PCT/US2020/029527, mailed Aug. 17, 2020.
International Preliminary Report on Patentability for Application No. PCT/US2020/029527, mailed Nov. 4, 2021.
Fitzpatrick et al., Influence of Pre-existing Anti-capsid Neutralizing and Binding Antibodies on AAV Vector Transduction. Mol Ther Methods Clin Dev. Feb. 13, 2018;9:119-129. doi: 10.1016/j.omtm. 2018.02.003.

(Continued)

*Primary Examiner* — Michael D Burkhart
(74) *Attorney, Agent, or Firm* — Wolf, Greenfield & Sacks, P.C.

(57) ABSTRACT

Aspects of the disclosure relate to compositions and methods for modulating the immune response of a subject (e.g., a human subject) to certain viral antigens (e.g., antigens derived from AAV capsid proteins). The disclosure is based, in part, on isolated nucleic acids and expression constructs encoding chimeric antigen receptors (CARs) that target AAV capsid proteins, and recombinant immune cells comprising such constructs (e.g., recombinant T-cell comprising a CAR (CAR T-cells), and recombinant T-regulatory cells comprising a CAR (CAR T-regs)).

16 Claims, 19 Drawing Sheets

Specification includes a Sequence Listing.

(56) References Cited

OTHER PUBLICATIONS

Mingozzi et al., CD8(+) T-cell responses to adeno-associated virus capsid in humans. Nat Med. Apr. 2007;13(4):419-22. doi: 10.1038/nm1549. Epub Mar. 18, 2007.

Rogers et al., Plasmacytoid and conventional dendritic cells cooperate in crosspriming AAV capsid-specific CD8+ T cells. Blood. Jun. 15, 2017;129(24):3184-3195. doi: 10.1182/blood-2016-11-751040. Epub May 3, 2017.

64-(Human)antiAAV-LongHinge(CH2CH3)-CD28-41BB-CD3z-E2A-FoxP3-E2A-CD19t
11,111 bp 64-(Human)antiAAV-LongHinge(CH2CH3)-CD28-41BB-CD3z-E2A-FoxP3-E2A-CD19t
11,111 bp CAR-T-cells Irradiated Feeder cells
( PBMCs + Hela-Cap)
IL21, IL 15,IL-7 ( TGF-B for T-Regs)

12 Days

CAR

CD3

AAV-CAR-T-cells
Before expansion

After expansion

AAV-CAR-T-cells
after expansion

AAV1-AAT+ AAV-CAR-Tcells
     AAV1-AAT+ PBS

Fig. 12E
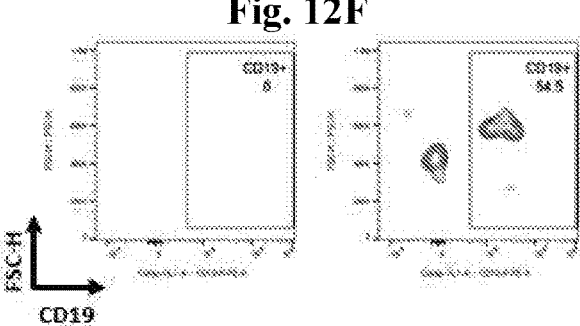
Fig. 12F
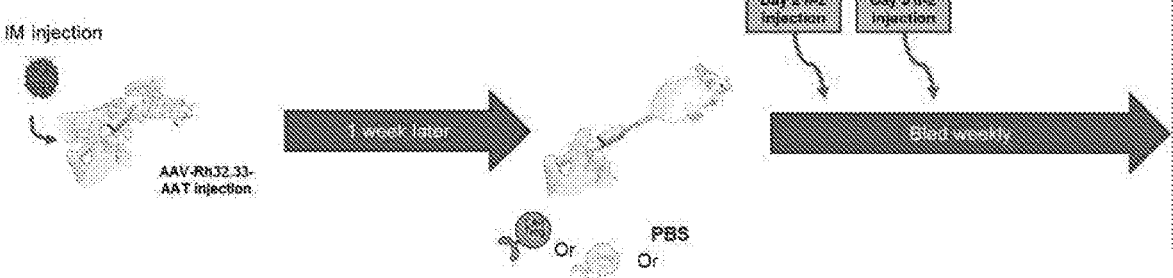
Fig. 13A

━⋙━ Rh32.33+ AAV-CAR-T-Regs

━⋙━ Rh32.33+ natural T-regs

━▲━ Rh32.33+ PBS

‑‑‑ OVA-AAV1 +CAR-T-regs

‑‑‑ OVA-AAV1 +T-regs

‑‑‑ OVA-AAV1+ PBS

‑‑‑ AAV1-chimp AAT+ AAV-CAR-Tregs
‑‑‑ AAV1-chimp AAT+ Tregs
‑‑‑ AAV1-chimp AAT+ PBS

SEQUENCE LISTING

<160> NUMBER OF SEQ ID NOS: 39

<210> SEQ ID NO 1
<211> LENGTH: 11147
<212> TYPE: DNA
<213> ORGANISM: Unknown
<220> FEATURE:
<223> OTHER INFORMATION: AAV-CAR-FoxP3-EGFRt

<400> SEQUENCE: 1

```
ctgttttaaa agaaaagggg ggattggggg gtacagtgca ggggaaagaa tagtagacat      60
aatagcaaca gacatacaaa ctaaagaatt acaaaaacaa attacaaaaa ttcaaaattt     120
tatcaacaag cttgatcgat ggctccggtg cccgtcagtg ggcagagcgc acatcgccca     180
cagtccccga gaagttgggg ggaggggtcg gcaattgaac cggtgcctag agaaggtggc     240
gcggggtaaa ctgggaaagt gatgtcgtgt actggctccg cctttttccc gagggtgggg     300
gagaaccgta tataagtgca gtagtcgccg tgaacgttct ttttcgcaac gggtttgccg     360
ccagaacaca ggtgtcgtga cgcggatcca cgcgtgcggc cgcacgcgta agcttagcgc     420
agaggcttgg ggcagccgag cggcagccag gccccggccc gggcctcggt tccagaaggg     480
agaggagccc gccaaggcgc gcaagagagc gggctgcctc gcagtccgag ccggagaggg     540
agcgcgagcc gcgccggccc cggacggcct cgccgccacc atggctctgc ccgtcaccgc     600
actgctgctg cctctggctc tgctgctgca cgccgcaaga ccagacattg tgctgacaca     660
gtctcctgct tccttagctg tatctctggg gcagagggcc accatctcat gcagggccag     720
ccaaagtgtc agttcatcta cctataattt tatacactgg tatcaacaga aatcaggaca     780
gccacccaaa ctcctcatca gtatgcatc caacctagaa tctggggtcc ctgtcaggtt     840
cagtggcagt gggtctggga cagacttctc cctcaacatc catcctgtgg aggaggagga     900
tactgcaaca tattactgtc agcacagttg ggagattcca tacacgttcg gagggggggc     960
caagttggag ataaaaggca gtactagcgg tggtggctcc ggggggcggtt ccggtggggg    1020 cggcagcagc caggtgcagc tgaaggagtc aggacctggc ctggtggcac cctcacagag    1080
cctgtccatc acatgcaccg tctcaggatt ctcattaagc ggctatggca taagctgggt    1140
tcgccagcct ccaggaaagc gtctggaatg gctgggattg atatggggtg atggaaccac    1200
agactataat tcagctctca aatccagact gagcatcagc aaggacaact ccaagagcca    1260 ggtttttctta aaaatgaaca gtctgcaaac tgatgacaca gccaggtact tctgtaccag    1320
agggcctccg gccttctata agtacctcta ctttgactac tggggccaag gcaccactct    1380
cacagtctcc tcagacaaaa ctcacacatg cccaccgtgc ccagcacctc ctgtggcagg    1440
accgtcagtc ttcctcttcc ccccaaaacc caaggacacc ctcatgatct cccggacccc    1500
tgaggtcaca tgcgtggtgg tggacgtgag ccacgaagac cctgaggtca agttcaactg    1560
gtacgtggac ggcgtggagg tgcataatgc caagacaaag ccgcgggagg agcagtacca    1620
gagcacgtac cgtgtggtca gcgtcctcac cgtcctgcac caggactggc tgaatggcaa    1680
ggagtacaag tgcaaggtct ccaacaaagc cctcccagcc cccatcgaga aaaccatctc    1740
caaagccaaa gggcagcccc gagaaccaca ggtgtacacc ctgccaccat cacgagatga    1800
gctgaccaag aaccaggtca gcctgacctg cctggtcaaa ggcttctatc ccagcgacat    1860
cgccgtggag tgggagagca atgggcagcc ggagaacaac tacaagacca cgcctcccgt    1920
gctggactcc gacggctcct tcttcctcta cagcaagctc accgtggaca gagcaggtg    1980 gcagcagggg aacgtcttct catgctccgt gatgcatgag gctctgcaca accactacac    2040
```

-continued

```
gcagaagagc ctctccctgt ctcccttttg ggtgctggtg gtggttggtg gagtcctggc   2100
ttgctatagc ttgctagtaa cagtggcctt tattattttc tgggtgagga gtaagaggag   2160
caggggaggt cacagtgact acatgaacat gactccccgc cgccccgggc ccacccgcaa   2220
gcattaccag ccctatgccc caccacgcga cttcgcagcc tatcgctcca aacggggcag   2280
aaagaaactc ctgtatatat tcaaacaacc atttatgaga ccagtacaaa ctactcaaga   2340
ggaagatggc tgtagctgcc gatttccaga agaagaagaa ggaggatgtg aactgagagt   2400
gaagttcagc aggagcgcag acgcccccgc gtaccagcag ggccagaacc agctctataa   2460
cgagctcaat ctaggacgaa gagaggagta cgatgttttg gacaagagac gtggccggga   2520
ccctgagatg gggggaaagc cgagaaggaa gaaccctcag gaaggcctgt acaatgaact   2580
gcagaaagat aagatggcgg aggcctacag tgagattggg atgaaaggcg agcgccggag   2640
gggcaagggg cacgatggcc tttaccaggg tctcagtaca gccaccaagg acacctacga   2700
cgcccttcac atgcaggccc tgccccctcg ccagtgtact aattatgctc tcttgaaatt   2760
ggctggagat gttgagagca accccgggcc ggaattcatg cccaacccta ggccagccaa   2820
gcctatggct ccttccttgg cccttggccc atccccagga gtcttgccaa gctggaagac   2880
tgcacccaag ggctcagaac ttctagggac caggggctct gggggaccct ccaaggtcg   2940 ggacctgcga agtggggccc acacctcttc ttccttgaac cccctgccac catcccagct   3000
gcagctgcct acagtgcccc tagtcatggt ggcaccgtct ggggcccgac taggtccctc   3060
accccaccta caggcccttc tccaggacag accacacttc atgcatcagc tctccactgt   3120
ggatgcccat gcccagaccc ctgtgctcca agtgcgtcca ctggacaacc cagccatgat   3180
cagcctccca ccaccttctg ctgccactgg ggtcttctcc ctcaaggccc ggcctggcct   3240
gccacctggg atcaatgtgg ccagtctgga atgggtgtcc agggagccag ctctactctg   3300
caccttccca cgctcgggta cacccaggaa agacagcaac cttttggctg cacccccaagg   3360 atcctaccca ctgctggcaa atggagtctg caagtggcct ggttgtgaga aggtcttcga   3420
ggagccagaa gagtttctca agcactgcca agcagatcat ctcctggatg agaaaggcaa   3480
ggcccagtgc ctcctccaga gagaagtggt gcagtctctg gagcagcagc tggagctgga   3540
aaaggagaag ctgggagcta tgcaggccca cctggctggg aagatggcgc tggccaaggc   3600
tccatctgtg gcctcaatgg acaagagctc ttgctgcatc gtagccacca gtactcaggg   3660
cagtgtgctc ccggcctggt ctgctcctcg ggaggctcca gacggcggcc tgtttgcagt   3720
gcggaggcac ctctggggaa gccatggcaa tagttccttc ccagagttct tccacacaat   3780
ggactacttc aagtaccaca atatgcgacc ccctttcacc tatgccaccc ttatccgatg   3840
ggccatcctg gaagccccgg agaggcagag gacactcaat gaaatctacc attggtttac   3900
tcgcatgttc gcctacttca gaaaccaccc cgccacctgg aagaatgcca tccgccacaa   3960
cctgagcctg cacaagtgct ttgtgcgagt ggagagcgag aagggagcag tgtggaccgt   4020
agatgaattt gagtttcgca agaagaggag ccaacgcccc aacaagtgct ccaatccctg   4080
ccctgaattc tctagacagt gtactaatta tgctctcttg aaattggctg agatgttga   4140 gagcaacccc gggccgatgc ttctcctggt gacaagcctt ctgctctgtg agttaccaca   4200
cccagcattc ctcctgatcc cacgcaaagt gtgtaacgga ataggtattg gtgaatttaa   4260
agactcactc tccataaatg ctacgaatat taaacacttc aaaaaactgca cctccatcag   4320 tggcgatctc cacatcctgc cggtggcatt taggggtgac tccttcacac atactcctcc   4380
```

-continued

```
tctggatcca caggaactgg atattctgaa aaccgtaaag gaaatcacag ggttttttgct    4440 gattcaggct tggcctgaaa acaggacgga cctccatgcc tttgagaacc tagaaatcat    4500
acgcggcagg accaagcaac atggtcagtt ttctcttgca gtcgtcagcc tgaacataac    4560
atccttggga ttacgctccc tcaaggagat aagtgatgga gatgtgataa tttcaggaaa    4620
caaaaatttg tgctatgcaa atacaataaa ctggaaaaaa ctgtttggga cctccggtca    4680
gaaaaccaaa attataagca acagaggtga aaacagctgc aaggccacag gccaggtctg    4740
ccatgccttg tgctcccccg agggctgctg gggcccggag cccagggact gcgtctcttg    4800
ccggaatgtc agccgaggca gggaatgcgt ggacaagtgc aaccttctgg agggtgagcc    4860
aagggagttt gtggagaact ctgagtgcat acagtgccac ccagagtgcc tgcctcaggc    4920
catgaacatc acctgcacag gacggggacc agacaactgt atccagtgtg cccactacat    4980
tgacggcccc cactgcgtca agacctgccc ggcaggagtc atgggagaaa acaacaccct    5040
ggtctggaag tacgcagacg ccggccatgt gtgccacctg tgccatccaa actgcaccta    5100
cggatgcact gggccaggtc ttgaaggctg tccaacgaat gggcctaaga tcccgtccat    5160
cgccactgga tctagataaa ttcgagcatc ttaccgccat ttattcccat atttgttctg    5220 ttttttcttga tttgggtata catttaaatg ttaataaaac aaaatggtgg ggcaatcatt    5280
tacattttta gggatatgta attactagtt caggtgtatt gccacaagac aaacatgtta    5340
agaaactttc ccgttattta cgctctgttc ctgttaatca acctctggat tacaaaattt    5400
gtgaaagatt gactgatatt cttaactatg ttgctccttt tacgctgtgt ggatatgctg    5460
ctttatagcc tctgtatcta gctattgctt cccgtacggc tttcgttttc tcctccttgt    5520
ataaatcctg gttgctgtct cttttagagg agttgtggcc cgttgtccgt caacgtggcg    5580
tggtgtgctc tgtgtttgct gacgcaaccc ccactggctg gggcattgcc accacctgtc    5640
aactcctttc tgggactttc gctttccccc tcccgatcgc cacggcagaa ctcatcgccg    5700
cctgccttgc ccgctgctgg acaggggcta ggttgctggg cactgataat tccgtggtgt    5760
tgtcggggaa gctgacgtcc tttcctcgag gggggccccg gtacctttaa gaccaatgac    5820
ttacaaggca gctgtagatc ttagccactt tttaaaagaa aaggggggac tggaagggct    5880
aattcactcc caacgaagac aagatctgct ttttgcttgt actgggtctc tctggttaga    5940
ccagatctga gcctgggagc tctctggcta actagggaac ccactgctta agcctcaata    6000
aagcttgcct tgagtgcttc aagtagtgtg tgcccgtctg ttgtgtgact ctggtaacta    6060
gagatccctc agacccttttt agtcagtgtg gaaaatctct agcagtagta gttcatgtca    6120
tcttattatt cagtatttat aacttgcaaa gaaatgaata tcagagagtg agaggaactt    6180
gtttattgca gcttataatg gttacaaata aagcaatagc atcacaaatt tcacaaataa    6240 agcattttttt tcactgcatt ctagttgtgg tttgtccaaa ctcatcaatg tatcttatca    6300
tgtctggctc tagctatccc gcccctaact ccgcccagtt ccgcccattc tccgccccat    6360
ggctgactaa ttttttttat ttatgcagag gccgaggccg cctcggcctc tgagctattc    6420
cagaagtagt gaggaggctt ttttggaggc ctaggctttt gcgtcgagac gtacccaatt    6480
cgccctatag tgagtcgtat tacgcgcgct cactggccgt cgttttacaa cgtcgtgact    6540
gggaaaaccc tggcgttacc caacttaatc gccttgcagc acatccccct ttcgccagct    6600
ggcgtaatag cgaagaggcc cgcaccgatc gcccttccca acagttgcgc agcctgaatg    6660
gcgaatggcg cgacgcgccc tgtagcggcg cattaagcgc ggcgggtgtg gtggttacgc    6720
gcagcgtgac cgctacactt gccagcgccc tagcgcccgc tcctttcgct ttcttccctt    6780
```

-continued

```
cctttctcgc cacgttcgcc ggctttcccc gtcaagctct aaatcggggg ctcccttag     6840 ggttccgatt tagtgcttta cggcacctcg accccaaaaa acttgattag ggtgatggtt     6900
cacgtagtgg gccatcgccc tgatagacgg tttttcgccc tttgacgttg gagtccacgt     6960
tctttaatag tggactcttg ttccaaactg gaacaacact caaccctatc tcggtctatt     7020
cttttgattt ataagggatt ttgccgattt cggcctattg gttaaaaaat gagctgattt     7080
aacaaaaatt taacgcgaat tttaacaaaa tattaacgtt tacaatttcc caggtggcac     7140
ttttcgggga aatgtgcgcg gaacccctat ttgtttattt ttctaaatac attcaaatat     7200
gtatccgctc atgagacaat aaccctgata aatgcttcaa taatattgaa aaaggaagag     7260
tatgagtatt caacatttcc gtgtcgccct tattcctttt tttgcggcat tttgccttcc     7320 tgttttttgct cacccagaaa cgctggtgaa agtaaaagat gctgaagatc agttgggtgc     7380
acgagtgggt tacatcgaac tggatctcaa cagcggtaag atccttgaga gttttcgccc     7440
cgaagaacgt tttccaatga tgagcacttt taaagttctg ctatgtggcg cggtattatc     7500
ccgtattgac gccgggcaag agcaactcgg tcgccgcata cactattctc agaatgactt     7560
ggttgagtac tcaccagtca cagaaaagca tcttacggat ggcatgacag taagagaatt     7620
atgcagtgct gccataacca tgagtgataa cactgcggcc aacttacttc tgacaacgat     7680
cggaggaccg aaggagctaa ccgcttttttt gcacaacatg ggggatcatg taactcgcct     7740
tgatcgttgg gaaccggagc tgaatgaagc cataccaaac gacgagcgtg acaccacgat     7800
gcctgtagca atggcaacaa cgttgcgcaa actattaact ggcgaactac ttactctagc     7860
ttcccggcaa caattaatag actggatgga ggcggataaa gttgcaggac cacttctgcg     7920
ctcggccctt ccggctggct ggtttattgc tgataaatct ggagccggtg agcgtgggtc     7980
tcgcggtatc attgcagcac tggggccaga tggtaagccc tcccgtatcg tagttatcta     8040
cacgacgggg agtcaggcaa ctatggatga acgaaataga cagatcgctg agataggtgc     8100
ctcactgatt aagcattggt aactgtcaga ccaagtttac tcatatatac tttagattga     8160
tttaaaactt catttttaat ttaaaaggat ctaggtgaag atccttttg ataatctcat     8220 gaccaaaatc ccttaacgtg agttttcgtt ccactgagcg tcagaccccg tagaaaagat     8280
caaaggatct tcttgagatc ctttttttct gcgcgtaatc tgctgcttgc aaacaaaaaa     8340
accaccgcta ccagcggtgg tttgtttgcc ggatcaagag ctaccaactc tttttccgaa     8400
ggtaactggc ttcagcagag cgcagatacc aaatactgtc cttctagtgt agccgtagtt     8460
aggccaccac ttcaagaact ctgtagcacc gcctacatac ctcgctctgc taatcctgtt     8520
accagtggct gctgccagtg gcgataagtc gtgtcttacc gggttggact caagacgata     8580
gttaccggat aaggcgcagc ggtcgggctg aacggggggt tcgtgcacac agcccagctt     8640
ggagcgaacg acctacaccg aactgagata cctacagcgt gagctatgag aaagcgccac     8700
gcttcccgaa gggagaaagg cggacaggta tccggtaagc ggcagggtcg aacaggaga     8760 gcgcacgagg gagcttccag ggggaaacgc ctggtatctt tatagtcctg tcgggtttcg     8820
ccacctctga cttgagcgtc gatttttgtg atgctcgtca gggggggcgga gcctatggaa     8880 aaacgccagc aacgcggcct ttttacggtt cctggccttt tgctggcctt ttgctcacat     8940
gttctttcct gcgttatccc ctgattctgt ggataaccgt attaccgcct ttgagtgagc     9000
tgataccgct cgccgcagcc gaacgaccga gcgcagcgag tcagtgagcg aggaagcgga     9060
agagcgccca atacgcaaac cgcctctccc cgcgcgttgg ccgattcatt aatgcagctg     9120
```

-continued

```
gcacgacagg tttcccgact ggaaagcggg cagtgagcgc aacgcaatta atgtgagtta        9180
gctcactcat taggcacccc aggctttaca ctttatgctt ccggctcgta tgttgtgtgg        9240
aattgtgagc ggataacaat ttcacacagg aaacagctat gaccatgatt acgccaagcg        9300
cgcaattaac cctcactaaa gggaacaaaa gctggagctg caagcttaat gtagtcttat        9360
gcaatactct tgtagtcttg caacatggta acgatgagtt agcaacatgc cttacaagga        9420
gagaaaaagc accgtgcatg ccgattggtg gaagtaaggt ggtacgatcg tgccttatta        9480
ggaaggcaac agacgggtct gacatggatt ggacgaacca ctgaattgcc gcattgcaga        9540
gatattgtat ttaagtgcct agctcgatac ataaacgggt ctctctggtt agaccagatc        9600
tgagcctggg agctctctgg ctaactaggg aacccactgc ttaagcctca ataaagcttg        9660
ccttgagtgc ttcaagtagt gtgtgcccgt ctgttgtgtg actctggtaa ctagagatcc        9720
ctcagaccct tttagtcagt gtggaaaatc tctagcagtg gcgcccgaac agggacttga        9780
aagcgaaagg gaaaccagag gagctctctc gacgcaggac tcggcttgct gaagcgcgca        9840
cggcaagagc cgaggggcgg cgactggtga gtacgccaaa aattttgact agcggaggct        9900
agaaggagag agatgggtgc gagagcgtca gtattaagcg ggggagaatt agatcgcgat        9960
gggaaaaaat tcggttaagg ccaggggggaa agaaaaaata taaattaaaa catatagtat       10020
gggcaagcag ggagctagaa cgattcgcag ttaatcctgg cctgttagaa acatcagaag       10080
gctgtagaca aatactggga cagctacaac catcccttca gacaggatca gaagaactta       10140
gatcattata taatacagta gcaaccctct attgtgtgca tcaaaggata gagataaaag       10200
acaccaagga agctttagac aagatagagg aagagcaaaa caaaagtaag accaccgcac       10260
agcaagcggc cgctgatctt cagacctgga ggaggagata tgagggacaa ttggagaagt       10320
gaattatata aatataaagt agtaaaaatt gaaccattag gagtagcacc caccaaggca       10380
aagagaagag tggtgcagag agaaaaaaga gcagtgggaa taggagcttt gttccttggg       10440
ttcttgggag cagcaggaag cactatgggc gcagcctcaa tgacgctgac ggtacaggcc       10500
agacaattat tgtctggtat agtgcagcag cagaacaatt tgctgagggc tattgaggcg       10560
caacagcatc tgttgcaact cacagtctgg ggcatcaagc agctccaggc aagaatcctg       10620
gctgtggaaa gatacctaaa ggatcaacag ctcctgggga tttgggggttg ctctggaaaa       10680 ctcatttgca ccactgctgt gccttggaat gctagttgga gtaataaatc tctggaacag       10740
atttggaatc acacgacctg gatggagtgg gacagagaaa ttaacaatta cacaagctta       10800
atacactcct taattgaaga atcgcaaaac cagcaagaaa agaatgaaca agaattattg       10860
gaattagata aatgggcaag tttgtggaat tggtttaaca taacaaattg gctgtggtat       10920
ataaaattat tcataatgat agtaggaggc ttggtaggtt taagaatagt ttttgctgta       10980
ctttctatag tgaatagagt taggcaggga tattcaccat tatcgtttca gacccacctc       11040
ccaaccccga ggggacccga caggcccgaa ggaatagaag aagaaggtgg agagagagac       11100
agagacagat ccattcgatt agtgaacgga tctcgacggt atcggtt                     11147
```

<210> SEQ ID NO 2
<211> LENGTH: 10047
<212> TYPE: DNA
<213> ORGANISM: Unknown
<220> FEATURE:
<223> OTHER INFORMATION: 14-2_Lenti-IF5-D3-NQ-28-BB-Z -continued

<400> SEQUENCE: 2

```
ctgttttaaa agaaaagggg ggattggggg gtacagtgca ggggaaagaa tagtagacat      60
aatagcaaca gacatacaaa ctaaagaatt acaaaaacaa attacaaaaa ttcaaaattt     120
tatcaacaag cttgatcgat ggctccggtg cccgtcagtg ggcagagcgc acatcgccca     180
cagtccccga gaagttgggg ggaggggtcg gcaattgaac cggtgcctag agaaggtggc     240
gcggggtaaa ctgggaaagt gatgtcgtgt actggctccg ccttttttccc gagggtgggg     300 gagaaccgta tataagtgca gtagtcgccg tgaacgttct ttttcgcaac gggtttgccg     360
ccagaacaca ggtgtcgtga cgcggatcca cgcgtgcggc cgcacgcgta agcttagcgc     420
agaggcttgg ggcagccgag cggcagccag gccccggccc gggcctcggt tccagaaggg     480
agaggagccc gccaaggcgc gcaagagagc gggctgcctc gcagtccgag ccggagaggg     540
agcgcgagcc gcgccggccc cggacggcct cgccgccacc atggagacag acacactcct     600
gctatgggtg ctgctgctct gggttccagg ttccactggt gacattgtgc tgacacagtc     660
tcctgcttcc ttagctgtat ctctggggca gagggccacc atctcatgca gggccagcca     720
aagtgtcagt tcatctacct ataatttttat acactggtat caacagaaat caggacagcc     780
acccaaactc ctcatcaagt atgcatccaa cctagaatct ggggtccctg tcaggttcag     840
tggcagtggg tctgggacag acttctccct caacatccat cctgtggagg aggaggatac     900
tgcaacatat tactgtcagc acagttggga gattccatac acgttcggag gggggccaa      960 gttggagata aaaggcagta ctagcggtgg tggctccggg ggcggttccg gtgggggcgg    1020
cagcagccag gtgcagctga aggagtcagg acctggcctg gtggcaccct cacagagcct    1080
gtccatcaca tgcaccgtct caggattctc attaagcggc tatggcataa gctgggttcg    1140
ccagcctcca ggaaagcgtc tggaatggct gggattgata tggggtgatg gaaccacaga    1200
ctataattca gctctcaaat ccagactgag catcagcaag gacaactcca agagccaggt    1260
tttcttaaaa atgaacagtc tgcaaactga tgacacagcc aggtacttct gtaccagagg    1320
gcctccggcc ttctataagt acctctactt tgactactgg ggccaaggca ccactctcac    1380
agtctcctca gacaaaactc acacatgccc accgtgccca gcacctcctg tggcaggacc    1440
gtcagtcttc ctcttccccc caaaacccaa ggacaccctc atgatctccc ggacccctga    1500
ggtcacatgc gtggtggtgg acgtgagcca cgaagaccct gaggtcaagt tcaactggta    1560
cgtggacggc gtggaggtgc ataatgccaa gacaaagccg cgggaggagc agtaccagag    1620
cacgtaccgt gtggtcagcg tcctcaccgt cctgcaccag gactggctga atggcaagga    1680
gtacaagtgc aaggtctcca acaaagccct cccagccccc atcgagaaaa ccatctccaa    1740
agccaaaggg cagccccgag aaccacaggt gtacaccctg ccaccatcac gagatgagct    1800
gaccaagaac caggtcagcc tgacctgcct ggtcaaaggc ttctatccca gcgacatcgc    1860
cgtggagtgg gagagcaatg ggcagccgga gaacaactac aagaccacgc ctcccgtgct    1920
ggactccgac ggctccttct tcctctacag caagctcacc gtggacaaga gcaggtggca    1980
gcaggggaac gtcttctcat gctccgtgat gcatgaggct ctgcacaacc actacacgca    2040
gaagagcctc tccctgtctc cctttttgggt gctggtggtg gttggtggag tcctggcttg    2100
ctatagcttg ctagtaacag tggcctttat tattttctgg gtgaggagta agaggagcag    2160
gggaggtcac agtgactaca tgaacatgac tccccgccgc cccgggccca cccgcaagca    2220
ttaccagccc tatgccccac cacgcgactt cgcagcctat cgctccaaac ggggcagaaa    2280
```

-continued

```
gaaactcctg tatatattca acaaccatt tatgagacca gtacaaacta ctcaagagga    2340
agatggctgt agctgccgat ttccagaaga agaagaagga ggatgtgaac tgagagtgaa    2400
gttcagcagg agcgcagacg cccccgcgta ccagcagggc cagaaccagc tctataacga    2460
gctcaatcta ggacgaagag aggagtacga tgttttggac aagagacgtg gccgggaccc    2520
tgagatgggg ggaaagccga gaaggaagaa ccctcaggaa ggcctgtaca atgaactgca    2580
gaaagataag atggcggagg cctacagtga gattgggatg aaaggcgagc gccgaggggg    2640 caagggggcac gatggccttt accagggtct cagtacagcc accaaggaca cctacgacgc    2700
ccttcacatg caggccctgc cccctcgcca gtgtactaat tatgctctct tgaaattggc    2760
tggagatgtt gagagcaacc ccgggccgat gcccaaccct aggccagcca agcctatggc    2820
tccttccttg gcccttggcc catccccagg agtcttgcca agctggaaga ctgcacccaa    2880
gggctcagaa cttctaggga ccaggggctc tgggggaccc ttccaaggtc gggacctgcg    2940
aagtggggcc cacacctctt cttccttgaa cccctgcca ccatcccagc tgcagctgcc    3000
tacagtgccc ctagtcatgg tggcaccgtc tggggcccga ctaggtccct caccccacct    3060 acaggcccctt ctccaggaca gaccacactt catgcatcag ctctccactg tggatgccca    3120
tgcccagacc cctgtgctcc aagtgcgtcc actggacaac ccagccatga tcagcctccc    3180
accaccttct gctgccactg gggtcttctc cctcaaggcc cggcctggcc tgccacctgg    3240
gatcaatgtg gccagtctgg aatgggtgtc cagggagcca gctctactct gcaccttccc    3300
acgctcgggt acacccagga aagacagcaa ccttttggct gcaccccaag gatcctaccc    3360
actgctggca aatggagtct gcaagtggcc tggttgtgag aaggtcttcg aggagccaga    3420
agagtttctc aagcactgcc aagcagatca tctcctggat gagaaaggca aggcccagtg    3480
cctcctccag agagaagtgg tgcagtctct ggagcagcag ctggagctgg aaaaggagaa    3540
gctgggagct atgcaggccc acctggctgg gaagatggcg ctggccaagg ctccatctgt    3600
ggcctcaatg gacaagagct cttgctgcat cgtagccacc agtactcagg gcagtgtgct    3660
cccggcctgg tctgctcctc gggaggctcc agacggcggc ctgtttgcag tgcggaggca    3720
cctctgggga agccatggca atagttcctt cccagagttc ttccacaaca tggactactt    3780
caagtaccac aatatgcgac ccccttcac ctatgccacc cttatccgat gggccatcct    3840
ggaagccccg gagaggcaga ggacactcaa tgaaatctac cattggttta ctcgcatgtt    3900
cgcctacttc agaaaccacc ccgccacctg gaagaatgcc atccgccaca acctgagcct    3960
gcacaagtgc tttgtgcgag tggagagcga gaagggagcg gtgtggaccg tagatgaatt    4020
tgagtttcgc aagaagagga gccaacgccc caacaagtgc tccaatccct gcccttgaaa    4080
ttcgagcatc ttaccgccat ttattcccat atttgttctg tttttcttga tttgggtata    4140
catttaaatg ttaataaaac aaaatggtgg ggcaatcatt tacatttta gggatatgta    4200 attactagtt caggtgtatt gccacaagac aaacatgtta agaaactttc ccgttattta    4260
cgctctgttc ctgttaatca acctctggat tacaaaattt gtgaaagatt gactgatatt    4320
cttaactatg ttgctccttt tacgctgtgt ggatatgctg ctttatagcc tctgtatcta    4380
gctattgctt cccgtacggc tttcgttttc tcctccttgt ataaatcctg gttgctgtct    4440
cttttagagg agttgtggcc cgttgtccgt caacgtggcg tggtgtgctc tgtgtttgct    4500
gacgcaaccc ccactggctg gggcattgcc accacctgtc aactcctttc tgggactttc    4560
gctttccccc tcccgatcgc cacggcagaa ctcatcgccg cctgccttgc ccgctgctgg    4620
acaggggcta ggttgctggg cactgataat tccgtggtgt tgtcggggaa gctgacgtcc    4680
```

```
tttcctcgag gggggccccg gtacctttaa gaccaatgac ttacaaggca gctgtagatc   4740
ttagccactt tttaaaagaa aaggggggac tggaagggct aattcactcc caacgaagac   4800
aagatctgct ttttgcttgt actgggtctc tctggttaga ccagatctga gcctgggagc   4860
tctctggcta actagggaac ccactgctta agcctcaata aagcttgcct tgagtgcttc   4920
aagtagtgtg tgcccgtctg ttgtgtgact ctggtaacta gagatccctc agaccctttt   4980
agtcagtgtg gaaaatctct agcagtagta gttcatgtca tcttattatt cagtatttat   5040
aacttgcaaa gaaatgaata tcagagagtg agaggaactt gtttattgca gcttataatg   5100
gttacaaata aagcaatagc atcacaaatt tcacaaataa agcatttttt tcactgcatt   5160
ctagttgtgg tttgtccaaa ctcatcaatg tatcttatca tgtctggctc tagctatccc   5220
gcccctaact ccgcccagtt ccgcccattc tccgccccat ggctgactaa tttttttttat   5280 ttatgcagag gccgaggccg cctcggcctc tgagctattc cagaagtagt gaggaggctt   5340
ttttggaggc ctaggctttt gcgtcgagac gtacccaatt cgccctatag tgagtcgtat   5400
tacgcgcgct cactggccgt cgttttacaa cgtcgtgact gggaaaaccc tggcgttacc   5460
caacttaatc gccttgcagc acatcccect ttcgccagct ggcgtaatag cgaagaggcc   5520
cgcaccgatc gcccttccca acagttgcgc agcctgaatg gcgaatggcg cgacgcgccc   5580
tgtagcggcg cattaagcgc ggcgggtgtg gtggttacgc gcagcgtgac cgctacactt   5640
gccagcgccc tagcgcccgc tcctttcgct ttcttccctt cctttctcgc cacgttcgcc   5700
ggctttcccc gtcaagctct aaatcggggg ctccctttag ggttccgatt tagtgcttta   5760
cggcacctcg accccaaaaa acttgattag ggtgatggtt cacgtagtgg gccatcgccc   5820
tgatagacgg ttttttcgccc tttgacgttg gagtccacgt tctttaatag tggactcttg   5880
ttccaaactg gaacaacact caaccctatc tcggtctatt cttttgattt ataagggatt   5940
ttgccgattt cggcctattg gttaaaaaat gagctgattt aacaaaaatt taacgcgaat   6000
tttaacaaaa tattaacgtt tacaatttcc caggtggcac ttttcgggga aatgtgcgcg   6060
gaacccctat ttgtttattt ttctaaatac attcaaatat gtatccgctc atgagacaat   6120
aaccctgata aatgcttcaa taatattgaa aaaggaagag tatgagtatt caacatttcc   6180
gtgtcgccct tattccctttt tttgcggcat tttgccttcc tgttttttgct cacccagaaa   6240 cgctggtgaa agtaaaagat gctgaagatc agttgggtgc acgagtgggt tacatcgaac   6300
tggatctcaa cagcggtaag atccttgaga gttttcgccc cgaagaacgt tttccaatga   6360
tgagcacttt taaagttctg ctatgtggcg cggtattatc ccgtattgac gccgggcaag   6420
agcaactcgg tcgccgcata cactattctc agaatgactt ggttgagtac tcaccagtca   6480
cagaaaagca tcttacggat ggcatgacag taagagaatt atgcagtgct gccataacca   6540
tgagtgataa cactgcggcc aacttacttc tgacaacgat cggaggaccg aaggagctaa   6600 ccgcttttttt gcacaacatg ggggatcatg taactcgcct tgatcgttgg gaaccggagc   6660
tgaatgaagc cataccaaac gacgagcgtg acaccacgat gcctgtagca atggcaacaa   6720
cgttgcgcaa actattaact ggcgaactac ttactctagc ttcccggcaa caattaatag   6780
actggatgga ggcggataaa gttgcaggac cacttctgcg ctcggccctt ccggctggct   6840
ggtttattgc tgataaatct ggagccggtg agcgtgggtc tcgcggtatc attgcagcac   6900
tggggccaga tggtaagccc tcccgtatcg tagttatcta cacgacgggg agtcaggcaa   6960
ctatggatga acgaaataga cagatcgctg agataggtgc ctcactgatt aagcattggt   7020
```

-continued

```
aactgtcaga ccaagtttac tcatatatac tttagattga tttaaaactt cattttttaat    7080 ttaaaaggat ctaggtgaag atccttttttg ataatctcat gaccaaaatc ccttaacgtg    7140
agttttcgtt ccactgagcg tcagacccccg tagaaaagat caaaggatct tcttgagatc    7200 cttttttttct gcgcgtaatc tgctgcttgc aaacaaaaaa accaccgcta ccagcggtgg    7260
tttgtttgcc ggatcaagag ctaccaactc tttttccgaa ggtaactggc ttcagcagag    7320
cgcagatacc aaatactgtc cttctagtgt agccgtagtt aggccaccac ttcaagaact    7380
ctgtagcacc gcctacatac ctcgctctgc taatcctgtt accagtggct gctgccagtg    7440
gcgataagtc gtgtcttacc gggttggact caagacgata gttaccggat aaggcgcagc    7500
ggtcgggctg aacggggggt tcgtgcacac agcccagctt ggagcgaacg acctacaccg    7560
aactgagata cctacagcgt gagctatgag aaagcgccac gcttcccgaa gggagaaagg    7620
cggacaggta tccggtaagc ggcagggtcg gaacaggaga gcgcacgagg gagcttccag    7680
ggggaaacgc ctggtatctt tatagtcctg tcgggtttcg ccacctctga cttgagcgtc    7740
gatttttgtg atgctcgtca ggggggcgga gcctatggaa aaacgccagc aacgcggcct    7800
ttttacggtt cctggccttt tgctggcctt ttgctcacat gttctttcct gcgttatccc    7860
ctgattctgt ggataaccgt attaccgcct ttgagtgagc tgataccgct cgccgcagcc    7920
gaacgaccga gcgcagcgag tcagtgagcg aggaagcgga agagcgccca atacgcaaac    7980
cgcctctccc cgcgcgttgg ccgattcatt aatgcagctg gcacgacagg tttcccgact    8040
ggaaagcggg cagtgagcgc aacgcaatta atgtgagtta gctcactcat taggcacccc    8100
aggctttaca ctttatgctt ccggctcgta tgttgtgtgg aattgtgagc ggataacaat    8160
ttcacacagg aaacagctat gaccatgatt acgccaagcg cgcaattaac cctcactaaa    8220
gggaacaaaa gctggagctg caagcttaat gtagtcttat gcaatactct tgtagtcttg    8280
caacatggta acgatgagtt agcaacatgc cttacaagga gagaaaaagc accgtgcatg    8340
ccgattggtg gaagtaaggt ggtacgatcg tgccttatta ggaaggcaac agacgggtct    8400
gacatggatt ggacgaacca ctgaattgcc gcattgcaga gatattgtat ttaagtgcct    8460
agctcgatac ataaacgggt ctctctggtt agaccagatc tgagcctggg agctctctgg    8520
ctaactaggg aacccactgc ttaagcctca ataaagcttg ccttgagtgc ttcaagtagt    8580
gtgtgcccgt ctgttgtgtg actctggtaa ctagagatcc ctcagaccct tttagtcagt    8640
gtggaaaatc tctagcagtg gcgcccgaac agggacttga aagcgaaagg gaaaccagag    8700
gagctctctc gacgcaggac tcggcttgct gaagcgcgca cggcaagagg cgaggggcgg    8760
cgactggtga gtacgccaaa aattttgact agcggaggct agaaggagag agatgggtgc    8820
gagagcgtca gtattaagcg ggggagaatt agatcgcgat gggaaaaaat tcggttaagg    8880
ccagggggaa agaaaaaata taattaaaa catatagtat gggcaagcag ggagctagaa    8940
cgattcgcag ttaatcctgg cctgttagaa acatcagaag gctgtagaca aatactggga    9000
cagctacaac catcccttca gacaggatca gaagaactta gatcattata taatacagta    9060
gcaaccctct attgtgtgca tcaaaggata gagataaaag acaccaagga agctttagac    9120
aagatagagg aagagcaaaa caaaagtaag accaccgcac agcaagcggc cgctgatctt    9180
cagacctgga ggaggagata tgagggacaa ttggagaagt gaattatata aatataaagt    9240
agtaaaaatt gaaccattag gagtagcacc caccaaggca aagagaagag tggtgcagag    9300
agaaaaaaga gcagtgggaa taggagcttt gttccttggg ttcttgggag cagcaggaag    9360
cactatgggc gcagcctcaa tgacgctgac ggtacaggcc agacaattat tgtctggtat    9420
```

-continued

```
agtgcagcag cagaacaatt tgctgagggc tattgaggcg caacagcatc tgttgcaact       9480
cacagtctgg ggcatcaagc agctccaggc aagaatcctg gctgtggaaa gatacctaaa       9540
ggatcaacag ctcctgggga tttggggttg ctctggaaaa ctcatttgca ccactgctgt       9600
gccttggaat gctagttgga gtaataaatc tctggaacag atttggaatc acacgacctg       9660
gatggagtgg gacagagaaa ttaacaatta cacaagctta atacactcct taattgaaga       9720
atcgcaaaac cagcaagaaa agaatgaaca agaattattg gaattagata aatgggcaag       9780
tttgtggaat tggtttaaca taacaaattg gctgtggtat ataaaattat tcataatgat       9840
agtaggaggc ttggtaggtt taagaatagt ttttgctgta ctttctatag tgaatagagt       9900
taggcaggga tattcaccat tatcgtttca gacccacctc ccaaccccga ggggacccga       9960
caggcccgaa ggaatagaag aagaaggtgg agagagagac agagacagat ccattcgatt      10020
agtgaacgga tctcgacggt atcggtt                                         10047
```

```
<210> SEQ ID NO 3
<211> LENGTH: 9836
<212> TYPE: DNA
<213> ORGANISM: Unknown
<220> FEATURE:
<223> OTHER INFORMATION: CD8leader-AAV-CAR-2A-EGFRt

<400> SEQUENCE: 3
```

```
ctgttttaaa agaaaagggg ggattggggg gtacagtgca ggggaaagaa tagtagacat         60
aatagcaaca gacatacaaa ctaaagaatt acaaaaacaa attacaaaaa ttcaaaattt        120
tatcaacaag cttgatcgat ggctccggtg cccgtcagtg ggcagagcgc acatcgccca        180
cagtccccga gaagttgggg ggaggggtcg gcaattgaac cggtgcctag agaaggtggc        240
gcggggtaaa ctgggaaagt gatgtcgtgt actggctccg ccttttttcc gagggtgggg        300
gagaaccgta tataagtgca gtagtcgccg tgaacgttct ttttcgcaac gggtttgccg        360
ccagaacaca ggtgtcgtga cgcggatcca cgcgtgcggc cgcacgcgta agcttagcgc        420
agaggcttgg ggcagccgag cggcagccag gccccggccc gggcctcggt tccagaaggg        480
agaggagccc gccaaggcgc gcaagagagc gggctgcctc gcagtccgag ccggagaggg        540
agcgcgagcc gcgccggccc cggacggcct cgccgccacc atggctctgc ccgtcaccgc        600
actgctgctg cctctggctc tgctgctgca cgccgcaaga ccagacattg tgctgacaca        660
gtctcctgct tccttagctg tatctctggg gcagagggcc accatctcat gcagggccag        720
ccaaagtgtc agttcatcta cctataattt tatacactgg tatcaacaga aatcaggaca        780
gccacccaaa ctcctcatca agtatgcatc caacctagaa tctggggtcc ctgtcaggtt        840
cagtggcagt gggtctggga cagacttctc cctcaacatc catcctgtgg aggaggagga        900
tactgcaaca tattactgtc agcacagttg ggagattcca tacacgttcg gagggggggc        960
caagttggag ataaaaggca gtactagcgg tggtggctcc ggggggcggtt ccggtggggg       1020 cggcagcagc caggtgcagc tgaaggagtc aggacctggc ctggtggcac cctcacagag       1080
cctgtccatc acatgcaccg tctcaggatt ctcattaagc ggctatggca taagctgggt       1140
tcgccagcct ccaggaaagc gtctggaatg gctgggatta atatggggtg atggaaccac       1200
agactataat tcagctctca aatccagact gagcatcagc aaggacaact ccaagagcca       1260
ggttttctta aaaatgaaca gtctgcaaac tgatgacaca gccaggtact ctgtaccag       1320 agggcctccg gccttctata agtacctcta ctttgactac tggggccaag gcaccactct       1380
```

-continued

```
cacagtctcc tcagacaaaa ctcacacatg cccaccgtgc ccagcacctc ctgtggcagg     1440
accgtcagtc ttcctcttcc ccccaaaacc caaggacacc ctcatgatct cccggacccc     1500
tgaggtcaca tgcgtggtgg tggacgtgag ccacgaagac cctgaggtca agttcaactg     1560
gtacgtggac ggcgtggagg tgcataatgc caagacaaag ccgcgggagg agcagtacca     1620
gagcacgtac cgtgtggtca gcgtcctcac cgtcctgcac caggactggc tgaatggcaa     1680
ggagtacaag tgcaaggtct ccaacaaagc cctcccagcc cccatcgaga aaaccatctc     1740
caaagccaaa gggcagcccc gagaaccaca ggtgtacacc ctgccaccat cacgagatga     1800
gctgaccaag aaccaggtca gcctgacctg cctggtcaaa ggcttctatc ccagcgacat     1860
cgccgtggag tgggagagca atgggcagcc ggagaacaac tacaagacca cgcctcccgt     1920
gctggactcc gacggctcct tcttcctcta cagcaagctc accgtggaca gagcaggtg     1980 gcagcagggg aacgtcttct catgctccgt gatgcatgag gctctgcaca accactacac     2040
gcagaagagc ctctccctgt ctccctttg ggtgctggtg gtggttggtg gagtcctggc     2100
ttgctatagc ttgctagtaa cagtggcctt tattattttc tgggtgagga gtaagaggag     2160
caggggaggt cacagtgact acatgaacat gactccccgc cgccccgggc ccacccgcaa     2220
gcattaccag ccctatgccc caccacgcga cttcgcagcc tatcgctcca aacggggcag     2280
aaagaaactc ctgtatatat tcaaacaacc atttatgaga ccagtacaaa ctactcaaga     2340
ggaagatggc tgtagctgcc gatttccaga agaagaagaa ggaggatgtg aactgagagt     2400
gaagttcagc aggagcgcag acgcccccgc gtaccagcag ggccagaacc agctctataa     2460
cgagctcaat ctaggacgaa gagaggagta cgatgttttg gacaagagac gtggccggga     2520
ccctgagatg gggggaaagc cgagaaggaa gaaccctcag gaaggcctgt acaatgaact     2580
gcagaaagat aagatggcgg aggcctacag tgagattggg atgaaaggcg agcgccggag     2640
gggcaagggg cacgatggcc tttaccaggg tctcagtaca gccaccaagg acacctacga     2700
cgcccttcac atgcaggccc tgccccctcg ccagtgtact aattatgctc tcttgaaatt     2760
ggctggagat gttgagagca accccgggcc gatgcttctc ctggtgacaa gccttctgct     2820
ctgtgagtta ccacacccag cattcctcct gatcccacgc aaagtgtgta acggaatagg     2880
tattggtgaa tttaaagact cactctccat aaatgctacg aatattaaac acttcaaaaa     2940
ctgcacctcc atcagtggcg atctccacat cctgccggtg gcatttaggg gtgactcctt     3000
cacacatact cctcctctgg atccacagga actggatatt ctgaaaaccg taaaggaaat     3060
cacagggttt ttgctgattc aggcttggcc tgaaaacagg acggacctcc atgcctttga     3120
gaacctagaa atcatacgcg gcaggaccaa gcaacatggt cagttttctc ttgcagtcgt     3180
cagcctgaac ataacatcct ggggattacg ctccctcaag gagataagtg atggagatgt     3240
gataatttca ggaaacaaaa atttgtgcta tgcaaataca ataaactgga aaaaactgtt     3300
tgggacctcc ggtcagaaaa ccaaaattat aagcaacaga ggtgaaaaca gctgcaaggc     3360
cacaggccag gtctgccatg ccttgtgctc ccccgagggc tgctggggcc cggagcccag     3420
ggactgcgtc tcttgccgga atgtcagccg aggcagggaa tgcgtggaca agtgcaacct     3480
tctggagggt gagccaaggg agtttgtgga gaactctgag tgcatacagt gccacccaga     3540
gtgcctgcct caggccatga acatcacctg cacaggacgg ggaccagaca actgtatcca     3600
gtgtgcccac tacattgacg gcccccactg cgtcaagacc tgcccggcag gagtcatggg     3660
agaaaacaac accctggtct ggaagtacgc agacgccggc catgtgtgcc acctgtgcca     3720
tccaaactgc acctacggat gcactgggcc aggtcttgaa ggctgtccaa cgaatgggcc     3780
```

```
taagatcccg tccatcgcca ctgggatggt gggggccctc ctcttgctgc tggtggtggc      3840
cctggggatc ggcctcttca tgtgaggaat tcgagcatct taccgccatt tattcccata      3900
tttgttctgt ttttcttgat ttgggtatac atttaaatgt taataaaaca aaatggtggg      3960
gcaatcattt acatttttag ggatatgtaa ttactagttc aggtgtattg ccacaagaca      4020
aacatgttaa gaaactttcc cgttatttac gctctgttcc tgttaatcaa cctctggatt      4080
acaaaatttg tgaaagattg actgatattc ttaactatgt tgctcctttt acgctgtgtg      4140
gatatgctgc tttatagcct ctgtatctag ctattgcttc ccgtacggct ttcgttttct      4200
cctccttgta taaatcctgg ttgctgtctc ttttagagga gttgtggccc gttgtccgtc      4260
aacgtggcgt ggtgtgctct gtgtttgctg acgcaacccc cactggctgg ggcattgcca      4320
ccacctgtca actcctttct gggactttcg ctttccccct cccgatcgcc acggcagaac      4380
tcatcgccgc ctgccttgcc cgctgctgga caggggctag gttgctgggc actgataatt      4440
ccgtggtgtt gtcggggaag ctgacgtcct ttcctcgagg ggggcccggg tacctttaag      4500
accaatgact tacaaggcag ctgtagatct tagccacttt ttaaaagaaa aggggggact      4560
ggaagggcta attcactccc aacgaagaca agatctgctt tttgcttgta ctgggtctct      4620
ctggttagac cagatctgag cctgggagct ctctggctaa ctagggaacc cactgcttaa      4680
gcctcaataa agcttgcctt gagtgcttca agtagtgtgt gcccgtctgt tgtgtgactc      4740
tggtaactag agatccctca gacccttta gtcagtgtgg aaaatctcta gcagtagtag      4800
ttcatgtcat cttattattc agtatttata acttgcaaag aaatgaatat cagagagtga      4860
gaggaacttg tttattgcag cttataatgg ttacaaataa agcaatagca tcacaaattt      4920
cacaaataaa gcattttttt cactgcattc tagttgtggt ttgtccaaac tcatcaatgt      4980
atcttatcat gtctggctct agctatcccg cccctaactc cgcccagttc cgcccattct      5040
ccgccccatg gctgactaat tttttttatt tatgcagagg ccgaggccgc ctcggcctct      5100
gagctattcc agaagtagtg aggaggcttt tttggaggcc taggcttttg cgtcgagacg      5160
tacccaattc gccctatagt gagtcgtatt acgcgcgctc actggccgtc gttttacaac      5220
gtcgtgactg ggaaaaccct ggcgttaccc aacttaatcg ccttgcagca catccccctt      5280
tcgccagctg gcgtaatagc gaagaggccc gcaccgatcg cccttccaa cagttgcgca      5340 gcctgaatgg cgaatggcgc gacgcgccct gtagcggcgc attaagcgcg gcgggtgtgg      5400
tggttacgcg cagcgtgacc gctacacttg ccagcgccct agcgcccgct cctttcgctt      5460
tcttcccttc ctttctcgcc acgttcgccg gctttccccg tcaagctcta aatcgggggc      5520
tccctttagg gttccgattt agtgctttac ggcacctcga ccccaaaaaa cttgattagg      5580
gtgatggttc acgtagtggg ccatcgccct gatagacggt ttttcgccct ttgacgttgg      5640
agtccacgtt ctttaatagt ggactcttgt tccaaactgg aacaacactc aaccctatct      5700
cggtctattc ttttgattta taagggattt tgccgatttc ggcctattgg ttaaaaaatg      5760
agctgattta acaaaaattt aacgcgaatt ttaacaaaat attaacgttt acaatttccc      5820
aggtggcact tttcggggaa atgtgcgcgg aaccctatt tgtttatttt tctaaataca      5880
ttcaaatatg tatccgctca tgagacaata accctgataa atgcttcaat aatattgaaa      5940
aaggaagagt atgagtattc aacatttccg tgtcgccctt attccctttt ttgcggcatt      6000
ttgccttcct gtttttgctc acccagaaac gctggtgaaa gtaaaagatg ctgaagatca      6060
gttgggtgca cgagtgggtt acatcgaact ggatctcaac agcggtaaga tccttgagag      6120
```

-continued

```
ttttcgcccc gaagaacgtt ttccaatgat gagcactttt aaagttctgc tatgtggcgc    6180
ggtattatcc cgtattgacg ccgggcaaga gcaactcggt cgccgcatac actattctca    6240
gaatgacttg gttgagtact caccagtcac agaaaagcat cttacggatg gcatgacagt    6300
aagagaatta tgcagtgctg ccataaccat gagtgataac actgcggcca acttacttct    6360
gacaacgatc ggaggaccga aggagctaac cgcttttttg cacaacatgg gggatcatgt    6420
aactcgcctt gatcgttggg aaccggagct gaatgaagcc ataccaaacg acgagcgtga    6480
caccacgatg cctgtagcaa tggcaacaac gttgcgcaaa ctattaactg gcgaactact    6540
tactctagct tcccggcaac aattaataga ctggatggag gcggataaag ttgcaggacc    6600
acttctgcgc tcggcccttc cggctggctg gtttattgct gataaatctg gagccggtga    6660
gcgtgggtct cgcggtatca ttgcagcact ggggccagat ggtaagccct cccgtatcgt    6720
agttatctac acgacgggga gtcaggcaac tatggatgaa cgaaatagac agatcgctga    6780
gataggtgcc tcactgatta agcattggta actgtcagac caagtttact catatatact    6840
ttagattgat ttaaaacttc attttttaatt taaaaggatc taggtgaaga tcctttttga    6900
taatctcatg accaaaatcc cttaacgtga gttttcgttc cactgagcgt cagacccgt     6960 agaaaagatc aaaggatctt cttgagatcc tttttttctg cgcgtaatct gctgcttgca    7020
aacaaaaaaa ccaccgctac cagcggtggt ttgtttgccg gatcaagagc taccaactct    7080
ttttccgaag gtaactggct tcagcagagc gcagatacca aatactgtcc ttctagtgta    7140
gccgtagtta ggccaccact tcaagaactc tgtagcaccg cctacatacc tcgctctgct    7200
aatcctgtta ccagtggctg ctgccagtgg cgataagtcg tgtcttaccg ggttggactc    7260
aagacgatag ttaccggata aggcgcagcg gtcgggctga acggggggtt cgtgcacaca    7320
gcccagcttg gagcgaacga cctacaccga actgagatac ctacagcgtg agctatgaga    7380
aagcgccacg cttcccgaag ggagaaaggc ggacaggtat ccggtaagcg gcagggtcgg    7440
aacaggagag cgcacgaggg agcttccagg gggaaacgcc tggtatcttt atagtcctgt    7500
cgggtttcgc cacctctgac ttgagcgtcg attttttgtga tgctcgtcag ggggggcggag   7560 cctatggaaa aacgccagca acgcggcctt tttacggttc ctggccttttt gctggccttt   7620 tgctcacatg ttctttcctg cgttatcccc tgattctgtg gataaccgta ttaccgcctt    7680
tgagtgagct gataccgctc gccgcagccg aacgaccgag cgcagcgagt cagtgagcga    7740
ggaagcggaa gagcgcccaa tacgcaaacc gcctctcccc gcgcgttggc cgattcatta    7800
atgcagctgg cacgacaggt ttcccgactg gaaagcgggc agtgagcgca acgcaattaa    7860
tgtgagttag ctcactcatt aggcacccca ggctttacac tttatgcttc cggctcgtat    7920
gttgtgtgga attgtgagcg gataacaatt tcacacagga aacagctatg accatgatta    7980
cgccaagcgc gcaattaacc ctcactaaag ggaacaaaag ctggagctgc aagcttaatg    8040
tagtcttatg caatactctt gtagtcttgc aacatggtaa cgatgagtta gcaacatgcc    8100
ttacaaggag agaaaaagca ccgtgcatgc cgattggtgg aagtaaggtg gtacgatcgt    8160
gccttattag gaaggcaaca gacgggtctg acatggattg gacgaaccac tgaattgccg    8220
cattgcagag atattgtatt taagtgccta gctcgataca taaacgggtc tctctggtta    8280
gaccagatct gagcctggga gctctctggc taactaggga acccactgct taagcctcaa    8340
taaagcttgc cttgagtgct tcaagtagtg tgtgcccgtc tgttgtgtga ctctggtaac    8400
tagagatccc tcagaccctt ttagtcagtg tggaaaatct ctagcagtgg cgcccgaaca    8460
gggacttgaa agcgaaaggg aaaccagagg agctctctcg acgcaggact cggcttgctg    8520
```

```
aagcgcgcac ggcaagaggc gaggggcggc gactggtgag tacgccaaaa attttgacta      8580
gcggaggcta gaaggagaga gatgggtgcg agagcgtcag tattaagcgg gggagaatta      8640
gatcgcgatg ggaaaaaatt cggttaaggc cagggggaaa gaaaaaatat aaattaaaac      8700
atatagtatg ggcaagcagg gagctagaac gattcgcagt taatcctggc ctgttagaaa      8760
catcagaagg ctgtagacaa atactgggac agctacaacc atcccttcag acaggatcag      8820
aagaacttag atcattatat aatacagtag caaccctcta ttgtgtgcat caaaggatag      8880
agataaaaga caccaaggaa gctttagaca agatagagga agagcaaaac aaaagtaaga      8940
ccaccgcaca gcaagcggcc gctgatcttc agacctggag gaggagatat gagggacaat      9000
tggagaagtg aattatataa atataaagta gtaaaaattg aaccattagg agtagcaccc      9060
accaaggcaa agagaagagt ggtgcagaga gaaaaaagag cagtgggaat aggagctttg      9120
ttccttgggt tcttgggagc agcaggaagc actatgggcg cagcctcaat gacgctgacg      9180
gtacaggcca gacaattatt gtctggtata gtgcagcagc agaacaattt gctgagggct      9240
attgaggcgc aacagcatct gttgcaactc acagtctggg gcatcaagca gctccaggca      9300
agaatcctgg ctgtggaaag atacctaaag gatcaacagc tcctggggat ttggggttgc      9360
tctggaaaac tcatttgcac cactgctgtg ccttggaatg ctagttggag taataaatct      9420
ctggaacaga tttggaatca cacgacctgg atggagtggg acagagaaat taacaattac      9480
acaagcttaa tacactcctt aattgaagaa tcgcaaaacc agcaagaaaa gaatgaacaa      9540
gaattattgg aattagataa atgggcaagt ttgtggaatt ggtttaacat aacaaattgg      9600
ctgtggtata taaaattatt cataatgata gtaggaggct tggtaggttt aagaatagtt      9660
tttgctgtac tttctatagt gaatagagtt aggcagggat attcaccatt atcgtttcag      9720
acccacctcc caaccccgag gggacccgac aggcccgaag gaatagaaga agaaggtgga      9780
gagagagaca gagacagatc cattcgatta gtgaacggat ctcgacggta tcggtt         9836
```

```
<210> SEQ ID NO 4
<211> LENGTH: 8711
<212> TYPE: DNA
<213> ORGANISM: Unknown
<220> FEATURE:
<223> OTHER INFORMATION: 13-1_Lenti-IF5-D3-NQ-28-BB-Z

<400> SEQUENCE: 4
ctgttttaaa agaaaagggg ggattggggg gtacagtgca ggggaaagaa tagtagacat        60
aatagcaaca gacatacaaa ctaaagaatt acaaaaacaa attacaaaaa ttcaaaattt       120
tatcaacaag cttgatcgat ggctccggtg cccgtcagtg gcagagcgc acatcgccca        180 cagtccccga gaagttgggg ggaggggtcg gcaattgaac cggtgcctag agaaggtggc       240
gcggggtaaa ctgggaaagt gatgtcgtgt actggctccg ccttttttcc gagggtgggg       300
gagaaccgta tataagtgca gtagtcgccg tgaacgttct ttttcgcaac gggtttgccg       360
ccagaacaca ggtgtcgtga cgcggatcca cgcgtgcggc cgcacgcgta agcttagcgc       420
agaggcttgg ggcagccgag cggcagccag gccccggccc gggcctcggt tccagaaggg       480
agaggagccc gccaaggcgc gcaagagagc gggctgcctc gcagtccgag ccggagaggg       540
agcgcgagcc gcgccggccc cggacggcct cgccgccacc atggagacag acacactcct       600
gctatgggtg ctgctgctct gggttccagg ttccactggt gacattgtgc tgacacagtc       660
tcctgcttcc ttagctgtat ctctggggca gagggccacc atctcatgca gggccagcca       720
```

-continued

```
aagtgtcagt tcatctacct ataattttat acactggtat caacagaaat caggacagcc     780
acccaaactc ctcatcaagt atgcatccaa cctagaatct gggggtccctg tcaggttcag    840 tggcagtggg tctgggacag acttctccct caacatccat cctgtggagg aggaggatac    900
tgcaacatat tactgtcagc acagttggga gattccatac acgttcggag ggggggccaa    960
gttggagata aaaggcagta ctagcggtgg tggctccggg ggcggttccg gtgggggcgg    1020
cagcagccag gtgcagctga aggagtcagg acctggcctg gtggcaccct cacagagcct    1080
gtccatcaca tgcaccgtct caggattctc attaagcggc tatggcataa gctgggttcg    1140
ccagcctcca ggaaagcgtc tggaatggct gggattgata tggggtgatg gaaccacaga    1200
ctataattca gctctcaaat ccagactgag catcagcaag gacaactcca agagccaggt    1260
tttcttaaaa atgaacagtc tgcaaactga tgacacagcc aggtacttct gtaccagagg    1320
gcctccggcc ttctataagt acctctactt tgactactgg ggccaaggca ccactctcac    1380
agtctcctca gacaaaactc acacatgccc accgtgccca gcacctcctg tggcaggacc    1440
gtcagtcttc ctcttccccc caaaacccaa ggacaccctc atgatctccc ggacccctga    1500
ggtcacatgc gtggtggtgg acgtgagcca cgaagaccct gaggtcaagt tcaactggta    1560
cgtggacggc gtggaggtgc ataatgccaa gacaaagccg cgggaggagc agtaccagag    1620
cacgtaccgt gtggtcagcg tcctcaccgt cctgcaccag gactggctga atggcaagga    1680
gtacaagtgc aaggtctcca acaaagccct cccagccccc atcgagaaaa ccatctccaa    1740
agccaaaggg cagccccgag aaccacaggt gtacaccctg ccaccatcac gagatgagct    1800
gaccaagaac caggtcagcc tgacctgcct ggtcaaaggc ttctatccca gcgacatcgc    1860
cgtggagtgg gagagcaatg ggcagccgga gaacaactac aagaccacgc ctcccgtgct    1920
ggactccgac ggctccttct tcctctacag caagctcacc gtggacaaga gcaggtggca    1980 gcagggaac gtcttctcat gctccgtgat gcatgaggct ctgcacaacc actacacgca     2040
gaagagcctc tccctgtctc cctttttgggt gctggtggtg gttggtggag tcctggcttg    2100
ctatagcttg ctagtaacag tggcctttat tattttctgg gtgaggagta agaggagcag    2160
gggaggtcac agtgactaca tgaacatgac tccccgccgc cccgggccca cccgcaagca    2220
ttaccagccc tatgccccac cacgcgactt cgcagcctat cgctccaaac ggggcagaaa    2280
gaaactcctg tatatattca aacaaccatt tatgagacca gtacaaacta ctcaagagga    2340
agatggctgt agctgccgat ttccagaaga agaagaagga ggatgtgaac tgagagtgaa    2400
gttcagcagg agcgcagacg cccccgcgta ccagcagggc cagaaccagc tctataacga    2460
gctcaatcta ggacgaagag aggagtacga tgttttggac aagagacgtg gccgggaccc    2520
tgagatgggg ggaaagccga gaaggaagaa ccctcaggaa ggcctgtaca atgaactgca    2580
gaaagataag atggcggagg cctacagtga gattgggatg aaaggcgagc gccggagggg    2640 caagggcac gatggccttt accagggtct cagtacagcc accaaggaca cctacgacgc    2700
ccttcacatg caggccctgc cccctcgctg agatatcgtg ggaattcgag catcttaccg    2760
ccatttattc ccatatttgt tctgtttttc ttgatttggg tatacattta aatgttaata    2820
aaacaaaatg gtggggcaat catttacatt tttaggata tgtaattact agttcaggtg     2880
tattgccaca agacaaacat gttaagaaac tttcccgtta tttacgctct gttcctgtta    2940
atcaacctct ggattacaaa atttgtgaaa gattgactga tattcttaac tatgttgctc    3000 ctttttacgct gtgtggatat gctgctttat agcctctgta tctagctatt gcttcccgta    3060
cggctttcgt tttctcctcc ttgtataaat cctggttgct gtctctttta gaggagttgt    3120
```

-continued

```
ggcccgttgt ccgtcaacgt ggcgtggtgt gctctgtgtt tgctgacgca accccactg      3180 gctggggcat tgccaccacc tgtcaactcc tttctgggac tttcgctttc cccctcccga      3240
tcgccacggc agaactcatc gccgcctgcc ttgcccgctg ctggacaggg gctaggttgc      3300
tgggcactga taattccgtg gtgttgtcgg ggaagctgac gtcctttcct cgaggggggg      3360
cccggtacct ttaagaccaa tgacttacaa ggcagctgta gatcttagcc actttttaaa      3420
agaaaagggg ggactggaag ggctaattca ctcccaacga agacaagatc tgcttttttgc      3480 ttgtactggg tctctctggt tagaccagat ctgagcctgg gagctctctg gctaactagg      3540
gaacccactg cttaagcctc aataaagctt gccttgagtg cttcaagtag tgtgtgcccg      3600
tctgttgtgt gactctggta actagagatc cctcagaccc ttttagtcag tgtggaaaat      3660
ctctagcagt agtagttcat gtcatcttat tattcagtat ttataacttg caaagaaatg      3720
aatatcagag agtgagagga acttgtttat tgcagcttat aatggttaca aataaagcaa      3780
tagcatcaca aatttcacaa ataaagcatt ttttcactg cattctagtt gtggtttgtc       3840
caaactcatc aatgtatctt atcatgtctg gctctagcta tcccgcccct aactccgccc      3900
agttccgccc attctccgcc ccatggctga ctaattttt ttatttatgc agaggccgag       3960
gccgcctcgg cctctgagct attccagaag tagtgaggag gctttttttgg aggcctaggc     4020 ttttgcgtcg agacgtaccc aattcgccct atagtgagtc gtattacgcg cgctcactgg      4080
ccgtcgtttt acaacgtcgt gactgggaaa accctggcgt tacccaactt aatcgccttg      4140
cagcacatcc cctttcgcc agctggcgta atagcgaaga ggcccgcacc gatcgccctt       4200
cccaacagtt gcgcagcctg aatggcgaat ggcgcgacgc gccctgtagc ggcgcattaa      4260
gcgcggcggg tgtggtggtt acgcgcagcg tgaccgctac acttgccagc gccctagcgc      4320
ccgctccttt cgctttcttc ccttcctttc tcgccacgtt cgccggcttt ccccgtcaag      4380
ctctaaatcg ggggctccct ttagggttcc gatttagtgc tttacggcac ctcgacccca      4440
aaaaacttga ttagggtgat ggttcacgta gtgggccatc gccctgatag acggtttttc      4500 gcccttttgac gttggagtcc acgttcttta atagtggact cttgttccaa actggaacaa     4560
cactcaaccc tatctcggtc tattctttttg atttataagg gattttgccg atttcggcct     4620
attggttaaa aaatgagctg atttaacaaa aatttaacgc gaattttaac aaaatattaa      4680
cgtttacaat ttcccaggtg gcactttttcg gggaaatgtg cgcggaaccc ctatttgttt     4740 attttttctaa atacattcaa atatgtatcc gctcatgaga caataaccct gataaatgct      4800
tcaataatat tgaaaaagga agagtatgag tattcaacat ttccgtgtcg cccttattcc      4860 ctttttttgcg gcattttgcc ttcctgtttt tgctcaccca gaaacgctgg tgaaagtaaa      4920
agatgctgaa gatcagttgg gtgcacgagt gggttacatc gaactggatc tcaacagcgg      4980
taagatcctt gagagttttc gccccgaaga acgttttcca atgatgagca cttttaaagt      5040
tctgctatgt ggcgcggtat tatcccgtat tgacgccggg caagagcaac tcggtcgccg      5100
catacactat tctcagaatg acttggttga gtactcacca gtcacagaaa agcatcttac      5160
ggatggcatg acagtaagag aattatgcag tgctgccata accatgagtg ataacactgc      5220
ggccaactta cttctgacaa cgatcggagg accgaaggag ctaaccgctt ttttgcacaa       5280
catgggggat catgtaactc gccttgatcg ttgggaaccg gagctgaatg aagccatacc      5340
aaacgacgag cgtgacacca cgatgcctgt agcaatggca acaacgttgc gcaaactatt      5400
aactggcgaa ctacttactc tagcttcccg gcaacaatta atagactgga tggaggcgga      5460
```

-continued

```
taaagttgca ggaccacttc tgcgctcggc ccttccggct ggctggttta ttgctgataa    5520
atctggagcc ggtgagcgtg ggtctcgcgg tatcattgca gcactggggc cagatggtaa    5580
gccctcccgt atcgtagtta tctacacgac ggggagtcag gcaactatgg atgaacgaaa    5640
tagacagatc gctgagatag gtgcctcact gattaagcat tggtaactgt cagaccaagt    5700
ttactcatat atactttaga ttgatttaaa acttcatttt taatttaaaa ggatctaggt    5760
gaagatcctt tttgataatc tcatgaccaa aatcccttaa cgtgagtttt cgttccactg    5820
agcgtcagac cccgtagaaa agatcaaagg atcttcttga gatccttttt ttctgcgcgt    5880
aatctgctgc ttgcaaacaa aaaaaccacc gctaccagcg gtggtttgtt tgccggatca    5940
agagctacca actctttttc cgaaggtaac tggcttcagc agagcgcaga taccaaatac    6000
tgtccttcta gtgtagccgt agttaggcca ccacttcaag aactctgtag caccgcctac    6060
atacctcgct ctgctaatcc tgttaccagt ggctgctgcc agtggcgata agtcgtgtct    6120
taccgggttg gactcaagac gatagttacc ggataaggcg cagcggtcgg gctgaacggg    6180
gggttcgtgc acacagccca gcttggagcg aacgacctac accgaactga gatacctaca    6240
gcgtgagcta tgagaaagcg ccacgcttcc cgaagggaga aaggcggaca ggtatccggt    6300
aagcggcagg tcggaacagg agagcgcac gagggagctt ccagggggaa acgcctggta    6360
tctttatagt cctgtcgggt ttcgccacct ctgacttgag cgtcgatttt tgtgatgctc    6420
gtcagggggg cggagcctat ggaaaaacgc cagcaacgcg gcctttttac ggttcctggc    6480
cttttgctgg ccttttgctc acatgttctt tcctgcgtta tcccctgatt ctgtggataa    6540
ccgtattacc gcctttgagt gagctgatac cgctcgccgc agccgaacga ccgagcgcag    6600
cgagtcagtg agcgaggaag cggaagagcg cccaatacgc aaaccgcctc tccccgcgcg    6660
ttggccgatt cattaatgca gctggcacga caggtttccc gactggaaag cgggcagtga    6720
gcgcaacgca attaatgtga gttagctcac tcattaggca ccccaggctt tacactttat    6780
gcttccggct cgtatgttgt gtggaattgt gagcggataa caatttcaca caggaaacag    6840
ctatgaccat gattacgcca agcgcgcaat taaccctcac taaagggaac aaaagctgga    6900
gctgcaagct taatgtagtc ttatgcaata ctcttgtagt cttgcaacat ggtaacgatg    6960
agttagcaac atgccttaca aggagagaaa aagcaccgtg catgccgatt ggtggaagta    7020
aggtggtacg atcgtgcctt attaggaagg caacagacgg gtctgacatg gattggacga    7080
accactgaat tgccgcattg cagagatatt gtatttaagt gcctagctcg atacataaac    7140
gggtctctct ggttagacca gatctgagcc tgggagctct ctggctaact agggaaccca    7200
ctgcttaagc ctcaataaag cttgccttga gtgcttcaag tagtgtgtgc ccgtctgttg    7260
tgtgactctg gtaactagag atccctcaga cccttttagt cagtgtggaa aatctctagc    7320
agtggcgccc gaacagggac ttgaaagcga aagggaaacc agaggagctc tctcgacgca    7380
ggactcggct tgctgaagcg cgcacggcaa gaggcgaggg gcggcgactg gtgagtacgc    7440
caaaaatttt gactagcgga ggctagaagg agagagatgg gtgcgagagc gtcagtatta    7500 agcggggggag aattagatcg cgatgggaaa aaattcggtt aaggccaggg ggaaagaaaa    7560
aatataaatt aaaacatata gtatgggcaa gcagggagct agaacgattc gcagttaatc    7620
ctggcctgtt agaaacatca gaaggctgta gacaaatact gggacagcta caaccatccc    7680
ttcagacagg atcagaagaa cttagatcat tatataatac agtagcaacc ctctattgtg    7740
tgcatcaaag gatagagata aaagacacca aggaagcttt agacaagata gaggaagagc    7800
aaaacaaaag taagaccacc gcacagcaag cggccgctga tcttcagacc tggaggagga    7860
```

```
gatatgaggg acaattggag aagtgaatta tataaatata aagtagtaaa aattgaacca   7920
ttaggagtag cacccaccaa ggcaaagaga agagtggtgc agagagaaaa aagagcagtg   7980
ggaataggag ctttgttcct tgggttcttg ggagcagcag gaagcactat gggcgcagcc   8040
tcaatgacgc tgacggtaca ggccagacaa ttattgtctg gtatagtgca gcagcagaac   8100
aatttgctga gggctattga ggcgcaacag catctgttgc aactcacagt ctggggcatc   8160
aagcagctcc aggcaagaat cctggctgtg gaaagatacc taaaggatca acagctcctg   8220
gggatttggg gttgctctgg aaaactcatt tgcaccactg ctgtgccttg gaatgctagt   8280
tggagtaata aatctctgga acagatttgg aatcacacga cctggatgga gtgggacaga   8340
gaaattaaca attacacaag cttaatacac tccttaattg aagaatcgca aaaccagcaa   8400
gaaaagaatg aacaagaatt attggaatta gataaatggg caagtttgtg gaattggttt   8460
aacataacaa attggctgtg gtatataaaa ttattcataa tgatagtagg aggcttggta   8520
ggtttaagaa tagtttttgc tgtactttct atagtgaata gagttaggca gggatattca   8580
ccattatcgt ttcagaccca cctcccaacc ccgaggggac ccgacaggcc cgaaggaata   8640
gaagaagaag gtggagagag agacagagac agatccattc gattagtgaa cggatctcga   8700
cggtatcggt t                                                        8711
```

<210> SEQ ID NO 5
<211> LENGTH: 5054
<212> TYPE: DNA
<213> ORGANISM: Unknown
<220> FEATURE:
<223> OTHER INFORMATION: EF1alpha

<400> SEQUENCE: 5

```
gtcgacattg attattgact agatcatcgc gtgaggctcc ggtgcccgtc agtgggcaga     60
gcgcacatcg cccacagtcc ccgagaagtt ggggggaggg gtcggcaatt gaaccggtgc    120
ctagagaagg tggcgcgggg taaactggga aagtgatgtc gtgtactggc tccgcctttt    180
tcccgagggt gggggagaac cgtatataag tgcagtagtc gccgtgaacg ttctttttcg    240
caacgggttt gccgccagaa cacaggtaag tgccgtgtgt ggttcccgcg ggcctggcct    300
ctttacgggt tatggccctt gcgtgccttg aattacttcc acgcccctgg ctgcagtacg    360
tgattcttga tcccgagctt cgggttggaa gtgggtggga gagttcgagg ccttgcgctt    420
aaggagcccc ttcgcctcgt gcttgagttg aggcctggcc tgggcgctgg ggccgccgcg    480
tgcgaatctg gtggcacctt cgcgcctgtc tcgctgcttt cgataagtct ctagccattt    540 aaaattttg atgacctgct gcgacgcttt ttttctggca agatagtctt gtaaatgcgg    600
gccaagatct gcacactggt atttcggttt ttggggccgc gggcggcgac ggggcccgtg    660
cgtcccagcg cacatgttcg gcgaggcggg cctgcgagc gcggccaccg agaatcggac    720
gggggtagtc tcaagctggc cggcctgctc tggtgcctgg cctcgcgccg ccgtgtatcg    780
ccccgccctg ggcggcaagg ctggcccggt cggcaccagt tgcgtgagcg gaaagatggc    840
cgcttccggg ccctgctgca gggagctcaa aatggaggac gcggcgctcg ggagagcggg    900
cgggtgagtc acccacacaa aggaaaaggg cctttccgtc ctcagccgtc gcttcatgtg    960
actccacgga gtaccgggcg ccgtccaggc acctcgatta gttctcgagc ttttggagta   1020
cgtcgtcttt aggttggggg gaggggtttt atgcgatgga gtttccccac actgagtggg   1080
tggagactga agttaggcca gcttggcact tgatgtaatt ctccttggaa tttgcccttt   1140
```

-continued

```
ttgagtttgg atcttggttc attctcaagc ctcagacagt ggttcaaagt ttttttcttc     1200
catttcaggt gtcgtgagga attctgcagt cgacggtacc gcgggcccgg gatccaccgg     1260
tcgccaccat ggtgagcaag ggcgaggagc tgttcaccgg ggtggtgccc atcctggtcg     1320
agctggacgg cgacgtaaac ggccacaagt tcagcgtgtc cggcgagggc gagggcgatg     1380
ccacctacgg caagctgacc ctgaagttca tctgcaccac cggcaagctg cccgtgccct     1440
ggcccaccct cgtgaccacc ctgacctacg gcgtgcagtg cttcagccgc taccccgacc     1500
acatgaagca gcacgacttc ttcaagtccg ccatgcccga aggctacgtc caggagcgca     1560
ccatcttctt caaggacgac ggcaactaca agacccgcgc cgaggtgaag ttcgagggcg     1620
acaccctggt gaaccgcatc gagctgaagg gcatcgactt caaggaggac ggcaacatcc     1680
tggggcacaa gctggagtac aactacaaca gccacaacgt ctatatcatg gccgacaagc     1740
agaagaacgg catcaaggtg aacttcaaga tccgccacaa catcgaggac ggcagcgtgc     1800
agctcgccga ccactaccag cagaacaccc ccatcggcga cggccccgtg ctgctgcccg     1860
acaaccacta cctgagcacc cagtccgccc tgagcaaaga ccccaacgag aagcgcgatc     1920
acatggtcct gctggagttc gtgaccgccg ccgggatcac tctcggcatg gacgagctgt     1980
acaagtaaag cggccgcact cctcaggtgc aggctgccta tcagaaggtg gtggctggtg     2040
tggccaatgc cctggctcac aaataccact gagatctttt tccctctgcc aaaaattatg     2100
gggacatcat gaagcccctt gagcatctga cttctggcta taaaggaaa tttattttca     2160 ttgcaatagt gtgttggaat tttttgtgtc tctcactcgg aaggacatat gggagggcaa     2220
atcatttaaa acatcagaat gagtatttgg tttagagttt ggcaacatat gcccatatgc     2280
tggctgccat gaacaaaggt tggctataaa gaggtcatca gtatatgaaa cagcccctg      2340 ctgtccattc cttattccat agaaaagcct tgacttgagg ttagatttt tttatatttt      2400 gttttgtgtt atttttttct ttaacatccc taaaattttc cttacatgtt ttactagcca     2460 gattttcct cctctcctga ctactcccag tcatagctgt ccctcttctc ttatggagat       2520
ccctcgacct gcagcccaag cttggcgtaa tcatggtcat agctgtttcc tgtgtgaaat     2580
tgttatccgc tcacaattcc acacaacata cgagccggaa gcataaagtg taaagcctgg     2640
ggtgcctaat gagtgagcta actcacatta attgcgttgc gctcactgcc cgctttccag     2700
tcgggaaacc tgtcgtgcca gcggatccgc atctcaatta gtcagcaacc atagtcccgc     2760
ccctaactcc gcccatcccg cccctaactc cgcccagttc cgcccattct ccgccccatg     2820
gctgactaat tttttttatt tatgcagagg ccgaggccgc ctcggcctct gagctattcc     2880
agaagtagtg aggaggcttt tttggaggcc taggctttg caaaaagcta acttgtttat      2940
tgcagcttat aatggttaca ataaagcaa tagcatcaca aatttcacaa ataaagcatt      3000 ttttcactg cattctagtt gtggtttgtc caaactcatc aatgtatctt atcatgtctg       3060
gatccgctgc attaatgaat cggccaacgc gcggggagag gcggtttgcg tattgggcgc     3120
tcttccgctt cctcgctcac tgactcgctg cgctcggtcg ttcggctgcg gcgagcggta     3180
tcagctcact caaaggcggt aatacggtta tccacagaat caggggataa cgcaggaaag     3240
aacatgtgag caaaaggcca gcaaaaggcc aggaaccgta aaaaggccgc gttgctggcg     3300 ttttttccata ggctccgccc ccctgacgag catcacaaaa atcgacgctc aagtcagagg    3360
tggcgaaacc cgacaggact ataaagatac caggcgtttc ccctggaag ctccctcgtg       3420 cgctctcctg ttccgaccct gccgcttacc ggatacctgt ccgcctttct cccttcggga     3480
agcgtggcgc tttctcatag ctcacgctgt aggtatctca gttcggtgta ggtcgttcgc     3540
```

```
tccaagctgg gctgtgtgca cgaaccccccc gttcagcccg accgctgcgc cttatccggt    3600
aactatcgtc ttgagtccaa ccccggtaaga cacgacttat cgccactggc agcagccact    3660
ggtaacagga ttagcagagc gaggtatgta ggcggtgcta cagagttctt gaagtggtgg    3720
cctaactacg gctacactag aagaacagta tttggtatct gcgctctgct gaagccagtt    3780
accttcggaa aaagagttgg tagctcttga tccggcaaac aaaccaccgc tggtagcggt    3840
ggtttttttg tttgcaagca gcagattacg cgcagaaaaa aaggatctca agaagatcct    3900
ttgatctttt ctacggggtc tgacgctcag tggaacgaaa actcacgtta agggattttg    3960
gtcatgagat tatcaaaaag gatcttcacc tagatccttt taaattaaaa atgaagtttt    4020
aaatcaatct aaagtatata tgagtaaact tggtctgaca gttaccaatg cttaatcagt    4080
gaggcaccta tctcagcgat ctgtctattt cgttcatcca tagttgcctg actccccgtc    4140
gtgtagataa ctacgatacg ggagggctta ccatctggcc ccagtgctgc aatgataccg    4200
cgagacccac gctcaccggc tccagattta tcagcaataa accagccagc cggaagggcc    4260
gagcgcagaa gtggtcctgc aactttatcc gcctccatcc agtctattaa ttgttgccgg    4320
gaagctagag taagtagttc gccagttaat agtttgcgca acgttgttgc cattgctaca    4380
ggcatcgtgg tgtcacgctc gtcgtttggt atggcttcat tcagctccgg ttcccaacga    4440
tcaaggcgag ttacatgatc ccccatgttg tgcaaaaaag cggttagctc cttcggtcct    4500
ccgatcgttg tcagaagtaa gttggccgca gtgttatcac tcatggttat ggcagcactg    4560
cataattctc ttactgtcat gccatccgta agatgctttt ctgtgactgg tgagtactca    4620
accaagtcat tctgagaata gtgtatgcgg cgaccgagtt gctcttgccc ggcgtcaata    4680
cgggataata ccgcgccaca tagcagaact ttaaaagtgc tcatcattgg aaaacgttct    4740
tcggggcgaa aactctcaag gatcttaccg ctgttgagat ccagttcgat gtaacccact    4800
cgtgcaccca actgatcttc agcatctttt actttcacca gcgtttctgg gtgagcaaaa    4860
acaggaaggc aaaatgccgc aaaaaaggga ataagggcga cacggaaatg ttgaatactc    4920
atactcttcc tttttcaata ttattgaagc atttatcagg gttattgtct catgagcgga    4980
tacatatttg aatgtattta gaaaaataaa caaatagggg ttccgcgcac atttccccga    5040
aaagtgccac ctgg    5054
```

```
<210> SEQ ID NO 6
<211> LENGTH: 80
<212> TYPE: DNA
<213> ORGANISM: Unknown
<220> FEATURE:
<223> OTHER INFORMATION: Woodchuck Hepatitis Virus Posttranscriptional
      Regulatory Element Alpha Component

<400> SEQUENCE: 6
gccacggcgg aactcatcgc cgcctgcctt gcccgctgct ggacaggggc tcggctgttg    60
ggcactgaca attccgtggt    80

<210> SEQ ID NO 7
<211> LENGTH: 592
<212> TYPE: DNA
<213> ORGANISM: Unknown
<220> FEATURE:
<223> OTHER INFORMATION: Woodchuck Hepatitis Virus Posttranscriptional
      Regulatory Element
```

-continued

<400> SEQUENCE: 7

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga ctttcgcttt cccctccct     300 attgccacgg cggaactcat cgccgcctgc cttgcccgct gctggacagg ggctcggctg     360
ttgggcactg acaattccgt ggtgttgtcg gggaagctga cgtcctttcc atggctgctc     420
gcctgtgttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgcc tg            592
```

```
<210> SEQ ID NO 8
<211> LENGTH: 18
<212> TYPE: PRT
<213> ORGANISM: Unknown
<220> FEATURE:
<223> OTHER INFORMATION: T2A
```

<400> SEQUENCE: 8

```
Glu Gly Arg Gly Ser Leu Leu Thr Cys Gly Asp Val Glu Glu Asn Pro
1               5                   10                  15

Gly Pro
```

```
<210> SEQ ID NO 9
<211> LENGTH: 19
<212> TYPE: PRT
<213> ORGANISM: Unknown
<220> FEATURE:
<223> OTHER INFORMATION: P2A
```

<400> SEQUENCE: 9

```
Ala Thr Asn Phe Ser Leu Leu Lys Gln Ala Gly Asp Val Glu Glu Asn
1               5                   10                  15

Pro Gly Pro
```

```
<210> SEQ ID NO 10
<211> LENGTH: 20
<212> TYPE: PRT
<213> ORGANISM: Unknown
<220> FEATURE:
<223> OTHER INFORMATION: E2A
```

<400> SEQUENCE: 10

```
Gln Cys Thr Asn Tyr Ala Leu Leu Lys Leu Ala Gly Asp Val Glu Ser
1               5                   10                  15

Asn Pro Gly Pro
            20
```

```
<210> SEQ ID NO 11
<211> LENGTH: 22
<212> TYPE: PRT
<213> ORGANISM: Unknown
<220> FEATURE:
<223> OTHER INFORMATION: F2A
```

<400> SEQUENCE: 11

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 12
<211> LENGTH: 21
<212> TYPE: PRT
<213> ORGANISM: Unknown
<220> FEATURE:
<223> OTHER INFORMATION: T2A

<400> SEQUENCE: 12

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 13
<211> LENGTH: 22
<212> TYPE: PRT
<213> ORGANISM: Unknown
<220> FEATURE:
<223> OTHER INFORMATION: P2A

<400> SEQUENCE: 13

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 14
<211> LENGTH: 23
<212> TYPE: PRT
<213> ORGANISM: Unknown
<220> FEATURE:
<223> OTHER INFORMATION: E2A

<400> SEQUENCE: 14

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 15
<211> LENGTH: 25
<212> TYPE: PRT
<213> ORGANISM: Unknown
<220> FEATURE:
<223> OTHER INFORMATION: F2A

<400> SEQUENCE: 15

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 16
<211> LENGTH: 11111
<212> TYPE: DNA
<213> ORGANISM: Unknown
<220> FEATURE:

-continued

<223> OTHER INFORMATION: 64-AAV-CAR-T-Regs

<400> SEQUENCE: 16

```
ctgttttaaa agaaaagggg ggattggggg gtacagtgca ggggaaagaa tagtagacat      60
aatagcaaca gacatacaaa ctaaagaatt acaaaaacaa attacaaaaa ttcaaaattt     120
tatcaacaag cttgatcgat ggctccggtg cccgtcagtg ggcagagcgc acatcgccca     180
cagtccccga gaagttgggg ggaggggtcg gcaattgaac cggtgcctag agaaggtggc     240
gcggggtaaa ctgggaaagt gatgtcgtgt actggctccg cctttttccc gagggtgggg     300
gagaaccgta tataagtgca gtagtcgccg tgaacgttct ttttcgcaac gggtttgccg     360
ccagaacaca ggtgtcgtga cgcggatcca cgcgtgcggc cgcacgcgta agcttagcgc     420
agaggcttgg ggcagccgag cggcagccag gccccggccc gggcctcggt tccagaaggg     480
agaggagccc gccaaggcgc gcaagagagc gggctgcctc gcagtccgag ccggagaggg     540
agcgcgagcc gcgccggccc cggacggcct cgccgccacc atggctctgc ccgtcaccgc     600
actgctgctg cctctggctc tgctgctgca cgccgcaaga ccagacattg tgctgacaca     660
gtctcctgct tccttagctg tatctctggg gcagagggcc accatctcat gcagggccag     720
ccaaagtgtc agttcatcta cctataattt tatacactgg tatcaacaga aatcaggaca     780
gccacccaaa ctcctcatca agtatgcatc caacctagaa tctggggtcc ctgtcaggtt     840
cagtggcagt gggtctggga cagacttctc cctcaacatc catcctgtgg aggaggagga     900
tactgcaaca tattactgtc agcacagttg ggagattcca tacacgttcg gaggggggggc     960 caagttggag ataaaaggca gtactagcgg tggtggctcc gggggcggtt ccggtggggg    1020
cggcagcagc caggtgcagc tgaaggagtc aggacctggc ctggtggcac cctcacagag    1080
cctgtccatc acatgcaccg tctcaggatt ctcattaagc ggctatggca taagctgggt    1140
tcgccagcct ccaggaaagc gtctggaatg gctgggattg atatggggtg atggaaccac    1200
agactataat tcagctctca aatccagact gagcatcagc aaggacaact ccaagagcca    1260 ggtttttctta aaaatgaaca gtctgcaaac tgatgacaca gccaggtact tctgtaccag    1320
agggcctccg gccttctata agtacctcta ctttgactac tggggccaag caccactct     1380 cacagtctcc tcactcgacc ccaaatcttc tgacaaaact cacacatgcc caccgtgccc    1440
agcacctcct gtggcaggac cgtcagtctt cctcttcccc ccaaaaccca aggacaccct    1500
catgatctcc cggacccctg aggtcacatg cgtggtggtg gacgtgagcc acgaagaccc    1560
tgaggtcaag ttcaactggt acgtggacgg cgtggaggtg cataatgcca agacaaagcc    1620
gcgggaggag cagtaccaga gcacgtaccg tgtggtcagc gtcctcaccg tcctgcacca    1680
ggactggctg aatggcaagg agtacaagtg caaggtctcc aacaaagccc tcccagcccc    1740
catcgagaaa accatctcca aagccaaagg gcagccccga gaaccacagg tgtacaccct    1800
gccaccatca cgagatgagc tgaccaagaa ccaggtcagc ctgacctgcc tggtcaaagg    1860
cttctatccc agcgacatcg ccgtggagtg ggagagcaat gggcagccgg agaacaacta    1920
caagaccacg cctcccgtgc tggactccga cggctccttc ttcctctaca gcaagctcac    1980
cgtggacaag agcaggtggc agcaggggaa cgtcttctca tgctccgtga tgcatgaggc    2040
tctgcacaac cactacacgc agaagagcct ctccctgtct cccttttggg tgctggtggt    2100
ggttggtgga gtcctggctt gctatagctt gctagtaaca gtggccttta ttattttctg    2160
ggtgaggagt aagaggagca ggggaggtca cagtgactac atgaacatga ctccccgccg    2220 cccccgggccc acccgcaagc attaccagcc ctatgcccca ccacgcgact cgcagcccta    2280
```

-continued

```
tcgctccaaa cggggcagaa agaaactcct gtatatattc aaacaaccat ttatgagacc    2340
agtacaaact actcaagagg aagatggctg tagctgccga tttccagaag aagaagaagg    2400
aggatgtgaa ctgagagtga agttcagcag gagcgcagac gccccgcgt accagcaggg     2460 ccagaaccag ctctataacg agctcaatct aggacgaaga gaggagtacg atgttttgga    2520
caagagacgt ggccgggacc ctgagatggg gggaaagccg agaaggaaga accctcagga    2580
aggcctgtac aatgaactgc agaaagataa gatggcggag gcctacagtg agattgggat    2640
gaaaggcgag cgccggaggg gcaaggggca cgatggcctt taccagggtc tcagtacagc    2700
caccaaggac acctacgacg cccttcacat gcaggccctg cccctcgcc agtgtactaa     2760 ttatgctctc ttgaaattgg ctggagatgt tgagagcaac cccgggccgg aattcatgcc    2820
caaccctagg ccagccaagc ctatggctcc ttccttggcc cttggcccat ccccaggagt    2880
cttgccaagc tggaagactg cacccaaggg ctcagaactt ctagggacca ggggctctgg    2940
gggacccttc caaggtcggg acctgcgaag tggggcccac acctcttctt ccttgaaccc    3000
cctgccacca tcccagctgc agctgcctac agtgccccta gtcatggtgg caccgtctgg    3060
ggcccgacta ggtccctcac cccacctaca ggcccttctc caggacagac cacacttcat    3120
gcatcagctc tccactgtgg atgcccatgc ccagacccct gtgctccaag tgcgtccact    3180
ggacaaccca gccatgatca gcctcccacc accttctgct gccactgggg tcttctccct    3240
caaggcccgg cctggcctgc cacctgggat caatgtggcc agtctggaat gggtgtccag    3300
ggagccagct ctactctgca ccttcccacg ctcgggtaca cccaggaaag acagcaacct    3360
tttggctgca ccccaaggat cctacccact gctggcaaat ggagtctgca agtggcctgg    3420
ttgtgagaag gtcttcgagg agccagaaga gtttctcaag cactgccaag cagatcatct    3480
cctggatgag aaaggcaagg cccagtgcct cctccagaga gaagtggtgc agtctctgga    3540
gcagcagctg gagctggaaa aggagaagct gggagctatg caggcccacc tggctgggaa    3600
gatggcgctg gccaaggctc catctgtggc ctcaatggac aagagctctt gctgcatcgt    3660
agccaccagt actcagggca gtgtgctccc ggcctggtct gctcctcggg aggctccaga    3720
cggcggcctg tttgcagtgc ggaggcacct ctggggaagc catggcaata gttccttccc    3780
agagttcttc cacaacatgg actacttcaa gtaccacaat atgcgacccc ctttcaccta    3840
tgccacccct atccgatggg ccatcctgga agccccggag aggcagagga cactcaatga    3900
aatctaccat tggtttactc gcatgttcgc ctacttcaga aaccacccg ccacctggaa      3960 gaatgccatc cgccacaacc tgagcctgca caagtgcttt gtgcgagtgg agagcgagaa    4020
gggagcagtg tggaccgtag atgaatttga gtttcgcaag aagaggagcc aacgccccaa    4080
caagtgctcc aatccctgcc cccagtgtac taattatgct ctcttgaaat tggctggaga    4140
tgttgagagc aaccccgggc cgatgccacc tcctcgcctc ctcttcttcc tcctcttcct    4200 caccccatg gaagtcaggc ccgaggaacc tctagtggtg aaggtggaag agggagataa      4260
cgctgtgctg cagtgcctca gggggacctc agatggcccc actcagcagc tgacctggtc    4320
tcgggagtcc ccgcttaaac ccttcttaaa actcagcctg gggctgccag gcctgggaat    4380
ccacatgagg cccctggcca tctggctttt catcttcaac gtctctcaac agatgggggg    4440
cttctacctg tgccagccgg ggccccctc tgagaaggcc tggcagcctg ctggacagt      4500 caatgtggag ggcagcgggg agctgttccg gtggaatgtt tcggacctag gtggcctggg    4560
ctgtggcctg aagaacaggt cctcagaggg ccccagctcc ccttccggga agctcatgag    4620
```

-continued

```
ccccaagctg tatgtgtggg ccaaagaccg ccctgagatc tgggagggag agcctccgtg    4680
tgtcccaccg agggacagcc tgaaccagag cctcagccag gacctcacca tggcccctgg    4740
ctccacactc tggctgtcct gtggggtacc ccctgactct gtgtccaggg gcccctctc     4800 ctggacccat gtgcaccca aggggcctaa gtcattgctg agcctagagc tgaaggacga     4860
tcgcccggcc agagatatgt gggtaatgga gacgggtctg ttgttgcccc gggccacagc    4920
tcaagacgct ggaaagtatt attgtcaccg tggcaacctg accatgtcat tccacctgga    4980
gatcactgct cggccagtac tatggcactg gctgctgagg actggtggct ggaaggtctc    5040
agctgtgact ttggcttatc tgatcttctg cctgtgttcc cttgtgggca ttcttcatct    5100
tcaaagagcc ctggtcctga ggaggaaaag atgatctaga taaattcgag catcttaccg    5160
ccatttattc ccatatttgt tctgtttttc ttgatttggg tatacattta aatgttaata    5220
aaacaaaatg gtggggcaat catttacatt tttagggata tgtaattact agttcaggtg    5280
tattgccaca agacaaacat gttaagaaac tttcccgtta tttacgctct gttcctgtta    5340
atcaacctct ggattacaaa atttgtgaaa gattgactga tattcttaac tatgttgctc    5400
cttttacgct gtgtggatat gctgctttat agcctctgta tctagctatt gcttcccgta    5460
cggctttcgt tttctcctcc ttgtataaat cctggttgct gtctctttta gaggagttgt    5520
ggcccgttgt ccgtcaacgt ggcgtggtgt gctctgtgtt tgctgacgca accccccactg   5580 gctggggcat tgccaccacc tgtcaactcc tttctgggac tttcgctttc ccctcccga     5640 tcgccacggc agaactcatc gccgcctgcc ttgcccgctg ctggacaggg gctaggttgc     5700
tgggcactga taattccgtg gtgttgtcgg ggaagctgac gtcctttcct cgaggggggg     5760
cccggtacct ttaagaccaa tgacttacaa ggcagctgta gatcttagcc actttttaaa    5820
agaaaagggg ggactggaag ggctaattca ctcccaacga agacaagatc tgcttttttgc   5880 ttgtactggg tctctctggt tagaccagat ctgagcctgg gagctctctg gctaactagg    5940
gaacccactg cttaagcctc aataaagctt gccttgagtg cttcaagtag tgtgtgcccg    6000
tctgttgtgt gactctggta actagagatc cctcagaccc ttttagtcag tgtggaaaat    6060
ctctagcagt agtagttcat gtcatcttat tattcagtat ttataacttg caaagaaatg    6120
aatatcagag agtgagagga acttgtttat tgcagcttat aatggttaca aataaagcaa    6180
tagcatcaca aatttcacaa ataaagcatt tttttcactg cattctagtt gtggtttgtc    6240
caaactcatc aatgtatctt atcatgtctg gctctagcta tcccgcccct aactccgccc    6300
agttccgccc attctccgcc ccatggctga ctaattttttt ttatttatgc agaggccgag    6360
gccgcctcgg cctctgagct attccagaag tagtgaggag gcttttttgg aggcctaggc    6420
ttttgcgtcg agacgtaccc aattcgccct atagtgagtc gtattacgcg cgctcactgg    6480
ccgtcgtttt acaacgtcgt gactgggaaa accctggcgt tacccaactt aatcgccttg    6540
cagcacatcc ccctttcgcc agctggcgta atagcgaaga ggcccgcacc gatcgccctt    6600
cccaacagtt gcgcagcctg aatggcgaat ggcgcgacgc gccctgtagc ggcgcattaa    6660
gcgcggcggg tgtggtggtt acgcgcagcg tgaccgctac acttgccagc gccctagcgc    6720
ccgctccttt cgctttcttc ccttcctttc tcgccacgtt cgccggcttt ccccgtcaag    6780
ctctaaatcg ggggctccct ttagggttcc gatttagtgc tttacggcac ctcgacccca    6840
aaaaacttga ttagggtgat ggttcacgta gtgggccatc gccctgatag acggtttttc    6900
gccctttgac gttggagtcc acgttcttta atagtggact cttgttccaa actggaacaa    6960
cactcaaccc tatctcggtc tattcttttg atttataagg gattttgccg atttcggcct    7020
```

-continued

```
attggttaaa aaatgagctg atttaacaaa aatttaacgc gaattttaac aaaatattaa    7080
cgtttacaat ttcccaggtg gcacttttcg gggaaatgtg cgcggaaccc ctatttgttt    7140 attttttctaa atacattcaa atatgtatcc gctcatgaga caataaccct gataaatgct    7200
tcaataatat tgaaaaagga agagtatgag tattcaacat ttccgtgtcg cccttattcc    7260
cttttttgcg gcattttgcc ttcctgtttt tgctcaccca gaaacgctgg tgaaagtaaa    7320
agatgctgaa gatcagttgg gtgcacgagt gggttacatc gaactggatc tcaacagcgg    7380
taagatcctt gagagttttc gccccgaaga cgtttttcca atgatgagca cttttaaagt    7440
tctgctatgt ggcgcggtat tatcccgtat tgacgccggg caagagcaac tcggtcgccg    7500
catacactat tctcagaatg acttggttga gtactcacca gtcacagaaa agcatcttac    7560
ggatggcatg acagtaagag aattatgcag tgctgccata accatgagtg ataacactgc    7620
ggccaactta cttctgacaa cgatcggagg accgaaggag ctaaccgctt ttttgcacaa    7680
catgggggat catgtaactc gccttgatcg ttgggaaccg gagctgaatg aagccatacc    7740
aaacgacgag cgtgacacca cgatgcctgt agcaatggca caacgttgc gcaaactatt    7800 aactggcgaa ctacttactc tagcttcccg gcaacaatta atagactgga tggaggcgga    7860
taaagttgca ggaccacttc tgcgctcggc ccttccggct ggctggttta ttgctgataa    7920
atctggagcc ggtgagcgtg ggtctcgcgg tatcattgca gcactggggc cagatggtaa    7980
gccctcccgt atcgtagtta tctacacgac ggggagtcag gcaactatgg atgaacgaaa    8040
tagacagatc gctgagatag gtgcctcact gattaagcat tggtaactgt cagaccaagt    8100
ttactcatat atactttaga ttgatttaaa acttcatttt taatttaaaa ggatctaggt    8160
gaagatcctt tttgataatc tcatgaccaa aatcccttaa cgtgagtttt cgttccactg    8220
agcgtcagac cccgtagaaa agatcaaagg atcttcttga tcctttttt ttctgcgcgt    8280 aatctgctgc ttgcaaacaa aaaaaccacc gctaccagcg gtggtttgtt tgccggatca    8340
agagctacca actctttttc cgaaggtaac tggcttcagc agagcgcaga taccaaatac    8400
tgtccttcta gtgtagccgt agttaggcca ccacttcaag aactctgtag caccgcctac    8460
atacctcgct ctgctaatcc tgttaccagt ggctgctgcc agtggcgata agtcgtgtct    8520
taccgggttg gactcaagac gatagttacc ggataaggcg cagcggtcgg ctgaacggg    8580 gggttcgtgc acacagccca gcttggagcg aacgacctac accgaactga gatacctaca    8640
gcgtgagcta tgagaaagcg ccacgcttcc cgaagggaga aaggcggaca ggtatccggt    8700
aagcggcagg tcggaacagg agagcgcac gagggagctt ccagggggaa acgcctggta    8760
tctttatagt cctgtcgggt ttcgccacct ctgacttgag cgtcgatttt tgtgatgctc    8820 gtcaggggg cggagcctat ggaaaaacgc cagcaacgcg gcctttttac ggttcctggc    8880
cttttgctgg ccttttgctc acatgttctt tcctgcgtta tccctgatt ctgtggataa    8940 ccgtattacc gcctttgagt gagctgatac cgctcgccgc agccgaacga ccgagcgcag    9000
cgagtcagtg agcgaggaag cggaagagcg cccaatacgc aaaccgcctc tccccgcgcg    9060
ttggccgatt cattaatgca gctggcacga caggtttccc gactggaaag cgggcagtga    9120
gcgcaacgca attaatgtga gttagctcac tcattaggca ccccaggctt tacactttat    9180
gcttccggct cgtatgttgt gtggaattgt gagcggataa caatttcaca caggaaacag    9240
ctatgaccat gattacgcca agcgcgcaat taaccctcac taaagggaac aaaagctgga    9300
gctgcaagct taatgtagtc ttatgcaata ctcttgtagt cttgcaacat ggtaacgatg    9360
```

-continued

```
agttagcaac atgccttaca aggagagaaa aagcaccgtg catgccgatt ggtggaagta    9420
aggtggtacg atcgtgcctt attaggaagg caacagacgg gtctgacatg gattggacga    9480
accactgaat tgccgcattg cagagatatt gtatttaagt gcctagctcg atacataaac    9540
gggtctctct ggttagacca gatctgagcc tgggagctct ctggctaact agggaaccca    9600
ctgcttaagc ctcaataaag cttgccttga gtgcttcaag tagtgtgtgc ccgtctgttg    9660
tgtgactctg gtaactagag atccctcaga cccttttagt cagtgtggaa aatctctagc    9720
agtggcgccc gaacagggac ttgaaagcga aagggaaacc agaggagctc tctcgacgca    9780
ggactcggct tgctgaagcg cgcacggcaa gaggcgaggg gcggcgactg gtgagtacgc    9840
caaaaatttt gactagcgga ggctagaagg agagagatgg gtgcgagagc gtcagtatta    9900 agcggggggag aattagatcg cgatgggaaa aaattcggtt aaggccaggg ggaaagaaa    9960 aatataaatt aaaacatata gtatgggcaa gcagggagct agaacgattc gcagttaatc    10020
ctggcctgtt agaaacatca gaaggctgta gacaaatact gggacagcta caaccatccc    10080
ttcagacagg atcagaagaa cttagatcat tatataatac agtagcaacc ctctattgtg    10140
tgcatcaaag gatagagata aaagacacca aggaagcttt agacaagata gaggaagagc    10200
aaaacaaaag taagaccacc gcacagcaag cggccgctga tcttcagacc tggaggagga    10260
gatatgaggg acaattggag aagtgaatta tataaatata aagtagtaaa aattgaacca    10320
ttaggagtag cacccaccaa ggcaaagaga agagtggtgc agagagaaaa aagagcagtg    10380
ggaataggag ctttgttcct tgggttcttg ggagcagcag gaagcactat gggcgcagcc    10440
tcaatgacgc tgacggtaca ggccagacaa ttattgtctg gtatagtgca gcagcagaac    10500
aatttgctga gggctattga ggcgcaacag catctgttgc aactcacagt ctggggcatc    10560
aagcagctcc aggcaagaat cctggctgtg aaagatacc taaaggatca acagctcctg    10620
gggatttggg gttgctctgg aaaactcatt tgcaccactg ctgtgccttg gaatgctagt    10680
tggagtaata aatctctgga acagatttgg aatcacacga cctggatgga gtgggacaga    10740
gaaattaaca attacacaag cttaatacac tccttaattg aagaatcgca aaaccagcaa    10800
gaaaagaatg aacaagaatt attggaatta gataaatggg caagtttgtg gaattggttt    10860
aacataacaa attggctgtg gtatataaaa ttattcataa tgatagtagg aggcttggta    10920
ggtttaagaa tagttttttgc tgtactttct atagtgaata gagttaggca gggatattca    10980
ccattatcgt ttcagaccca cctcccaacc ccgaggggac ccgacaggcc cgaaggaata    11040
gaagaagaag gtggagagag agacagagac agatccattc gattagtgaa cggatctcga    11100
cggtatcggt t                                                         11111
```

```
<210> SEQ ID NO 17
<211> LENGTH: 9764
<212> TYPE: DNA
<213> ORGANISM: Unknown
<220> FEATURE:
<223> OTHER INFORMATION: 65-AAV-CAR-T-Cells

<400> SEQUENCE: 17
ctgttttaaa agaaaagggg ggattggggg gtacagtgca gggaaagaa tagtagacat      60 aatagcaaca gacatacaaa ctaaagaatt acaaaaacaa attacaaaaa ttcaaaattt     120
tatcaacaag cttgatcgat ggctccggtc ccgtcagtg ggcagagcgc acatcgccca      180
cagtccccga gaagttgggg ggaggggtcg gcaattgaac cggtgcctag agaaggtggc     240
gcggggtaaa ctgggaaagt gatgtcgtgt actggctccg cctttttccc gagggtgggg     300
```

-continued

```
gagaaccgta tataagtgca gtagtcgccg tgaacgttct ttttcgcaac gggtttgccg   360
ccagaacaca ggtgtcgtga cgcggatcca cgcgtgcggc cgcacgcgta agcttagcgc   420
agaggcttgg ggcagccgag cggcagccag gccccggccc gggcctcggt tccagaaggg   480
agaggagccc gccaaggcgc gcaagagagc gggctgcctc gcagtccgag ccggagaggg   540
agcgcgagcc gcgccggccc cggacggcct cgccgccacc atggctctgc ccgtcaccgc   600
actgctgctg cctctggctc tgctgctgca cgccgcaaga ccagacattg tgctgacaca   660
gtctcctgct tccttagctg tatctctggg gcagagggcc accatctcat gcagggccag   720
ccaaagtgtc agttcatcta cctataattt tatacactgg tatcaacaga aatcaggaca   780
gccacccaaa ctcctcatca agtatgcatc caacctagaa tctggggtcc ctgtcaggtt   840
cagtggcagt gggtctggga cagacttctc cctcaacatc catcctgtgg aggaggagga   900
tactgcaaca tattactgtc agcacagttg ggagattcca tacacgttcg gaggggggc    960 caagttggag ataaaaggca gtactagcgg tggtggctcc gggggcggtt ccggtggggg   1020
cggcagcagc caggtgcagc tgaaggagtc aggacctggc ctggtggcac cctcacagag   1080
cctgtccatc acatgcaccg tctcaggatt ctcattaagc ggctatggca taagctgggt   1140
tcgccagcct ccaggaaagc gtctggaatg gctgggattg atatggggtg atggaaccac   1200
agactataat tcagctctca aatccagact gagcatcagc aaggacaact ccaagagcca   1260
ggttttctta aaaatgaaca gtctgcaaac tgatgacaca gccaggtact tctgtaccag   1320
agggcctccg gccttctata agtacctcta ctttgactac tggggccaag caccactct    1380 cacagtctcc tcactcgacc ccaaatcttc tgacaaaact cacacatgcc caccgtgccc   1440
agcacctcct gtggcaggac cgtcagtctt cctcttcccc ccaaaaccca aggacaccct   1500
catgatctcc cggacccctg aggtcacatg cgtggtggtg gacgtgagcc acgaagaccc   1560
tgaggtcaag ttcaactggt acgtggacgg cgtggaggtg cataatgcca agacaaagcc   1620
gcgggaggag cagtaccaga gcacgtaccg tgtggtcagc gtcctcaccg tcctgcacca   1680
ggactggctg aatggcaagg agtacaagtg caaggtctcc aacaaagccc tcccagcccc   1740
catcgagaaa accatctcca aagccaaagg gcagccccga gaaccacagg tgtacaccct   1800
gccaccatca cgagatgagc tgaccaagaa ccaggtcagc ctgacctgcc tggtcaaagg   1860
cttctatccc agcgacatcg ccgtggagtg ggagagcaat gggcagccgg agaacaacta   1920
caagaccacg cctcccgtgc tggactccga cggctccttc ttcctctaca gcaagctcac   1980
cgtggacaag agcaggtggc agcaggggaa cgtcttctca tgctccgtga tgcatgaggc   2040
tctgcacaac cactacacgc agaagagcct ctccctgtct cccttttggg tgctggtggt   2100
ggttggtgga gtcctggctt gctatagctt gctagtaaca gtggccttta ttattttctg   2160
ggtgaggagt aagaggagca ggggaggtca cagtgactac atgaacatga ctccccgccg   2220 cccccgggccc acccgcaagc attaccagcc ctatgcccca ccacgcgact cgcagcccta   2280
tcgctccaaa cggggcagaa agaaactcct gtatatattc aaacaaccat ttatgagacc   2340
agtacaaact actcaagagg aagatggctg tagctgccga tttccagaag aagaagaagg   2400
aggatgtgaa ctgagagtga agttcagcag gagcgcagac gcccccgcgt accagcaggg   2460
ccagaaccag ctctataacg agctcaatct aggacgaaga gaggagtacg atgttttgga   2520
caagagacgt ggccgggacc ctgagatggg gggaaagccg agaaggaaga accctcagga   2580
aggcctgtac aatgaactgc agaaagataa gatggcggag gcctacagtg agattgggat   2640
```

```
gaaaggcgag cgccggaggg gcaaggggca cgatggcctt taccagggtc tcagtacagc    2700
caccaaggac acctacgacg cccttcacat gcaggccctg ccccctcgcc agtgtactaa    2760
ttatgctctc ttgaaattgg ctggagatgt tgagagcaac cccgggccgg aattcatgcc    2820
acctcctcgc ctcctcttct tcctcctctt cctcaccccc atggaagtca ggcccgagga    2880
acctctagtg gtgaaggtgg aagagggaga taacgctgtg ctgcagtgcc tcaaggggac    2940
ctcagatggc cccactcagc agctgacctg gtctcgggag tccccgctta aacccttctt    3000
aaaactcagc ctggggctgc caggcctggg aatccacatg aggcccctgg ccatctggct    3060
tttcatcttc aacgtctctc aacagatggg gggcttctac ctgtgccagc cggggccccc    3120
ctctgagaag gcctggcagc ctggctggac agtcaatgtg gagggcagcg gggagctgtt    3180
ccggtggaat gtttcggacc taggtggcct gggctgtggc ctgaagaaca ggtcctcaga    3240
gggccccagc tccccttccg ggaagctcat gagcccccaag ctgtatgtgt gggccaaaga    3300
ccgccctgag atctgggagg gagagcctcc gtgtgtccca ccgagggaca gcctgaacca    3360
gagcctcagc caggacctca ccatggcccc tggctccaca ctctggctgt cctgtgggggt    3420 acccctgac tctgtgtcca ggggcccccct ctcctggacc catgtgcacc ccaagggggcc    3480 taagtcattg ctgagcctag agctgaagga cgatcgcccg gccagagata tgtgggtaat    3540
ggagacgggt ctgttgttgc cccgggccac agctcaagac gctggaaagt attattgtca    3600
ccgtggcaac ctgaccatgt cattccacct ggagatcact gctcggccag tactatggca    3660
ctggctgctg aggactggtg gctggaaggt ctcagctgtg actttggctt atctgatctt    3720
ctgcctgtgt tcccttgtgg gcattcttca tcttcaaaga gccctggtcc tgaggaggaa    3780
aagatgatct agataaattc gagcatctta ccgccattta ttcccatatt tgttctgttt    3840
ttcttgattt gggtatacat ttaaatgtta ataaaacaaa atggtggggc aatcatttac    3900 attttttaggg atatgtaatt actagttcag gtgtattgcc acaagacaaa catgttaaga    3960
aactttcccg ttatttacgc tctgttcctg ttaatcaacc tctggattac aaaatttgtg    4020
aaagattgac tgatattctt aactatgttg ctccttttac gctgtgtgga tatgctgctt    4080
tatagcctct gtatctagct attgcttccc gtacggcttt cgttttctcc tccttgtata    4140
aatcctggtt gctgtctctt ttagaggagt tgtggcccgt tgtccgtcaa cgtggcgtgg    4200
tgtgctctgt gtttgctgac gcaacccccca ctggctgggg cattgccacc acctgtcaac    4260
tcctttctgg gactttcgct ttccccctcc cgatcgccac ggcagaactc atcgccgcct    4320
gccttgcccg ctgctggaca ggggctaggt tgctgggcac tgataattcc gtggtgttgt    4380
cggggaagct gacgtccttt cctcgagggg gggcccggta cctttaagac caatgactta    4440
caaggcagct gtagatctta gccacttttt aaaagaaaag gggggactgg aagggctaat    4500
tcactcccaa cgaagacaag atctgctttt tgcttgtact gggtctctct ggttagacca    4560
gatctgagcc tgggagctct ctggctaact agggaaccca ctgcttaagc ctcaataaag    4620
cttgccttga gtgcttcaag tagtgtgtgc ccgtctgttg tgtgactctg gtaactagag    4680
atccctcaga cccttttagt cagtgtggaa aatctctagc agtagtagtt catgtcatct    4740
tattattcag tatttataac ttgcaaagaa atgaatatca gagagtgaga ggaacttgtt    4800
tattgcagct tataatggtt acaaataaag caatagcatc acaaatttca caaataaagc    4860
atttttttca ctgcattcta gttgtggttt gtccaaactc atcaatgtat cttatcatgt    4920
ctggctctag ctatcccgcc cctaactccg cccagttccg cccattctcc gccccatggc    4980
tgactaattt ttttttattta tgcagaggcc gaggccgcct cggcctctga gctattccag    5040
```

-continued

```
aagtagtgag gaggcttttt tggaggccta ggcttttgcg tcgagacgta cccaattcgc   5100
cctatagtga gtcgtattac gcgcgctcac tggccgtcgt tttacaacgt cgtgactggg   5160
aaaaccctgg cgttacccaa cttaatcgcc ttgcagcaca tccccctttc gccagctggc   5220
gtaatagcga agaggcccgc accgatcgcc cttcccaaca gttgcgcagc ctgaatggcg   5280
aatggcgcga cgcgccctgt agcggcgcat taagcgcggc gggtgtggtg gttacgcgca   5340
gcgtgaccgc tacacttgcc agcgccctag cgcccgctcc tttcgctttc ttcccttcct   5400
ttctcgccac gttcgccggc tttccccgtc aagctctaaa tcgggggctc cctttagggt   5460
tccgatttag tgctttacgg cacctcgacc ccaaaaaact tgattagggt gatggttcac   5520
gtagtgggcc atcgccctga tagacggttt ttcgcccttt gacgttggag tccacgttct   5580
ttaatagtgg actcttgttc caaactggaa caacactcaa ccctatctcg gtctattctt   5640
ttgatttata agggattttg ccgatttcgg cctattggtt aaaaaatgag ctgatttaac   5700
aaaaatttaa cgcgaatttt aacaaaatat taacgtttac aatttcccag gtggcacttt   5760
tcggggaaat gtgcgcggaa cccctatttg tttattttc taaatacatt caaatatgta   5820
tccgctcatg agacaataac cctgataaat gcttcaataa tattgaaaaa ggaagagtat   5880
gagtattcaa catttccgtg tcgcccttat tcccttttt gcggcatttt gccttcctgt   5940
ttttgctcac ccagaaacgc tggtgaaagt aaaagatgct gaagatcagt tgggtgcacg   6000
agtgggttac atcgaactgg atctcaacag cggtaagatc cttgagagtt ttcgccccga   6060
agaacgtttt ccaatgatga gcacttttaa agttctgcta tgtggcgcgg tattatcccg   6120
tattgacgcc gggcaagagc aactcggtcg ccgcatacac tattctcaga atgacttggt   6180
tgagtactca ccagtcacag aaaagcatct tacggatggc atgacagtaa gagaattatg   6240
cagtgctgcc ataaccatga gtgataacac tgcggccaac ttacttctga caacgatcgg   6300
aggaccgaag gagctaaccg cttttttgca caacatgggg gatcatgtaa ctcgccttga   6360
tcgttgggaa ccggagctga atgaagccat accaaacgac gagcgtgaca ccacgatgcc   6420
tgtagcaatg gcaacaacgt tgcgcaaact attaactggc gaactactta ctctagcttc   6480
ccggcaacaa ttaatagact ggatggaggc ggataaagtt gcaggaccac ttctgcgctc   6540
ggcccttccg gctggctggt ttattgctga taaatctgga gccggtgagc gtgggtctcg   6600
cggtatcatt gcagcactgg ggccagatgg taagccctcc cgtatcgtag ttatctacac   6660
gacggggagt caggcaacta tggatgaacg aaatagacag atcgctgaga taggtgcctc   6720
actgattaag cattggtaac tgtcagacca agtttactca tatatacttt agattgattt   6780
aaaacttcat ttttaattta aaaggatcta ggtgaagatc cttttgata atctcatgac   6840 caaaatccct taacgtgagt tttcgttcca ctgagcgtca gaccccgtag aaaagatcaa   6900
aggatcttct tgagatcctt tttttctgcg cgtaatctgc tgcttgcaaa caaaaaaacc   6960
accgctacca gcggtggttt gtttgccgga tcaagagcta ccaactcttt ttccgaaggt   7020
aactggcttc agcagagcgc agataccaaa tactgtcctt ctagtgtagc cgtagttagg   7080
ccaccacttc aagaactctg tagcaccgcc tacatacctc gctctgctaa tcctgttacc   7140
agtggctgct gccagtggcg ataagtcgtg tcttaccggg ttggactcaa gacgatagtt   7200
accggataag gcgcagcggt cgggctgaac ggggggttcg tgcacacagc ccagcttgga   7260
gcgaacgacc tacaccgaac tgagatacct acagcgtgag ctatgagaaa gcgccacgct   7320
tcccgaaggg agaaaggcgg acaggtatcc ggtaagcggc agggtcggaa caggagagcg   7380
```

-continued

```
cacgagggag cttccagggg gaaacgcctg gtatctttat agtcctgtcg ggtttcgcca      7440
cctctgactt gagcgtcgat ttttgtgatg ctcgtcaggg gggcggagcc tatggaaaaa      7500
cgccagcaac gcggcctttt tacggttcct ggccttttgc tggccttttg ctcacatgtt      7560
ctttcctgcg ttatcccctg attctgtgga taaccgtatt accgcctttg agtgagctga      7620
taccgctcgc cgcagccgaa cgaccgagcg cagcgagtca gtgagcgagg aagcggaaga      7680
gcgcccaata cgcaaaccgc ctctccccgc gcgttggccg attcattaat gcagctggca      7740
cgacaggttt cccgactgga aagcgggcag tgagcgcaac gcaattaatg tgagttagct      7800
cactcattag gcaccccagg ctttacactt tatgcttccg gctcgtatgt tgtgtggaat      7860
tgtgagcgga taacaatttc acacaggaaa cagctatgac catgattacg ccaagcgcgc      7920
aattaaccct cactaaaggg aacaaaagct ggagctgcaa gcttaatgta gtcttatgca      7980
atactcttgt agtcttgcaa catggtaacg atgagttagc aacatgcctt acaaggagag      8040
aaaaagcacc gtgcatgccg attggtggaa gtaaggtggt acgatcgtgc cttattagga      8100
aggcaacaga cgggtctgac atggattgga cgaaccactg aattgccgca ttgcagagat      8160
attgtattta agtgcctagc tcgatacata aacgggtctc tctggttaga ccagatctga      8220
gcctgggagc tctctggcta actagggaac ccactgctta agcctcaata aagcttgcct      8280
tgagtgcttc aagtagtgtg tgcccgtctg ttgtgtgact ctggtaacta gagatccctc      8340
agaccctttt agtcagtgtg gaaaatctct agcagtggcg cccgaacagg gacttgaaag      8400
cgaaagggaa accagaggag ctctctcgac gcaggactcg gcttgctgaa gcgcgcacgg      8460
caagaggcga ggggcggcga ctggtgagta cgccaaaaat tttgactagc ggaggctaga      8520
aggagagaga tgggtgcgag agcgtcagta ttaagcgggg gagaattaga tcgcgatggg      8580
aaaaaattcg gttaaggcca ggggggaaaga aaaaatataa attaaaacat atagtatggg      8640
caagcaggga gctagaacga ttcgcagtta atcctggcct gttagaaaca tcagaaggct      8700
gtagacaaat actgggacag ctacaaccat cccttcagac aggatcagaa gaacttagat      8760
cattatataa tacagtagca accctctatt gtgtgcatca aaggatagag ataaaagaca      8820
ccaaggaagc tttagacaag atagaggaag agcaaaacaa aagtaagacc accgcacagc      8880
aagcggccgc tgatcttcag acctggagga ggagatatga gggacaattg gagaagtgaa      8940
ttatataaat ataaagtagt aaaaattgaa ccattaggag tagcacccac caaggcaaag      9000
agaagagtgg tgcagagaga aaaaagagca gtgggaatag gagctttgtt ccttgggttc      9060
ttgggagcag caggaagcac tatgggcgca gcctcaatga cgctgacggt acaggccaga      9120
caattattgt ctggtatagt gcagcagcag aacaatttgc tgagggctat tgaggcgcaa      9180
cagcatctgt tgcaactcac agtctggggc atcaagcagc tccaggcaag aatcctggct      9240
gtggaaagat acctaaagga tcaacagctc ctggggattt ggggttgctc tggaaaactc      9300
atttgcacca ctgctgtgcc ttggaatgct agttggagta ataaatctct ggaacagatt      9360
tggaatcaca cgacctggat ggagtgggac agagaaatta caattacac aagcttaata      9420 cactccttaa ttgaagaatc gcaaaaccag caagaaaaga atgaacaaga attattggaa      9480
ttagataaat gggcaagttt gtggaattgg tttaacataa caaattggct gtggtatata      9540
aaattattca taatgatagt aggaggcttg gtaggtttaa gaatagtttt tgctgtactt      9600
tctatagtga atagagttag gcagggatat tcaccattat cgtttcagac ccacctccca      9660
accccgaggg gacccgacag gcccgaagga atagaagaag aaggtggaga gagagacaga      9720
gacagatcca ttcgattagt gaacggatct cgacggtatc ggtt      9764
```

-continued

```
<210> SEQ ID NO 18
<211> LENGTH: 291
<212> TYPE: DNA
<213> ORGANISM: Unknown
<220> FEATURE:
<223> OTHER INFORMATION: EF1-alpha

<400> SEQUENCE: 18
aacaagcttg atcgatggct ccggtgcccg tcagtgggca gagcgcacat cgcccacagt       60
ccccgagaag ttggggggag gggtcggcaa ttgaaccggt gcctagagaa ggtggcgcgg      120
ggtaaactgg gaaagtgatg tcgtgtactg gctccgcctt tttcccgagg gtgggggaga      180
accgtatata agtgcagtag tcgccgtgaa cgttcttttt cgcaacgggt ttgccgccag      240
aacacaggtg tcgtgacgcg gatccacgcg tgcggccgca cgcgtaagct t                291

<210> SEQ ID NO 19
<211> LENGTH: 584
<212> TYPE: DNA
<213> ORGANISM: Unknown
<220> FEATURE:
<223> OTHER INFORMATION: CMV

<400> SEQUENCE: 19
ggcattgatt attgactagt tattaatagt aatcaattac ggggtcatta gttcatagcc       60
catatatgga gttccgcgtt acataactta cggtaaatgg cccgcctggc tgaccgccca      120
acgacccccg cccattgacg tcaataatga cgtatgttcc catagtaacg ccaataggga      180
ctttccattg acgtcaatgg gtggagtatt tacggtaaac tgcccacttg gcagtacatc      240
aagtgtatca tatgccaagt ccgcccccta ttgacgtcaa tgacggtaaa tggcccgcct      300
ggcattatgc ccagtacatg accttacggg actttcctac ttggcagtac atctacgtat      360
tagtcatcgc tattaccatg gtgatgcggt tttggcagta caccaatggg cgtggatagc      420
ggtttgactc acggggattt ccaagtctcc accccattga cgtcaatggg agtttgtttt      480
ggcaccaaaa tcaacgggac tttccaaaat gtcgtaataa ccccgccccg ttgacgcaaa      540
tgggcggtag gcgtgtacgg tgggaggtct atataagcag aggt                       584

<210> SEQ ID NO 20
<211> LENGTH: 450
<212> TYPE: DNA
<213> ORGANISM: Unknown
<220> FEATURE:
<223> OTHER INFORMATION: MND2

<400> SEQUENCE: 20
ggccgccagt gtgatggata tctgcagaat tcgcccttat ggggatccga acagagagac       60
agcagaatat gggccaaaca ggatatctgt ggtaagcagt tcctgccccg gctcagggcc      120
aagaacagtt ggaacagcag aatatgggcc aaacaggata tctgtggtaa gcagttcctg      180
ccccggctca gggccaagaa cagatggtcc ccagatgcgg tcccgccctc agcagtttct      240
agagaaccat cagatgtttc cagggtgccc caaggacctg aaatgaccct gtgccttatt      300
tgaactaacc aatcagttcg cttctcgctt ctgttcgcgc gcttctgctc cccgagctct      360
atataagcag agctcgttta gtgaaccgtc agatcgcctg gagacgccat ccacgctgtt      420
ttgacctcca tagaagacac cgactctaga                                       450

<210> SEQ ID NO 21
```

```
<211> LENGTH: 408
<212> TYPE: DNA
<213> ORGANISM: Unknown
<220> FEATURE:
<223> OTHER INFORMATION: SFFV

<400> SEQUENCE: 21
gtaacgccat tttgcaaggc atggaaaaat accaaaccaa gaatagagaa gttcagatca      60
agggcgggta catgaaaata gctaacgttg ggccaaacag gatatctgcg gtgagcagtt     120
tcggccccgg cccgggggcca agaacagatg gtcaccgcag tttcggcccc ggcccgaggc     180
caagaacaga tggtccccag atatggccca accctcagca gtttcttaag acccatcaga     240
tgtttccagg ctcccccaag gacctgaaat gaccctgcgc cttatttgaa ttaaccaatc     300
agcctgcttc tcgcttctgt tcgcgcgctt ctgcttcccg agctctataa aagagctcac     360
aacccctcac tcggcgcgcc agtcctccga cagactgagt cgcccggg               408

<210> SEQ ID NO 22
<211> LENGTH: 750
<212> TYPE: DNA
<213> ORGANISM: Unknown
<220> FEATURE:
<223> OTHER INFORMATION: AAV-ScFv

<400> SEQUENCE: 22
gacattgtgc tgacacagtc tcctgcttcc ttagctgtat ctctggggca gagggccacc      60
atctcatgca gggccagcca aagtgtcagt tcatctacct ataattttat acactggtat     120
caacagaaat caggacagcc acccaaactc ctcatcaagt atgcatccaa cctagaatct     180
ggggtccctg tcaggttcag tggcagtggg tctgggacag acttctccct caacatccat     240
cctgtggagg aggaggatac tgcaacatat tactgtcagc acagttggga gattccatac     300
acgttcggag ggggggccaa gttggagata aaaggcagta ctagcggtgg tggctccggg     360
ggcggttccg gtggggggcgg cagcagccag gtgcagctga aggagtcagg acctggcctg     420
gtggcaccct cacagagcct gtccatcaca tgcaccgtct caggattctc attaagcggc     480
tatggcataa gctgggttcg ccagcctcca ggaaagcgtc tggaatggct gggattgata     540
tggggtgatg gaaccacaga ctataattca gctctcaaat ccagactgag catcagcaag     600
gacaactcca agagccaggt tttcttaaaa atgaacagtc tgcaaactga tgacacagcc     660
aggtacttct gtaccagagg gcctccggcc ttctataagt acctctactt tgactactgg     720
ggccaaggca ccactctcac agtctcctca                                      750

<210> SEQ ID NO 23
<211> LENGTH: 672
<212> TYPE: DNA
<213> ORGANISM: Unknown
<220> FEATURE:
<223> OTHER INFORMATION: IgG1 hinge-IgG2 hinge, IgG1 CH2CH3

<400> SEQUENCE: 23
gacaaaactc acacatgccc accgtgccca gcacctcctg tggcaggacc gtcagtcttc      60
ctcttccccc caaaacccaa ggacaccctc atgatctccc ggacccctga ggtcacatgc     120
gtggtggtgg acgtgagcca cgaagaccct gaggtcaagt tcaactggta cgtggacggc     180
gtggaggtgc ataatgccaa gacaaagccg cgggaggagc agtaccagag cacgtaccgt     240
gtggtcagcg tcctcaccgt cctgcaccag gactggctga atggcaagga gtacaagtgc     300
aaggtctcca acaaagccct cccagccccc atcgagaaaa ccatctccaa agccaaaggg     360
```

-continued

```
cagccccgag aaccacaggt gtacaccctg ccaccatcac gagatgagct gaccaagaac     420
caggtcagcc tgacctgcct ggtcaaaggc ttctatccca gcgacatcgc cgtggagtgg     480
gagagcaatg ggcagccgga gaacaactac aagaccacgc ctcccgtgct ggactccgac     540
ggctccttct tcctctacag caagctcacc gtggacaaga gcaggtggca gcaggggaac     600
gtcttctcat gctccgtgat gcatgaggct ctgcacaacc actacacgca gaagagcctc     660
tccctgtctc cc                                                         672
```

```
<210> SEQ ID NO 24
<211> LENGTH: 117
<212> TYPE: DNA
<213> ORGANISM: Unknown
<220> FEATURE:
<223> OTHER INFORMATION: CD28 extracellular domain

<400> SEQUENCE: 24
attgaagtta tgtatcctcc tccttaccta gacaatgaga agagcaatgg aaccattatc      60
catgtgaaag ggaaacacct ttgtccaagt cccctatttc ccggaccttc taagccc        117
```

```
<210> SEQ ID NO 25
<211> LENGTH: 81
<212> TYPE: DNA
<213> ORGANISM: Unknown
<220> FEATURE:
<223> OTHER INFORMATION: CD28 transmembrane domain

<400> SEQUENCE: 25
ttttgggtgc tggtggtggt tggtggagtc ctggcttgct atagcttgct agtaacagtg      60
gcctttatta ttttctgggt g                                               81
```

```
<210> SEQ ID NO 26
<211> LENGTH: 123
<212> TYPE: DNA
<213> ORGANISM: Unknown
<220> FEATURE:
<223> OTHER INFORMATION: Human CD28 signaling domain

<400> SEQUENCE: 26
aggagtaaga ggagcagggg aggtcacagt gactacatga acatgactcc ccgccgcccc      60
gggcccaccc gcaagcatta ccagccctat gccccaccac gcgacttcgc agcctatcgc     120
tcc                                                                   123
```

```
<210> SEQ ID NO 27
<211> LENGTH: 123
<212> TYPE: DNA
<213> ORGANISM: Unknown
<220> FEATURE:
<223> OTHER INFORMATION: Murine CD28 signaling domain

<400> SEQUENCE: 27
aacagcagaa gaaacagagg cggccagagc gactacatga acatgacccc cagaaggcca      60
ggcctgacca gaaagcccta ccagccctac gccctgcca gagacttcgc cgcctacaga     120
ccc                                                                   123
```

```
<210> SEQ ID NO 28
<211> LENGTH: 126
<212> TYPE: DNA
<213> ORGANISM: Unknown
<220> FEATURE:
```

-continued

---

<223> OTHER INFORMATION: Human 4-1BB signaling domain

<400> SEQUENCE: 28
aaacggggca gaaagaaact cctgtatata ttcaaacaac catttatgag accagtacaa        60
actactcaag aggaagatgg ctgtagctgc cgatttccag aagaagaaga aggaggatgt       120
gaactg                                                                  126

<210> SEQ ID NO 29
<211> LENGTH: 144
<212> TYPE: DNA
<213> ORGANISM: Unknown
<220> FEATURE:
<223> OTHER INFORMATION: Murine 4-1BB signaling domain

<400> SEQUENCE: 29
tctgtgctca aatggatcag gaaaaaattc ccccacatat tcaagcaacc atttaagaag        60
accactggag cagctcaaga ggaagatgct tgtagctgcc gatgtccaca ggaagaagaa       120
ggaggaggag gaggctatga gctg                                              144

<210> SEQ ID NO 30
<211> LENGTH: 336
<212> TYPE: DNA
<213> ORGANISM: Unknown
<220> FEATURE:
<223> OTHER INFORMATION: Human CD3z

<400> SEQUENCE: 30
agagtgaagt tcagcaggag cgcagacgcc cccgcgtacc agcagggcca gaaccagctc        60
tataacgagc tcaatctagg acgaagagag gagtacgatg ttttggacaa gagacgtggc       120
cgggaccctg agatgggggg aaagccgaga aggaagaacc ctcaggaagg cctgtacaat       180
gaactgcaga agataagat ggcggaggcc tacagtgaga ttgggatgaa aggcgagcgc       240
cggaggggca aggggcacga tggcctttac cagggtctca gtacagccac caaggacacc       300
tacgacgccc ttcacatgca ggccctgccc cctcgc                                 336

<210> SEQ ID NO 31
<211> LENGTH: 342
<212> TYPE: DNA
<213> ORGANISM: Unknown
<220> FEATURE:
<223> OTHER INFORMATION: Murine CD3z

<400> SEQUENCE: 31
agagccaagt tcagcagatc cgccgagaca gccgccaacc tgcaggatcc caaccagctg        60
tacaacgagc tgaacctggg cagacgggag gaatacgacg tgctggaaaa gaagagagcc       120
agggaccccg agatgggcgg caagcagcag agaagaagaa accctcagga aggcgtctac       180
aacgccctgc agaaagacaa gatggccgag gcctacagcg agatcggcac caagggcgag       240
agaagaaggg gcaagggcca cgatggcctg taccagggcc tgtccaccgc caccaaggac       300
acctacgacg ccctgcacat gcagaccctg gcccccagat ga                          342

<210> SEQ ID NO 32
<211> LENGTH: 969
<212> TYPE: DNA
<213> ORGANISM: Unknown
<220> FEATURE:
<223> OTHER INFORMATION: CD19 extracellular domain -continued

<400> SEQUENCE: 32

```
atgccacctc ctcgcctcct cttcttcctc ctcttcctca cccccatgga agtcaggccc      60
gaggaacctc tagtggtgaa ggtggaagag ggagataacg ctgtgctgca gtgcctcaag     120
gggacctcag atggccccac tcagcagctg acctggtctc gggagtcccc gcttaaaccc     180
ttcttaaaac tcagcctggg gctgccaggc ctggaatcc acatgaggcc cctggccatc     240 tggctttca tcttcaacgt ctctcaacag atggggggct tctacctgtg ccagccgggg     300
cccccctctg agaaggcctg gcagcctggc tggacagtca atgtggaggg cagcggggag     360
ctgttccggt ggaatgtttc ggacctaggt ggcctgggct gtggcctgaa gaacaggtcc     420
tcagagggcc ccagctcccc ttccgggaag ctcatgagcc ccaagctgta tgtgtgggcc     480
aaagaccgcc tgagatctg ggaggagag cctccgtgtg tcccaccgag ggacagcctg     540
aaccagagcc tcagccagga cctcaccatg gccctggct ccacactctg ctgtcctgt     600 ggggtacccc ctgactctgt gtccaggggc ccctctcct ggacccatgt gcaccccaag     660
gggcctaagt cattgctgag cctagagctg aaggacgatc gcccggccag agatatgtgg     720
gtaatggaga cgggtctgtt gttgccccgg gccacagctc aagacgctgg aaagtattat     780
tgtcaccgtg gcaacctgac catgtcattc cacctggaga tcactgctcg gccagtacta     840
tggcactggc tgctgaggac tggtggctgg aaggtctcag ctgtgacttt ggcttatctg     900
atcttctgcc tgtgttccct tgtgggcatt cttcatcttc aaagagccct ggtcctgagg     960
aggaaaaga                                                               969
```

<210> SEQ ID NO 33
<211> LENGTH: 1021
<212> TYPE: DNA
<213> ORGANISM: Unknown
<220> FEATURE:
<223> OTHER INFORMATION: EGFR extracellular domain

<400> SEQUENCE: 33

```
atgcttctcc tggtgacaag ccttctgctc tgtgagttac cacacccagc attcctcctg      60
atcccacgca aagtgtgtaa cggaataggt attggtgaat ttaaagactc actctccata     120
aatgctacga atattaaaca cttcaaaaac tgcacctcca tcagtggcga tctccacatc     180
ctgccggtgg catttagggg tgactccttc acacatactc ctcctctgga tccacaggaa     240
ctggatattc tgaaaaccgt aaaggaaatc acagggtttt tgctgattca ggcttggcct     300
gaaaacagga cggacctcca tgcctttgag aacctagaaa tcatacgcgg caggaccaag     360
caacatggtc agttttctct tgcagtcgtc agcctgaaca taacatcctt gggattacgc     420
tccctcaagg agataagtga tggagatgtg ataattcag gaaacaaaaa tttgtgctat     480
gcaaatacaa taaactggaa aaaactgttt gggacctccg tcagaaaac caaaattata     540 agcaacagag gtgaaaacag ctgcaaggcc acaggccagg tctgccatgc cttgtgctcc     600
cccgagggct gctggggccc ggagcccagg gactgcgtct cttgccggaa tgtcagccga     660
ggcagggaat gcgtggacaa gtgcaacctt ctggagggtg agccaaggga gtttgtggag     720
aactctgagt gcatacagtg ccacccagag tgcctgcctc aggccatgaa catcacctgc     780
acaggacggg gaccagacaa ctgtatccag tgtgcccact acattgacgg cccccactgc     840
```

-continued

```
gtcaagacct gcccggcagg agtcatggga gaaaacaaca ccctggtctg gaagtacgca      900
gacgccggcc atgtgtgcca cctgtgccat ccaaactgca cctacggatg cactgggcca      960
ggtcttgaag gctgtccaac gaatgggcct aagatcccgt ccatcgccac tggatctaga     1020
t                                                                       1021

<210> SEQ ID NO 34
<211> LENGTH: 60
<212> TYPE: DNA
<213> ORGANISM: Unknown
<220> FEATURE:
<223> OTHER INFORMATION: E2A

<400> SEQUENCE: 34
cagtgtacta attatgctct cttgaaattg gctggagatg ttgagagcaa ccccgggccg       60

<210> SEQ ID NO 35
<211> LENGTH: 54
<212> TYPE: DNA
<213> ORGANISM: Unknown
<220> FEATURE:
<223> OTHER INFORMATION: T2A

<400> SEQUENCE: 35
gaaggtcgtg gatcactact tacgtgcggt gatgtagaag agaatccggg tccg             54

<210> SEQ ID NO 36
<211> LENGTH: 57
<212> TYPE: DNA
<213> ORGANISM: Unknown
<220> FEATURE:
<223> OTHER INFORMATION: P2A

<400> SEQUENCE: 36
gccacaaact tctctctgct aaagcaagca ggtgatgttg aagaaaaccc cgggcct          57

<210> SEQ ID NO 37
<211> LENGTH: 2214
<212> TYPE: DNA
<213> ORGANISM: Unknown
<220> FEATURE:
<223> OTHER INFORMATION: AAV8-capsid

<400> SEQUENCE: 37
atggctgccg atggttatct tccagattgg ctcgaggaca acctctctga gggcattcgc       60
gagtggtggg cgctgaaacc tggagccccg aagcccaaag ccaaccagca aaagcaggac      120
gacggccggg gtctggtgct tcctggctac aagtacctcg gacccttcaa cggactcgac      180 aaggggggagc ccgtcaacgc ggcggacgca gcggccctcg agcacgacaa ggcctacgac      240
cagcagctgc aggcgggtga caatccgtac ctgcggtata accacgccga cgccgagttt      300
caggagcgtc tgcaagaaga tacgtctttt gggggcaacc tcgggcgagc agtcttccag      360
gccaagaagc gggttctcga acctctcggt ctggttgagg aaggcgctaa gacggctcct      420
ggaaagaaga gaccggtaga gccatcaccc cagcgttctc agactcctc tacgggcatc      480 ggcaagaaag ccaacagcc cgccagaaaa agactcaatt ttggtcagac tggcgactca      540
gagtcagttc cagaccctca acctctcgga gaacctccag cagcgccctc tggtgtggga      600
cctaatacaa tggctgcagg cggtggcgca ccaatggcag acaataacga aggcgccgac      660
ggagtgggta gttcctcggg aaattggcat tgcgattcca catggctggg cgacagagtc      720
```

-continued

```
atcaccacca gcacccgaac ctgggccctg cccacctaca acaaccacct ctacaagcaa    780
atctccaacg ggacatcggg aggagccacc aacgacaaca cctacttcgg ctacagcacc    840 ccctggggt attttgactt taacagattc cactgccact tttcaccacg tgactggcag     900
cgactcatca acaacaactg gggattccgg cccaagagac tcagcttcaa gctcttcaac    960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctgcctcc gttcccggcg gacgtgttca tgattcccca gtacggctac   1140
ctaacactca caacggtag tcaggccgtg ggacgctcct ccttctactg cctggaatac   1200
tttccttcgc agatgctgag aaccggcaac aacttccagt ttacttacac cttcgaggac   1260 gtgccttttcc acagcagcta cgcccacagc cagagcttgg accggctgat gaatcctctg   1320
attgaccagt acctgtacta cttgtctcgg actcaaacaa caggaggcac ggcaaatacg   1380
cagactctgg gcttcagcca aggtgggcct aatacaatgg ccaatcaggc aaagaactgg   1440
ctgccaggac cctgttaccg ccaacaacgc gtctcaacga caaccgggca aaacaacaat   1500
agcaactttg cctggactgc tgggaccaaa taccatctga atggaagaaa ttcattggct   1560
aatcctggca tcgctatggc aacacacaaa gacgacgagg agcgttttt tcccagtaac   1620 gggatcctga ttttggcaa acaaaatgct gccagagaca atgcggatta cagcgatgtc   1680
atgctcacca gcgaggaaga aatcaaaacc actaaccctg tggctacaga ggaatacggt   1740
atcgtggcag ataacttgca gcagcaaac acggctcctc aaattggaac tgtcaacagc   1800 caggggggcct tacccggtat ggtctggcag aaccgggacg tgtacctgca gggtcccatc   1860
tgggccaaga ttcctcacac ggacggcaac ttccacccgt ctccgctgat gggcggcttt   1920
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg aaattgaatg ggagctgcag aaggaaaaca gcaagcgctg gaaccccgag   2100
atccagtaca cctccaacta ctacaaatct acaagtgtgg actttgctgt taatacagaa   2160
ggcgtgtact ctgaaccccg ccccattggc acccgttacc tcacccgtaa tctg         2214
```

```
<210> SEQ ID NO 38
<211> LENGTH: 2080
<212> TYPE: DNA
<213> ORGANISM: Unknown
<220> FEATURE:
<223> OTHER INFORMATION: AAV9-capsid

<400> SEQUENCE: 38
```

```
atggctgccg atggttatct tccagattgg ctcgaggaca accttagtga aggaattcgc     60
gagtggtggg ctttgaaacc tggagccct caacccaagg caaatcaaca acatcaagac    120
aacgctcgag gtcttgtgct tccgggttac aaataccttg acccggcaa cggactcgac    180 aaggggagc cggtcaacgc agcagacgcg gcggccctcg agcacgacaa ggcctacgac    240
cagcagctca aggccggaga caacccgtac ctcaagtaca ccacgccga cgccgagttc    300 caggagcggc tcaaagaaga tacgtctttt ggggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
```

-continued

```
cttacaatgg cttcaggtgg tggcgcacca gtggcagaca ataacgaagg tgccgatgga      660
gtgggtagtt cctcgggaaa ttggcattgc gattcccaat ggctggggga cagagtcatc      720
accaccagca cccgaacctg ggccctgccc acctacaaca atcacctcta caagcaaatc      780
tccaacagca catctggagg atcttcaaat gacaacgcct acttcggcta cagcaccccc      840
tgggggtatt ttgacttcaa cagattccac tgccacttct caccacgtga ctggcagcga      900
ctcatcaaca caactggggg attccggcct aagcgactca acttcaagct cttcaacatt      960
caggtcaaag aggttacgga caacaatgga gtcaagacca tcgccaataa ccttaccagc     1020
acggtccagg tcttcacgga ctcagactat cagctcccgt acgtgctcgg tcggctcac      1080 gagggctgcc tcccgccgtt cccagcggac gttttcatga ttcctcagta cgggtatctg     1140
acgcttaatg atggaagcca ggccgtgggt cgttcgtcct tttactgcct ggaatatttc     1200
ccgtcgcaaa tgctaagaac gggtaacaac ttccagttca gctacgagtt tgagaacgta     1260
cctttccata gcagctacgc tcacagccaa agcctggacc gactaatgaa tccactcatc     1320
gaccaatact tgtactatct ctcaaagact attaacggtt ctggacagaa tcaacaaacg     1380
ctaaaattca gtgtggccgg acccagcaac atggctgtcc agggaagaaa ctacatacct     1440
ggacccagct accgacaaca acgtgtctca accactgtga ctcaaaacaa caacagcgaa     1500
tttgcttggc ctggagcttc ttcttgggct ctcaatggac gtaatagctt gatgaatcct     1560
ggacctgcta tggccagcca caagaagga gaggaccgtt tctttccttt gtctggatct     1620 ttaattttg gcaaacaagg aactggaaga gacaacgtgg atgcggacaa agtcatgata     1680
accaacgaag aagaaattaa aactactaac ccggtagcaa cggagtccta tggacaagtg     1740
gccacaaacc accagagtgc ccaagcacag gcgcagaccg gctgggttca aaaccaagga     1800
atacttccgg gtatggtttg gcaggacaga gatgtgtacc tgcaaggacc catttgggcc     1860
aaaattcctc acacggacgg caactttcac ccttctccgc tgatgggagg gtttggaatg     1920
aagcacccgc ctcctcagat cctcatcaaa aacacacctg tacctgcgga tcctccaacg     1980
gccttcaaca aggacaagct gaactctttc atcacccagt attctactgg ccaagtcagc     2040
gtggagatcg agtgggagct gcagaaggaa aacagcaagc                           2080
```

```
<210> SEQ ID NO 39
<211> LENGTH: 250
<212> TYPE: PRT
<213> ORGANISM: Unknown
<220> FEATURE:
<223> OTHER INFORMATION: AAV-ScFv

<400> SEQUENCE: 39

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Ser Ser
            20                  25                  30

Thr Tyr Asn Phe Ile His Trp Tyr Gln Gln Lys Ser Gly Gln Pro Pro
        35                  40                  45

Lys Leu Leu Ile Lys Tyr Ala Ser Asn Leu Glu Ser Gly Val Pro Val
    50                  55                  60

Arg Phe Ser Gly Ser Gly Ser Gly Thr Asp Phe Ser Leu Asn Ile His
65                  70                  75                  80

Pro Val Glu Glu Glu Asp Thr Ala Thr Tyr Tyr Cys Gln His Ser Trp
                85                  90                  95
```

-continued

```
Glu Ile Pro Tyr Thr Phe Gly Gly Gly Ala Lys Leu Glu Ile Lys Gly
            100             105             110

Ser Thr Ser Gly Gly Gly Ser Gly Gly Gly Ser Gly Gly Gly Gly Ser
        115             120             125

Ser Gln Val Gln Leu Lys Glu Ser Gly Pro Gly Leu Val Ala Pro Ser
    130             135             140

Gln Ser Leu Ser Ile Thr Cys Thr Val Ser Gly Phe Ser Leu Ser Gly
145             150             155             160

Tyr Gly Ile Ser Trp Val Arg Gln Pro Pro Gly Lys Arg Leu Glu Trp
            165             170             175

Leu Gly Leu Ile Trp Gly Asp Gly Thr Thr Asp Tyr Asn Ser Ala Leu
            180             185             190

Lys Ser Arg Leu Ser Ile Ser Lys Asp Asn Ser Lys Ser Gln Val Phe
        195             200             205

Leu Lys Met Asn Ser Leu Gln Thr Asp Asp Thr Ala Arg Tyr Phe Cys
    210             215             220

Thr Arg Gly Pro Pro Ala Phe Tyr Lys Tyr Leu Tyr Phe Asp Tyr Trp
225             230             235             240

Gly Gln Gly Thr Thr Leu Thr Val Ser Ser
            245             250
```

AAV CAPSID CHIMERIC ANTIGEN RECEPTORS AND USES THEREOF

CROSS-REFERENCE TO RELATED APPLICATIONS

This application is a national stage filing under 35 U.S.C. § 371 of international PCT application PCT/US2020/029527, filed Apr. 23, 2020, which claims priority under 35 U.S.C. § 119(e) to U.S. provisional patent application, U.S. Ser. No. 62/838,288, filed Apr. 24, 2019, the entire contents of each of which are incorporated herein by reference.

BACKGROUND OF THE INVENTION

Clinical trials with recombinant Adeno-associated virus (rAAV) have been observed to elicit T-cell mediated immune responses against the Adeno-associated virus (AAV) capsid of the recombinant virus. Different responses have been observed. For example, in trials for hemophilia where rAAVs were injected into the hepatic artery, a cytotoxic CD8+ T-cell response against capsid was responsible for elevated liver enzymes and clearance of transfected cells. In other clinical trials, for example alpha-1-anti-trypsin deficiency and lipoprotein lipase deficiency, where the injection site was intramuscular, a CD4+ T-regulatory response was observed with long-term expression of transgene without steroids.

SUMMARY OF THE INVENTION

Embodiments of the disclosure relate to compositions and methods for modulating the immune response of a subject (e.g., a human subject) to certain viral antigens (e.g., AAV capsid proteins or antigens derived from AAV capsid proteins). The disclosure is based, in part, on isolated nucleic acids and expression constructs encoding chimeric antigen receptors (CARs), and recombinant immune cells comprising such constructs (e.g., recombinant T-cell comprising a CAR (CAR T-cells), and recombinant T-regulatory cells comprising a CAR (CAR T-regs)). In some embodiments, CAR T-cells described herein are useful for killing immune cells (e.g., antigen presenting cells (APCs)) which induce immune responses against AAV capsid proteins, thereby dampening (e.g., inhibiting or suppressing) the host immune response against the AAV capsid protein. In some embodiments, CAR T-reg cells described herein are useful for inhibiting the killing of immune cells (e.g., APCs) which induce immune responses against AAV capsid proteins, thereby increasing (e.g., promoting or inducing) the host immune response against AAV capsid protein.

Accordingly, in some embodiments, the disclosure provides an isolated nucleic acid comprising an expression construct encoding a CAR, wherein the CAR comprises: an antigen binding domain that targets (e.g., specifically binds) one or more AAV capsid protein epitopes; a transmembrane domain; and a cytoplasmic signaling domain.

In some embodiments, the nucleic acid encodes a CAR with an antigen binding domain with a first portion comprising a monoclonal antibody or a single chain variable fragment (scFv). In some embodiments, the nucleic acid encodes an antigen binding domain comprising an scFv having a variable heavy chain domain (VH) derived from an AAV capsid protein-targeting antibody linked to a variable light chain domain (VL). In some embodiments, the nucleic acid encodes an antigen binding domain comprising an scFv having a variable heavy chain domain (VH) derived from an AAV capsid protein-targeting antibody linked to a variable light chain domain (VL) derived from an AAV capsid protein-targeting antibody.

In some embodiments, the nucleic acid encodes a VH domain and a VL domain linked by a linking molecule. In some embodiments, the linking molecule is a peptide linker. In some embodiments, the peptide linker is a glycine-rich linker (e.g., a (GGGGS)n linker, where n is an integer between 1 and 10).

In some embodiments, the nucleic acid encodes an antigen binding domain further comprising an IgG1 heavy chain constant domain 2 (IgG1 CH2) and/or an IgG1 heavy chain constant domain 3 (IgG1 CH3). In some embodiments, the IgG CH2 and/or the IgG1 CH3 domain are linked to a nucleotide sequence encoding an antibody or scFv by a linking molecule. In some embodiments, a linking sequence encodes a molecule comprising an IgG1 hinge linker and/or an IgG2 hinge linker.

In some embodiments, the nucleic acid encodes an antigen binding domain targeting (e.g., specifically binds to) an epitope of an AAV capsid protein having a serotype selected from AAV1, AAV2, AAV3, AAV3b, AAV4, AAV5, AAV6, AAV7, AAV8, AAVrh.8, AAV9, AAV10, AAVrh.10, AAVrh.39, AAVrh.43, AAV.PHPB, AAV.PHPB.e, AAVrh32.33, or a variant thereof. In some embodiments, the nucleic acid encodes an antigen binding domain targeting an AAV2 epitope or an AAV6 epitope.

In some embodiments, the nucleic acid encodes a CAR comprising a transmembrane domain which is a CD28 transmembrane domain. In some embodiments, the nucleic acid encodes a CAR comprising a cytoplasmic signaling domain comprising one or more of a CD28 signaling domain, a 4-1BB signaling domain, and a CD3 signaling domain. In some embodiments, the cytoplasmic domain comprises a CD28 signaling domain, a 4-1BB signaling domain, and a CD3 signaling domain.

In some embodiments, an expression construct further comprises a promoter operably linked to a nucleic acid sequence encoding a CAR. In some embodiments, a promoter is an EF1alpha (EF1α) promoter. In some embodiments, an expression construct further comprises a Woodchuck Hepatitis Virus Posttranscriptional Regulatory Element (WPRE). In some embodiments, an EF1alpha promoter is positioned 5' to a nucleic acid sequence encoding a CAR, and a WPRE is positioned 3' to the nucleic acid sequence encoding the CAR.

In some embodiments, an expression construct further comprises a forkhead box P3 (FoxP3) encoding nucleic acid sequence. In some embodiments, a FoxP3 encoding nucleic acid sequence is linked to a nucleic acid sequence encoding a CAR. In some embodiments, a FoxP3 encoding sequence and a nucleic acid sequence encoding a CAR are linked by a nucleic acid sequence encoding a 2A self-cleaving peptide.

In some embodiments, an expression construct is flanked by viral long terminal repeats (LTRs). In some embodiments, the LTRs are retroviral LTRs. In some embodiments, LTRs are HIV LTRs.

In some embodiments, the disclosure provides a vector comprising an isolated nucleic acid as described herein. In some embodiments, the vector is a plasmid. In some embodiments, the vector is a viral vector, for example a lentiviral vector, retroviral vector, or an adenoviral vector.

In some embodiments, the disclosure provides a host cell comprising an isolated nucleic acid or a vector as described herein. In some embodiments, the host cell comprises a CAR encoded by a nucleic acid as described herein. In some embodiments, a host cell is a mammalian cell. In some embodiments, a mammalian cell is a human cell.

In some embodiments, a host cell is an immune cell. In some embodiments, an immune cell is a T-cell or a regulatory T-cell (T-reg).

In some embodiments, the disclosure provides a composition comprising a host cell as described herein. In some embodiments, a composition comprises a plurality of host cells. In some embodiments, a composition further comprises a pharmaceutically acceptable excipient. In some embodiments, a pharmaceutically acceptable excipient is a cryoprotectant.

In some embodiments, the disclosure provides a method for modulating an immune response of a subject to an AAV capsid protein, the method comprising administering to the subject a host cell (e.g., a composition comprising a plurality of host cells) as described herein. In some embodiments, the host cells are autologous host cells (e.g., derived from the subject). In some embodiments, the host cells are heterologous (e.g., derived from a different subject of the same species as the subject) or xenogeneic (e.g., derived from a different species than the subject) host cells.

In some embodiments, a subject is a human. In some embodiments, a subject has previously been administered an rAAV, or is contemplated to be administered an rAAV (e.g., a therapeutic rAAV).

In some embodiments, the method comprises administering to the subject a CAR T-cell such that the immune response of the subject to the AAV capsid protein is inhibited relative to a control or a subject not having been administered the CAR T-cell.

In some embodiments, the method comprises administering to the subject a CAR T-reg such that the immune response of the subject to the AAV capsid protein is induced relative to a control or a subject not having been administered the CAR T-reg.

In some embodiments, the methods further comprise administering a therapeutic rAAV to the subject. In some embodiments, the rAAV is administered in combination with a CAR T-cell. In some embodiments, the rAAV is administered prior to the administration of a CAR T-cell. In some embodiments, the rAAV is administered after the administration of a CAR T-cell. In some embodiments, the therapeutic rAAV comprises a capsid protein having the same serotype as the capsid protein targeted by the CAR.

In some embodiments, the disclosure relates to a vector carrying a nucleic acid encoding a CAR. In some embodiments, the vector is a lentiviral vector. In some embodiments, the lentiviral vector comprises a nucleic acid encoding a CAR having the sequence as set forth in SEQ ID NO: 1. In some embodiments, the lentiviral vector comprises a nucleic acid encoding a CAR having the sequence as set forth in SEQ ID NO: 2. In some embodiments, the lentiviral vector comprises a nucleic acid encoding a CAR having the sequence as set forth in SEQ ID NO: 3. In some embodiments, the lentiviral vector comprises a nucleic acid encoding a CAR having the sequence as set forth in SEQ ID NO: 4.

These and other aspects and embodiments will be described in greater detail herein. The description of some exemplary embodiments of the disclosure are provided for illustration purposes only and not meant to be limiting. Additional compositions and methods are also embraced by this disclosure.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, Drawings, Examples, and Claims.

BRIEF DESCRIPTION OF DRAWINGS

FIG. 2A: 3rd generation Lentiviral vector for CAR-Regulatory-T-cells. Vector contains ScFv anti-AAV capsid derived from D3 antibody with reactivity against major AAV capsid variants, human CD28 domain, human 4-1BB domain, human CD3z domain. Included after a self-cleavage domain are FoxP3 transcription factor and CD19 truncated extracellular domain. Different versions include: murine and human genes, shorter Fc linker, 2nd generation CARs with either CD28 domain or 41BB domain, other co-stim, other reporter genes (CD19 or EGFR). FIG. 2B: 3rd generation Lentiviral vector for CAR-T-cells. Vector contains ScFv anti-AAV capsid derived from D3 antibody with reactivity against major AAV capsid variants, human CD28 domain, human 4-1BB domain, human CD3z domain. Included after a self-cleavage domain is CD19 truncated extracellular domain. Different versions include: murine and human genes, shorter Fc linker, 2nd generation CARs with either CD28 domain or 41BB domain, other co-stim, other reporter genes (CD19 or EGFR).

FIGS. 10A-10G. FIG. 10A: graphical schematic of AAV-CAR-T-cells and AAV-CAR-Regulatory-T-cells expansion. FIG. 10B: Representative flow cytometry plots of transfected cells before and after expansion. FIG. 10C: Flow cytometry plots of IL-2 production by AAV-CAR-T-cells after different stimulation conditions. FIG. 10D: IL-2 concentration of AAV-CAR-T-cells after different stimulation conditions by ELISA. FIG. 10E: Flow cytometry plots of IFN-y production by AAV-CAR-T-cells after different stimulation conditions. FIG. 10F: Flow cytometry plots of IFN-y production by AAV-CAR-T-cells co-cultured with AAV-CAR-Regulatory-T-cells after different stimulation conditions. FIG. 10G: IFN-γ concentration of AAV-CAR-T-cells with or without AAV-CAR-Regulatory-T-cells after different stimulation conditions by ELISA.

FIGS. 11A-11E. FIG. 11A: Graphical schematic of a luciferase killing assay and inhibition of luciferase killing assay. FIG. 11B: Quantitative results of killing assay and inhibition of killing assay for AAV1, AAV6, AAV3b and Rh32.33 capsid variants. FIG. 11C: Graphical schematic of a luciferase killing assay and inhibition of luciferase killing assay. FIG. 11D: Quantitative results of killing assay and inhibition of killing assay against AAV6 transfected-Raji cells (CD20+) and Raji cells (CD20+) using AAV-CAR-T-cells and CD20-CAR-Tregs. FIG. 11E: Quantitative results of killing assay and inhibition of killing assay against AAV6 transfected-Raji cells (CD20+) and Raji cells (CD20+) using CD20-CAR-T-cells and AAV-CAR-Tregs.

FIGS. 12A-12F. FIG. 12A: Graphical schematic of in vivo CAR-T-cell response. Intramuscular injections of AAV1-human AAT [$5*10^{10}$ viral titer]. At week 3, intravenous injection of AAV-CAR-T-cells [$5*10^6$ cells] or PBS followed by intraperitoneal of IL-2 [45000 IU] for 3 days. FIG. 12B: Time course of serum human AAT protein levels of control animals and animals that received AAV-CAR-T-cells (left). Normalized human AAT protein levels to the baseline at week 3 for control animals and animals that received AAV-CAR-T-cells (right). Arrows represents delivery of CAR T-cell delivery. FIGS. 12C-F: Flow cytometry plots of isolated T-cells from the muscles of AAV1-human AAT injected animals or AAV1-human AAT injected animals with AAV-CAR-T-cells. Populations of CD3+ (FIG. 12C); CD3+, CD8+, or CD4+ (FIG. 12D); CD3+, CD90.2+ (FIG. 12E); CD3+, CD90.2+, CD19+ (FIG. 12F).

FIGS. 13A-13F. FIG. 13A: Graphical schematic of in vivo CAR-Regulatory-T-cell suppression immune response against AAV-Rh32.33. Intra muscular injections of AAV-Rh32.33-human AAT [5*1010 viral titer]. At week 1, intravenous injection of AAV-CAR-Regulatory-T-cells [5*106 cells] or natural expanded regulatory T-cells [5*106 cells] or PBS followed by Intraperitoneal of IL-2 [45000 IU] for 3 days. FIG. 13B: Time course of serum human AAT protein levels of control animals and animals that received AAV-CAR-Regulatory-T-cells and expanded natural regulatory-T-cells (left). Normalized human AAT protein levels to the baseline at week 1 for control animals and animals that received AAV-CAR-Regulatory-T-cells and expanded natural regulatory-T-cells (right). Red arrow represents CAR T-Reg delivery. FIG. 13C: Graphical schematic of in vivo CAR-Regulatory T-cell suppression immune response against Ovalbumin-AAV1 in C57BL/6 animals. Intra muscular injections of Ovalbumin-AAV1 [5*1010 viral titer]. At week 1, intravenous injection of AAV-CAR-Regulatory-T-cells [5*106 cells] or natural expanded regulatory T-cells [5*106 cells] or PBS followed intraperitoneal of IL-2 [45000 IU] for 3 days. FIG. 13D: Time course of serum Ovalbumin levels of control animals and animals that received AAV-CAR-Regulatory-T-cells and expanded natural regulatory-T-cells (left). Normalized Ovalbumin protein levels to the baseline at week 1 for control animals and animals that received AAV-CAR-Regulatory-T-cells and expanded natural regulatory-T-cells (right). Red arrow represents CAR T-Reg delivery. FIG. 13E: Graphical schematic of in vivo CAR-Regulatory-T-cell suppression immune response against chimpanzee AAT-AAV1 in Balb/C animals. Intra muscular injections of chimpanzee AAT-AAV1 [5*1010 viral titer]. At week 1, intravenous injection of AAV-CAR-Regulatory-T-cells [5*106 cells] or natural expanded regulatory T-cells [5*106 cells] or PBS followed by intraperitoneal of IL-2 [45000 IU] for 3 days. FIG. 13F: Time course of serum chimpanzee AAT protein levels of control animals and animals that received AAV-CAR-Regulatory-T-cells and expanded natural regulatory-T-cells (left). Normalized chimpanzee AAT protein levels to the baseline at week 1 for control animals and animals that received AAV-CAR-Regulatory-T-cells and expanded natural regulatory-T-cells (right). Red arrow represents CAR T-reg delivery.

DETAILED DESCRIPTION OF CERTAIN EMBODIMENTS

Figure 1A:
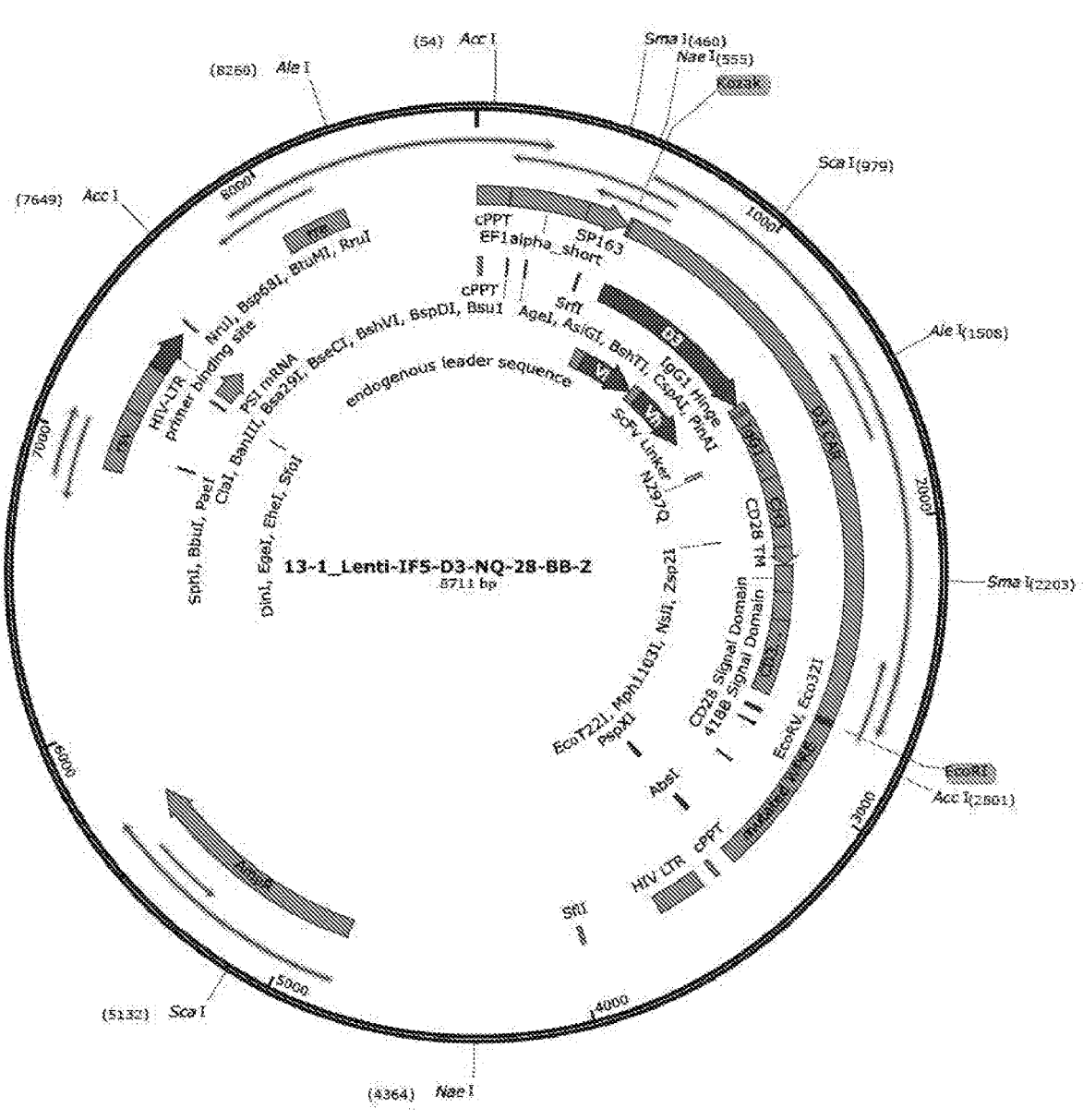
FIGS. 1A-1B are schematics depicting two embodiments of CAR T-cell constructs that recognize (e.g., specifically bind to) AAV2 capsid protein (e.g., SEQ ID NO: 1-2).

Embodiments of the disclosure relate to compositions and methods for modulating the immune response of a subject (e.g., a human subject) to certain viral antigens (e.g., antigens derived from AAV capsid proteins). The disclosure is based, in part, on isolated nucleic acids and expression constructs encoding chimeric antigen receptors (CARs), and recombinant immune cells comprising such expression constructs (e.g., CAR T-cells and CAR T-regs). In some embodiments, CAR T-cells described herein are useful for killing immune cells (e.g., APCs), which APCs induce immune responses against AAV capsid proteins, thereby dampening (e.g., inhibiting or suppressing) the host immune response against the AAV capsid protein. In some embodiments, CAR T-reg cells described herein are useful for inhibiting the killing of immune cells (e.g., APCs), which APCs induce immune responses against AAV capsid proteins, thereby increasing (e.g., promoting or inducing) the host immune response against AAV capsid protein.

Chimeric Antigen Receptors (CARs)

Aspects of the disclosure relate to compositions (e.g., isolated nucleic acids, vectors such as viral vectors, cells, etc.) encoding one or more chimeric antigen receptors (CARs). For example, in aspects, the disclosure relates to CARs having an antigen binding domain that is specific for an AAV capsid protein epitope. As used herein, a "chimeric antigen receptor" or "CAR" refers to a recombinant cell receptors which redirects the specificity or function of a cell (e.g., an immune cell) by providing both antigen-binding and cell activating functions. Generally, CARs are a fusion protein comprising one or more antigen binding domains (e.g., extracellular domain), a transmembrane domain, and at least one cytoplasmic signaling domain (e.g., intracellular domain), which combination of extracellular domain, transmembrane domain, and cytoplasmic signaling domain, do not naturally occur together in nature. A cell expressing a CAR may produce, in some embodiments, an atypical cellular response (e.g., increased, decreased, or different cellular response relative to a naturally-occurring cell).

Antigen Binding Domain

A CAR may comprise one or more (e.g., 1, 2, 3, etc.) antigen binding domains (e.g., an extracellular domain). As used herein, an "antigen binding domain," refers to the domain of a protein or polypeptide external to the cellular membrane, which domain's main function is to recognize (e.g., bind) and respond to a type of ligand (e.g., antigen). As used herein, "binding affinity" refers to the apparent association constant or KA. The KA is the reciprocal of the dissociation constant (KD). The antigen binding domain (e.g., antibody, scFv, etc.) described herein may have a binding affinity (KA) of at least $10^5$, $10^6$, $10^7$, $10^8$, $10^9$, $10^{10}$ M, or higher. An increased binding affinity corresponds to a decreased KD. Higher affinity binding of an antigen binding domain to a first target relative to a second target can be indicated by a higher KA (or a smaller numerical value KD) for binding the first target than the KA (or numerical value KD) for binding the second target. In such cases, the antigen binding domain has specificity for the first target relative to the second target. Differences in binding affinity between the first target relative to the second target (e.g., for specificity or other comparisons) can be greater than 1, for example at least 1.5; 2; 3; 4; 5; 10; 15; 20; 37.5; 50; 70; 80; 91; 100; 500; 1,000; 10,000, or 100,000 fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in, e.g., TRIS-buffer (50 mM TRIS, 150 mM NaCl, 5 mM CaCl2 at pH7.5). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation: [Bound]=[N][Free]/(Kd+[Free]).

It is not always necessary to make an exact determination of KA, though, since sometimes it is sufficient to obtain a quantitative measurement of affinity, e.g., determined using a method such as ELISA or FACS analysis, is proportional to KA, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

Each of the antigen binding domains may bind to the same target (e.g., the same peptide, protein, epitope, etc.), or each antigen binding domain may bind to a separate target (e.g., a different peptide, protein, epitope, etc., for example as in the case of a bi-specific CAR).

An antigen binding domain, may be part of a polypeptide which crosses the cellular membrane multiple times, which results in a multiple exposures of the polypeptide with loops intersecting the membrane as well as an end with a singular intersection. In some embodiments, extracellular ligand-binding domain or moiety is in the form of a binding protein, small molecule, a peptide, a targeting agent, a protein agonist, or a protein antagonist.

The antigen binding domain can be any domain that binds to the antigen including, but not limited to, monoclonal antibodies, scFvs, polyclonal antibodies, synthetic antibodies, human antibodies, humanized antibodies, and fragments thereof. In some instances, it is beneficial for the antigen binding domain to be derived from the same species in which the CAR will ultimately be used. For example, for use in humans, it may be beneficial for the antigen binding domain of the CAR to comprise a human antibody or fragment thereof. In some embodiments, the antigen binding domain comprises a human antibody or a fragment thereof. In some embodiments, the binding protein is an antibody, an antigen-binding portion of an antibody (e.g., a scFv), a ligand, a cytokine, or a receptor. In some embodiments, an antigen binding domain may comprise a site derived from a monoclonal antibody or a scFv. In some embodiments, the antigen binding fragment is a scFv or an Fab fragment. In some embodiments, the antigen binding domain may bind an AAV capsid protein epitope. In some embodiments, an scFv fragment is encoded by a nucleic acid sequence comprising a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 22. In some embodiments, an scFv fragment is encoded by a nucleic acid sequence comprising a sequence of SEQ ID NO: 22. In some embodiments the chimeric antigen receptors of the disclosure comprise a CD19 extracellular domain. In some embodiments, the CD19 extracellular domain is encoded by a nucleic acid sequence comprising a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 32. In some embodiments, the CD19 extracellular domain is encoded by a nucleic acid sequence comprising a sequence of SEQ ID NO: 32. In some embodiments the chimeric antigen receptors of the disclosure comprise an EGFR extracellular domain. In some embodiments, the EGFR extracellular domain is encoded by a nucleic acid sequence comprising a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 33. In some embodiments, the EGFR extracellular domain is encoded by a nucleic acid sequence comprising a sequence of SEQ ID NO: 33.

In some embodiments, a CAR may be configured to have an antigen binding domain which recognizes an epitope of a capsid protein of an AAV. Each serotype of AAV has a capsid comprising 3 capsid proteins (e.g. VP1, VP2, VP3), and which capsid expresses a variety of receptors. Of the AAV serotypes the capsid proteins contain 12 hypervariable regions which capsid proteins affect the tissue specificity of the AAV. The serotypes and capsids also express a number of stimulating epitopes. In some embodiments, the nucleic acid encodes a CAR with an antigen binding domain targets (e.g., specifically binds to) an epitope of an AAV capsid protein. In some embodiments, the nucleic acid encodes a CAR with an antigen binding domain targets (e.g., specifically binds to) an epitope of an AAV capsid protein having a serotype selected from AAV1, AAV2, AAV3, AAV3b, AAV4, AAV5, AAV6, AAV7, AAV8, AAVrh.8, AAV9, AAV10, AAVrh.10, AAVrh.39, AAVrh.43, AAV.PHPB, AAV.PHPB.e, AAVrh32.33, or a variant thereof. In some embodiments, the nucleic acid encodes a CAR with an antigen binding domain which targets an AAV2 epitope or an AAV6 epitope.

In some embodiments, the antigen binding domain targets an epitope of an AAV capsid protein having a serotype selected from AAV1, AAV2, AAV3, AAV3b, AAV4, AAV5, AAV6, AAV7, AAV8, AAVrh.8, AAV9, AAV10, AAVrh.10, AAVrh.39, AAVrh.43, AAV.PHPB, AAV.PHPB.e, AAVrh32.33, or a variant thereof. In some embodiments, the nucleic acid may encode an antigen binding domain which targets an epitope of a capsid protein of any of AAV1, AAV2, AAV3, AAV3b, AAV4, AAV5, AAV6, AAV7, AAV8, AAVrh.8, AAV9, AAV10, AAVrh.10, AAVrh.39, AAVrh.43, AAV.PHPB, AAV.PHPB.e, AAVrh32.33, or a variant thereof, AAV serotypes. In some embodiments, the antigen binding domain targets an AAV2 epitope or an AAV6 epitope. In some of the embodiments, nucleic acid may encode an antigen binding domain which targets an epitope of a capsid protein of either AAV2 or AAV6, AAV serotypes. In some of the embodiments, the antigen binding domain targets an epitope of a capsid protein of AAV serotype AAV2. In some embodiments, the antigen binding domain has a nucleic acid comprising SEQ ID NO: 22. In some embodiments, the nucleic acid encodes an antigen binding domain having an amino acid comprising SEQ ID NO: 39. In some of the embodiments, the antigen binding domain targets an epitope of a capsid protein of AAV serotype AAV6.

The antigen binding domain may comprise an scFv having a variable heavy chain domain (VH) derived from an AAV capsid protein-targeting antibody linked to a variable light chain domain (VL) derived from an AAV capsid protein-targeting antibody. In some embodiments, the nucleic acid encodes a CAR with an antigen binding domain which comprises a scFv. Single chain variable fragments are well known in the art, they are generally known to consist of a fusion protein of the VH and VL of the subject antibody connected by a linker peptide.

In some embodiments, a CAR may have increased cytotoxic effects on a cell bearing a target antigen or epitope. In some embodiments, a CAR may have increased cytotoxic effects on a cell bearing a target antigen or epitope resulting from expressing a target antigen binding domain on a T-Cell to target APCs. In some embodiments, a CAR may have decreased cytotoxic effects on a cell bearing a target antigen or epitope. In some embodiments, a CAR may have decreased cytotoxic effects on a cell bearing a target antigen or epitope resulting from expressing a target antigen binding domain on a T-reg cell to induce APCs.

In some embodiments, a nucleic acid encoding a CAR is disclosed, wherein the antigen binding domain comprises a first portion comprising a monoclonal antibody or a single chain variable fragment (scFv). In some embodiments, the nucleic acid encodes a CAR with an antigen binding domain comprising a "monoclonal antibody" (mAb). In some embodiments, the antigen binding domain may be a mAb. In some embodiments, the mAb may be an mAb to, or targets, an epitope of AAV capsid. In some embodiments, the mAb may be an mAb to, or targets, an epitope of AAV1, AAV2, AAV3, AAV3b, AAV4, AAV5, AAV6, AAV7, AAV8, AAVrh.8, AAV9, AAV10, AAVrh.10, AAVrh.39, AAVrh.43, AAV.PHPB, AAV.PHPB.e, AAVrh32.33, or a variant thereof. In some embodiments, the mAb may be an mAb, or targets, AAV2 capsid epitope or an AAV6 capsid epitope. mAbs are antibodies that are made by immune cells (e.g., leukocytes) that are identical and bind to a shared epitope. Antibodies (e.g., immunoglobulins) are well known in the art, but generally are known to be large "Y" shaped proteins in the immune system which neutralize antigens. Each protein consist of two identical heavy chains and two identical light chains each having a variable (e.g., variable domain of heavy chain (VH) and variable domain of light chain (VL)). The variable domains contain complementarity determining regions, which specify the antigen the antibody will recognize (i.e. bind). In addition to the variable domains, the light chain a constant domain (CL) and the heavy chain has three constant domains, which are numbered 1-3 as you move farther from the VH domain (e.g., CH1, CH2, CH3). Production of mAbs in all forms (e.g., humanized) are well known in the art and include traditional means such as animal based techniques. For example, the techniques generally entail: 1) exposing a subject (e.g., mouse, rabbit) to an antigen (e.g., capsid protein); 2) fusion into immortalized cell lines (e.g., myeloma cells); 3) cell culture and antibody screening; and 4) selection and recovery of cells presenting the mAb of interest) as well as other techniques such as phage display (generally: 1) the target proteins or nucleic acid sequences (e.g., capsid proteins) are immobilized to the wells of a microtiter plate; 2) a variety of nucleic acid sequences are expressed in a bacteriophage library in the form of fusions with the bacteriophage coat protein, so that they are displayed on the surface of the viral particle. The protein displayed corresponds to the genetic sequence within the phage; 3) this phage-display library is added to the microtiter plat allowing the phage time to bind, the dish is subsequently washed; 4) bound phage-displaying proteins remain attached to the dish, while all others are washed away; 5) attached phage may be enriched (through elution and culture, etc.) and steps 3 to 5 are optionally repeated one or more times, further enriching the phage library in binding proteins; 6) following further bacterial-based culture, the nucleic acids within in the interacting phage is sequenced to identify the interacting proteins or protein fragments). Any method of generating mAbs known in the art may be used to generate the mAbs of the instant disclosure.

In some embodiments, the nucleic acid of the instant disclosure encoding the antigen binding domain may further encode an immunoglobulin G1 (IgG1) constant domain 2 (IgG1 CH2). In some embodiments, the nucleic acid of the instant disclosure, may further encode for an IgG1 constant domain 3 (IgG1 CH3). IgG is a type of antibody which represents, by some estimates, nearly 75% of the serum antibodies in humans. IgG is created by B-cells and has two antigen binding sites. IgG is a versatile immunoglobulin, exploiting a variety of mechanisms to mediate the immune response, for example through classical pathways, toxin neutralization, complement pathways, opsonization, agglutination, antibody dependent cell-mediated cytotoxicity, and others. IgG is further differentiated into 4 subclasses (G1, G2, G3, and G4). The structure of the hinge region which links the CH1 domain with the CH2 domain, determines the properties and subclass of IgG molecules. The hinge region also affects the affinity of IgG to immunoglobulin receptor (e.g. Fc receptor) on a variety of immune cells, thereby affecting the specificity and activity of the sub-class IgG.

In some embodiments, the antigen binding domain may further comprise an extracellular recognition domain. A recognition domain may be used to identify the cells upon action or inaction when the protein is used in vitro or in vivo, for example by release of visible light, or by being detectable by different modalities (e.g., x-ray, luminescence, radiation, or other detectable means). Such domains (e.g., tags) are known in the art and will be readily appreciated by the skilled artisan (e.g., GFP, EGFP, etc.). In some embodiments, the antigen binding domain further comprises EGFP.

Transmembrane Domain

As used herein, a "transmembrane domain," refers to the domain of a protein or polypeptide which spans the cellular membrane connecting the antigen binding domain with the cytoplasmic signaling domain. The transmembrane domain may span the cellular membrane multiple times and is responsible for communicating the activation of the antigen binding domain (e.g., through binding of a ligand or antigen) with the cytoplasmic signaling domain. Any transmembrane domain is contemplated for use herein as long as the domain is capable of anchoring a CAR comprising the domain to a cell membrane. In some embodiments, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex. Various mechanisms exist for signaling, such as conformational changes and changes to the cellular membrane (e.g., conformational or changes to membrane pores), and are known in the art.

The transmembrane domain may be selected from any known transmembrane domain which can be incorporated into the nucleic acid and expressed as a fusion protein. Transmembrane domains of particular use in this invention may be derived from (e.g., comprise at least the transmembrane domain(s) of) the alpha, beta or zeta chain of the T-cell receptor, CD28, CD3 epsilon, CD45, CD4, CD5, CD8, CD9, CD16, CD22, CD33, CD37, CD64, CD80, CD86, C 5 D134, CD137, and CD154. Transmembrane domains can be identified using any method known in the art or described herein, e.g., by using the UniProt Database.

In some embodiments, the transmembrane domain is a CD28 transmembrane domain.

CD28 is a costimulatory receptor for T-cells which is primarily responsible for delivering a second signal for T-cell activation. In some embodiments, the nucleic acid encoding a transmembrane domain has a nucleic acid sequence comprising a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to SEQ ID NO: 25. The terms "percent identity," "sequence identity," "% identity," "% sequence identity," and % identical," as they may be interchangeably used herein, refer to a quantitative measurement of the similarity between two sequences (e.g., nucleic acid or amino acid). The percent identity of genomic DNA sequence, intron and exon sequence, and amino acid sequence between humans and other species varies by species type, with chimpanzee having the highest percent identity with humans of all species in each category. Percent identity can be determined using the algorithms of Karlin and Altschul, Proc. Natl. Acad. Sci. USA 87:2264-68, 1990, modified as in Karlin and Altschul, Proc. Natl. Acad. Sci. USA 90:5873-77, 1993. Such algorithms is incorporated into the NBLAST and XBLAST programs (version 2.0) of Altschul et al., J. Mol. Biol. 215:403-10, 1990. BLAST protein searches can be performed with the XBLAST program, score=50, word length=3, to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used. When a percent identity is stated, or a range thereof (e.g., at least, more than, etc.), unless otherwise specified, the endpoints shall be inclusive and the range (e.g., at least 70% identity) shall include all ranges within the cited range (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.). In some embodiments, the transmembrane domain is encoded by a nucleic acid sequence comprising the sequence of SEQ ID NO: 25. In some embodiments, the antigen binding domain and the transmembrane domain are connected (e.g., joined) by a linker.

Cytoplasmic Signaling Domain

In some embodiments, a CAR comprises a cytoplasmic signaling domain. As used herein, "cytoplasmic signaling domain" (e.g., intracellular domain) refers to one or more domains (e.g., co-stimulatory domains, signaling domains) of a protein or polypeptide internal to the cellular membrane, which domain's main function is to relay the signal from the antigen binding and transmembrane domains to interact with the interior of the cell. The interaction can be by various mechanisms (e.g., protein-protein interactions, enzymatic activity) and are known in the art. The cytoplasmic signaling domain may be part of a polypeptide which crosses the cellular membrane multiple times, which results in a multiple exposures of the polypeptide with loops intersecting the membrane as well as an end with a singular intersection. Cytoplasmic signaling domains transmit an activation signal to the cell following binding of the antigen binding domain (i.e., extracellular domain). Cytoplasmic signaling domain can be any intracellular signaling domain of interest that is known in the art. For example, cytoplasmic signaling domains can include, without limitation, CD3-zeta. This signaling in turn "activates" or causes a function of the cell (i.e., effector function). Additionally, while an entire intracellular signaling domain (i.e., not truncated) can be employed, in cases it may not be necessary to use the entire domain, for example a truncated portion of the intracellular signaling domain may function as the intracellular domain with equivalent, or modulated, function. Such truncated portion may be used in place of the intact domain as long as it transduces the effector function signal. The term intracellular signaling domain is thus meant to include any truncated portion of the intracellular signaling domain sufficient to transduce the effector function signal.

In some embodiments, the cytoplasmic signaling domain comprises domain selected from: a CD28 signaling domain, a 4-1BB signaling domain, a CD3 signaling domain, or combination thereof. In some embodiments, the cytoplasmic signaling domain comprises a CD28 signaling domains. In some embodiments, the cytoplasmic signaling domain comprises a 4-1BB signaling domains. In some embodiments, the cytoplasmic signaling domain comprises a CD3 signaling domains. In some embodiments, the cytoplasmic signaling domain comprises all three of CD28, 4-1BB, and CD3 signaling domains.

The cytoplasmic signaling domain of CD28 is a B7 (e.g., CD80 and CD 86) receptor constitutively expressed on naive T-cells and can initiate a variety of pathways to stimulate a T-cell response. The cytoplasmic signaling domain of 4-1BB is a co-stimulatory molecule with roles in expansion, acquisition of effector function, survival, and development of T cell memory. It is a signaling domain with a role in pathways which induce the expression of survival genes encoding surviving, Bcl-2, Bcl-XL, and Bfl-1 and decrease the expression of pro-apoptotic Bim, which can promote different type cells to live. CD3 is a T-cell co-receptor integral to T-cell activation. CD3 molecules, along with the t-cell receptor, associate to comprise the t-cell receptor complex, which activation is necessary for native T-cell activation. In some embodiments, the nucleic acid may encode a CAR having a cytoplasmic signaling domain which is a CD28 signaling domain. In some embodiments, the CD28 signaling domain is encoded by a nucleic acid sequence comprising a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 26. In some embodiments, the CD28 signaling domain is encoded by a nucleic acid sequence comprising a sequence of SEQ ID NO: 26. In some embodiments, the CD28 signaling domain is encoded by a nucleic acid sequence comprising a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 27. In some embodiments, the CD28 signaling domain is encoded by a nucleic acid sequence comprising a sequence of SEQ ID NO: 27. In some embodiments, the nucleic acid may encode a CAR having a cytoplasmic signaling domain which is a 4-1BB signaling domain. In some embodiments, the CD28 signaling domain is encoded by a nucleic acid sequence comprising a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 28. In some embodiments, the CD28 signaling domain is encoded by a nucleic acid sequence comprising a sequence of SEQ ID NO: 28. In some embodiments, the CD28 signaling domain is encoded by a nucleic acid sequence comprising a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 29. In some embodiments, the CD28 signaling domain is encoded by a nucleic acid sequence comprising a sequence of SEQ ID NO: 29. In some embodiments, the nucleic acid may encode a cytoplasmic signaling domain which is a CD3 signaling domain. In some embodiments, the CD3 signaling domain is a CD3z signaling domain. In some embodiments, the CD3 signaling domain is encoded by a nucleic acid sequence comprising a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 30. In some embodiments, the CD3 signaling domain is encoded by a nucleic acid sequence comprising a sequence of SEQ ID NO: 30. In some embodiments, the CD28 signaling domain is encoded by a nucleic acid sequence comprising a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 31. In some embodiments, the CD28 signaling domain is encoded by a nucleic acid sequence comprising a sequence of SEQ ID NO: 31.

The three domains, antigen binding domains, transmembrane domains, and cytoplasmic signaling domains, as well as the general function and architecture are known in the art. The three domains (e.g., antigen binding domain, transmembrane domain, and cytoplasmic signaling domain), operate to effect some change in the host cell, for example increased cellular activity (e.g. protein production), which can result in various internal or external effects (e.g. cytotoxic effect on antigen bearing cell).

Linkers

In some embodiments, the disclosure relates to a CAR comprising a linker. In some embodiments, domains of the CAR may be joined by a linker. In some embodiments, at least one linker is used to join each domain of a CAR. The term "linker," as used herein, refers to a molecule linking two other molecules or moieties. Linkers are well known in the art and can comprise any suitable combination of nucleic acids or amino acids to facilitate the proper function of the structures they join. The linker can be a series of amino acids. The linker can be an amino acid sequence in the case of a linker joining two fusion proteins. For example, a fusion protein (e.g., a CAR) comprising various domains (e.g., antigen binding domain, transmembrane domain, intracellular domain) can be fused to by an amino acid linker sequence. The linker can also be a nucleotide sequence in the case of joining two nucleotide sequences together. In other embodiments, the linker is an organic molecule, group, polymer, or chemical moiety. In some embodiments, the linker is 1-100 amino acids in length, for example: 1; 2; 3; 4; 5; 6; 7; 8; 9; 10; 11; 12; 13; 14; 15; 16; 17; 18; 19; 20; 21; 22; 23; 24; 25; 26; 27; 28; 29; 30; 30-35; 35-40; 40-45; 45-50; 50-60; 60-70; 70-80; 80-90; 90-100; 100-150; or 150-200 amino acids in length. In some embodiments, the linker is 5-1,000 nucleotides in length, for example: 5; 6; 7; 8; 9; 10; 11; 12; 13; 14; 15; 16; 17; 18; 19; 20; 21; 22; 23; 24; 25; 26; 27; 28; 29; 30; 30-35; 35-40; 40-45; 45-50; 50-60; 60-70; 70-80; 80-90; 90-100; 100-150; 150-200; 200-300; 300-500; 500-1,000; 1,000-2,000; or 2,000-5,000 nucleotides. Longer or shorter linkers are also contemplated. In some embodiments, a CAR comprises at least one linker. In some embodiments, a CAR comprises at least one linker. In some embodiments, a CAR comprises at least two linkers. In some embodiments, a CAR comprises at least three linkers. In some embodiments, a CAR comprises at least four linkers. In some embodiments, a CAR comprises at least five linkers. In some embodiments, a CAR comprises more than five linkers. In some embodiments, all of the linkers used are the same (e.g., identical). In some embodiments, not all of the linkers are identical (e.g., at least one linker is distinct from at least one other linker). In some embodiments, each linker is distinct from each other linker.

In some embodiments, a linker is referred to as a hinge or hinge domain. As used herein, a hinge domain generally means any polypeptide that functions to provide flexibility to the CAR, or domains thereof, and/or prevent steric hindrance of the CAR, or domains thereof. In some embodiments, a hinge domain may comprise up to 300 amino acids, preferably 10 to 100 amino acids and most preferably 1 to 20 amino acids. It also should be appreciated that one or more hinge domains may be included in other regions of a CAR, as aspects of the disclosure are not limited in this respect. In some embodiments, the hinge is encoded by a nucleic acid sequence having at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 23. In some embodiments, the hinge is encoded by a nucleic acid sequence comprising a sequence of SEQ ID NO: 23. In some embodiments, the hinge is encoded by a nucleic acid sequence having at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 24. In some embodiments, the hinge is encoded by a nucleic acid sequence comprising a sequence of SEQ ID NO: 24.

In some embodiments the VH and the VL are linked by a linking molecule. In some embodiments, the linking molecule is a peptide linker. The linkers may be rich in glycine (e.g., a (GGGGS)n linker, where n is an integer between 1 and 10) for flexibility and in serine or threonine for solubility (i.e., hinge). In some embodiments, the peptide linker is a glycine-rich linker. The linker may connect the N-terminus of either VH or VL to the C-terminus of the other. In some embodiments, the linker joins the N-terminus of the VH to the C-terminus of the VL. In some embodiments, the linker joins the N-terminus of the VL to the C-terminus of the VH. In some embodiments, an antigen binding domain may be an scFv having a VH derived from an AAV capsid protein-targeting antibody linked to a VL derived from an AAV capsid protein-targeting antibody.

In some embodiments, the nucleic acid comprises IgG CH2 and IgG1 CH3 domains are joined by a linker. In some embodiments, the linker comprises an IgG1 hinge linker and/or an IgG2 hinge linker. In some embodiments, the nucleic acid of the instant disclosure encoding the antigen binding domain may further encode for an immunoglobulin G1 (IgG1) constant domain 2 (IgG1 CH2) and constant domain 3 (IgG1 CH3) joined by a linker. In some embodiments, the linker comprises a linker native to IgG1. In some embodiments, the nucleic acid of the instant disclosure encoding the antigen binding domain may further encode for an immunoglobulin G1 (IgG1) constant domain 2 (IgG1 CH2) and constant domain 3 (IgG1 CH3) linked to the first portion by a hinge linker native to IgG1.

In some embodiments, a CAR is encoded by a nucleic acid sequence having at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 1-4 and 16-17. In some embodiments, a CAR is encoded by a nucleic acid comprising a sequence of SEQ ID NO: 1-4 and 16-17.

Isolated Nucleic Acids

In some embodiments, a CAR is encoded by an isolated nucleic acid. As used herein, the term "isolated," refers to the characteristic of a material as provided herein being removed from its original or native environment (e.g., the natural environment if it is naturally occurring). Therefore, a naturally-occurring polynucleotide or protein or polypeptide present in a living animal is not isolated, but the same polynucleotide or polypeptide, separated by human intervention from some or all of the coexisting materials in the natural system, is isolated. An artificial or engineered material, for example, a non-naturally occurring nucleic acid construct, such as the expression constructs and vectors described herein, are, accordingly, also referred to as isolated. A material does not have to be purified in order to be isolated. Accordingly, a material may be part of a vector and/or part of a composition, and still be isolated in that such vector or composition is not part of the environment in which the material is found in nature.

As used herein, the term "nucleic acid," refers to a polymer of nucleotides. The term includes, but is not limited to, oligonucleotides and polynucleotides, both single-stranded and double-stranded forms, including hybrids, for example, of DNA and RNA strands, or of strands comprising ribonucleotides, deoxyribonucleotides, and/or modified nucleotides. The polymer may include natural nucleosides (i.e., adenosine, thymidine, guano sine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5 bromouridine, C5 fluorouridine, C5 iodouridine, C5 propynyl uridine, C5 propynyl cytidine, C5 methylcytidine, 7 deazaadenosine, 7 deazaguanosine, 8 oxoadenosine, 8 oxoguanosine, O(6) methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5' N phosphoramidite linkages).

In some embodiments, the isolated nucleic acid encoding a CAR may be a portion of an expression construct. The term "expression construct," as used herein, refers to a nucleic acid construct comprising nucleic elements sufficient for the expression of a gene product. Typically, an expression construct comprises a nucleic acid encoding a gene product operatively linked to a promoter sequence. The term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (e.g., the coding sequence is under the transcriptional control of the promoter). Encoding sequences can be operatively linked to regulatory sequences in sense or antisense orientation. In some embodiments, the promoter is a heterologous promoter.

The term "promoter," as used herein, refers to a nucleotide sequence capable of controlling the expression of a coding sequence or functional nucleic acid. In general, a nucleic acid sequence encoding a gene product is located 3' of a promoter sequence. In some embodiments, a promoter sequence consists of proximal and more distal upstream elements and can comprise an enhancer element. An "enhancer" is a nucleotide sequence that can stimulate promoter activity and may be an innate element of the promoter or a heterologous element inserted to enhance the level or tissue-specificity of a promoter. In some embodiments, the promoter is derived in its entirety from a native gene. In some embodiments, the promoter is composed of different elements derived from different naturally occurring promoters. In some embodiments, the promoter comprises a synthetic nucleotide sequence. It will be understood by those skilled in the art that different promoters will direct the expression of a gene in different tissues or cell types, or at different stages of development, or in response to different environmental conditions or to the presence or the absence of a drug or transcriptional co-factor.

Ubiquitous, cell-type-specific, tissue-specific, developmental stage-specific, and conditional promoters, for example, drug-responsive promoters (e.g., tetracycline-responsive promoters) are well known to those of skill in the art. In some embodiments, the promoter is a RNA polymerase I promoter. In some embodiments, the promoter is a RNA polymerase II promoter. In some embodiments, the promoter is a RNA polymerase III promoter. Promoters mediating transcription by recruiting RNA polymerase I (e.g., most rRNA gene promoters), II (e.g., U6 and H1 promoters), or III (e.g., most promoters of protein-encoding genes), are well known to those of skill in the art. The term "heterologous promoter," as used herein, refers to a promoter that is not found to be operatively linked to a given encoding sequence in nature. In some embodiments, an expression construct may comprise additional elements, for example, an intron, an enhancer, a polyadenylation site, a WPRE, and/or other elements known to affect expression levels of the encoding sequence. Without wishing to be bound by theory, inclusion of an intron in an expression construct, for example, between the transcriptional start site and an encoding nucleic acid sequence, for example, a protein-encoding cDNA sequence, is believed to result in increased expression levels of the encoding nucleic acid and the encoded gene product as compared to an expression construct not including an intron. In some embodiments, the promoter may be an EF1-alpha promoter. In some embodiments, the EF1-alpha promoter comprises a nucleic acid sequence having at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 5 or 19. In some embodiments, the EF1-alpha promoter comprises a nucleic acid sequence comprising a sequence of SEQ ID NO: 5 or 19. In some embodiments, the promoter may be a cytomegalovirus (CMV) promoter. In some embodiments, the CMV promoter comprises a nucleic acid sequence having at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 19. In some embodiments, the CMV promoter comprises a nucleic acid sequence comprising a sequence of SEQ ID NO: 19. In some embodiments, the promoter may be a MND2 promoter. In some embodiments, the MND2 promoter comprises a nucleic acid sequence having at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 20. In some embodiments, the MND2 promoter comprises a nucleic acid sequence comprising a sequence of SEQ ID NO: 20. In some embodiments, the promoter may be a SFFV promoter. In some embodiments, the SFFV promoter comprises a nucleic acid sequence having at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 21. In some embodiments, the SFFV promoter comprises a nucleic acid sequence comprising a sequence of SEQ ID NO: 21.

The term "gene product," as used herein, refers to any product encoded by a nucleic acid sequence. Accordingly, a gene product may, for example, be a primary transcript, a mature transcript, a processed transcript, or a protein or peptide encoded by a transcript. Examples for gene products, accordingly, include mRNAs, rRNAs, tRNAs, hairpin RNAs, microRNAs (miRNAs), shRNAs, siRNAs, and peptides and proteins, for example, reporter proteins or therapeutic proteins. In some embodiments, the expression construct further comprises a promoter operably linked to a nucleic acid sequence encoding the CAR. The term "operably linked," as may be used herein, refers to functional linkage between a regulatory sequence and a heterologous nucleic acid sequence (e.g., transgene) resulting in expression of the heterologous nucleic acid sequence (e.g., transgene). For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in the same reading frame.

In addition to the conventional control elements necessary, the nucleic acids may also include elements which are operably linked to the transgene in a manner which permits its transcription, translation and/or expression in a cell transfected with the plasmid vector or infected with the virus produced by the invention. In some embodiments, a promotor is contiguous with the gene of interest and expression control sequences that act in trans or at a distance to control the transgene. Expression control sequences include appropriate transcription initiation, termination, promoter, and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product (e.g., enhancers, post-transcriptional regulatory elements). In some embodiments, the polyA signal is an SV40 polyA signal. A great number of expression control sequences, including promoters which are native, constitutive, inducible, and/or tissue-specific, are known in the art and may be utilized. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV 40 promoter, the dihydrofolate reductase promoter, the beta-actin promoter, the phosphoglycerol kinase (PGK) promoter, and the EF1alpha promoter [Invitrogen]. In some embodiments, EF1alpha has a sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 5. In some embodiments, EF1alpha has a sequence of SEQ ID NO: 5.

In some embodiments, the nucleic acid is has a promoter operably linked to the nucleic acid sequence encoding a CAR.

In some embodiments, the promoter comprises an EF1alpha promoter. EF1alpha is a constitutive promotor which is especially useful in instances where other promoter sequences have diminished activity, or where other promoters may experience silencing or interferences from other cellular responses or activities. It is a common promoter used in driving ectopic gene expression in vivo. In some embodiments, the EF1alpha promoter may be operably linked to the transgene.

In some embodiments, the nucleic acids comprise a post-transcriptional regulatory element (PRE). Post-transcriptional regulatory elements, control gene expression through a variety of mechanisms (e.g., capping, splicing, polyadenylation, editing, stability manipulation, binding), but generally effect control at the RNA level, thus influence gene expression post-transcription, but pre-translation. PRE's may be cis- or trans-acting, and may be operably linked to the transgene. An example of a PRE, is woodchuck hepatitis virus PRE (WPRE), which is a nucleic acid sequence that in its transcribed form creates a tertiary structure which enhances gene expression. It's comprised of three component elements, alpha, beta, and gamma, which alpha being able to effect enhancement by itself, but in a reduced capacity. In some embodiments, the nucleic acid may encode a PRE. In some embodiments, the PRE comprises a Woodchuck Hepatitis Virus Posttranscriptional Regulatory Element (WPRE). In some embodiments, the WPRE may have an alpha component comprising a nucleic acid sequence with at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to SEQ ID NO: 6. In some embodiments, the WPRE may have an alpha component with a nucleic acid sequence comprising SEQ ID NO: 6. In some embodiments, the nucleic acid may comprise a WPRE having an alpha component comprising an amino acid sequence of SEQ ID NO: 6. In some embodiments, the nucleic acid comprises a WPRE with at least 70% identity to SEQ ID NO: 7. In some embodiments, the WPRE has a nucleic acid sequence comprising SEQ ID NO: 7. In some embodiments, there is more than one PRE encoded in the nucleic acid, and the more than one PRE can include WPRE, or a mixture thereof. In some embodiments, the nucleic acid does not include a PRE.

In some embodiments, the EF1alpha promoter is positioned 5' to a nucleic acid sequence encoding the CAR, and the WPRE is positioned 3' to the nucleic acid sequence encoding the CAR. Either the EF1alpha promoter or the WPRE may be positioned anywhere such that they effectuate transcription of the CAR. In some embodiments, the EF1alpha promoter may be positioned 5' to the nucleic acid encoding the CAR. In some embodiments, the WPRE may be positioned 3' to the nucleic acid encoding the CAR. The transgene can be positioned anywhere within the nucleic acid which to effectuate its expression (e.g., operably linked to its regulatory elements (e.g., promoter)). In instances where the transgene isn't protein coding, it may be positioned in any untranslated portion of the nucleic acid, including, for example, an intron, a 5' or 3' untranslated region, etc.

In some embodiments, the nucleic acid may encode genes and/or gene products useful in modulating the immune response. For example, forkhead box P3 (FoxP3) is a gene involved in regulating immune system responses. The protein produced by FoxP3 has been observed to be a regulator of the pathway of the development and function of T-regs. In some embodiments, the nucleic acid described herein, may further comprise a nucleic acid sequence encoding FoxP3. In some embodiments, the FoxP3 encoding nucleic acid sequence is linked to the nucleic acid sequence encoding the CAR. In some embodiments, the FoxP3 encoding nucleic acid sequence is linked to the nucleic acid sequence encoding the CAR, wherein the sequences are linked by a nucleic acid sequence encoding a 2A self-cleaving peptide. 2A self-cleaving peptides are generally 18-22 amino acids long and induce cleaving of a recombinant protein between the proline and glycine in the C-terminus of the 2A peptide. The 2A peptide sequence allows for the recombinant protein to be severed in to two smaller proteins and function independent of the other and free from any effects experienced by the larger fusion protein. Four variants of the 2A sequence are commonly used; T2A (SEQ ID NO: 8 and 35), P2A (SEQ ID NO: 9 and 36), E2A (SEQ ID NO: 10 and 34), and F2A (SEQ ID NO: 11). In some embodiments, the 2A peptide linker is selected from T2A, P2A, E2A, and F2A. In some embodiments, the 2A peptide linker is T2A. In some embodiments, the 2A peptide linker is P2A. In some embodiments, the 2A peptide linker is E2A. In some embodiments, the 2A peptide linker is F2A. In some embodiments, the 2A peptide linker is selected from SEQ ID NOs: 8-11 and 34-36. In some embodiments, the 2A linker peptide includes a GSG sequence (glycine (G)-serine (S)-glycine (G)) on the N-terminus, which may increase cleavage efficiency and is selected from SEQ ID NOs: 12-15 or GSG added to SEQ ID NO: 34-36.

In some embodiments, the nucleic acid encoding FoxP3 may be linked to the nucleic acid encoding the CAR. However, in some instances, it may be beneficial to have FoxP3 protein and CAR accessible in vivo as separate proteins. This may be accomplished by encoding the genes as separable expression constructs with the necessary additional transcriptional factors (e.g. promoters and others as described herein). In some embodiments, the nucleic acids encoding FoxP3 and the CAR are separated and separately transcribed as separate expression constructs. Separable proteins may also result from post-transcriptional modification or cleavage, for example, by the inclusion of a 2A self-cleaving peptide. In some embodiments, the nucleic acids encoding FoxP3 and the CAR may be linked by a nucleic acid sequence encoding a 2A self-cleaving peptide.

Vectors

In some aspects, the disclosure relates to nucleic acids comprising a vector. The term "vector" refers to a nucleic acid construct useful for transfer of genetic material onto a cell. A vector may comprise a nucleic acid construct in single-stranded or double-stranded form, and may comprise additional molecules, for example, DNA-associated proteins or viral capsid or envelope proteins. Vectors for eukaryotic and prokaryotic cells are well known to those in the art and include, for example, linear and circular DNA or RNA (e.g., plasmids), viral vectors (e.g., retroviral and parvoviral vectors, such as lentivirus-derived, Moloney murine leukemia virus-derived, adenovirus-derived, and AAV-derived vectors).

In some embodiments, the vector comprises a viral capsid. In some embodiments, the viral capsid is an adeno-associated viral (AAV) capsid protein. In some embodiments, the AAV is of serotype AAV8. In some embodiments, viral capsid protein is encoded by an nucleic acid sequence having at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 37. In some embodiments, the viral capsid protein is encoded by a nucleic acid sequence comprising a sequence of SEQ ID NO: 37. In some embodiments, the AAV is of serotype AAV8. In some embodiments, viral capsid protein is encoded by an nucleic acid sequence having at least 70% identity (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) to the sequence of SEQ ID NO: 38. In some embodiments, the viral capsid protein is encoded by a nucleic acid sequence comprising a sequence of SEQ ID NO: 38.

In some embodiments, the vector is a plasmid. In some embodiments, the vector carrying any nucleic acids disclosed herein may be a plasmid. Plasmids are well known in the art, but are generally known to be small DNA molecules which are independent and separate from the chromosomal DNA, and are also self-replicating. Plasmids are most commonly found to be small circular double stranded DNA molecules, which typically do not carry any essential nucleic acid sequences (e.g., genes), but rather carry auxiliary or acquired genes such as nucleic acids encoding antibiotic resistance genes as well as transgenes incorporated artificially. Plasmids (both natural and artificial) are very useful and common delivery mechanisms (e.g., vectors) in molecular cloning for their ability to introduce foreign nucleic acids into a host cell. At their most basic, a plasmid vector will comprise an origin of replication, promoter region, and insert (e.g. transgene).

In some embodiments, the vector carrying any nucleic acid as disclosed herein is a viral vector. Viruses used as vectors are well known in the art, but generally known to be selected for their various characteristics and ability to introduce foreign material (e.g., nucleic acids, genes) into a separate organism, nucleic acid, or genome. Some viruses may carry and insert plasmids into the organism and some may have the ability to integrate foreign genetic material into the organism's DNA. In some embodiments, the viral vector is selected a retroviral vector (e.g., lentiviral vector), adenoviral (Ad) vector, or an Adeno-associated viral vector (e.g., AAV vector). In some embodiments, the viral vector is an AAV vector. In some embodiments, the viral vector is an adenoviral (Ad) vector. In some embodiments, the vector is a lentiviral vector.

In some embodiments, the expression construct is flanked by viral long terminal repeats (LTRs). In some embodiments, the LTRs are retroviral LTRs. In some embodiments, the LTRs are HIV LTRs. The nucleic acids disclosed herein may comprise a 5' long terminal repeat (LTR) and a 3' LTR. The 5' LTR and/or 3' LTR may be the native 5' LTR and native 3' LTR of a viral genome. Alternatively, either one may be modified, (e.g., including deletions, insertions, and/or mutations) relative to the native sequences. In some examples, the 3' LTR may further comprise a polyadenylation (e.g., AAUAAA) (polyA) enhancer signal sequence, which is located upstream of the cleavage/polyA site and function to increase the polyA site efficiency and thus polyadenylation efficiency. Exemplary polyadenylation enhancer signal sequences include upstream sequence element (USE) from a suitable viral gene, for example, simian virus 40 (SV40) late gene or human immunodeficiency virus (HIV). Inclusion of such a polyA enhancer signal sequence may facilitate transcription termination and reduce read-through of vector transcript and improving packaging efficiency, which would lead to increased viral titer. In some embodiments, the LTRs may be native to the viral vector used. In some embodiments, the LTRs may be HIV LTRs.

In some embodiments, the vector is an adeno-associated viral (AAV) based vector. Adeno-associated virus (AAV) is a small (20 nm) replication-defective, nonenveloped DNA virus, that depends on the presence of a second virus, for example, adenovirus or herpesvirus, for productive infection. AAV is not known to cause disease and induces a very mild immune response. AAV can infect both dividing and non-dividing cells and stably incorporates its genome into that of the host cell. Various serotypes of AAV are known in the art. AAV serotype affects tissue tropism of the respective viral particles and allows to target specific cell types or tissues, making AAV vectors attractive for in vivo gene delivery applications in which only a specific cell type or tissue is targeted and/or gene transfer into non-targeted cells or tissues is not desirable. Wild type AAV particles harbor a single-stranded DNA genome comprising two genes: The AAV rep gene encodes proteins controlling viral replication, structural gene expression, and integration into the host genome. The AAV cap gene encodes capsid structural proteins. The 5' and 3' termini each comprise an inverted terminal repeat region (ITR), which is involved in multiplication of the AAV genome. In some embodiments, an AAV ITR sequence comprises 145 nucleotides. In general, an AAV ITR sequence is a self-complementary nucleic acid structure that is able to form a hairpin, which plays a role in AAV self-priming for synthesis of the second DNA AAV strand during the viral life cycle. In some embodiments, the disclosure relates to an AAV vector comprising the nucleic acids as disclosed herein flanked by AAV ITRs. In some embodiments, the capsid protein is an AAV1, AAV2, AAV3, AAV3b, AAV4, AAV5, AAV6, AAV7, AAV8, AAVrh.8, AAV9, AAV10, AAVrh.10, AAVrh.39, AAVrh.43, AAV.PHPB, AAV.PHPB.e, AAVrh32.33, or a variant thereof, capsid protein.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned. The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. The vectors can be suitable for replication and integration into eukaryotes. Typical cloning vectors contain transcription and translation terminators, initiation sequences, and promoters useful for regulation of the expression of the desired nucleic acid sequence. The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector. The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like, and fluorescent genes such as GFP, YFP, RFP and the like. In some embodiments, reporter genes or selectable marker genes are excluded from a CAR polypeptide used in a therapy as described herein. Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property (e.g., enzymatic activity, antibiotic resistance, fluorescence). Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter driven transcription. Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. In some embodiments, the host cell is a T cell.

Physical methods for introducing a polynucleotide into a host cell include calcium phosphate precipitation, lipofection, particle bombardment, microinjection, electroporation, electroporation in addition to a plasmid, and the like. Other suitable methods include the use of transposons (natural and synthetic, for example Sleeping Beauty transposon method), ssDNA, and circular ssDNA. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection. Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362. Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid.

In some embodiments, the disclosure teaches a vector carrying a nucleic acid as described herein, where the vector comprises a nucleic acid sequence of SEQ ID NO: 1. In some embodiments, the disclosure teaches a vector carrying a nucleic acid encoding a CAR as described herein. In some embodiments, the CAR has an antigen binding domain comprising a nucleic acid, wherein the nucleic acid has at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.) identity to the sequence of SEQ ID NO: 22 or 32-33. In some embodiments, the CAR has an antigen binding domain comprising a nucleic acid, wherein the nucleic acid has a sequence of SEQ ID NO: 22 or 32-33. In some embodiments, the CAR has transmembrane domain comprising a nucleic acid, wherein the nucleic acid has at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.) identity to the sequence of SEQ ID NO: 25. In some embodiments, the CAR has an transmembrane domain comprising a nucleic acid, wherein the nucleic acid has a sequence of SEQ ID NO: 25. In some embodiments, the CAR has cytoplasmic signaling domain comprising a nucleic acid, wherein the nucleic acid has at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.) identity to the sequence of SEQ ID NO: 26-29. In some embodiments, the CAR has an cytoplasmic signaling domain comprising a nucleic acid, wherein the nucleic acid has a sequence of SEQ ID NO: 26-29.

In some embodiments, the disclosure teaches a vector carrying a nucleic acid as described herein, where the vector comprises a nucleic acid sequence with at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.) identity to of any of the sequences SEQ ID NOs: 1-4. In some embodiments, the disclosure teaches a vector carrying a nucleic acid as described herein, where the vector comprises a nucleic acid sequence of any of the sequences SEQ ID NOs: 1-4. In some embodiments, the disclosure teaches a vector carrying a nucleic acid as described herein, where the vector comprises a nucleic acid with at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.) identity to the sequence of SEQ ID NO: 1. In some embodiments, the disclosure teaches a vector carrying a nucleic acid as described herein, where the vector comprises a nucleic acid with at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.) identity to the sequence of SEQ ID NO: 2. In some embodiments, the disclosure teaches a vector carrying a nucleic acid as described herein, where the vector comprises a nucleic acid sequence of SEQ ID NO: 2. In some embodiments, the disclosure teaches a vector carrying a nucleic acid as described herein, where the vector comprises a nucleic acid with at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.) identity to the sequence of SEQ ID NO: 3. In some embodiments, the disclosure teaches a vector carrying a nucleic acid as described herein, where the vector comprises a nucleic acid sequence of SEQ ID NO: 3. In some embodiments, the disclosure teaches a vector carrying a nucleic acid as described herein, where the vector comprises a nucleic acid with at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.) identity to the sequence of SEQ ID NO: 4. In some embodiments, the disclosure teaches a vector carrying a nucleic acid as described herein, where the vector comprises a nucleic acid sequence of SEQ ID NO: 4.

Cells

In an aspect, the disclosure relates to a host cell comprising the nucleic acids and/or vectors as disclosed herein. The term "host cell" generally refers to any cell from a living organism which holds, carries, or is infected with material of another organism (e.g., human cell transduced with a virus carrying a transgene). Suitable host cells may be readily selected by one of skill in the art in view of the indication for which the application is directed. For example, one suitable host cell is a mammalian immune cell. The cells may be autologous (i.e. obtained from the same subject into which they will be returned) or allogenic (i.e. derived from a subject other than the subject they are to be given, but of the same species). In some embodiments, host cell may be mammalian (e.g., a human, mouse, rat, cat, dog, sheep, rabbit, horse, cow, goat, pig, guinea pig, hamster, chicken, turkey, or a non-human primate (e.g., Marmoset, Macaque)). In some embodiments, the mammalian cell is a human cell. Host cells or tissues can be isolated from a subject by any suitable method. For example, cells or tissues may be isolated by surgery, biopsy (e.g., biopsy of skin tissue, lung tissue, liver tissue, adipose tissue), or collection of biological fluids such as blood. In some embodiments, cells are isolated from bone marrow. In some embodiments, cells are isolated from adipose tissue. In some embodiments, cells are isolated from a lipoaspirate. Appropriate methods for isolating cells from adipose tissue for ex vivo transfection are known in the art. See, e.g., Kuroda, M., et al., (2011), Journal of Diabetes Investigation, 2: 333-340; Kouki Morizono, et al. Human Gene Therapy. January 2003, 14(1): 59-66; and Patricia A. Zuk, Viral Transduction of Adipose-Derived Stem Cells, Methods in Molecular Biology, 1, Volume 702, Adipose-Derived Stem Cells, Part 4, Pages 345-357.

In some embodiments, the host cell is an immune cell. Immune cells (e.g., leukocytes) are well known in the art and generally known to constitute cells which comprise the immune system and mediate the immune response of a living organism. Examples of immune cells are lymphocytes (e.g., T-cells, T-regulatory cells (T-regs), and NK-cells), phagocytes (e.g., monocytes and macrophages), granulocytes (e.g., neutrophils, basophils and eosinophils), and dendritic cells. In some embodiments, the disclosure relates to a plurality of the host cells disclosed herein. The plurality of cells may be greater than 2 (e.g., 10; 100; 1,000; 10,000; $10^6$; $10^9$; $10^{12}$, or more) host cells. The plurality of cells should be substantially pure, meaning the plurality of cells are substantially free of other cells (e.g., lineages, cells containing other foreign nucleic acids, or otherwise contaminated), proteins, and/or agents.

In some embodiments, the immune cells are T-cells. In some embodiments, the immune cells are T-regs. T-cells and T-regs are well known in the art, but are known as a subtypes of white blood cells (e.g., leukocytes) and play a central role in cell-mediated immunity. T-cells are a form of lymphocytes which develop in the thymus, contain T-cell receptor (TCR), and either modulate an immune response upon recognition of a ligand or directly kill a ligand presenting cell. T-regs (formerly known as suppressors cells) are a subset of T-cells (which are a subset of leukocytes), which generally modulate the immune reaction of a subject by suppressing and downregulating the induction and proliferation of T-cells. In doing so, they inhibit cytotoxic effects of T-cells due to T-reg recognition of an antigen.

Compositions

In some aspects, the disclosure relates to a composition comprising the nucleic acids, vectors, host cells, or combination thereof, as disclosed herein. In some embodiments, the host cells or nucleic acids disclosed herein may be in a composition, including the pharmaceutical forms suitable for injectable use include sterile aqueous solutions or dispersions and sterile powders for the extemporaneous preparation of sterile injectable solutions or dispersions.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the nucleic acid or active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In some embodiments, the composition comprises a plurality of the nucleic acids, vectors, host cells, or a combination thereof, as disclosed herein. The nucleic acids or host cells of the instant disclosure may be delivered to a subject in compositions according to any appropriate methods known in the art. The compositions of the invention may comprise a nucleic acid or host cell alone, or in combination with one or more other nucleic acids or host cells (e.g., a second nucleic acid or host cell encoding having one or more different nucleic acid (e.g., CAR). In some embodiments, the composition may contain a carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. Suitable carriers may be readily selected by one of skill in the art in view of the indication for which the nucleic acid or host cell is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. Still others will be apparent to the skilled artisan. Optionally, the compositions of the invention may contain, in addition to the nucleic acid or host cell and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like. In some embodiments, the compositions of the disclosure are delivered by a delivery vehicle, including but not limited to, liposomes, nanocapsules, microparticles, microspheres, lipid particles, vesicles, and the like.

Such formulations may be preferred for the introduction of pharmaceutically acceptable formulations of the nucleic acids, vectors, or host cells disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat Nos. 5,567,434; 5,552,157; 5,565,213; 5,738,868 and 5,795,587).

In some embodiments, the excipient is a cryoprotectant. A cryoprotectant is a substance used to protect tissues or samples (e.g., nucleic acids, vectors, host cells) from damage caused or related to cold temperatures (e.g., freezing, temperatures below ambient). For example damage can occur by a variety of mechanisms, but often is the result of either mechanical damage to the cell by the distortion caused by ice crystal formation, or chemical damage due to changes in the solutes surrounding the cells (e.g., dehydration due to increased salt concentration due extracellular fluids freezing). Cryoprotectants work by lowering the melting point of water, thereby increasing the ranges of temperatures cells remain viable and avoid the issues surrounding cold temperatures. Suitable cryoprotectants may be readily selected by one of skill in the art in view of the indication for which the nucleic acid or host cell is directed. For example, one suitable cryoprotectant includes glycerol, which may be formulated with a variety of buffering solutions (e.g., phosphate buffered saline). Other exemplary cryoprotectants include: sucrose, trehalose, dextrose, polyvinylpyrrolidone (PVP), methylcellulose, dimethyl sulfoxide (DMSO), ethylene glycol, polyethylene glycol (PEG), and propylene glycol.

Methods of Manufacture

In some aspects, the disclosure relates to methods of making the CAR T-cells and CAR T-reg cells as disclosed herein.

In some embodiments T-cells are transfected with the CARs as disclosed herein and following transfection are co-cultured with Hela cells. In some embodiments T-cells are transfected with the CARs as disclosed herein and following transfection are co-cultured with peripheral blood mononuclear cells (PBMCs). In some embodiments T-cells are transfected with the CARs as disclosed herein and following transfection are co-cultured with Hela cells and PBMCs. In some embodiments T-cells are transfected with the CARs as disclosed herein and following transfection are co-cultured with IL-7, IL21, IL15 cytokines, and anti-CD3 antibodies. In some embodiments T-cells are transfected with the CARs as disclosed herein and following transfection are co-cultured with Hela cells and IL-7, IL21, IL15 cytokines, and anti-CD3 antibodies. In some embodiments T-cells are transfected with the CARs as disclosed herein and following transfection are co-cultured with peripheral blood mononuclear cells (PBMCs) and IL-7, IL21, IL15 cytokines, and anti-CD3 antibodies. In some embodiments T-cells are transfected with the CARs as disclosed herein and following transfection are co-cultured with Hela cells, peripheral blood mononuclear cells (PBMCs), and IL-7, IL21, IL15 cytokines and anti-CD3 antibodies.

In some embodiments, the T-cells are transfected at least 12 hours prior to co-culturing. In some embodiments, the T-cells are transfected at least 18 hours prior to co-culturing. In some embodiments, the T-cells are transfected at least 24 hours prior to co-culturing. In some embodiments, the T-cells are co-cultured with at least $1 \times 10^5$ Hela cells. In some embodiments, the T-cells are co-cultured with at least $1 \times 10^6$ Hela cells. In some embodiments, the T-cells are co-cultured with at least $1 \times 10^7$ Hela cells. In some embodiments, the T-cells are co-cultured with at least $1 \times 10^8$ Hela cells. In some embodiments, the Hela cells are irradiated prior to co-culturing. In some embodiments, the Hela cells are irradiated with about 100 gray (gy) of radiation prior to co-culturing. In some embodiments, the Hela cells are irradiated with about 125 gy of radiation prior to co-culturing. In some embodiments, the Hela cells are irradiated with about 135 gy of radiation prior to co-culturing. In some embodiments, the Hela cells express an AAV capsid protein. In some embodiments, the Hela cells express an AAV1 capsid protein. In some embodiments, the Hela cells express an AAV2 capsid protein. In some embodiments, the Hela cells express an AAV3b capsid protein. In some embodiments, the Hela cells express an AAV6 capsid protein. In some embodiments, the Hela cells express an AAV7 capsid protein. In some embodiments, the Hela cells express an AAV8 capsid protein. In some embodiments, the Hela cells express an AAV9 capsid protein. In some embodiments, the Hela cells express an AAV10 capsid protein. In some embodiments, the Hela cells express an AAV-rh32.331 capsid protein.

In some embodiments, the T-cells are co-cultured with at least $5 \times 10^5$ peripheral blood mononuclear cell (PBMCs). In some embodiments, the T-cells are co-cultured with at least $5 \times 10^6$ PBMCs. In some embodiments, the T-cells are co-cultured with at least $5 \times 10^7$ PBMCs. In some embodiments, the T-cells are co-cultured with at least $5 \times 10^8$ PBMCs. In some embodiments, the PBMCs are irradiated prior to co-culturing. In some embodiments, the PBMCs are irradiated with about 20 gy of radiation prior to co-culturing. In some embodiments, the PBMCs are irradiated with about 30 gy of radiation prior to co-culturing. In some embodiments, the PBMCs are irradiated with about 35 gy of radiation prior to co-culturing.

In some embodiments, the IL-7 cytokines are co-cultured at a concentration of about 2 nanograms (ng) per milliliter (ml) (ng/ml). In some embodiments, the IL-7 cytokines are co-cultured at a concentration of about 3 ng/ml. In some embodiments, the IL-7 cytokines are co-cultured at a concentration of about 4 ng/ml. In some embodiments, the IL-7 cytokines are co-cultured at a concentration of about 5 ng/ml. In some embodiments, the IL-7 cytokines are co-cultured at a concentration of about 6 ng/ml. In some embodiments, the IL-7 cytokines are co-cultured at a concentration of about 7 ng/ml.

In some embodiments, the IL21 cytokines are co-cultured at a concentration of about 15 ng/ml. In some embodiments, the IL21 cytokines are co-cultured at a concentration of about 20 ng/ml. In some embodiments, the IL21 cytokines are co-cultured at a concentration of about 23 ng/ml. In some embodiments, the IL21 cytokines are co-cultured at a concentration of about 25 ng/ml. In some embodiments, the IL21 cytokines are co-cultured at a concentration of about 27 ng/ml. In some embodiments, the IL21 cytokines are co-cultured at a concentration of about 30 ng/ml.

In some embodiments, the IL15 cytokines are co-cultured at a concentration of about 0.2 ng/ml. In some embodiments, the IL15 cytokines are co-cultured at a concentration of about 0.3 ng/ml. In some embodiments, the IL15 cytokines are co-cultured at a concentration of about 0.4 ng/ml. In some embodiments, the IL15 cytokines are co-cultured at a concentration of about 0.5 ng/ml. In some embodiments, the IL15 cytokines are co-cultured at a concentration of about 0.6 ng/ml. In some embodiments, the IL15 cytokines are co-cultured at a concentration of about 0.7 ng/ml.

In some embodiments, the anti-CD3 antibodies are co-cultured at a concentration of about 20 ng/ml. In some embodiments, the anti-CD3 antibodies are co-cultured at a concentration of about 25 ng/ml. In some embodiments, the anti-CD3 antibodies are co-cultured at a concentration of about 27 ng/ml. In some embodiments, the anti-CD3 antibodies are co-cultured at a concentration of about 30 ng/ml. In some embodiments, the anti-CD3 antibodies are co-cultured at a concentration of about 33 ng/ml. In some embodiments, the anti-CD3 antibodies are co-cultured at a concentration of about 35 ng/ml.

In some embodiments, the media is changed at least every 2 days. In some embodiments, a portion of the media is changed. In some embodiments, about two-thirds of the media is changed about every 2 days. In some embodiments, the new media contains new cytokines and/or antibodies.

In some embodiments T-reg cells are transfected with the CARs as disclosed herein and following transfection are co-cultured with Hela cells. In some embodiments T-reg cells are transfected with the CARs as disclosed herein and following transfection are co-cultured with peripheral blood mononuclear cells (PBMCs). In some embodiments T-reg cells are transfected with the CARs as disclosed herein and following transfection are co-cultured with Hela cells and PBMCs. In some embodiments T-reg cells are transfected with the CARs as disclosed herein and following transfection are co-cultured with IL-7, IL21, IL15 cytokines, TGF-beta, and anti-CD3 antibodies. In some embodiments T-reg cells are transfected with the CARs as disclosed herein and following transfection are co-cultured with Hela cells and IL-7, IL21, IL15 cytokines, TGF-beta, and anti-CD3 antibodies. In some embodiments T-reg cells are transfected with the CARs as disclosed herein and following transfection are co-cultured with peripheral blood mononuclear cells (PBMCs) and IL-7, IL21, IL15 cytokines, TGF-beta, and anti-CD3 antibodies. In some embodiments T-reg cells are transfected with the CARs as disclosed herein and following transfection are co-cultured with Hela cells, peripheral blood mononuclear cells (PBMCs), and IL-7, IL21, IL15 cytokines, TGF-beta, and anti-CD3 antibodies.

In some embodiments, the T-reg cells are transfected at least 12 hours prior to co-culturing. In some embodiments, the T-reg cells are transfected at least 18 hours prior to co-culturing. In some embodiments, the T-reg cells are transfected at least 24 hours prior to co-culturing. In some embodiments, the T-reg cells are co-cultured with at least $1 \times 10^5$ Hela cells. In some embodiments, the T-reg cells are co-cultured with at least $1 \times 10^6$ Hela cells. In some embodiments, the T-reg cells are co-cultured with at least $1 \times 10^7$ Hela cells. In some embodiments, the T-reg cells are co-cultured with at least $1 \times 10^8$ Hela cells. In some embodiments, the Hela cells are irradiated prior to co-culturing. In some embodiments, the Hela cells are irradiated with about 100 gray (gy) of radiation prior to co-culturing. In some embodiments, the Hela cells are irradiated with about 125 gy of radiation prior to co-culturing. In some embodiments, the Hela cells are irradiated with about 135 gy of radiation prior to co-culturing. In some embodiments, the Hela cells express an AAV capsid protein. In some embodiments, the Hela cells express an AAV1 capsid protein. In some embodiments, the Hela cells express an AAV2 capsid protein. In some embodiments, the Hela cells express an AAV3b capsid protein. In some embodiments, the Hela cells express an AAV6 capsid protein. In some embodiments, the Hela cells express an AAV7 capsid protein. In some embodiments, the Hela cells express an AAV8 capsid protein. In some embodiments, the Hela cells express an AAV9 capsid protein. In some embodiments, the Hela cells express an AAV10 capsid protein. In some embodiments, the Hela cells express an AAV-rh32.331 capsid protein.

In some embodiments, the T-reg cells are co-cultured with at least $5\times10^5$ PBMCs. In some embodiments, the T-reg cells are co-cultured with at least $5\times10^6$ PBMCs. In some embodiments, the T-reg cells are co-cultured with at least $5\times10^7$ PBMCs. In some embodiments, the T-reg cells are co-cultured with at least $5\times10^8$ PBMCs. In some embodiments, the PBMCs are irradiated prior to co-culturing. In some embodiments, the PBMCs are irradiated with about 20 gy of radiation prior to co-culturing. In some embodiments, the PBMCs are irradiated with about 30 gy of radiation prior to co-culturing. In some embodiments, the PBMCs are irradiated with about 35 gy of radiation prior to co-culturing.

In some embodiments, the IL-7 cytokines are co-cultured at a concentration of about 2 nanograms (ng) per milliliter (ml) (ng/ml). In some embodiments, the IL-7 cytokines are co-cultured at a concentration of about 3 ng/ml. In some embodiments, the IL-7 cytokines are co-cultured at a concentration of about 4 ng/ml. In some embodiments, the IL-7 cytokines are co-cultured at a concentration of about 5 ng/ml. In some embodiments, the IL-7 cytokines are co-cultured at a concentration of about 6 ng/ml. In some embodiments, the IL-7 cytokines are co-cultured at a concentration of about 7 ng/ml.

In some embodiments, the IL21 cytokines are co-cultured at a concentration of about 15 ng/ml. In some embodiments, the IL21 cytokines are co-cultured at a concentration of about 20 ng/ml. In some embodiments, the IL21 cytokines are co-cultured at a concentration of about 23 ng/ml. In some embodiments, the IL21 cytokines are co-cultured at a concentration of about 25 ng/ml. In some embodiments, the IL21 cytokines are co-cultured at a concentration of about 27 ng/ml. In some embodiments, the IL21 cytokines are co-cultured at a concentration of about 30 ng/ml.

In some embodiments, the IL15 cytokines are co-cultured at a concentration of about 0.2 ng/ml. In some embodiments, the IL15 cytokines are co-cultured at a concentration of about 0.3 ng/ml. In some embodiments, the IL15 cytokines are co-cultured at a concentration of about 0.4 ng/ml. In some embodiments, the IL15 cytokines are co-cultured at a concentration of about 0.5 ng/ml. In some embodiments, the IL15 cytokines are co-cultured at a concentration of about 0.6 ng/ml. In some embodiments, the IL15 cytokines are co-cultured at a concentration of about 0.7 ng/ml.

In some embodiments, the TGF-beta is co-cultured at a concentration of about 2 ng/ml. In some embodiments, the TGF-beta is co-cultured at a concentration of about 3 ng/ml. In some embodiments, the TGF-beta is co-cultured at a concentration of about 4 ng/ml. In some embodiments, the TGF-beta is co-cultured at a concentration of about 5 ng/ml. In some embodiments, the TGF-beta is co-cultured at a concentration of about 6 ng/ml. In some embodiments, the TGF-beta is co-cultured at a concentration of about 7 ng/ml.

In some embodiments, the anti-CD3 antibodies are co-cultured at a concentration of about 20 ng/ml. In some embodiments, the anti-CD3 antibodies are co-cultured at a concentration of about 25 ng/ml. In some embodiments, the anti-CD3 antibodies are co-cultured at a concentration of about 27 ng/ml. In some embodiments, the anti-CD3 antibodies are co-cultured at a concentration of about 30 ng/ml. In some embodiments, the anti-CD3 antibodies are co-cultured at a concentration of about 33 ng/ml. In some embodiments, the anti-CD3 antibodies are co-cultured at a concentration of about 35 ng/ml.

In some embodiments, the media is changed at least every 2 days. In some embodiments, a portion of the media is changed. In some embodiments, about two-thirds of the media is changed about every 2 days. In some embodiments, the new media contains new cytokines and/or antibodies.
Administration In some embodiments, the nucleic acids carried by a vector or host cells, which may be suspended in a physiologically compatible carrier (e.g., in a composition), may be administered to a subject (e.g., a human, mouse, rat, cat, dog, sheep, rabbit, horse, cow, goat, pig, guinea pig, hamster, chicken, turkey, or a non-human primate (e.g., Marmoset, Macaque)).

Administration of the nucleic acids, vectors, and/or host cells as described herein may be used to modulate the immune reaction (i.e., response) to target antigens (e.g., AAV capsid proteins). For example, by designing a CAR in a T-cell to recognize target antigens (e.g., AAV capsid proteins) the T-cell can be used to kill the APCs presenting the antigen, thereby inhibiting the immune response related to the target antigen. In some embodiments, a CAR targeting an antigen is expressed in a CD8+ T-cell for use in suppressing the immune response related to the target antigen. Conversely, transcriptional regulators (e.g., FOXP3) can be used to create regulatory T cells (i.e., T-regs) for the opposite effect. In some embodiments, the a T-regulatory cell expresses a CAR designed to recognize a target antigen (e.g., AAV capsid). By introducing the CAR into a T-reg cell and expressing the transcriptional regulator FOXP3, the T-reg cell is designed and functions inhibit the killing of an APC presenting the target antigen, thereby suppressing any suppression of the immune system with respect to the target antigen (e.g., AAV capsid), in other words, promote or increase the immune response with respect to the target antigen (e.g., AAV capsid). In some embodiments, a CAR targeting an antigen is expressed in a CD4+ T-cell for use in promoting or increasing the immune response related to the target antigen. In some embodiments, a CAR targeting an antigen is expressed in a T-cell expressing FOXP3 for use in promoting or increasing the immune response related to the target antigen. In some embodiments, the CAR T-reg cells of the disclosure are used to modulate the immune response. In some embodiments, the modulation is of response to AAV capsids. In some embodiments, the modulation is performed in combination with steroid treatment. In some embodiments, the modulation is done in lieu of steroid treatment(s). In some embodiments, the modulation is performed to modulate previous administration of an AAV capsid. In some embodiments, the modulation is performed in a subject with a pre-existing immunity to an AAV or antigen. In some embodiments, the subject has circulating neutralizing antibodies against an AAV capsid protein. In some embodiments, the subject has previously been administered an AAV. In some embodiments, the subject has previously been administered a recombinant AAV (rAAV). In some embodiments, the subject has circulating neutralizing antibodies against an AAV capsid protein and has previously been administered an AAV and/or recombinant AAV (rAAV).

In some embodiments, the administration of the nucleic acids, vectors, and/or host cells as described herein may be used to modulate the expression or immune reaction to transgenes, for example in CRIM-negative subjects (see, Am J Med Genet C Semin Med Genet. 2012 Feb. 15; 160C(1): 40-9. doi: 10.1002/ajmg.c.31319. Epub 2012 Jan. 17). In some embodiments, the transgenes are introduced by an rAAV. In some embodiments, the CAR T-cells are administered to reduce immunogenicity due to expression of the transgene. In some embodiments, the transgene is A1AT. In some embodiments, the nucleic acids, vectors, and/or host cells as described herein may be used to allow for the redosing of a subject with an AAV based therapy. For example, in some embodiments, the CAR T-cells are administered to increase the efficacy of a subsequent exposures or administrations of AAV based therapies. In some embodiments, the CAR T-reg cells are administered to decrease the efficacy of a subsequent exposures or administrations of AAV based therapies.

In some embodiments, the nucleic acids, vectors, and/or host cells as described herein may be used to modulate the immune reaction to gene editing tools. For example, in some embodiments, the CAR T-cells of the disclosure may be administered to decrease the immune response to gene editing tools (e.g., Cas proteins), introduced into a subject by an rAAV. In some embodiments, the CAR T-reg cells of the disclosure may be administered to increase the immune response to gene editing tools (e.g., Cas proteins), introduced into a subject by an rAAV. In some embodiments, the gene editing tool may be an AAV6+ CRISPR-Cas9 system, which may, in some embodiments, employ TRAC locus or genomic safe harbor based techniques.

In some embodiments, the nucleic acids, vectors, and/or host cells as described herein may be used in combination of a gene editing tool (e.g., CRISPR-Cas) to increase the expression of the CAR T-cells and CAR T-reg cells of the disclosure. In some embodiments, the increased expression allows for multiple re-administrations to a subject of AAV based therapies.

In some embodiments, administration of the nucleic acids, vectors, and/or host cells as described herein may be used to model immune reaction (i.e., response) to target antigens (e.g., AAV capsid proteins). As disclosed above, the CAR T-cells and CAR T-reg cells can be used to modulate the immune response, and thus can be designed to model a response to a given antigen in vitro.

In some embodiments, the CAR T-cells and CAR T-reg cells of the disclosure are used as adjuvant therapies or with an adjuvant therapy. The term "adjuvant," as may be used herein, refers to any therapy or treatment (e.g., composition, drug, or method based) which is used as an adjunct to the primary or initial therapy or treatment. Adjuvants may be administered concurrently (e.g., at the same time, simultaneously) with the primary or initial treatment or shortly after the administration of the primary or initial treatment. In some, but not all, cases an adjuvant modulates (e.g., increases, decreases) the effect of the primary or initial treatment. In some, but not all, cases an adjuvant is used to modulate (e.g., increase, decrease) a side effect of the primary or initial treatment. In some, but not all, cases an adjuvant is used to prepare (e.g., condition) a subject in anticipation of the primary or initial treatment or aid in the primary or initial treatment's effects or sustain or aid in the recovery of the subject after the primary or initial treatment. In some embodiments, the CAR T-cells and CAR T-reg cells of the disclosure are administered to modulate the immune response to a given treatment. In some embodiments, the CAR T-cells and CAR T-reg cells of the disclosure are administered in connection with treatment of SMA. In some embodiments, the CAR T-cells and CAR T-reg cells of the disclosure are administered in connection with administration of Zolgensma. In some embodiments, the CAR T-cells and CAR T-reg cells of the disclosure are administered in connection with the treatment of Leber's congenital amaurosis. In some embodiments, the CAR T-cells and CAR T-reg cells of the disclosure are administered in connection with the administration of Luxturna.

In some embodiments, the CAR T-cells and CAR T-reg cells of the disclosure can be used to treat a disease or disorder. In some embodiments, the disease or disorder is an autoimmune or neuroinflammatory disease. In some embodiments, the disease or disorder is diabetes, multiple sclerosis, Amyotrophic lateral sclerosis, or Alzheimer's Disease.

Conventional and pharmaceutically acceptable routes of administration include, but are not limited to, direct delivery to the selected tissue (e.g., liver tissue, lung tissue) and administration subcutaneously, intraopancreatically, intranasally, parenterally, intravenously, intramuscularly, intrathecally, intracerebrally, orally, intraperitoneally, by inhalation or by another route. Routes of administration may be combined, if desired.

Delivery according the methods of the disclosure to a subject may be, for example, by administration into the bloodstream of the subject. Administration into the bloodstream may be by injection into a vein, an artery, or any other vascular conduit. Moreover, in certain instances, it may be desirable to deliver the nucleic acids, vectors, host cells, or a combination thereof to brain tissue, meninges, neuronal cells, glial cells, astrocytes, oligodendrocytes, cereobrospinal fluid (CSF), interstitial spaces and the like. In some embodiments, nucleic acids, vectors, host cells, or a combination thereof may be delivered directly to the spinal cord or brain (e.g., prefrontal cortex) by injection into the ventricular region, as well as to the striatum (e.g., the caudate nucleus or putamen of the striatum), and neuromuscular junction, or cerebellar lobule, with a needle, catheter or related device, using neurosurgical techniques known in the art, such as by stereotactic injection (see, e.g., Stein et al., J. Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

In certain circumstances it will be desirable to deliver the nucleic acids, vectors, host cells, or a combination thereof in suitably formulated pharmaceutical compositions disclosed herein either intrathecally, intracerebrally, intravenously, subcutaneously, intraopancreatically, intranasally, parenterally, intravenously, intramuscularly, orally, intraperitoneally, or by inhalation.

It can be appreciated by one skilled in the art that desirable administration of nucleic acids, vectors, host cells, or combination thereof can also include ex vivo administration. In some embodiments, ex vivo administration comprises (1) isolation of cells or tissue(s) of interest from a subject, (2) contacting the cells or tissue(s) with viral vectors in sufficient amounts to transfect the cells or tissue to provide sufficient levels of gene transfer and expression without undue adverse effect, and (3) transferring cells or tissue back into the subject. In some embodiments, cells or tissues may be cultured ex vivo for several days before and/or after transfection.

In an embodiment, cells or tissue(s) are transduced at a multiplicity of infection (MOI) of at least 10 infectious units (i.u.) of viral vectors per cell (for example: 10; 100; 1,000; 5,000; 10,000; 100,000 or more i.u.) or at a functionally equivalent viral copy number. In one embodiment, cells or tissue(s) are transduced at a MOI of 10 to 10,000 i.u. Routes for transfer of transfected cells or tissue(s) into a subject include, but are not limited to, subcutaneously, intraopancreatically, intranasally, parenterally, intravenously, intravascularly, intramuscularly, intrathecally, intracerebrally, intraperitoneally, or by inhalation. In some embodiments, transfected cells are administered by hepatic portal vein injection. In some embodiments, transfected cells are administered intravascularly. Methods for ex vivo administration of nucleic acids and/or vectors are well known in the art (see, e.g., Naldini, L. Nature Reviews Genetics (2011) 12, 301-315, Li, H. et al. Molecular Therapy (2010) 18, 1553-1558, and Loiler et al. Gene Therapy (2003) 10, 1551-1558).

The nucleic acids, vectors, host cells, or combination thereof of the disclosure may be administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected tissue (e.g., liver tissue, lung tissue) and administration subcutaneously, intraopancreatically, intranasally, parenterally, intravenously, intramuscularly, intrathecally, intracerebrally, orally, intraperitoneally, by inhalation or by another route. Routes of administration may be combined, if desired.

In some embodiments, the subject is a human. The human subject may be a male or female of any age (e.g., infant, child, adolescent, adult). In some embodiments, the subject has previously been administered a vector or host cell as described herein, or is contemplated to be administered a vector or host cell as described herein. In some embodiments, the subject has previously received administration of a vector or host cell as described herein, such as those disclosed herein. In some embodiments, the subject is contemplated to receive administration of a vector or host cell as described herein, such as those disclosed herein.

In an aspect, the disclosure relates to a method comprising administering to the subject a recombinant T-cell comprising a CAR, such that the immune response of the subject to the AAV capsid protein is inhibited. In some embodiments, the nucleic acids disclosed herein comprise a T-cell and CAR, which are administered to a subject such that the immune response to an AAV capsid protein is inhibited. By administering a T-cell comprising a CAR which recognizing an epitope of an AAV capsid protein, immune response may be modulated by recognizing antigen binding sites on circulating immune cells (e.g. APCs) which recognize the AAV epitope. It is believed these immune cells are reduced in number due to the cytotoxic effect of the CAR T-cells, thus lessening the immune response to any contemporaneously or subsequently administered cell comprising an AAV capsid protein epitope. The duration of the reduced immunity state with respect to the targeted epitope may be temporary or long lasting, the time to administration of any subsequent therapy will be timed to exploit the reduced immunity state, which will be readily apparent to one of ordinary skill without undue experimentation.

In an aspect the disclosure relates to a method comprising, administering to the subject a recombinant T-regulatory cell comprising a CAR, such that the immune response of the subject to the AAV capsid protein is induced. In some embodiments, the nucleic acids disclosed herein comprise a T-reg and CAR, which are administered to a subject such that the immune response to an AAV capsid protein is inhibited. By administering a T-reg comprising a CAR which recognizing an epitope of an AAV capsid protein, immune response may be modulated by recognizing antigen binding sites on circulating immune cells (e.g. APCs) which recognize the AAV epitope. It is believed these immune cells will reducing in number CAR T-cells targeting any APCs expressing the AAV epitope, thus increasing or restoring to baseline levels such APCs, thus increasing the immune response to any contemporaneously or subsequently administered cell comprising an AAV capsid protein epitope. The duration of the reduced immunity state with respect to the targeted epitope may be temporary or long lasting, the time to administration of any subsequent therapy will be timed to exploit the reduced immunity state, which will be readily apparent to one of ordinary skill without undue experimentation.

In an aspect, the disclosure relates to a method, comprising administering a therapeutic host cells to the subject. In some embodiments, the nucleic acids disclosed herein are administered to a subject therapeutically, or for the purpose of inducing a therapeutic effect. The dose of nucleic acids or host cells required to achieve a desired effect or "therapeutic effect," e.g., the units of dose in vector genomes/per kilogram of body weight (vg/kg), will vary based on several factors including, but not limited to: the route of administration, the level of gene or RNA expression required to achieve a therapeutic effect, the specific disease or disorder being treated, and the stability of the gene or RNA product. One of skill in the art can readily determine an vector dose range to treat a subject having a particular disease or disorder based on the aforementioned factors, as well as other factors that are well known in the art. An effective amount of the nucleic acids is generally in the range of from about 10 µl to about 100 ml of solution containing from about $10^9$ to $10^{16}$ genome copies per subject. Other volumes of solution may be used. The volume used will typically depend, among other things, on the size of the subject, the dose of the nucleic acids, and the route of administration. For example, for intravenous administration a volume in range of 10 µl to 100 µl, 100 µl to 1 ml, 1 ml to 10 ml, or more may be used. In some cases, a dosage between about $10^{10}$ to $10^{12}$ rAAV genome copies per subject is appropriate. In some embodiments the rAAV is administered at a dose of $10^{10}$, $10^{11}$, $10^{12}$, $10^{13}$, $10^{14}$, or $10^{15}$ genome copies per subject. In some embodiments the rAAV is administered at a dose of $10^{10}$, $10^{11}$, $10^{12}$, $10^{13}$, or $10^{14}$, genome copies per kg.

In some embodiments, the therapeutic rAAV comprises a capsid protein having the same serotype as the capsid protein targeted by the CAR. In some embodiments the rAAV has the same capsid protein as the capsid protein targeted by the nucleic acid expressing the CAR of the rAAV.

Kits

The recombinant nucleic acids, compositions, vectors, host cells etc. described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a subject, such as a syringe, topical application devices, or intravenous needle tubing and bag.

Exemplary embodiments of the invention are described in more detail by the following examples. These embodiments are exemplary of the invention, which one skilled in the art will recognize is not limited to the exemplary embodiments.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

This example describes CAR T-cell constructs that recognizes AAV capsid proteins. Two versions of CAR T-cell constructs were produced; one construct that is characterized by cytotoxic T-cell function, and another construct that is characterized by FoxP3 transcription regulator encoded as part of the CAR construct to create CAR T-regs against AAV capsid.

Figure 1B:
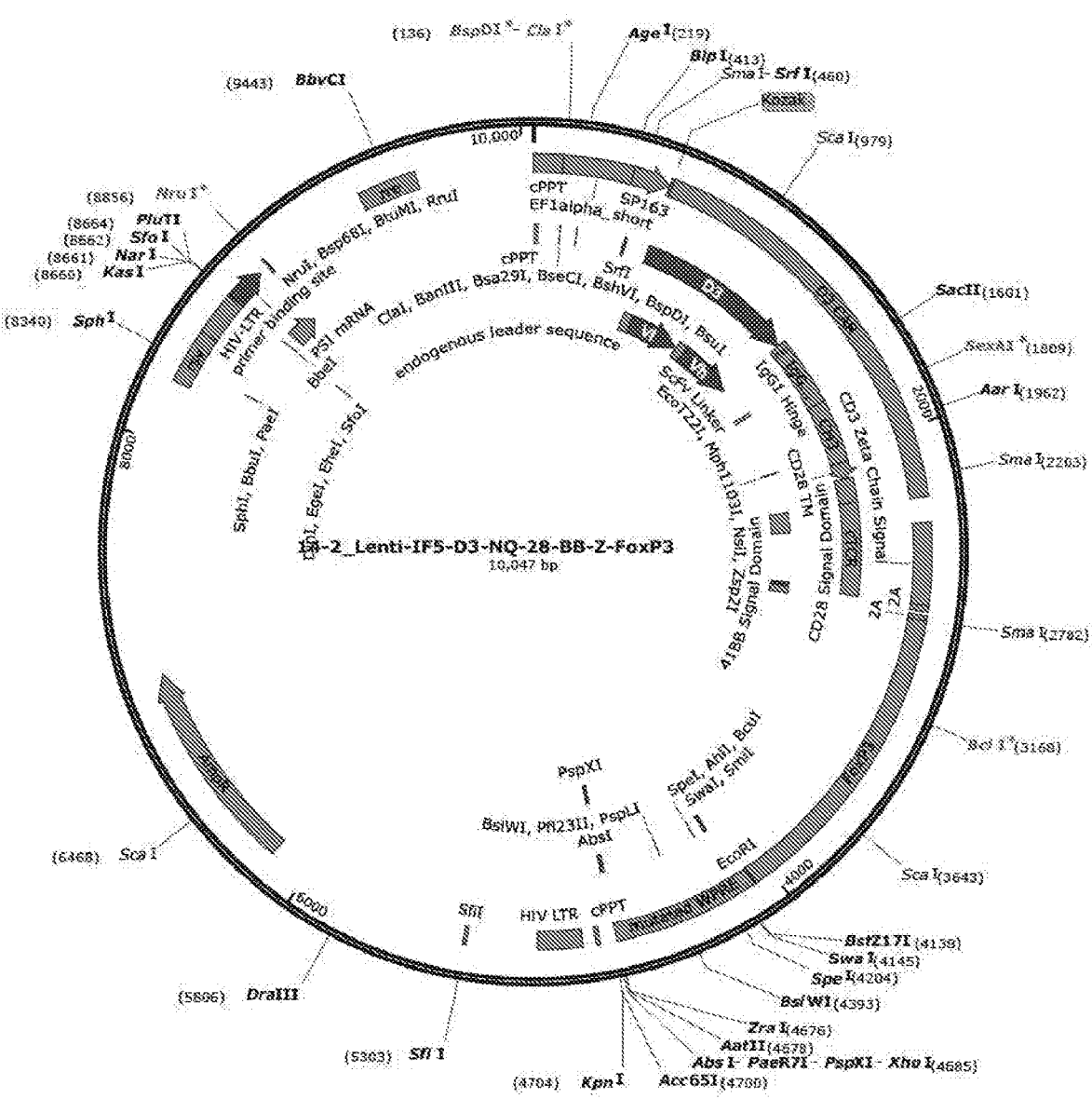
Figure 2A:
FIGS. 2A-2B are schematics depicting two embodiment of third generation CAR T and CAR T-reg cells (e.g., SEQ ID NO: 16-17).
Figure 2B:
Figure 3A:
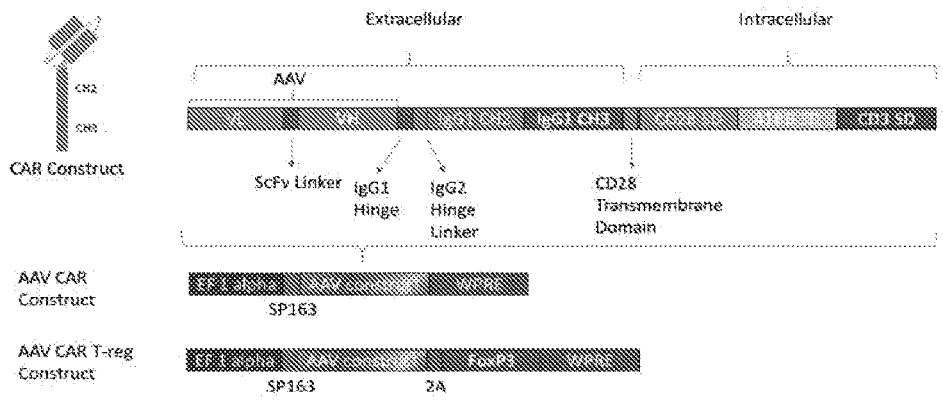
FIGS. 3A-3B show schematics depicting embodiments of CAR T-cell and CAR T-reg cell constructs (e.g., SEQ ID NO: 1-2 and 16-17).
Figure 3B:
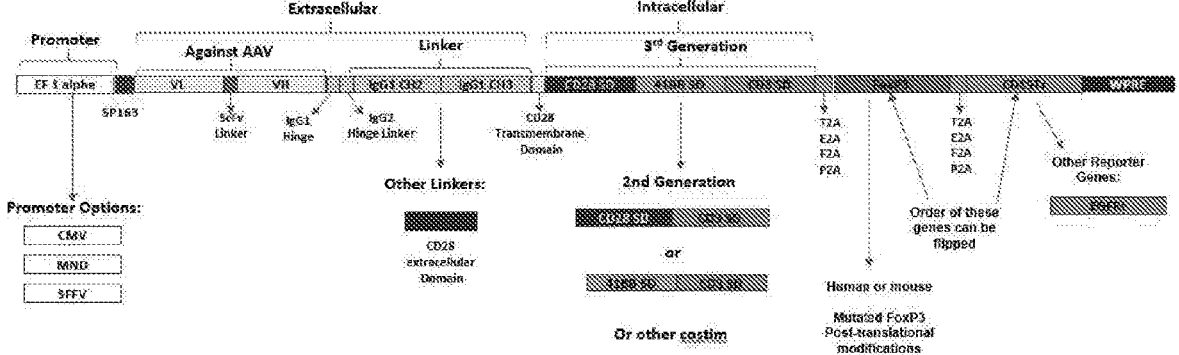

The CAR T-cell constructs comprise an anti-AAV2 capsid protein antibody (e.g., D3 antibody) and lack the iCaspase9 gene and 2A sequence, and a CD19 truncated sequence. Constructs were introduced into a lentiviral backbone and expressed from the EF1alpha promoter. In some embodiments, the constructs contain, endogenous leader sequence, D3 AAV specific antibody variable light and variable heavy domains with an scFv linker, a human IgG1 hinge and IgG2 linker, IgG1 CH2 and CH3 domains with the CD28 transmembrane domain, and internal CD28, 41BB and CD3 cytoplasmic signaling domains. The CAR T-regs construct further comprises a 2A self-cleaving sequence followed by the FoxP3 sequence. In some embodiments, the D3 endogenous leader sequence is replaced by a CD8 endogenous leader sequence. In some embodiments, a 2A self-cleaving sequence and EGFRt receptor sequence are added to the constructs. Examples of constructs described herein are shown in FIGS. 1-3.

Constructs were packaged into 3rd generation lentiviruses. Lentiviruses were transduced into human T-cells, isolated from human donor peripheral blood mononuclear cells (PBMCs), Jurkat cell lines (human T-cell line), and mouse T-cells. CAR T-regs against AAV were produced in two different ways. In some embodiments, CAR T-regs are isolated from human donors and then infected them with AAV CAR constructs. In some embodiments, CAR T-regs are produced by transducing cells with lentivirus encoding CAR that contains 2A and FoxP3, transcription regulator.

Figure 4:
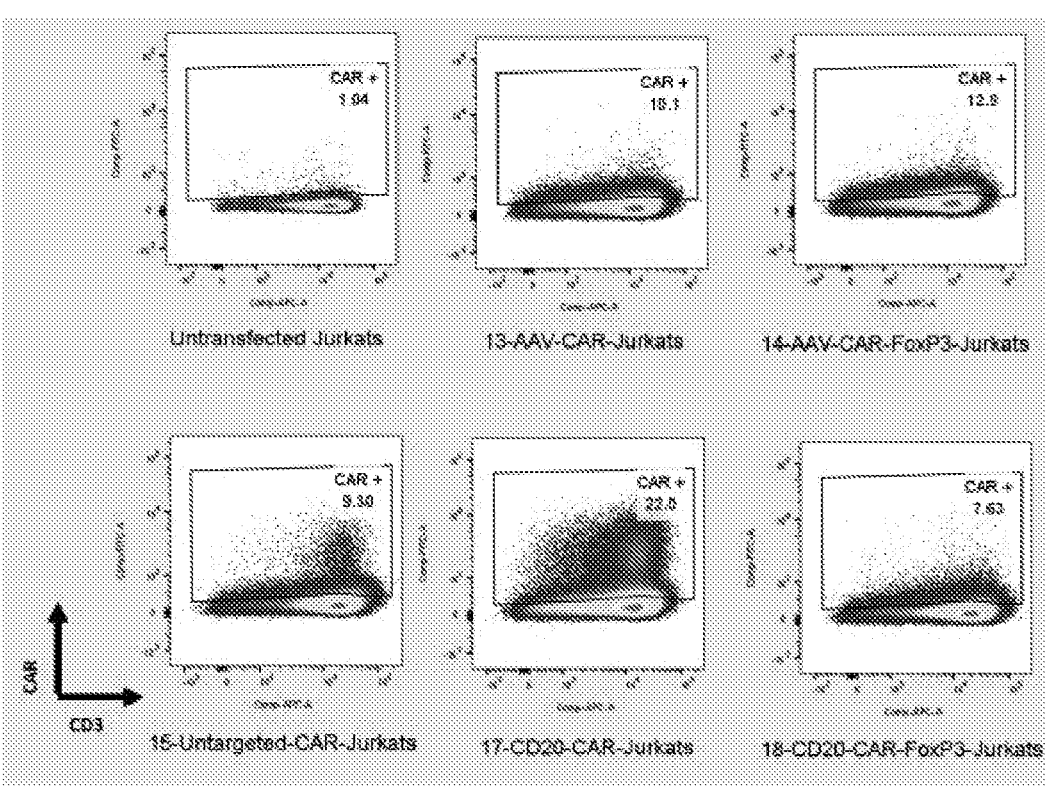
FIG. 4 shows representative Fluorescence Assisted Cell Sorting (FACS) data of CARs expression on the surface of cells using an antibody to detect the CH2-CH3 constant domain of the CAR.

To determine the transduction efficiency of the lentiviral transduction of T-cells, CAR expression on the surface of the cell is analyzed using an antibody to detect the CH2-CH3 constant domain of the CAR, as shown in FIG. 4.

Figure 5:
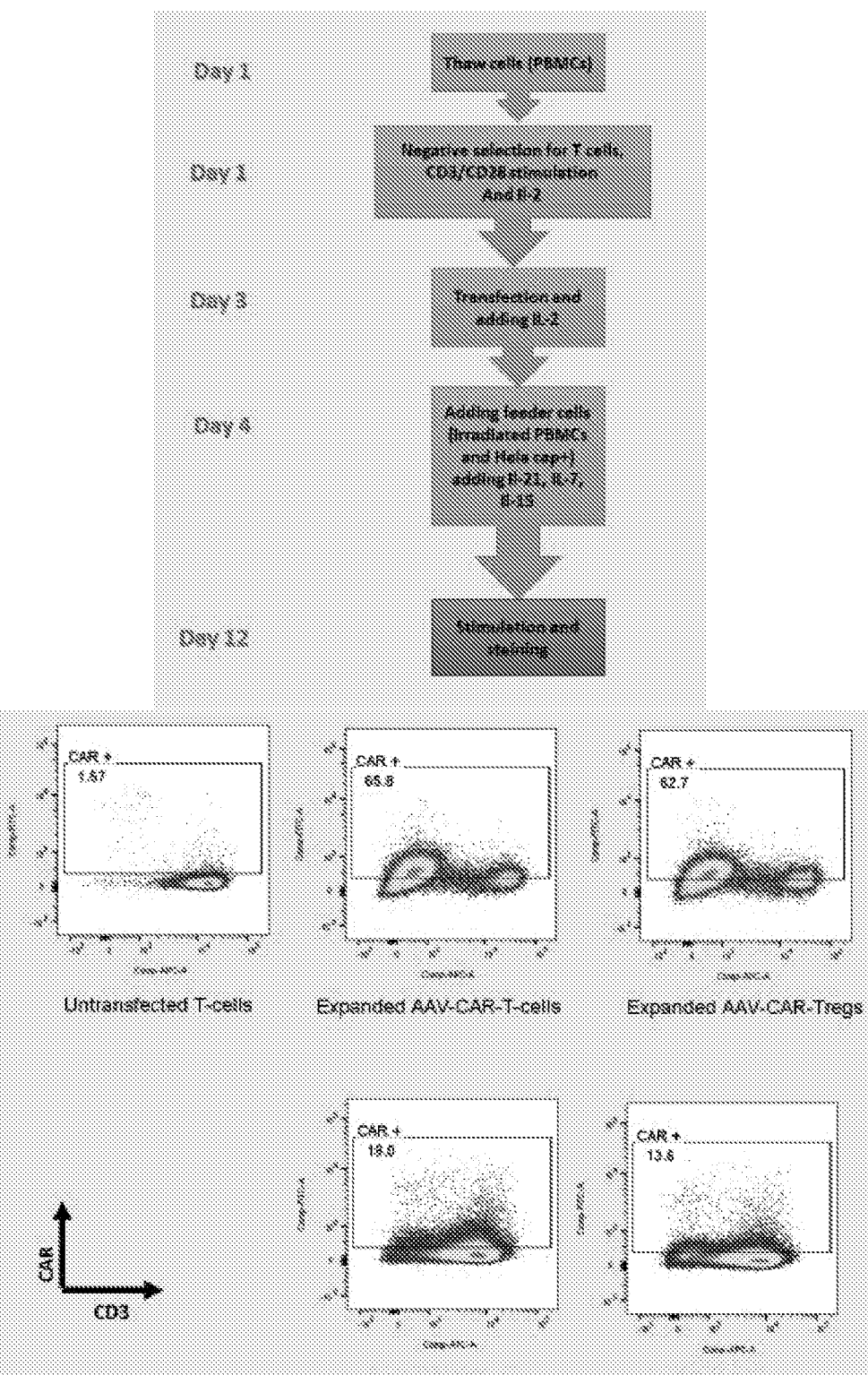
FIG. 5 is a schematic depicting one embodiment of a CAR T-cell expansion protocol. Representative FACS data indicating increased CAR T-cell population is also shown.

Cell transduction is enhanced by an expansion protocol. Briefly, after stimulation and transduction with lentivirus expressing CAR constructs, the cells are cultured with irradiated feeder cells (e.g., different cell lines than are being tested) in the presence of IL-2, Il-7 and IL-15 (FIG. 5). After 8 days of culturing under these conditions, expansion of CAR T-cells population has been observed to be 65% (FIG. 5). The purity of this population can further be enhanced by sorting based on the presence of EGFRt receptor.

Figure 6:
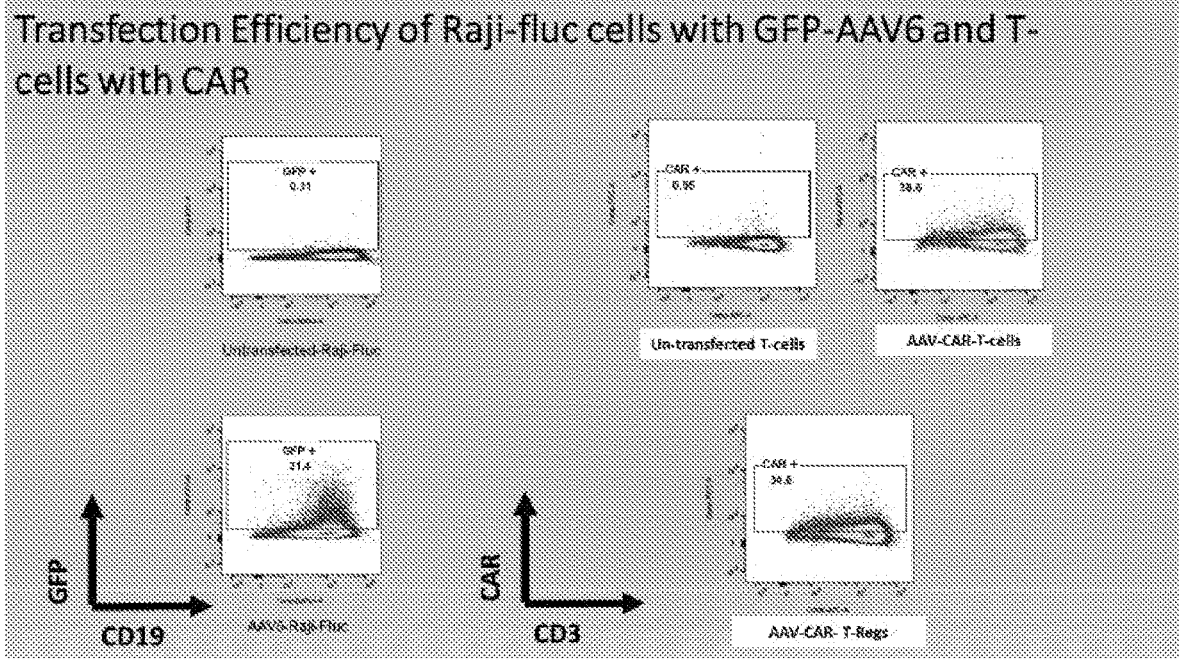
FIG. 6 shows representative FACS data for transfection efficiency of Raji-fluc cells with GFP-AAV6 and T-cells with CAR constructs.
Figure 7:
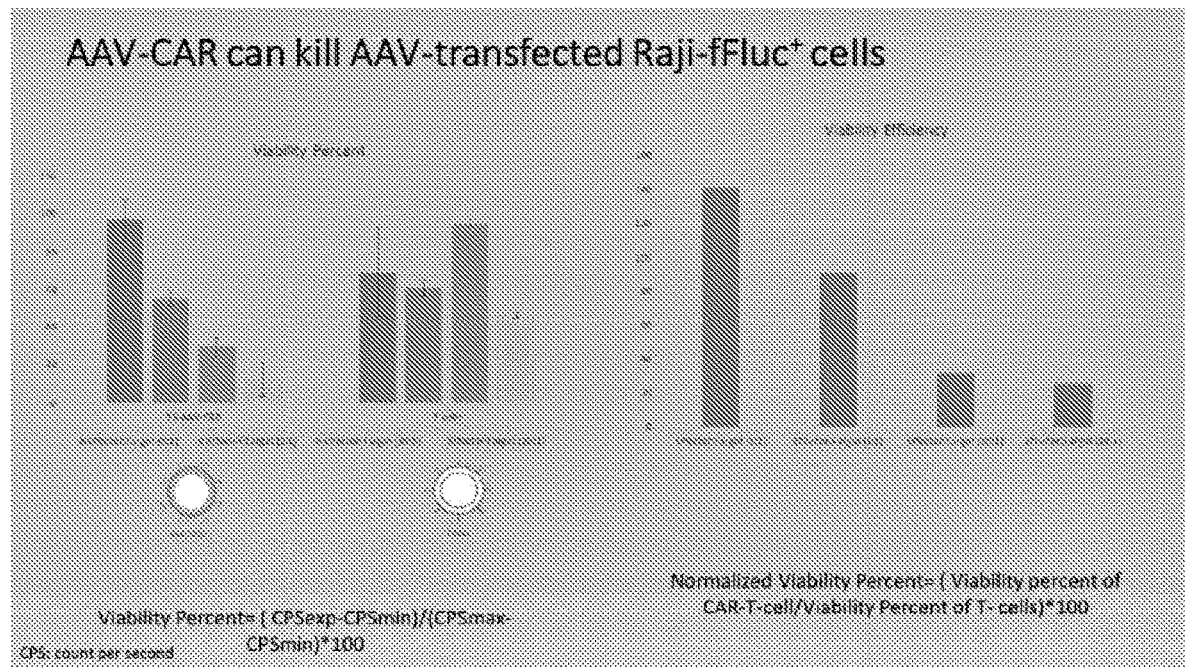
FIG. 7 shows representative data indicating that AAV-CAR constructs kill AAV-transfected Raji-fFluc+ cells.

Efficacy of CAR and CAR-Treg constructs has been investigated using luciferase-based Killing and Inhibition of Killing assays. In brief, the cytotoxicity of CARs is determined by a luciferase readout, as well as the inhibition of cytotoxicity of the CAR T-regs. Raji cells constitutively express luciferase and are used as target cells. For AAV specific CARs, cells are they are infected with rAAVs containing GFP so transduction efficiency of AAVs can be determined. After co-culturing target cells with CAR effector cells (for 6-24 hrs) luciferase activity is read on the plate. Decreased luciferase indicates decreased cell viability and efficient cytotoxic ability, whereas increased luciferase activity indicates increased cell viability and inhibition of cytotoxic ability. For these experiments AAV6 was used to infect the Raji cells. With increasing amounts of Effector AAV CARs (from 1:1 Effector to Target, to 1:20 Effector to Target) a dose dependent killing of the AAV infected Raji cells. This effect was not observed in untransfected T-cells cells, and when killing in normalized to untransfected T-cells dose dependent result is still observed. Representative data are shown in FIGS. 6 and 7.

Figure 8:
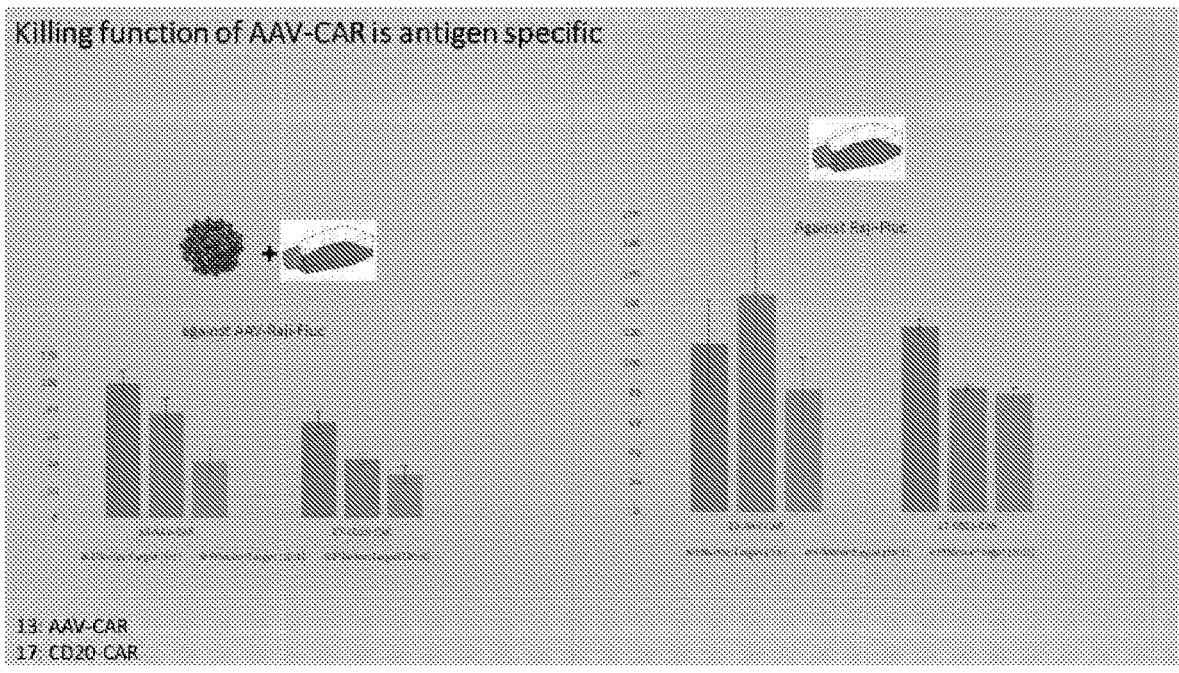
FIG. 8 shows representative data indicating the antigen-specific killing activity of AAV-CAR T-cells.

Importantly, this response is antigen specific and only observed when Raji cells are infected with AAV virus (FIG. 8). When AAV-CARs undergo the same assay but with cells that are not infected with AAV they do not display dose dependent killing. When Raji-cells are infected with AAV, dose dependent killing is observed.

Figure 9:
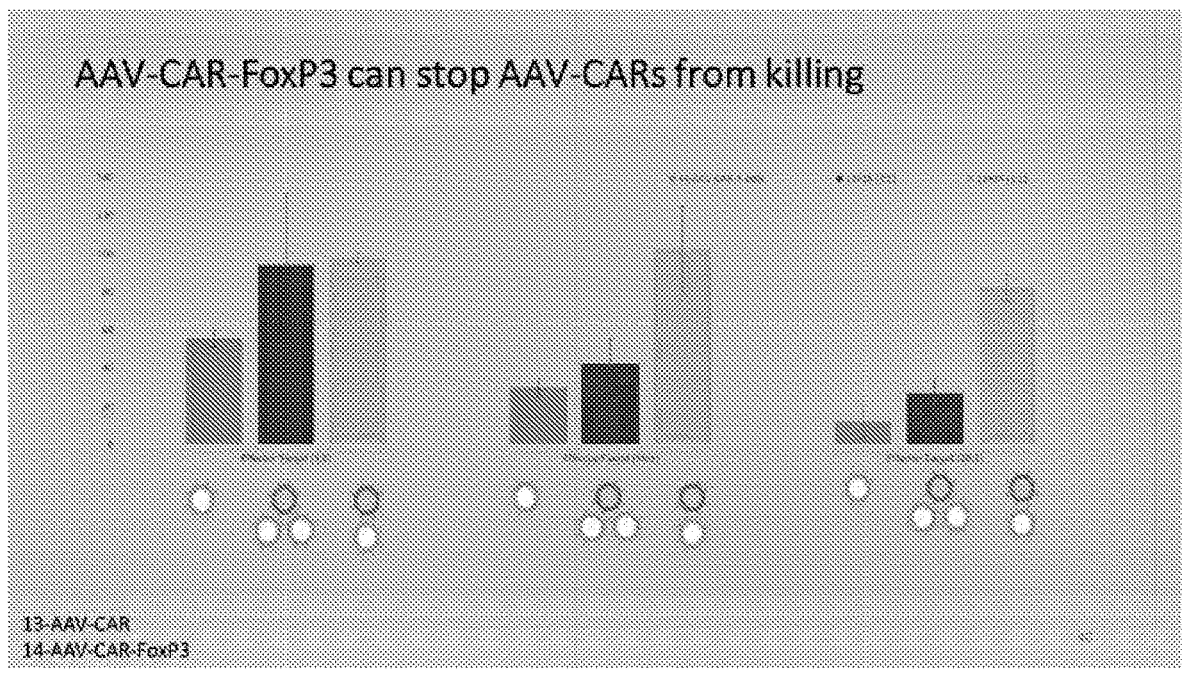
FIG. 9 shows representative data indicating that CAR T-regs (AAV-CAR-FoxP3) inhibit antigen specific killing by AAV-CAR T-cells.

The T-regulatory assays are performed in the same manner, except that Target cells are mixed with both CAR-AAV target cells as well as CAR-AAV T-regulatory cells. At 10:1 and 20:1 Effector to Target ratios, when CAR T-Cells and CAR T-regs are mixed at equal ratios robust inhibition of killing is observed (FIG. 9). The CAR T-reg response is able to inhibit antigen specific killing.

Example 2

Figures 10A, 10B:
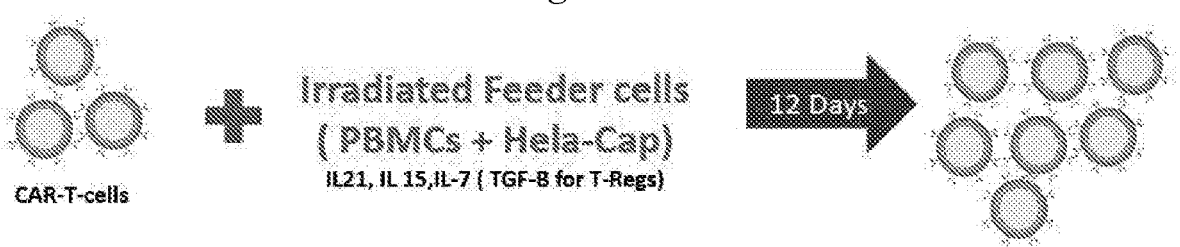
Figures 10C, 10D:
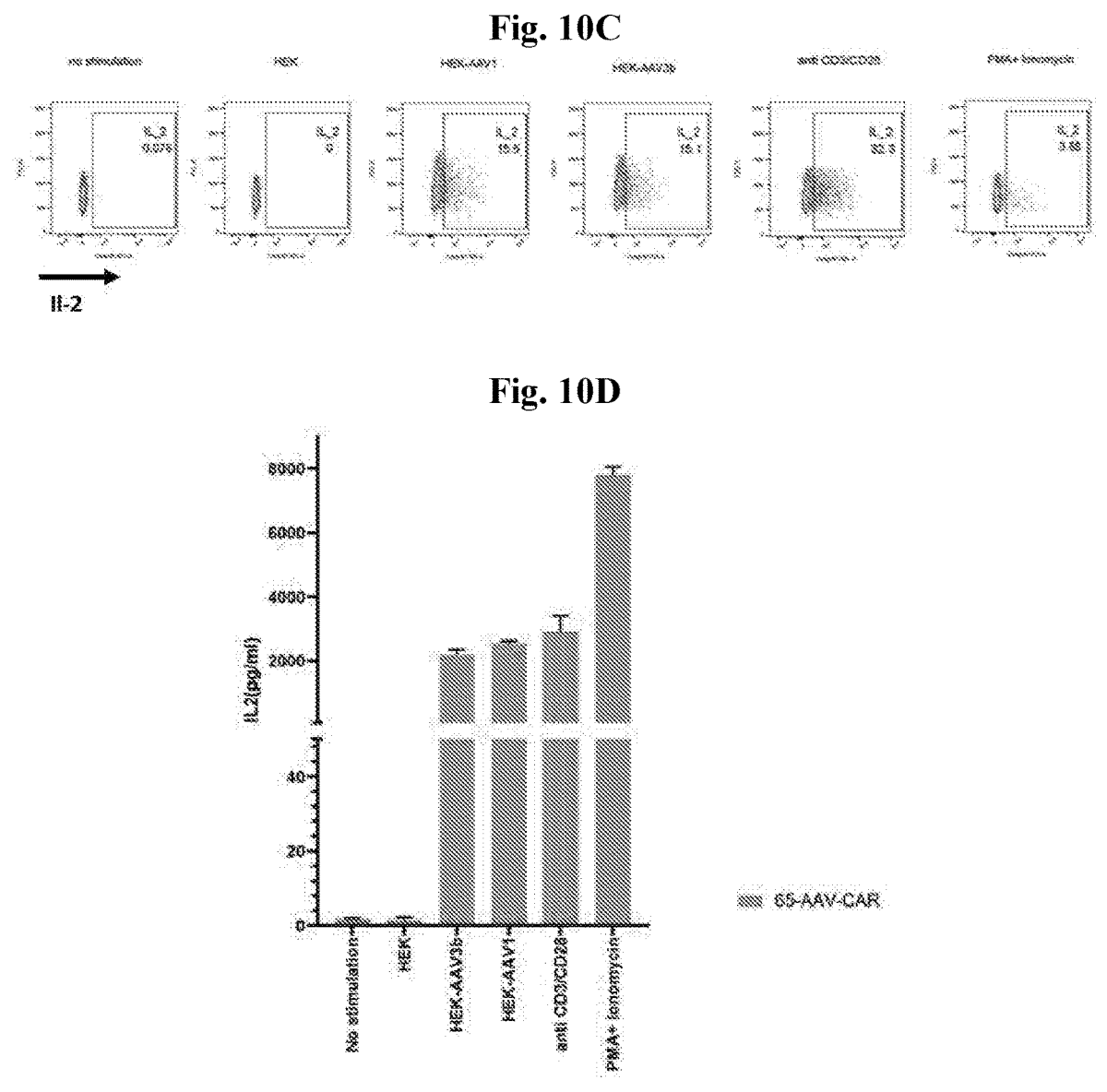
Figures 10E, 10F, 10G:
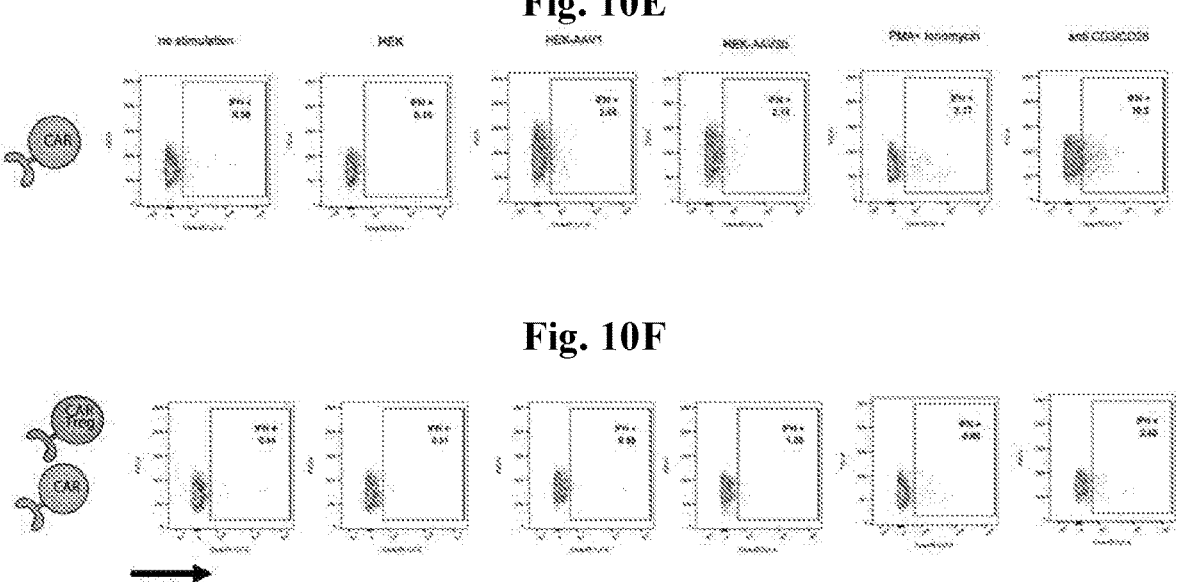

AAV-CAR-T-cells and AAV-CAR-Regulatory-T-cells were put through an expansion protocol (FIGS. 10A-10G) and measured by representative flow cytometry plots of transfected cells before and after expansion (FIG. 10B). Flow cytometry plots of IL-2 production by AAV-CAR-T-cells after different stimulation conditions (FIG. 10C). IL-2 concentration of AAV-CAR-T-cells after different stimulation conditions by ELISA (FIG. 10D). Flow cytometry plots of IFN-γ production by AAV-CAR-T-cells after different stimulation conditions (FIG. 10E). Flow cytometry plots of IFN-γ production by AAV-CAR-T-cells co-cultured with AAV-CAR-Regulatory-T-cells after different stimulation conditions (FIG. 10F). IFN-γ concentration of AAV-CAR-T-cells with or without AAV-CAR-Regulatory-T-cells after different stimulation conditions by ELISA (FIG. 10G).

Example 3

Figures 11A, 11B:
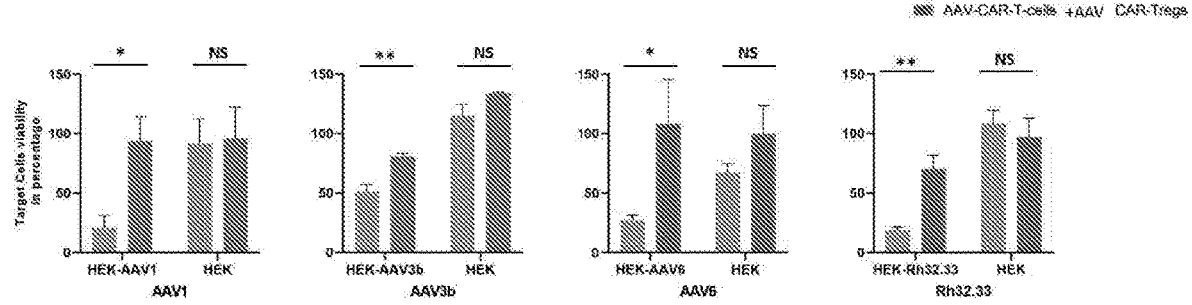
Figure 11C:
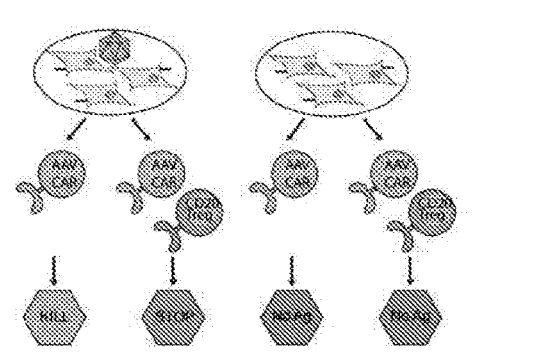
Figure 11C:
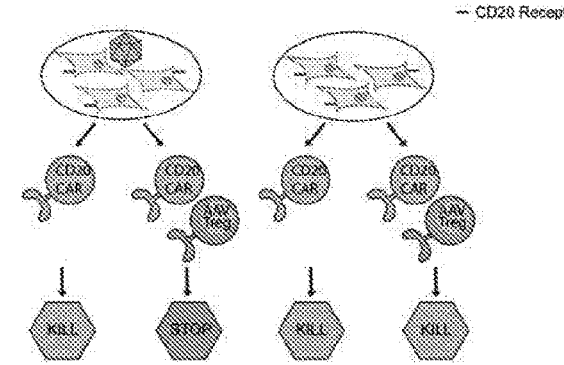
Figure 11D:
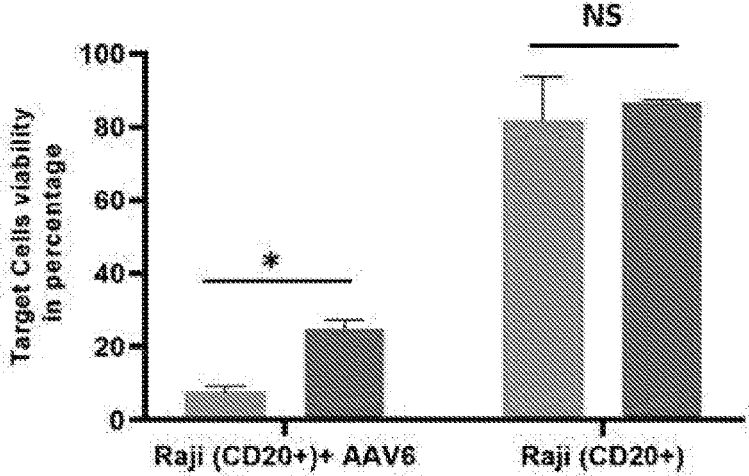
Figures 11E, 12A:
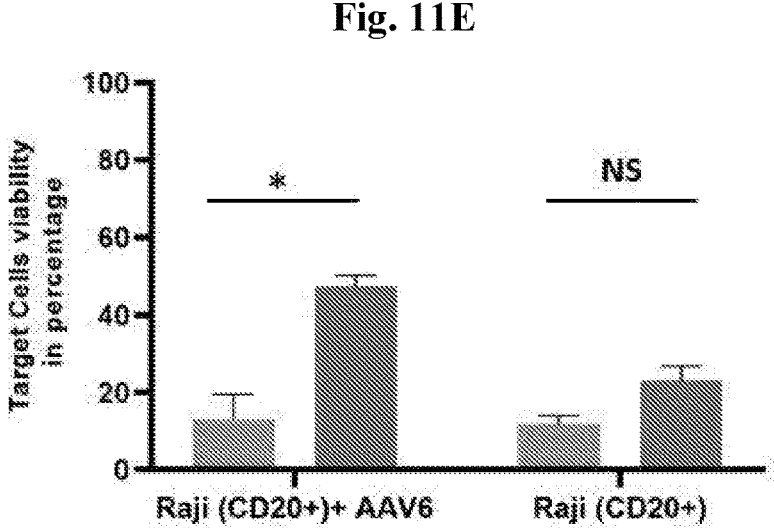

FIGS. 11A-11E. FIG. 11A: Graphical schematic of a luciferase killing assay and inhibition of luciferase killing assay. FIG. 11B: Quantitative results of killing assay and inhibition of killing assay for AAV1, AAV6, AAV3b and Rh32.33 capsid variants. FIG. 11C: Graphical schematic of a luciferase killing assay and inhibition of luciferase killing assay. FIG. 11D: Quantitative results of killing assay and inhibition of killing assay against AAV6 transfected-Raji cells (CD20+) and Raji cells (CD20+) using AAV-CAR-T-cells and CD20-CAR-Tregs. FIG. 11E: Quantitative results of killing assay and inhibition of killing assay against AAV6 transfected-Raji cells (CD20+) and Raji cells (CD20+) using CD20-CAR-T-cells and AAV-CAR-Tregs.

Example 4

Figure 12B:
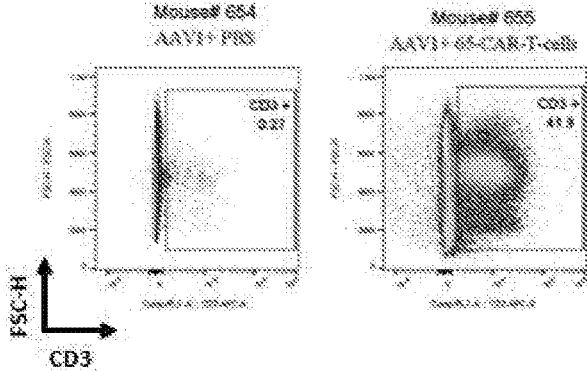
Figure 12C:
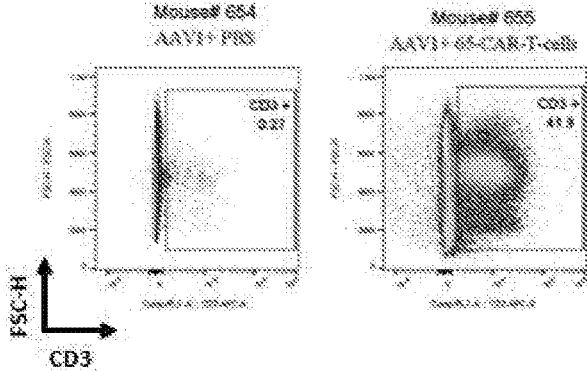
Figure 12D:
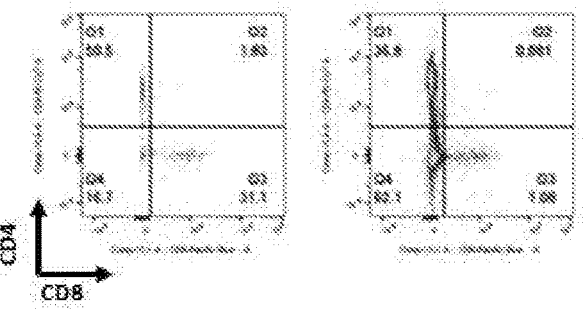

FIGS. 12A-12F. FIG. 12A: Graphical schematic of in vivo CAR-T-cell response. Intramuscular injections of AAV1-human AAT [5*10$^{10}$ viral titer]. At week 3, intravenous injection of AAV-CAR-T-cells [5*10$^6$ cells] or PBS followed by intraperitoneal of IL-2 [45000 IU] for 3 days. FIG. 12B: Time course of serum human AAT protein levels of control animals and animals that received AAV-CAR-T-cells (left). Normalized human AAT protein levels to the baseline at week 3 for control animals and animals that received AAV-CAR-T-cells (right). Arrows represents delivery of CAR T-cell delivery. FIGS. 12C-F: Flow cytometry plots of isolated T-cells from the muscles of AAV1-human AAT injected animals or AAV1-human AAT injected animals with AAV-CAR-T-cells. Populations of CD3+ (FIG. 12C); CD3+, CD8+, or CD4+ (FIG. 12D); CD3+, CD90.2+ (FIG. 12E); CD3+, CD90.2+, CD19+ (FIG. 12F).

Example 5

Figure 13B:
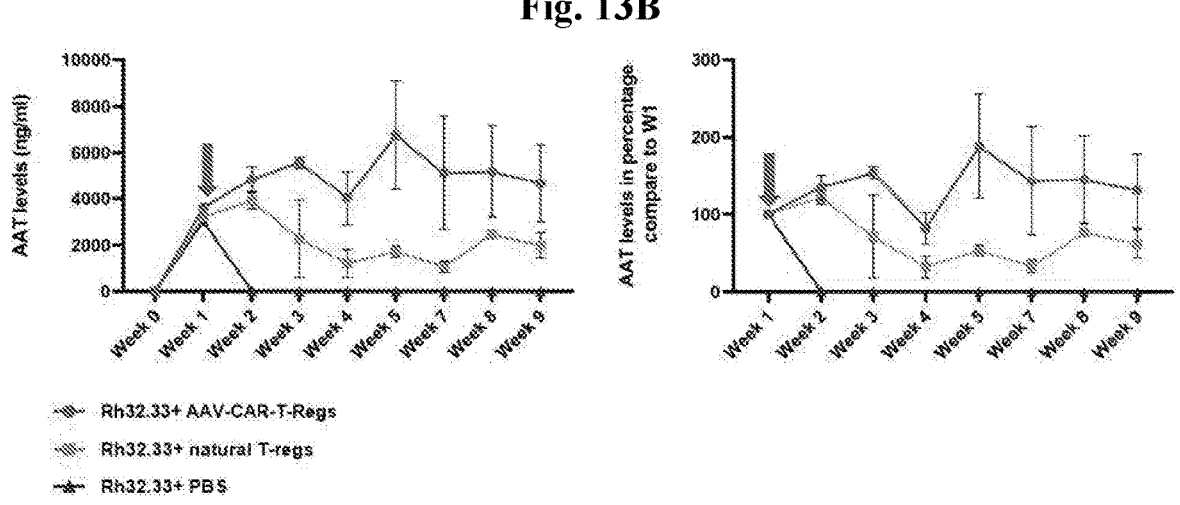
Figure 13C:
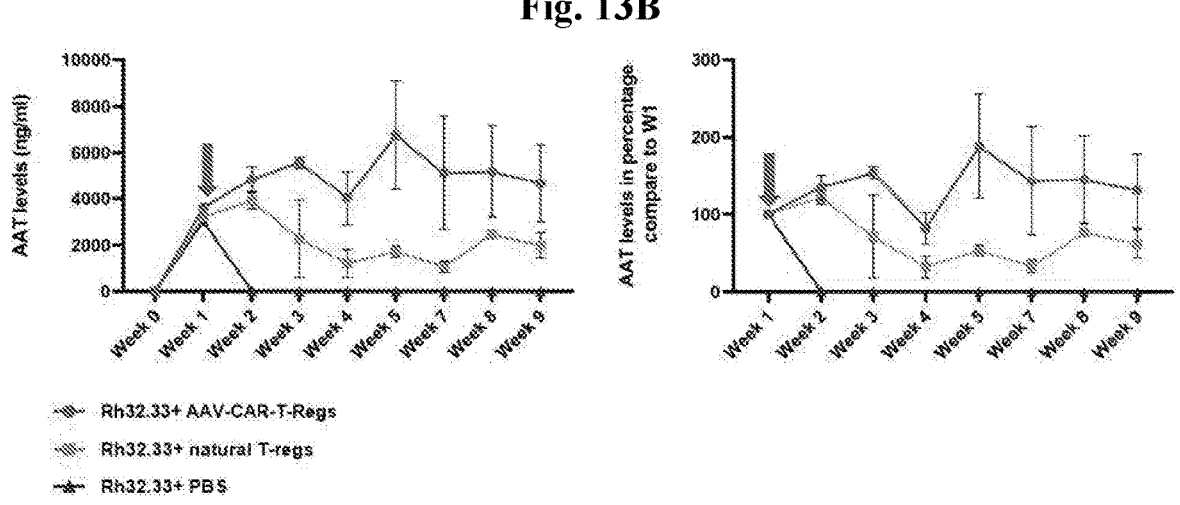
Figure 13D:
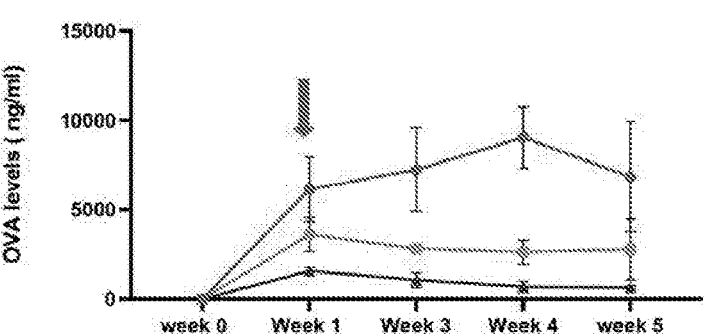
Figure 13E:
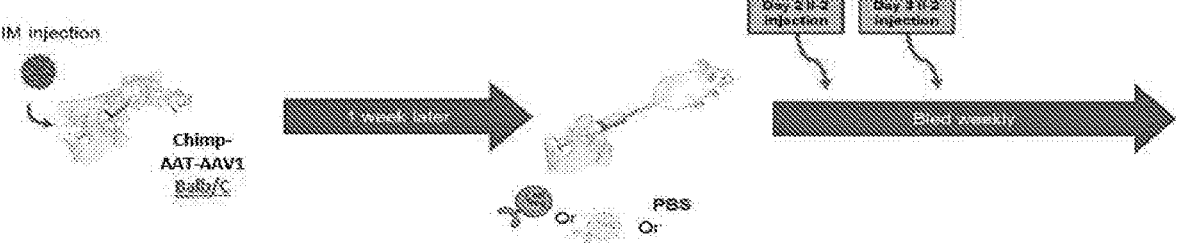
Figure 13F:
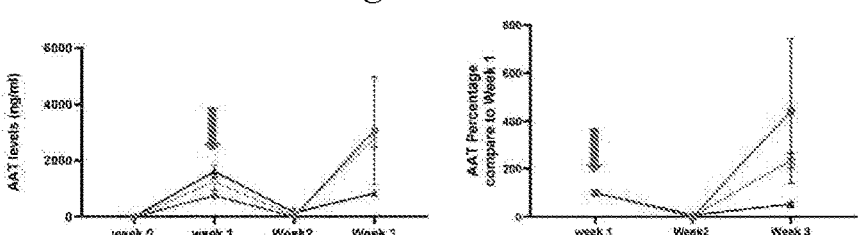

FIGS. 13A-13F. FIG. 13A: Graphical schematic of in vivo CAR-Regulatory-T-cell suppression immune response against AAV-Rh32.33. Intra muscular injections of AAV-Rh32.33-human AAT [5*1010 viral titer]. At week 1, intravenous injection of AAV-CAR-Regulatory-T-cells [5*106 cells] or natural expanded regulatory T-cells [5*106 cells] or PBS followed by Intraperitoneal of IL-2 [45000 IU] for 3 days. FIG. 13B: Time course of serum human AAT protein levels of control animals and animals that received AAV-CAR-Regulatory-T-cells and expanded natural regulatory-T-cells (left). Normalized human AAT protein levels to the baseline at week 1 for control animals and animals that received AAV-CAR-Regulatory-T-cells and expanded natural regulatory-T-cells (right). Red arrow represents CAR T-Reg delivery. FIG. 13C: Graphical schematic of in vivo CAR-Regulatory T-cell suppression immune response against Ovalbumin-AAV1 in C57BL/6 animals. Intra muscular injections of Ovalbumin-AAV1 [5*1010 viral titer]. At week 1, intravenous injection of AAV-CAR-Regulatory-T-cells [5*106 cells] or natural expanded regulatory T-cells [5*106 cells] or PBS followed intraperitoneal of IL-2 [45000 IU] for 3 days. FIG. 13D: Time course of serum Ovalbumin levels of control animals and animals that received AAV-CAR-Regulatory-T-cells and expanded natural regulatory-T-cells (left). Normalized Ovalbumin protein levels to the baseline at week 1 for control animals and animals that received AAV-CAR-Regulatory-T-cells and expanded natural regulatory-T-cells (right). Red arrow represents CAR T-Reg delivery. FIG. 13E: Graphical schematic of in vivo CAR-Regulatory-T-cell suppression immune response against chimpanzee AAT-AAV1 in Balb/C animals. Intra muscular injections of chimpanzee AAT-AAV1 [5*1010 viral titer]. At week 1, intravenous injection of AAV-CAR-Regulatory-T-cells [5*106 cells] or natural expanded regulatory T-cells [5*106 cells] or PBS followed by intraperitoneal of IL-2 [45000 IU] for 3 days. FIG. 13F: Time course of serum chimpanzee AAT protein levels of control animals and animals that received AAV-CAR-Regulatory-T-cells and expanded natural regulatory-T-cells (left). Normalized chimpanzee AAT protein levels to the baseline at week 1 for control animals and animals that received AAV-CAR-Regulatory-T-cells and expanded natural regulatory-T-cells (right). Red arrow represents CAR T-reg delivery.

Exemplary Sequences

This Table exhibits some exemplary sequences as disclosed by the instant Specification, but is not limiting. This Specification includes a Sequence Listing submitted concurrently herewith as a text file in ASCII format. The Sequence Listing and all of the information contained therein are expressly incorporated herein and constitute part of the instant Specification as filed.

TABLE 1

Exemplary Sequences

| SEQ ID NO: | Sequence* Nucleic Acid | Description |
|---|---|---|
| 1 | ctgttttaaaagaaagggggattggggggtacagtgcaggggaaagaatagtagacataatagcaaca<br>gacatacaaactaaagaattacaaaaacaaattacaaaaatttatcaacaagcttgatcgatggct<br>ccgtgccctgcagtgggcagagcgcacatcgcccacagtccccgagaagttgggggaggggtcggc<br>aattgaaccggtgcctagagaaggtggccgggggtaaactgggaaagtgatgtcgtgtactggctccgcct<br>tttccgaggtggggagaaacctatataagtgcagtagtcgccgtgaacgttctttttcgcaacgggtttg<br>ccgcagaacaacagtgtcgtgacgcggatccacgcgtggcccacgcgtcttagcgcagagg<br>cttgggcagccgagcgagcgggctcgctccgcagtccgagccggagggggagcgcgcgcggc<br>ccaggcgcgcaaggagcgggctcgctccgcaccATGGAGACAGACAGCACTCCTGCTATGGGT<br>GCTGTCTGCTGGGTTCCAGTTCCACTGGTGCATTGTGCTGAC<br>ACAGTCTCCTGCTTCCTTAGCTGTATCTCTGGGGCAGAGGGCAC<br>CATCTCATGCAGGGCCAGCCAAAGTGTCAGTTCATCTACCTATA<br>ATTTTATACACTGGTATCAACAGAAATCAGGACAGCCACCCAAA<br>CTCCTCATCAAGTATGCATCCAACCTAGAATCTGGGGTCCCTGTC<br>AGGTTCAGTGCAGTGGGTCTCGGGACAGACTTCTCCCTCAACAT<br>CCATCCTGTGGAGGAGGAGATACTGCAACATATTACTGTCAGC<br>ACAGTTGGGAGATTCCATACACGTTCGGAGGGGGGCCAAGTTG<br>GAGATAAAAggcagtactagcggtggtggctccggggcggttccggtggggggcggcagcag<br>cCAGGTGCAGCTGAAGGAGTCAGGACCTGGCCTGGTGGCACCCT<br>CACAGAGCCTGTCCATCACCTGCACCGTCTCAGGATTCTCATTAA<br>GCGCTATGGCATAAGCTGGGTTCGCCAGCCTCCAGGAAAGCGT<br>CTGGAATGGCTGGGATTGATATGGGGTGATGGAACCACAGACTA<br>TAATTCAGCTCTCAAATCCAGACTGAGCATCAGCAAGGACAACT<br>CCAAGAGCCAGGTTTTCTTAAAAATGAACAGTCTGCAAACTGAT<br>GACACCAGCCAGGTACTTCTGTACCAGAGGGCCTCCGGCCTTCTA<br>TAAGTACCTCTACTTTGACTACTGGGGCCAAGGCACCACTCTCAC<br>AGTCTCCTCAgacaaaaactcacacatgcccaccgtgcccagcacctcctgtggcaggaccgtca<br>gtcttcctcttcccccaaaacccaaggacacctcccgaccctgaggtcacatgcgtggtg<br>gtggacgtgagccacgaagaccctgaggtcaagttcaactggtacgtggacggcgtggaggtgcataatg<br>ccaagacaaagccgcgggaggagcagtacaacagcacgtaccgtgtggtcagcgtcctcaccgtcctgc<br>accaggactggctgaatggcaaggagtacaagtgcaaggtctccaacaaagccctcccagcccccatcga<br>gaaaccatctccaaagccaaagggcagccccgagaaccacaggtgtacaccctgcccccatcacgagga<br>tgagctgaccaagaaccaggtcagcctgacctgcctggtcaaaggcttctatcccagcgacatcgccgtgg<br>agtgggagagcaatgggcagccggagaacaactacaagaccacgcctcccgtgctggactccgacggct<br>ccttcttcctctacagcaagctcaccgtggacaagagcaggtggcagcaggggaacgtcttctcatgctccg<br>tgatgcatgaggctctgcacaaccactacacgcagaagagcctctccctgtctccgggtaaatg<br>ggtggtgagtctagctccttcctatagctgctagcagtggccttctggttttctgggtgctggtggtggt<br>gagcaggggggtcacagtctccttcctatagctgttaacagtggagggccttcctggggggagagtaagag<br>gcagcggggaggtcacagtgtcacactgacctccaaaggaggcagagaagaaactcctgtata<br>ccagccctatgccccaccacgacttcgaatgcagcctatgacacatgtgtccaaacagggcagggccagcatta<br>tattcaaacaaccatttatgagaccaagtgaactgagagtgaactactcaagaggaagatggctgactgcgattccaga<br>agaagaagaggagatgtgaactgagagtgaactgagagtcagcaggaggcagacccccgtaccagc<br>agggccagaaccctctataacgagctcaatctaggacgaagagaagaacccctaggagggcctgtacaatg<br>acgtgccggaaccctgagccggagggctcacagtgagattggatgaaagcgagcgccggagggc<br>aactgcagaaagatagtgcgggaggcctacagtgatgagattggatgaaagcgagcgccggagggc<br>aagggcacgatgcctctgctagggtctccagtacagcaccaagagaccaccaaggactcttaccatgc<br>aggccctgcccctgctgagatatcgtgggaattcgagcatctccacacacctgtctctgatt | 13-1_Lenti-IF5-<br>D3-NQ-28-BB-Z |

TABLE 1-continued

Exemplary Sequences

| SEQ ID NO: | Sequence*Nucleic Acid | Description |
|---|---|---|
| | tctgtattgggtatacatttaatgttaataaacaaatggtggggcaatcattcatttaggatatgtaat | |
| | tactagttcaggtgtgatgccacagacaaacatgttaagaaacttccgtattacgctcctcgttcctgtaatc | |
| | aacctctgattacaaaattgtgaaagattgactgatattcttaactagtgtcctttacgctgtgtgatatg | |
| | ctgcttatagccctgtatctagctattgctccgtacggcttcgtttctcctcctgataaatcctggttgct | |
| | gtctcttttagaggagttgtggccgttgccgtcaacggcgtggtgctctgtgtgttgctgacgcaaccc | |
| | ccactggctgggcattgccccaccaccgtcaacctctttctggacttctgcccctcccgatcgccacg | |
| | gcagaactcatcgcgccgctctgcccgctgccgcgtgacaagggcaggtgctggcactgataattccgt | |
| | ggtgtgtcggggaagcgacgtcacgtccttcctgaggggggcccgtacctttaagacaatgacttacaag | |
| | gcagtcgtagatcttagccacttttaaaaagaaaagggggggactcgaagggctaattcactcccaacgaaga | |
| | caagatctgctttttcgttctcctctgttagaccagatcctgagccggggagctctctggctaacta | |
| | gggaaccacctgcttaagcctcaataaagctccttgagtgcttcaagtagtgtgcgcgtcgtgtgtga | |
| | ctctggtaactagagatcctcagacccctttagtcagtgtggaaaatctctagcagtagtagttcatgtcatctt | |
| | attatcaagtatattataactgcaagaaatgaatatcagagagtgagaggaactgttattgcagcttataatg | |
| | gttacaaataaagcaataagcatcacaaatttcacaaatttcactgcattctagttgtggtttgtcc | |
| | aaactcatcaatgtatcttatcatgtctgcctcagctatcccgccccctaactccgcccagtccgcccattctc | |
| | cgccccatggctgactaatttttttattatgcagaggccgaggccgcctcggcctcgactattccagaag | |
| | tagtgaggaggcttttttggaggcctaggcttttgctcggcctctgagctgttctttcctctcctttctcg | |
| | acggcgcgctcactggccgtcgttttacaacgtcgtgactgggaaaaccctggcgttacccaacttaatcgcct | |
| | tgcagcacatccccctttcgccagctggcgtaatagcgaagaggcccgcaccgatcgcccttcccaacagt | |
| | tgcgcagcctgaatggcgaatggcgcgacgcgccctgtagcggcgcattaagcgcggcgggtgtggtgg | |
| | ttacggcgagccgtgaccgctacactggccagcgccctagcgcccgctcctttcgctttcttcccttctcg | |
| | ccacgttcgccggctttccccgtcaagctctaaatcgggggctccctttagggttccgatttagtgctttacgg | |
| | caccctgacctgcccaaaaaacttgattagggtgatggttcacgtagtgggccatcgccctgatagacggtttc | |
| | gccctttgacgttggagtccacgttctttaatagtggactcctgttccaaactggaacaacactcaacctatct | |
| | cggtctattctttgatttataaggggattttgccgatttcggcctattggttaaaaaatgagctgatttaacaaaaat | |
| | ttaacgcgaatttttaacaaaatattaacgtttacaatttccaggtggcacttttcggggaaatgtgcgcggaac | |
| | ccctattgtttatttttctaaatacattcaaatatgtatccgctcatgagacaataaccctgataaatgcttcaata | |
| | atattgaaaaaggaagagtatgagtattcaacatttccgtgtcgcccttattcccttttttgcggcattttgccttc | |
| | ctgtttttgctcacccagaaacgctggtgaaagtaaaagatgctgaagatcagttgggtgcacgagtgggtta | |
| | catcgaactggatctcaacagcggtaagatccttgagagttttcgccccgaagaacgttttccaatgatgagc | |
| | acttttaaagttctgctatgtggcgcggtattatcccgtattgacgccgggcaagagcaactcggtcgccgca | |
| | tacacattattctcagaatgacttggttgagtactcaccagtcacagaaaagcatcttacggatggcatgacagta | |
| | agagaattatgcagtgctgccataaccatgagtgataacactgcggccaacttacttctgacaacgatcgga | |
| | ggaccgaaggagctaaccgcttttttgcacaacatgggggatcatgtaactcgccttgatcgttgggaaccg | |
| | gagctgaatgaagccataccaaacgacgagcgtgacaccacgatgcctgcagcaatggcaacaacgttgc | |
| | gcaaactattaactggcgaactacttactctagcttcccggcaacaattaatagactggatggaggcggataa | |
| | agttgcaggaccacttctgcgctcggcccttccggctggctggtttattgctgataaatctggagccggtgag | |
| | cgtgggtctcgcggtatcattgcagcactggggccagatggtaagccctcccgtatcgtagttatctacacg | |
| | acggggagtcaggcaactatggatgaacgaaatagacagatcgctgagataggtgcctcactgattaagca | |
| | ttggtaactgtcagaccaagtttactcatatatactttagattgatttaaaacttcatttttaatttaaaaggatctag | |
| | gtgaagatcctttttgataatctcatgaccaaaatcccttaacgtgagttttcgttccactgagcgtcagaccc | |
| | gtagaaaagatcaaaggatcttcttgagatcctttttttctgcgcgtaatctgctgcttgcaaacaaaaaaacca | |
| | ccgctaccagcggtggtttgtttgccggatcaagagctaccaactctttttccgaaggtaactggcttcagca | |
| | gagcgcagataccaaatactgtccttctagtgtagccgtagttaggccaccacttcaagaactctgtagcacc | |
| | gcctacatacctcgctctgctaatcctgttaccagtggctgctgccagtggcgataagtcgtgtcttaccgggt | |
| | tggactcaagacgatagttaccggataaggcgcagcggtcgggctgaacggggggttcgtgcacacagc | |
| | ccagcttggagcgaacgacctacaccgaactgagatacctacagcgtgagctatgagaaagcgccacgct | |
| | tcccgaagggagaaaggcggacaggtatccggtaagcggcagggtcggaacaggagagcgcacgagg | |

TABLE 1-continued

Exemplary Sequences

| SEQ ID NO: | Sequence* Nucleic Acid | Description |
|---|---|---|
| | gagcttccaggggaaacgcctggtatctttatagtcctgtcggttcgccacctctgacttgagcgtcgatt<br>ttgtgatgtcgtcaggggggcggagccatggaaaacgccagcaacgcggccttttacggtcctggc<br>ctttgctggccttttgcttcacatgttcttttcctggttatccctgattctgtggataaccgtattaccgccctttga<br>gtgagctgataccgctcgccgacgaccgagcgcagcgagtcagtgagcgaggaagcggaa<br>gagcgcccaatacgcaaaccgcctctcccccgcgttggccgattcattaatgcagctggcacgacaggtt<br>tcccgactggaaagcgggcagtgagcgcaacgcaattaatgtgagttagctcactcattaggcacccagg<br>ctttacacttatgtctccggctccgtatgttgtgtggaattgtgagcggataacaatttcacacaggaaacagct<br>atgaccatgattacgccaagcgcgcaattaaccctcactaaagggaacaaaagtggagctgcaagcttaa<br>tgtagtcttatgcaatactccttgtagtcttgtcaacatggtaacgatgagttagcaacatgccttacaaggagag<br>aaaaagcaccgtgcatgccgattggtggagtggcggaaatgctcattaagaaggccaacagac<br>gggctgacatggattggacgaaccactgaattgccgcattgcagagatattgtatttaagtgctagctcgat<br>acataaacgggtctctctgttagaccagatctgagctggagcctctggactagttgtgtgactctggtaactaga<br>gatcccctcagacccttttagtcagtgtggaaaatctctagcagtggcgcccgaacaggggcacttgaaagcgaa<br>agggaaaccagagagctctctcgacgcaggactcggcttgctgaagcgcgcacggcaagaggcgagg<br>ggcggcgactggtgagtacgccaaaaattttgactagcggaggctagaaggagagagatgggtgcgaga<br>gcgcagtattaagcgggggagaattagatcgcgatgggaaaaaattcggttaaggccaggggaaagaa<br>aaaatataaattaaaacatatagtatgggcaagcagggagctagaacgattcgcagttaatcctggcctgtta<br>gaaacatcagaaggctgtagacaaatactgggacagctacaaccatcccttcagacaggatcagaagaact<br>tagatcattatataatacagtagcaaccctctattgtgtgcatcaaaggatagagataaaagacaccaaggaa<br>gctttagacaagatagaggaagagcaaaacaaaagtaagaccaccgcacagcaagcggccgctgatcttc<br>ccattaggaggagatggagattgaggaagtagaagtagaagcaaagaagaagagcagtgggaat<br>aggagcttgttcctcttgggagcagcaggaagcactatggcgcagcctcaatgacgctgacggt<br>acagccagacaattattgtctggtatagtgcagcagcagaacaatttgctgagggctattgaggcgcaaca<br>gcatctgttgcaactcacagtctggggcatcaagcagctccaggcaagaatcctggctgtggaaagatacct<br>aaaggatcaacagctcctggggatttggggttgctctggaaaactcatttgcaccactgctgtgccttggaat<br>gctagttggagtaataaatctctggaacagatttggaataacacgacctggatggagtgggacagagaaatt<br>aacaattacacaagcttaatacactccttaattgaagaatcgcaaaaccagcaagaaaagaatgaacaagaa<br>ttattggaattagataaatggcaagtttgtggaattggtttaacataacaaattggctgtggtatataaaattatt<br>cataatgatagtaggaggcttggtaggtttaagaatagtttttgctgtactttctatagtgaatagagttaggcag<br>ggatattcaccattatcgtttcagacccacctcccaaccccgaggggacccgacaggcccgaaggaatag<br>aagaagaaggtggagagagacagagacagatccattcgattagtgaacggatctcgacggtatcggtt<br>ctgtttaaagaaaaggggggattggggggtacagtgcaggggaaagaataatagacataacaaca | |
| 2 | gacatacaaactaaagaattacaaaaacaaattcaaaattttatcaaaagttatcgatggct<br>ccggtgccctgcagtgggcagagcgcacatcgcccacagtcccgagaagttgggggggaggggtcggc<br>aattgaaccggtgcctagagaaggtggcgcggggtaaactgggaaagtgatgtcgtgtactggctccgcct<br>ttttcccgagggtggggaggacccgtataaagtgtataaagtcagtagtccgcacgtctcttttcgcaacggg<br>cttgggcagcagcggaagcggctgcctcacggacccgcgggaggatcttcagagggagagccgc<br>ccgaggactcgagagagcggcgcctcgcagtccgagacggaggggagcggagcccgcggc<br>GCTGCTGCTTGGGTTCCAGGTTCCACTGTGACATTGTGCTGAC<br>ACAGTCTCCTGCTTCCTTAGCTGTATCTCTGGGCAGAGGCCAC<br>CATTTATACACTGGTATCAACAGAAATCAGGACAGCCACCCAAA<br>CTCCTCATCAAGTATGCATCCAACCTAGAATCTGGGGTCCCTGTC | 14-2_Lenti-IF5-<br>D3-NQ-28-BB-Z |

TABLE 1-continued

Exemplary Sequences

| SEQ ID NO: | Sequence*Nucleic Acid | Description |
|---|---|---|

AGGTTCAGTGCAGTGGGTCTGGGACAGAGACTTCTCCCTCAACAT
CCATCCTGTGGAGGAGGAGGATACTGCAACATATTACTGTCAGC
ACAGTTGGGAGATTCCATACACGTTCGGAGGGGGGGCCAAGTTG
GAGATAAAAggcagtactagcgtggtggctccgggggcggtccggtgggggcggcagcag
cCAGTGCAGCTGAAGGAGTCAGGACCTGGCCTGGTGGCACCCT
CACAGAGCCCTGTCCATCACATGCACCGTCTCAGGATTTCTCATTAA
GCGGCTATGGCATAAGCTGGGTTCCGCCAGCCTCCAGGAAAGCGT
CTGGAATGGCTGGGATTGATATGGGGGTGATTGGACCACAGACTA
TAATTCAGCTCTCAAATCCAGACTGAGCATCAGCAAGGACAACT
CCAAGAGCCAGGTTTTCTTAAAAATGAACAGTCTGCAAACTGAT
GACACAGCCAGGTACTTCTGTACCAGAGGGCCTCCGGCCTTCTA
TAAGTACCTCTACTTTGACTACTGGGGCCAAGGACCACTCTCAC
AGTCTCCTCAgacacaaaactcacacatgcccaccgtgcccagcacctccgtgtggcaggaccgtca
gtcttcctcctccccccaaaacccaaggacaccctcatgatcctccgaccccctgaggtcacatgcgtggtg
gtggacgtgagccacgaagacccctgaggtcaagttcaactggtacgtggacggcgtgaggtgcataatg
ccaagacaaagccgcgggaggagcagtaccagagcacgtaccgtgtggtcagcgtcctcaccgtcctgc
accaggactggctgaatggcaaggagtacaagtgcaaggtctccaacaaagcctccaggacccccatcga
gaaaaccatctccaaagccaaagggcagccccgagaaccacaggtgtacaccctgcccccatcccgggatga
tgagtgaccaagaaccaggtcagcctgacctgcctggtcaaaggcttctatcccagcgacatcgccgtgg
agtgggagagcaatgggcagccggagaacaactacaagaccacgcctcccgtgctggactccgacggct
ccttcttcctctacagcaagctcaccgtggacaagagcaggtggcagcaggggaacgtcttctcatgctccg
tgatgcatgaggctctgcacaaccactacacgcagaagagcctctccctgtctccgggtaaatgagtgcgacggccggt
ggttgtggtggagtcccggcctgctatagctgctgctagtaacagtggccttattatttctgggtgaggagtaagag
gagcaggggaggtcacagtgactacatgaacatgaccctcccccgcccccgggccaccccgaagcatta
ccagccctatgccccaccccggactcctcgcagcctatcgctccaaacggggcagaagaaactcctgtata
tattcaaacaacattatgagaccagtacaaactactcaagagagaagaggacaagagaatggctgcgattccaga
agaagaaggaggatgtgaactgaagtgcaggtcagcgagagagacgccccgctaccagc
aggccagaaccagctctataacgagctcaatcctaggacgaaggaagaaaccctcaggaaggcctgtaccaatg
acgtggccggaaccctgagtgggggggaaagccgagatgggggatgaaggcagcgccggagggc
aagggcacgatggccttttaccagatgtctcagtctcagcgccaccaagagaccctacgcccttcacatgc
aggccctgccccctgcccagtgtactaattatgctcttctgaaattggctgagagtgtgagagcaaccccgg
gccaATGCCCAACCTCAGCCTCCATCCCCCAGGAGTCTTGCCCAAGCTGGAAGACTGC
ACCCAAGGGCTCAGAACTTCTAGGGACCACGGGGGCTCTGGGGGAC
CCTTCCAAGGTCGGGACCTGCGAAGTGGGGGCCCACACCTCTTCTT
CCTTGAACCCCTGCCACCATCCCAGCTGCAGCTGCCTACAGTGC
CCCTAGTCATGGTGCGACCGTCTGGGGCCCGACTAGGTCCCTCA
CCCCATTACCAGCGCCCTTCTCCAGGACAGACCACACTTCATGCAT
CAGCTCTCCACTGTGGATGCCATGCCCAGACCCCTGTGCTCCAA
GTGCGTCCACTGGACAACCCAGCCATGATCAGCCTCCCACCACC
TTCTGCTGCGCCACTGGGGTCTTTCTCCCTCAAGGCCCGGCCTGGCCT
GCCACCTGGGATCAATGTGCCCAGTCTCGGAATGGGTGTCCAGGG
AGCCAGCTCTACTCTGCACCTTCCCACGCTCGGGTACACCCAGG
AAAGACAGCAACCTTTTGGCTGCACCCCAAGGAATCCTACCCACT
GCTGGCAAATGGAGTCTGCAAGTGCCCTGGTTGTGAGAAGGTCT
TCGAGGAGCCAGAAGAGTTTCTCAGCACTGCCAAGCAGATCAT
CTCCTGGATGAGAAAGGCAAGGCCCAGTGCCTCCTCCAGAGAGA TABLE 1-continued Exemplary Sequences

| SEQ ID NO: | Sequence* Nucleic Acid | Description |
|---|---|---|
|  | AGTGTGTGCAGTCTCTGGAGCAGCAGCTGGAGCTGAAAAGGAG<br>AAGCTGGGAGCTATGCAGGCCCACCTGGCTGGGAAGAGATGCGCT<br>GGCCAAGGCTCCATCTGTGGCCTCAATGGACAAGAGCTCTTGCT<br>GCATCGTAGCCACCAGTACTCAGGGCAGTGCTCCCGGCCTGG<br>TCTGCTCCTCGGGAGGCTCCAGACGGCGGCCTGTTTGCAGTGCG<br>GAGGCACCCTCTGGGAAGCCATGGCAATAGTTCCTCCCCAGAGT<br>TCTTCCACACATGGACTACTTCAAGTACCACAATATGCGACCCC<br>CTTTCACCTATGCCACCCTTATCCGATGGGCCATCCTGGAAGCCC<br>CGGAGAGGCAGAGGACACTCAATGAAATCTACCATTGGTTTACT<br>CGCATGTTCGCCTACTTCAGAAACACCCGCCACCTGGAAGAA<br>TGCCATCCGCCACACCTGAGCCTGCACAAGTGCTTTGTGCGAG<br>TGGAGGCAGAAGGAGAGCAGGCAGTGTGGACCGTAGATGAATTTGA<br>GTTTCGCAAGAAGAGGAGGAGCCAAGCGCCCCACACAAGTGCTCCAATC<br>CCTGCCCTTGAaattcgagcattcacggccattattcccatatttgttctgttttcttgatttgggtat<br>acatttaaatgttaataaacaaaatgttgggcaatcattacattttaggatatgtaattactagtcaggtg<br>tattgccacaagacaaacatgttaagaaactttccgtattacgtcctgttcctgttaatcaacctggattac<br>aaaatttgaaagattgactgatattcttaactatgtgctctttacgctgtgtggatatgctgctttatagcct<br>ctgtatctagcttattgctccgtacgagctgtcgttcgtttctgttctctccctgtataaatcctggttgtgtctcttttagagg<br>agttggtggccgttgtccgtcaactggcgtggtcgtctgtgtttgctgacgcaaccccccactggctgggg<br>cattgccaccacctgtcaactccttttctgggacttcgcttccccctccgatcgccacggcagaactcatcg<br>ccgctgccttgcccgcctgctggacaggggctagttgctgggcactgataattccggtggtgttgtcggga<br>agctgacgtcctttctctcgagggggccggtaccttaagacacaatgacttacaaggcagctgtagatctt<br>agccacttttaaaagaaaggggaacctggaaggctaattcactcccaacgagacaagatctgctttt<br>gctgtactggtctctcggttagaccagatctgagcctggaactcgagctgtgcccgctcttgtgtgactcggtaactaga<br>ttaagcctcaataaagcttgcctgagtgcttcagtcagtgtgcagtagtcatgtcatctattattcagtatttat<br>gatccctcagaccctttagtcagtgtggaaaatctctagcagtagtagcttattggcttgctcatgtttgacctaaagagcgtgtggcgcggcacgc<br>aactgcaagagaaactgaatcagagagtgggaacctgtttattgcacgtttaatggttaacaaataaagc<br>aatagcatcacaaattcacaaataaagcatttttcactgcattcagtgttggttgtccaaactcatcaatgta<br>tctatcatgtctgctctagctatcccgccctccaacctcggcctctgagcattccagaagtagtgaggaggctga<br>ttggaggcgcctcattatgcagaggccgaggccgcctccgagtctgagcttgcctaaacgtcagcgtcactg<br>gccgtcgtttacacgtcgtgactgggaaaaccctggcgttacccaacttaatcgccttgcagcacatcccc<br>cttcgccagctggcgtaatagcgaagaggcccgcaccgatcgcccttcccaacagttgcgcagcctgaat<br>ggcgaatggcgcgacgcgccctgtagcggcgcattaagcgcggcgggtgtggtggttacgcgcagcgtg<br>accgctacactcgccagctcgccgccgcctctctcccttcccttggggtcccattaagtgcttcacgcaccctcgaccccaa<br>tttccccgtcaagctctaaatcgggggctccctttagggttccgatttagtgctttacggcacctcgaccccgggttgg<br>aaacttgattaggggtgatggttcacgtagtgggccatcgccctgatagacggtttttcgcccttgacgttgg<br>agtccacgttctttaatagtggactcttgttccaaactggaacaacactcaaccctatcggggctattctttgat<br>ttataaggattttgccgatttcggcctattggttaaaaaatgagctgatttaacaaaaatttaacgcgaatttaa<br>caaaatattaacgtttacaattccaggtggcacttttcggggaaatgtgcgcggaacccctatttgtttattttt<br>ctaaatacattcaaatatgtatccgctcatgagacaataaccctgataaatgcttcaataatattgaaaaaggaa<br>gagtatgagtattcaacatttccgtgtcgcccttattcccttttttgcggcattttgccttcctgtttttgctcacccca<br>gaaacgctggtgaaagtaaaagatgctgaagatcagttgggtgcacgagtgggttacatcgaactggatctt<br>caacagcggtaagatccttgagagttttcgccccgaagaacgttttccaatgatgagcacttttaaagttctgct<br>atgtggcgcggtattatcccgtattgacgccgggcaagagcaactcggtcgccgcatacactattctcagaa<br>tgacttggttgagtactcaccagtcacagaaaagcatcttacggatggcatgacagtaagagaattatgcagt<br>gctgccataaccatgagtgataacactgcggccaacttacttctgacaacgatcggaggaccgaaggagct<br>aaccgcttttttgcacaacatgggggatcatgtaactcgccttgatcgttgggaaccggagctgaatgaagcc |  |

TABLE 1-continued

Exemplary Sequences

| SEQ ID NO: | Sequence* Nucleic Acid | Description |
|---|---|---|

```
ataccaaacgacgagcgacaccacgatgcctgagcaatggcaacaacgttcgcaaactattaactgg
cgaactacttactccagctccggcaacaattaatagacgaggcggataaagtgcaggaccactt
ctgcgctcggccctccggctgctggttattgtcgataaatctggagccgtgagcgtggtctcgcggta
tcattgcagcactgggcagatggtaagccctccgtatccgtagttatctacacgacgggagtcaggca
actatggatgaacgaaatagacagatcgctgagataggtgcctcactgattaagcattggtaactgtcagac
caagttaccatatatatactagattgattaaaacttcattttaaaaggatctaggtgaagatcctttttga
taatccatgaccaaaatcccttaacgtgagttttcgttccactgagcgtcagaccccgtagaaaagatcaaa
ggatcttcttgagatcctttttttctgcgcgtaatctgctgcttgcaaacaaaaaaaccaccgctaccagcggtg
gtttgtttgccggatcaagagctaccaactctttttccgaaggtaactggcttcagcagagcgcagataccaa
atactgtcctctagtgtagccgtagttagcgccaccacttcaagaactctgtagcaccgcctacatacctcgct
ctgctaatcctgttaccagtggctgctgccagtggcgataagtcgtgtcttaccgggttggactcaagacgat
agttaccggataaggcgcagcggtcgggctgaacggggggttcgtgcacacagcccagcttggagcgaa
cgacctacaccgaactgagatacctacagcgtgagctatgagaaagcgccacgcttcccgaagggaga
aaggcggacaggtatccggtaagcggcagggtcggaacaggagagcgcacgagggagcttccaggggg
aaacggggcgggagctccatggaaaaacgccagcaacgcggcctttttacggttcctggccttttgctgcttttt
gacacatgcagctcctgttatcccctgattctgtggataaccctgtattaccgcctttgagtgagctgataccg
ctcgccgcagccgaacgaccgagcgcagcgagtcagtgagcgaggaagcggaagagcgcccaatacg
caaaccgcctctccccgcgcgttggccgattcattaatgcagctggcacgacaggtttcccgactggaaag
cggcagtgagcgcaacgcaattaatgtgagttagctcactcattaggcaccccaggctttacacttttatgct
ccgctcgtatgttgtgtggaattgtgagcggataacaatttcacacaggaaacagctatgaccatgattacg
ccaggcgcaattaaccactaaaggagaacaaaagtcggagctgcaagatactggtagctagtaaacgg
actatgtagtagtcaacatgtaacaactgcctacaggtagagctgcttagcactgagatactggtagtatcacttatgat
atgccgattggtgaagtaaggtgtacatcgtgcctattaggaaggcaacagacgggtcgacatggat
tggacgaaccactgaattgccgattgcgagagatattgtattaagtgcctagctcgatacataaacgggtac
tctggttagacccagatctgagcctgggagactcctgctcgtgtgttaactagggaaaccacctgcttaagcctcaataaa
gatgcctgagtgatcaagtagtagtgtgccccgtcgtgtgtgtaactcagagatccacagaccct
tttagtcagtgtggaaaatctctagcagtggcgcccgaacaggactgaaggcgaaaaggaaaaccagag
gagactacgacgcaggactcggctgctgaagcgcgcacgggagggagcggagcggcgcacgcgcactggt
cgggggagaattagatcgcgatgggaaaaaatctcggttaaggccagggggaaaagaaaaaatataaaaattaa
aacatatagtatggcaagcagggagctagaacgattcgagttcgagccctgtagaaacatcagaag
gctgtagacaaatactggacagctacaaccatccctcagacaggatagagtaaaagacaacttagatcattatataa
tacagtagcacccctctattgtgtgcatcaaaggtagagataaagacaaagacaaggaagctttagacaagat
agaggaagagcaaaacaaaagtaagaaaaaagcacagcaagcagcagctgacacaggacacaacagccaggtcagccaa
ggagatatgagggacaattggagaagtgaattatataaatatgtagtagagggggatctataagaaattgaccattaggagtag
cacccaccaaggcaaagagaagagtggtgcagagagaaaaagagcagtggtacgctgggagctttgttccttgg
ttggctcttgggatggcagtccagagttattctaggctcattgctactgtatttgtctataaatattcataatgatagta
ttattgtctgtatagtagggtgtaatcaaatagctattacataatgcacaaatataggccaccatcctgttgcaa
ctcacagtctgggggatcctttgcttggagaatctggggcttgagtctgtggaagatacccaaagaggatcaaca
gctcctgggatttgggggttgctctggaaaactcattttgcacactgctgtgccttggaatgctagttggagta
gtaataggtctggaatagatttggaataacaacatcctgttaatataaagtacagcagaattacaacaattggagt
gcttaatacctcctaattgaagaatctgcaaaacaacaatggctggtatataaaatattcataatgatagta
taaatgggcaagtttgtgtggaattggtttaacataacaaattggctgtggtatataaaattattcataatgatagta
ggaggcttgtgtaggtttaagaatagtttttgctgtgactttctatagtgaatagagttaggcagggatattcaccat
tatcgtttcagacccacctcccaaccccgaggggacccgacaggcccgaaggaatagaagaagaaggtg
gagagagagacagagacagatccattcgattagtgaacggatctcgacggtatcggtt
```

TABLE 1-continued

Exemplary Sequences

| SEQ ID NO: | Sequence* Nucleic Acid | Description |
|---|---|---|
| 3 | ctgtttaaagaagaaaaggggggattggggggtacagtgcaggggaaagaatagtagacataatagcaaca<br>gacatacaaactaaagaattacaaaaacaattacaaaaatttattacaagacttgatcgatggct<br>ccgtgccctgcagtgggcagagcgcacatcgcccacagtccccgagaagttgggggaggggtcggc<br>aattgaaccggtgcctagagaagtggcgcgggtaaactgggaaagtgatgtcgtgtactggctccgcct<br>ttttcccgaggtggggagaaaccgtatataagtgcagtagtcgccgtgaacgtcttttcgcaacgggttg<br>cgccagacacagtgtcgtgacccgagtccaccgcgatctccgcgtaagcttagcgcagagg<br>cttgggcagccgagcggcagcaggccccgccccgggctcggttccagaagggaggagcccgc<br>caaggccgcaagagagcgggctgcctccgcagtccgagccgaggagcgcgagccgcgccggc<br>ccgacggcctcgcccgccaccATGGCTTCTGCCCGTCACCGCACTGCTGCTG<br>CCTCTGCTTCTGCTGCCACGCCCGCAAGACCAGACATTGTGCTG<br>ACACAGTCTCCTGCTCCTTAGCTGTATCTCTGGGGCAGAGGCC<br>ACCATCTCATGCAGGGCCAGCCAAAGTGTCAGTTCATCTACCTAT<br>AATTTTATACACTGTATCAACAGAAATCAGGACAGCCACCCAA<br>ACTCCTCATCAAGTATGCATCCAACCTAGAATCTGGGGTCCCTGT<br>CAGGTTCAGTGGCAGTGGGTCTGGGACAGACTTCTCCCTCAACA<br>TCCATCCTGTGGAGGAGGAGGATACTGCAACATATTACTGTCAG<br>CAGTTGGGAGATTCCATACACGTTCGGAGGGGGGCCAAGTT<br>GGAGATAAAggcagtactagcggtggtgttccggtggggggcggcagca<br>gcCAGGTGCAGCTGGAAGAGTCAGGACCTGGCCTGGTGGCACCC<br>TCACAGAGCCTGTCCATCACATGCACCGTCTCAGGATTCTCATTA<br>AGCGGCTATGGCATAAGCTGGGTTCGCCAGCCTCAGGAAAGCG<br>TCTGGAATGGCTGGGATTGATATGGGTGATGGAACCACAGACT<br>ATAATTCAGTCTCAAATCCAGACTGAGCATCAGCAAGGACAAC<br>TCCAAGAGCCAGGTTTTCTTAAAAATGAACAGTCTGCAAACTGA<br>TGACACAGCCCAGGTACTTCTGTACCAGAGGGCCTCCGGCCTTCT<br>ATAAGTACCCTACTTTGACTACTTGGGCCAAGGCACCACTCTCA<br>CAGTCTCCTCAgacaaaactcacacatgcccaccgtgcccactcctgtggcaggaccgtc<br>agtctcctcttccccccaaaaccccaaggacaccctcatgatctccggaccctgaggtcacatgcgtggt<br>ggtgacgtgagcccacgaagacccctgaggtcaagttcaactggtacgtggacggcgtggaggtgcataat<br>gccaagacaaagccgcgggaggagcagtacaacagcacgtaccgtgtggtcagcgtcctcaccgtcctg<br>caccaggactggctgaatggcaaggagtacaagtgcaaggtctccaacaaagccctcccagcccccatcg<br>agaaaaccatctccaaagccaaagggcagccccgagaaccacaggtgtacaccctgcccccatcacgag<br>atgagctgaccaagaaccaggtcagcctgacctgcctggtcaaaggcttctatcccagcgacatcgccgtg<br>gagtgggagagcaatgggcagccggagaacaactacaagaccacgcctcccgtgctggactccgacggg<br>ctccttcttcctctacagcaagctcaccgtggacaagagcaggtggcagcaggggaacgtcttctcatgctc<br>cgtgatgcatgaggctctgcacaaccactacacgcagaagagcctctccctgtctccgggtaaatga<br>gtggttggagctctggactctgtatacactgtagtaacatgacctcccccgggcccaccgtggtgaggagtaag<br>aggagcaggtggagagagtcacgtcctgctatatcttctctgagagagctagcagtggctgtgccgattcc<br>ttaccagacctatgcccaccacgattatgacaccagtacaaactactcaagaggaagatgctgtagctgccgattcc<br>atatattcaaacaacattatgacaacgatacaaactactcaagaggaagatgctgtagctgccgattcc<br>agaagaagaagaaggagagatgtgaactgagaagtgaagttcagcaggacgaaggaagaaccctcaggaaggcctgtac<br>agcaggccagaaccagctctataacgagctcaatctaggacgaaggaagaaggaaccctcaggaaggcctgtac<br>aatgaactgcagaaagataagatgccgagacctacagtgaggtgggatgaagaaggcgagcgcggag<br>gggcaagggcaccgatggctcccctgccagtgctaccaggtcttcagtacagcaccaaggacaccacgccctcac<br>ccgggccgatgctctccggtgacaagtcctctgctgcttgtggtgtaccacacagaattccctgatccca<br>cgcaaagtgtaacggaataggtattgggaattaaagactcactctccataaatgctcacagatattaaaca | CD81eader-AAV-<br>CAR-2A-EGFRt |

TABLE 1-continued

Exemplary Sequences

| SEQ ID NO: | Sequence* Nucleic Acid | Description |
|---|---|---| cttcaaaaactgcacctccatcagtggcgatctccacatcctgccggtggtgcattagggtgactccttcaca
catactcctctctgatccacaggaactgatatctcgaaaacgtaaaggaatcacaggggttttgctgat
tcaggcttggcctgaaaacaggacggacctccatgccttgagaacctagaaatcatacgcggcaggacca
agcaacatggtcagttttccttgcagtcgtcagcctgaacataacatccttgggatacgctccctcaaggag
ataagtggatggagatgtgataattcaggaaaacaaaaattgtgctatgcaaatacaataaactggaaaaact
gtttggaccttccgtcagaaaacaaaattataagcaacaagtgaaaacagctgcaaggccacagc
caggctgcgccatgcctgtctcccccgaggctgctgggggcccggagcccaggggactcgtcttgcc
ggaatgtcagccgaggcaggaatgcgtgacaccagagtcgctgcctcaggccatgaacatcacctgcacagga
cgggaccagacaactgtacacagtgcccactacattgacgcgccccactgctcaagaccctgcccgg
caggagtcatgggagaaaacaacaccctgtctggaagtacgcagacgcggccatgtgtgccacctgtg
ccatccaaactgcacctacggatgcaactggccaggcttgaaggctgtccaacgaatggcctaagatcc
tgtgaggaattcggacattcatccccgcaattcctcttggcatttggtggtgtatacattaaatgt
taataaaacaaaatggtgggcaatcattacattacattataggatatgtaattactacaggtgtattgccacaa
gacaaacatgttaagaaacttccgttatttacgctctgttcctgttaatcaacctctggattacaaaaattgtga
aagattgactgatattcctaactatgagtccattacgctgtggatatgctgctttatagcctctgatctcagct
attgcaccgtacgcgttctcctcctccgctataaaatcctggagctgtctcattaggagggagtggccc
gttgtccgtcaacgtcggggtgttcgtcgtgtgtgcgtacgcaacccccactggctgggcattgccacca
cctgtcaactccttctggacttcgcttccccctccgcatccgtggtcgtggggaagtgagtc
gccgctgtggacaggggctaggtgctggcactgataattccgtggtgtcgggaagtgagtc
ctaactccgagggggggccgtaccaagaccatagcagctgtagatcttagccactatt
aaaagaaagggggactgaagggctaatcactcccaacgagacaagatctgcttttgcttgtactgg
gtctctcggttgaccagatctgagctggagctagtagtgtgccgctgtgtgactcggtaactagagatccctcga
cccattagtcagtgtggaaaatctctagcagtagacatgtcatcttcttatttatttatcagttgcaaag
aaatgaatatcagagagtgagaggaacttgtatattgtcagcgatttagcagctgtacaataaagcaatagcatcac
aaatttcacaaataaagcattataacactccgccctaactccgcccatctccgccccatggctgactaattttttatt
tatgcagaggccgaggccgcctcggcctctgagctattccagaagtagtgaggaggcattaggaggccta
ggcatcggcgagacgctaccaatcgacctatagtgagtcgtattacgcgcgctcgagctggcggtcgatta
caacctcgtgactggaaaaccctggcgttacccaacttaatcgccttgcagcacatcccccctttcgccagct
ggcgtaatagcgaagaggccgcaccgatcgcccttcccaacagttgcgcagcctgaatggcgaatggc
gcgacgcgccctgtagcggcgcattaagcgcggcgggtgtggtggttacgcgcagcgtgaccgctacac
ttgccagcgccctagcgcccgctcctttcgctttcttcccttcctttctcgccacgttcgccggctttccccgtca
agctctaaatcggggctccctttagggttccgatttagtgctttacggcaccgccaaaacttgatt
aggtgatggttcacgtagtgggccatcgccctgatagacggtttttcgccctttgagtgtccacgttc
ataatagtggactcgaacaaccaacctccaatctcggtctattcttttgatttataaggggat
agccggactccctattggttaacaacctaacgactgctttaacggcctcctttaacaaatattaa
cgtttacaattcccaggtggcactttcgggaatgtgcgcggaacccctatttgtttattttctaaatacatt
caaatatgtatccgctcatgagacaataaccctgataaatgcttcaataatattgaaaaaggaagagtatgagt
attcaacatttccgtgtcgcccttattcccttttttgcggcattttgccttcctgtttttgctcacccagaaacgctg
gtgaaagtaaaagatgctgaagatcagttgggtgcacgagtgggttacatcgaactggatctcaacagcggg
taagatccttgagagttttcgccccgaagaacgttttccaatgatgagcacttttaaagttctgctatgtggcgc
ggtattatcccgtattgacgccgggcaagagcaactcggtcgccgcatacactattctcagaatgacttggttg
gagtactcaccagtcacagaaaagcatcttacggatggcatgacagtaagagaattatgcagtgctgccata
accatgagtgataacactgcggccaacttacttctgacaacgatcggaggaccgaaggagctaaccgcttttttg
cacaacatgggggatcatgtaactcgccttgatcgttgggaaccggagctgaatgaagccataccaaac TABLE 1-continued Exemplary Sequences

| SEQ ID NO: | Sequence*-Nucleic Acid | Description |
|---|---|---|

```
gacgagcgtgacaccacgatgcctgtagcaatggcaacaacgttgcgcaaactattaactggcgaactact
tactctagatcccggcaacaattaatagactgatggaggcggataaaagacaggaccaactgcgctc
ggccttccggctgctggttattgctgataaatctgagccggtgagcgtggtctcgcggtatcattgca
gcactgggccagatggctaagcccctcccgatcgtagctcatcacacgacgggagtcaggcaactatgga
tgaacgaaatagacagatcgctgagataggtgcctcactgattaagcattggtaactggcagaccaagttac
tcatatactcttagatgattaaaactcatctttaaaaggatctagtgaagatcccttttgataatctcat
gaccaaatccctaacgtgagtttcgttccactgagcgtcgaaccccctagaaaagatcaaagatcttctt
gagatccttttttctgcgcgtaactctgctgcttgcaacaaaaacaccgctaccagcggtggtttgtttgc
cggatcaagagctaccaactctttttccgaaggtaactggcttcagcagagcgcagataccaaatactgcct
tctagtgtagccgtagttaggccaccacttcaagaactctgctacacctgctctgcaatcc
tgttaccagtggctgctgccagtggcgataagtcgtgtcttaccgggttggactcaagacgatagttaccgga
taaggcgcagcggtcgggctgaacggggggttcgtgcacacagcccagcttgagcgaacgacctacac
cgaactgagatacctcacacgtgagcagagggagttcaggggggaaacgcctggt
gtatccggtaagcggcaggggtcggaacaggagagcgcacgagggagcttccaggggggaaacgcctggt
atattatagtcctgtcgggaggtctcctgacttgagcgtcgatatttgatcgtccagggggcgga
gcctatgaaaaacgccagcaacggccctttacgttccgtcctggcctttgctccaatgttctt
tcctcgctatcccctgattctggataacgtattaccgcctttgagtgagctgataccgctcgccgcagcc
gaacgaccgagcgcagcgagtcagtgagcgaggaagcggaagagcgcccaatacgcaaaccgcctct
ccccgcgttggccgattcattaatgcgacgcacgcagcggttcccgactgaaagcgggcagtgag
cgcaacgcaattaatgtgagttagctcactcattaggcaccccaggctttacactttatgcttccggctcgtatg
ttgtgtggaattgtgagcggataacaatttcacacaggaaacagctatgaccatgattacgccaagcgcgca
attaaccctcactaaagggaacaaaagctggagctgcaagcttaatgtagtcttatgcaatactcttgtagtctt
gcaacatgggtaacagtgagtagcaacaatccttcaaggagagaaaagcaccctgattggctatggtg
gaagtaaggtggtacgatcgtgccttattaggaaggcaacagacgggctgacatggtggacgaaccac
tgaattgccgcattgcagagatattgtatttaagtgcctagctcgatacataaacggtctctcggttagacca
gatctgagcctgggagctctgctaactagggaaccccactgttaagcctcaataaagcttggcctgagtg
cttcaagtagtgtgtgccctcgtgtgtggtaactagagatcccagacccttttagtcagtgtgg
aaaatctcagcagtggggcccgaacaggactgaaagcgaaaggagcagggagagctcctcgac
gcaggactcggctgctgaagcgaggcagaggagagagtggtcggagagcgtcagtatttaagcggggagaatt
aatttgactagcggaggctagaaggagagagtggtcggagagcgtcagtattaagcggggagaatt
agatgcaggggaaaaatcggcaggggaaaaataccagggggaaaaataaattaaaacatatagtatg
ggcaagcaggagctagaacgattcgcagttaatcctggctgttagaaacatcagaagctgtagacaa
tactggacagctacaaccatccctcagacaggatcagaagaacttagatcattatataataacagtagcaac
cctctattgtgtgcatcaaaggatagagataaaagacacaaggaagcttagacaagatagaggaagagc
aaaacaaaagtaagacaaccaccgcacagcaagcggccgctgatcctcagacctgaggaggagatatgagg
gacaattgggaagtgaattatcataaatataaaagtagtagaacattgaaccattaggagtagcaccaccaag
gcaaagagagagtggtgcagagagaaaaaagagcagtgggaataggagctttgttccttgggttccttggg
agcagcaggagcactatgggcgcagtcgtggcagctattgaaacagtacagcagcaacattgctggtga
tactggacagcctacaacatccctcagacaggatcagaagaacttagatcattatataatacagtagcaac
gcatcaagcagctcaggcaagaatcctggctgtggaaagatacctaaaggatcaacagctcctcgggggatt
tggggttgctctggaaaactcatttgcaccactgctgtgccttggaatgctagttggagtaataaatctctgga
acagatttggaataacacgacctggatggagtgggacagagaaattaacaattacacaagcttaatacactc
tttggtgaagaatcgcaaaccaacaagaaaagaatggaacaagatttattggcattggataagtgggcaag
ggtttaagaatagtttttgctgtactttctatagtgaatagagttaggcaggatattcaccattatcgttcagac
ccacctcccaaccccgaggggacccgacaggcccgaaggaatagaagaagaaggtggagagagac
agagacagatcccattcgattagtgaacggatctcgacggtatcggt
```

TABLE 1-continued

Exemplary Sequences

| SEQ ID NO: | Sequence* Nucleic Acid | Description |
|---|---|---|
| 4 | ctgtttaaagaagaaggggattggggggtacagtgcaggggaaagaatagtagacataatagcaaca gacatacaaactaaagaattacaaaaacaaattacaaaaatttatcaacaagcttgatcgatggct ccgtgccctgcagtgggcagagcgcacatcgccgcgggtaaactgggaaaagtgatgtcgtgactggctccgcct aattgaaccggtgcctagagaagtggccgggggagaaccgtatataagtcagtagtcgccgtgaacgttctttcgcaacgggtttg cgccagaacacagtgtcgtgacccgatccaccgtgccacgcgtaagccgtaagctttagcgcagagg cttgggcagccgacgcgagcgagcgggctgcctcgccagtccgagccgaggaggagcgcgagccgcggc caaggccgcaagagagcgggctctcgccgccaccATGGCTCTGCCCGTCACCGCACTGCTGCTG CCTCTGGCTCTGCTGCTGCACGCCGCAAGACCAGCATTGTGCTG ACACAGTCTCCTGCTTCCTTAGCTGTATCTCTGGGGCAGAGGGCC ACCATCTCATGCAGGGCCAGCCAAAGTGTCAGTTCATCTACCTAT AATTTTATACACTGTATCAACAGAAATCAGGACAGCCACCCAA ACTCCTCATCAAGTATGCATCCAACCTAGAATCTGGGGTCCCTGT CAGGTTCAGTGGCAGTGGGTCTGGGACAGACTTCTCCCTCAACA TCCATCCTGTGGAGGAGGAGGATACTGCAACATATTACTGTCAG GCAGGTTGGGGAGATTCCATACACGTTCGGAGGGGGGCCAAGTT GGAGATAAAggcagtactagcggtggtgttcgggggcggttccggtggggcggcagca gcCAGGTGCAGCTGGAGGAGTCAGGACCTGGCCTGGTGGCACCC TCACAGAGCCTGTCCATCACCTGCACCGTCTCAGGATTCTCATTA AGCGGCTATGGCATAAGCTGGGTTCGCCAGCCTCCAGGAAAGCG TCTGGAATGGCTGGGATTGATATGGGTGATGGAACCACAGACT ATAATTCAGTCTCAAATCCAGACTGAGCATCAGCAAGGACAAC TCCAAGAGCCAGGTTTCTTAAAAATGAACAGTCTGCAAACTGA TGAACAGCCAGGTACTTCTGTACCAGAGGCCTCCGGCCTTCT ATAAGTACCCTACTTTGACTACTGGGGCCAAGGCACCACTCTCA CAGTCTCCTCAgacaaaactcacacatgcccaccctgtggcaggaccgtc agtctcctcctcccccaaaacccaaggacaccctcatgatctccggacccctgaggtcacatgcgtggt ggtgacgtgagccacgaagaccctgaggtcaagttcaactggtacgtggacggcgtggaggtgcataat gccaagacaaagccgcgggaggagcagtacaacagcacgtaccgtgtggtcagcgtcctcaccgtcctg caccaggactggctgaatggcaaggagtacaagtgcaaggtctccaacaaagccctcccagcccccatcg agaaaaccatctccaaagccaaagggcagccccgagaaccacaggtgtacaccctgcccccatcacgag atgagctgaccaagaaccaggtcagcctgacctgcctggtcaaaggcttctatcccagcgacatcgccgtg gagtgggagagcaatgggcagccggagaacaactacaagaccacgcctcccgtgctggactccgacg gctccttcttcctctacagcaagctcaccgtggacaagagcaggtggcagcaggggaacgtcttctcatgctc cgtgatgcatgaggctctgcacaaccactacacgcagaagagcctctccctgtctccgggtaaatga gtggttggtggaggctcctggtcatgagagcctgtgtatagctgtgtgtagtacagtgacgtgttcctctggtgtctggtg aggagcaggggagtaagcggcacgttgagaggacgccctcctccccggccccaccgcaagca ttaccagccctatgcccaccaccaacttatgaccacaagctcaagagttcaggaagaaactcctgt atatttcaaacaacattatgaccacagtacaaactactcaagaggaagatgctgtagtcgcgatttcc agaagaagaagaggatgtgaactgagagtgaagttcagcaggaatgcctgacgccccggtacc agcaggccagaaccagctctataacgagctcaatctaggacgaagaagaacctcaggaaggcctgtac aatgaactgcagaaagataagatgcgggaccctacagtgaggtacctggatggaagcgagcgccgag gggcaaggggcacgatgcccctcgccagtgactacaataatatgtctcctctgaaattggcaccaccacgacgccctcac atgcagggccgGAATTCATGCCCATCCCAGGGCTCTTGCCAAGCTGG CCTTCCTTGGCCCTGGCCCATCCCCAGGAGTCTTGCCAAGCTGG | AAV-CAR-FoxP3-EGFRt |

TABLE 1-continued

Exemplary Sequences

| SEQ ID NO: | Sequence*Nucleic Acid | Description |
|---|---|---|
| | AAGACTGCACCCAAGGGCTCAGAACTTCTTAGGGACCAGGGGCTC | |
| | TGGGGACCCTTCCAAGGTGGGACCTGCAAGTGGGGCCCACA | |
| | CCTCTTCTTCCTTGAACCCCTGCCACCATCCCAGCTGCAGCTGC | |
| | CTACAGTGCCCCTAGTCATGGTGGCACCGTCTGGGGCCCGACTA | |
| | GGTCCCTCACCCCACCACTACAGGCCCTTCTTCCAGGACAGACCACA | |
| | CTTCATGCATCAGCTCTCCACTGTGGATGCCCATGCCCAGACCCC | |
| | TGTGCTCCAAGTGCGTCCACTGGACAACCCAGCCATGATCAGCC | |
| | TCCACCACCTTCTGTCTGCCACTGGGATCAATGTGGCCAGTCTGGAATGG | |
| | GGCCTGGCCTGCCACCTGGGATCAATGTGGCCAGTCTGGAATGG | |
| | GTGTCCAGGGAGCCAGCTCTACTCTGCACCTTCCCACGCTCGGGT | |
| | ACACCCAGGAAAGACAGCAACCTTTTGGCTGCACCCCAAGGATC | |
| | CTACCCACTGCTGGCCAAATGGAGTCTGCAAGTGGCCTGGTTGTG | |
| | AGAAGGTCTTCGAGGAGCCAGAAGAGTTTCTCAAGCACTGCCAA | |
| | GCAGATCATCTCCTGGATGAGAAAGGCAAGGCCCAGTGCCTCCT | |
| | CCAGAGAGAAGTGGTGCAGTCTCTGGAGCAGCAGCTGGAGCTGG | |
| | AAAAGGAGAAGCTGGGAGCTATGCAGGCCCACCTGGCTGGGAA | |
| | GATGGCGCTGGCCAAGGCTCCATCTGTGGCCTCAATGGACCAAGA | |
| | GCTCTTGCTGCATCGTAGCCACCAGTACTCAGGGCAGTGTGCTCC | |
| | CGGCCTGGTCTGCTCCTCGGGAGGCTCCAGACGGCGGCCCTGTTT | |
| | GCAGTGCGGAGGCACCCTCTGGGGAAGCCATGGCAATAGTTCCTT | |
| | CCCAGAGTTCTTCCACAACATGGACTACTTCAAGTACCACCAATAT | |
| | GCGACCCCCTTTCACCTATGCCACCCTTATCCGATGGGCCATCCT | |
| | GGAAGCCCCCGGAGAGGCAGAGGACACTCAATGAAATCTACCATT | |
| | GGTTTACTCGCCATGTTCGCCTACTTCAGAAAACCACCCCGCCACCT | |
| | GGAAGAATGCCATCCGCCCACAACCTGAGCCTGCCAAGTGCTTT | |
| | GTGCGAGTGGAGGAGCGGGAGAGGAGGCCAACGCCCCAACAAGTGC | |
| | AATTGAGTTTCGCAAGAAGGAGCCAACGCCCCAACAAGTGC | |
| | TCCAATCCCTGCCCTGAATTCTTAGAcagtgtactaattatgctctcttgaaattgg | |
| | ctggagatgttgagagcaacccggccgatgcttcctcggtgacaagccttcgtcctgtgagttaccaca | |
| | cccagcattcctcctgatcccacgcaaagtgtaacggaataagtattggtgaatttaaagactcactctcca | |
| | taaatgctacgaatattcaaacaactcaaaaactgcaactgcaactcccacatcctgccggtggc | |
| | atttagggtgactccttcacacatactcctccctcggatcccacaggaactggatatctgaaaaccgtcaagg | |
| | aaatcacaggtattgctgattcaggctttcggcttctccttcttgcccctgaaaacaggacagacctccatgcctcttgagaacctaga | |
| | aatcatacggccggcaggacaagcaacatgtcagtttggtcagttcttcttcttgcagtcgtcagcctgaacataacatccttg | |
| | ggattacgccccctccaaggagataaggagatgtgataattcaggaaaacaaaatttgtgctatgcaa | |
| | atacaataaactggaaaaactgtttgggacctccggtcagaaaccaaaattataagcaacagaggtgaa | |
| | aacagtgcaaggccacaggccagtctcctgcccggaatgtcagccgaggcagggaatgcgtggacaagtgcaacctctgg | |
| | cccaggggactggctgcctctcctgccgccggaatgtcagcgaggggatgcgtggacaagtgcaacctctgg | |
| | aggtgagccaaggacgttgtggaagaactctgagtgcataacgagtgcataccttcaggc | |
| | catgaacatcacctgcacaggacgggaccagacaactgtatccagtgtgcccactacattgacgtgcccc | |
| | cactgcgtcaagacctgcccggcaggagtcatgggagaaaaacaacaccctggtctggaagtacgagac | |
| | gccggccatgtgtgcccacctgtgccatccaaactgcacctacggatgcactggccaggtcctgaaggctg | |
| | tccaacgaatgggctaagatccctaagcagtgcctgattggtatacattaaatgttaatcaaacaaaatggtgggcaatcat | |
| | ttattcccatatttgttctgatttcttgattggtatacattaaatgttaatcaaacaaaatggtgggcaatcat | |
| | ttacatttttaggatatgtaattactagttcagttgattacaaagcacaaagcaaacaaacatttgtaagaaaactttccgtta | |
| | tttacgctcgttcctgttaatcaacctctggattacaaaattgtgaaagattgactgatatcttaactatgttgct | |
| | cctttacgtgtggtgggatatgcctgcttcccttcccttatagctctgtatgctgtttccgtacggctttcgttttctcct | |
| | cctgtataaatcctggttgctgtctctttatgaggagttgtggcccgttgtccgtcaacgtggcgtggtgtgctcc | |

TABLE 1-continued

Exemplary Sequences

| SEQ ID NO: | Sequence* Nucleic Acid | Description |
|---|---|---|
|  | tgtgttggtgacgcaacccccactggctggggcattgcacccactgtgcaccacctgtcaactccttctggacttcgcttt<br>cccctcccgatgccacggcagagactcatcgcgccctgccggctgccggctgtggacaggggctaggttg<br>ctggcactgataattccggtggttgtcgggaagctgacgtccttctctcgaggggggccgtacctt<br>aagaccaatgactacaaggcagctgagtgtagatcctgctttttggtgtttgctctgtgtactggtctctcggttgaccagatctgagcct<br>taattcactcccaacgaagacaagatctgctttttggtgtttgctctgtgtactggtctctcggttgaccagatctgagcct<br>gggagctctcggctcaaccaggagaaccccactcaagctcaagacttgccttgagtgcttcaagtagt<br>gtgtcccgctcgttgtgtgactcggtaactagagatccctcagaccctttagtcagtgtgaaaatcctag<br>cagtagtcatgtcatcttattattcagtattataactgcaaagaaatgaatcagaggagtgagga<br>cttgtttattgcagcttataatggttacaaataaagcaatagcatcaccaaataaagcattattccact<br>gcattcatgtcgtgttgtcccaaactcatcaatgtctcatctatcctggctctatccccgcccctaactcc<br>gcccagtccgcccattctccgcccatggctgacctaattttttttattttatgcagaggccgaggccgcctcgg<br>cctctgagctattccagaagtagtgaggaggcttttttggaggcctaggcttttgcctgaacgtaccaaatt<br>cgtaccccttatcgattctgaccgccctccccttcgccagctgatggtgatggctcacgtagtgggccat<br>cgatcgccctccaacagtcgcgagccgtagccgtacaattgccagccgcctagcgccgcctcttt<br>agcgcggggttgtggttacggcagcgtgaccgctacacttgccagtcgccctagccgcctctt<br>gttccgattcagttagtgcttcacggcacctcgacccaaaaaacttgattaggtgatggttcacgtagtgggccat<br>cgcctgatagacgtttctcgccccttgacgttggagtccagtcacgttcttaatagtgactcttgttccaaactgg<br>aacaacactcaaccctatctcgtctctattctttgatttataaggattcacaaaaatattaacgttacaattcccaggtggcactttc<br>atgagctgattcacaaaatttaacgaagactattaacgttacaattcaaatacattcaaatatgtatccgctcatgagacaata<br>gggaaatgtgcgcggaaccccctatttgtttatttttctcaaatacattccaaatacattcaaatatgtatccgctcatgagacaata<br>acccgataaatgctcaataaaccagccattgtcaataataatcattcaacattccgtctgcccttattcc<br>cttattgcggcatttttgccttcctgtttttgctcaccagaaacgctggtgaaagtaaaagatgctgaagatcag<br>ttggtgcacgagtgggttacatcgaactggatctcaacagcggtaagatccttgagagttttcgccccgaa<br>gaacgttttccaatgatgagcactttaaagttctgctatgtggcgcggtattatcccgtattgacgccgggcaa<br>gagcaactcggtcgccgcatacactattctcagaatgacttggttgagtactcaccagtcacagaaaagcat<br>cttacggatggcatgacagtaagagaattatgcagtgctgccataaccatgagtgataacactgcggccaac<br>ttacttctgacaacgatcgggaggaccgaaggagctaaccgcttttttgcacaacatgggggatcatgtaactc<br>gccttgatcgttgggaaccggagctgaatgaagccataccaaacgacgagcgtgacaccacgatgcctgt<br>agcaatggcaacaacgttgcgcaaactattaactggcgaactacttactctagcttcccggcaacaattaata<br>gactggatggaggcggataaagttgcaggaccacttctgcgctcggcccttccggctggctggtttattgct<br>gataaatctggagccggtgagcgtgggtctcgcggtatcattgcagcactggggccagatggtaagccctc<br>ccgtatcgtagttatctacacgacggggagtcaggcaactatggatgaacgaaatagacagatcgctgaga<br>taggtgcctcactgattaagcattggtaactgtcagaccaagtttactcatatatactttagattgatttaaaacttc<br>catttttaatttaaaaggatctaggtgaagatcctttttgataatctcatgaccaaaatcccttaacgtgagttttcg<br>ttccactgagcgtcagaccccgtagaaaagatcaaaggatcttcttgagatccttttttctgcgcgtaatctgc<br>tgcttgcaaacaaaaaaaccaccgctaccagcggtggtttgtttgccggatcaagagctaccaactcttttcc<br>gaaggtaactggcttcagcagagcgcagataccaaatactgtccttctagtgtagccgtagttaggccacca<br>cttcagaactctgtagcaccgcctacatacctcgctctgctaatcctgttaccagtggctgctgccagtggc<br>gataagtcgtgtcttaccgggttggactcaagacgatagttaccggataaggcgcagcggtcgggctgaac<br>ggggggttcgtgcacacagcccagcttggagcgaacgacctacaccgaactgagatacctacagcgtga<br>gctatgagaaagcgccacgcttcccgaagggagaaaggcggacaggtatccggtaagcggcagggtcg<br>gaacaggagagcgcacgagggagcttccagggggaaacgcctggtatctttatatagtcctgtcgggtttcgc<br>cacctctgacttgagcgtcgatttttgtgatgctcgtcaggggggcggagcctatggaaaaacgccagcaac<br>gcggcctttttacggttcctggccttttgctggccttttgctcacatgttctttcctgcgttatcccctgattctgtg<br>gataaccgtattaccgcctttgagtgagctgataccgctcgccgcagccgaacgaccgagcgcagcgagt<br>cagtgagcgaggaagcggaagagcgcccaatacgcaaaccgcctctccccgcgcgttggccgattcatta | |

TABLE 1-continued

Exemplary Sequences

| SEQ ID NO: | Sequence*·Nucleic Acid | Description |
|---|---|---|
|  | atgcagctgcacgacaggttcccgactggaagcgggcagtgagcgcaacgcaattaatgtgagttag | |
|  | ctcactcattaggcaccccaggctttacacttatgcttccggctcgtatgttgtgtggaattgtgagcggataa | |
|  | caatttcacacaggaaacagctatgaccatgattacgccaagcgcgcaattaaccctcactaaagggaaca | |
|  | aaagctggagctgcaagcttaatgtagtcttatgcaatactcctgtagtcttgcaacatgtacgatgagttag | |
|  | caacatgccttacaaggagagaaaaagcaccgtgcatgccgattggtggaagtaggtggtacgatcgtg | |
|  | ccttattaggaaggcaacacggtctgacaacgatccgcccacgtgaattgcgcattgcgcattcgcagagat | |
|  | attgtatttaagtgcctagctcgatacataaacggttctctcttgttagccagatctgagcctggggagctctct | |
|  | ggctaactagggaaccccactgcttaagcctcaataaagcttgccttgagtgcttcaagtagtgtgtgcccgtct | |
|  | gaacagggactcttgaaagcgaaagggaaaccagaggagctctcgcagagacccggcttgctgaagc | |
|  | gcgcacggcaagaggcgaggggcggcgactggtgagtacgccaaaaattttgactagcggaggctaga | |
|  | aggagagagatggtgcgagagcgtcagtattaagcgggggagaattagatcggatgggagaaaattc | |
|  | ggttaagccagggggaaagaaaaaatataaattaaaacatatagtatgggcaagcagggagctagaacg | |
|  | attccgcagttaatcctggcctgttagaacaggctgtgacaaatactggacagctacaaccatc | |
|  | cctcagacaggatcagaagaacttagatcattatataatacacagtagcaaccctctattgtgtgcatcaaagga | |
|  | tagagataaaagacaccaaggaagctttagacaagatagaggaagagcaaaacaaaagtaagaccaccg | |
|  | cacagcaagcggccgctgatcctcagacctggaggaggagatatgagggacaattggagaagtgaattat | |
|  | ataaatataaagtagtaaaattggaaccattaggagtagcacccaccaaggcaaagagaagagtggtgcag | |
|  | agagaaaaaagagcagtgggaataggagctttgttccttgggttcttgggagcagcaggaagcactatggg | |
|  | cgcagcgtcaatgacgctgacggtacaggccagacaattattgtctggtatagtgcagcagcagaacaattt | |
|  | gctgagggctattgaggcgcaacagcatctgttgcaactcacagtctggggcatcaagcagctccaggcaa | |
|  | gaatcctggctgtggaaagatacctaaaggatcaacagctcctggggatttggggttgctctggaaaactca | |
|  | tttgcaccactgctgtgccttggaatgctagttggagtaataaatctctggaacagatttggaatcacacgacc | |
|  | tggatggagtgggacagagaaattaacaattacacaagcttaatacactccttaattgaagaatcgcaaaacc | |
|  | agcaagaaaagaatgaacaagaattattggaattagataaatgggcaagtttgtggaattggtttaacataac | |
|  | aaattggctgtggtatataaaattattcataatgatagtaggaggcttgtaggtttaagaatagtttttgctgtgac | |
|  | ttctatagtgaatagagttaggcagggatattcaccattatcgtttcagacccacctcccaaccccgaggggg | |
|  | acccgacaggcccgaaggaatagaagaagaaggtggagagagacagagacagatccattcgattagt | |
|  | gaacggatccgacggtatcggtt | |
| 5 | GTCGACATTGATTATTGACTAGATCATCGCGTGAGGCTCCGGTGC | EF1 alpha |
|  | CCGTCAGTGGGCAGAGCGCACATCGCCCACAGTCCCCGAGAAGT | |
|  | TGGGGGGAGGGGTCGGCAATTGAACCGGTGCCTAGAGAAGGTG | |
|  | GCGCGGGGTAAACTGGGAAAGTGATGTCGTGTACTGGCTCCGCC | |
|  | TTTTTCCCGAGGGTGGGGGAGAACCGTATATAAGTGCAGTAGTC | |
|  | GCCGTGAACGTTCTTTTTCGCAACGGGTTTGCCGCCAGAACACA | |
|  | GGTAAGTGCCGTGTGTGGTTCCCGCGGGCCTGGCCTCTTTACGGG | |
|  | TTATGGCCCTTGCGTGCCTTGAATTACTTCCACGCCCCTGGCTGC | |
|  | AGTACGTGATTCTTGATCCCGAGCTTCGGGTTGGAAGTGGGTGG | |
|  | GAGAGTTCGAGGCCTTGCGCTTAAGGAGCCCCTTCGCCTCGTGCT | |
|  | TGAGTTGAGGCCTTGCCGCTGGGCGCCGGCCGCCGCGTGCGAAT | |
|  | CTGGTGGCACCTTCGCGCCTGTCTCGCTGCTTTCGATAAGTCTCT | |
|  | AGCCATTTAAAATTTTGATGACCTGCGCGACGCCTTTTTTTCTG | |
|  | GCAAGATAGTCTTGTAAATGCGGGCCAAGATCTGCACACTGGTA | |
|  | TTTCGGTTTTTGGGGCCGCGGGGCGGCGACGGGGCCCGTGCGTCC | |
|  | CAGCGCACATGTTCGGCGAGGCGGGGCCTTGCGAGCGCGGCCACC | |
|  | GAGAATCGGACGGGGGTAGTCTCAAGCTGGCCGGCCTGCTCTGG | |
|  | TGCCTGGCCTCGCGCCGCCGTGTATCGCCCCGCCCTGGGCGGGCA | |

TABLE 1-continued

Exemplary Sequences

| SEQ ID NO: | Sequence* Nucleic Acid | Description |
|---|---|---|
| | AGGCTGGCCCGGTCGGCACCAGTTGCGTGAGCGGAAAGATGGCC | |
| | GCTTCCCGGCCCTGCTGCAGGGAGCTCAAAATGGAGGACGCGGC | |
| | GCTCGGGAGACGCGGCGCGGTGAGTCACCCACACAAAGGAAAAG | |
| | GGCCTTTCCCGTCCTCAGCCGTCGCTTCATGTGACTCCACGGAGTA | |
| | CCGGGCGCCGTCCAGGCACCTCGATTAGTTCTCGAGCTTTTGGAG | |
| | TACGTCGTCTTAGGTTGGGGGAGGGGGTTTATGCGATGGAGTT | |
| | TCCCACACTGAGTGGGTGGAGACTGAAGTTAGGCCAGCTTGGC | |
| | ACTTGATGTAATTCTCCTTGGAATTGCCCTTTTTGAGTTTGGATC | |
| | TTGGTTCATTCTCAAGCCTCAGACAGTGGTTCAAAGTTTTTTTCTT | |
| | CCATTTCAGGTGTCTGAGGAATTCTGCAGTCGACGGTACCGCG | |
| | GGCCCGGGATCCACCCGGTCGCCACCATGGTGAGCAAGGGCGAG | |
| | GAGCTGTTCACCGGGGTGGTGCCCATCCTGGTCGAGCTGGACGG | |
| | CGACGTAAACGGCCACAAGTTCAGCGTGTCCGGCGAGGGCGAG | |
| | GGCGATGCCACCTACGGCAAGCTGACCCTGAAGTTCATCTGCAC | |
| | CACCGGCAAGCTGCCCGTGCCCTGGCCCACCCTCGTGACCACCC | |
| | TGACCTACGGCGTGCAGTGCTTCAGCCGCTACCCCGACCACATG | |
| | AAGCAGCACGACTTCTTCAAGTCCGCCATGCCCGAAGGCTACGT | |
| | CCAGGAGCGCACCATCTTCTTCAAGGACGACGGCAACTACAAGA | |
| | CCCGCGCCGAGGTGAAGTTCGAGGGCGACACCCTGGTGAACCGC | |
| | ATCGAGCTGAAGGGCATCGACTTCAAGGAGGACGGCAACATCCT | |
| | GGGGCACAAGCTGGAGTACAACTACAACAGCCACAACGTCTATA | |
| | TCATGGCCGACAAGCAGAAGAACGGCATCAAGGTGAACTTCAA | |
| | GATCCGCCACAACATCGAGGACGGCAGCGTGCAGCTCGCCGACC | |
| | ACTACCAGCAGAACACCCCCATCGGCGACGGCCCCGTGCTGCTG | |
| | CCCGACAACCACTACCTGAGCACCCAGTCCGCCCTGAGCAAAGA | |
| | CCCCAACGAGAAGCGCGATCACATGGTCCTGCTGGAGTTCGTGA | |
| | CCGCCGCCGGGATCACTCTCGGCATGGACGAGCTGTACAAGTAA | |
| | AGCGGCCGCACTCCTCCAGGTGCAGGCTGCCTATCAGAAGGTGGT | |
| | GGCTGGTGTGGCCAATGCCCTGGCTCACAAATACCACTGAGATC | |
| | TTTTTCCCTCTGCCAAAAATTATGGGGACATCATGAAGCCCCTTG | |
| | AGCATCTGACTTCTGCTAATAAAGGAAATTTATTTTCATTGCAA | |
| | TAGTGTTGTTGGAATTTTTGTGTCTTCACTCGGAAGGACATATG | |
| | GGAGGGCAAATCATTTAAAACATCAGAATGAGTATTTGGTTTAG | |
| | AGTTTGGCAACATATGCCCATATGCTGGCTGCCATGAACAAAGG | |
| | TTGGCTATAAAGAGGTCATCAGTATATGAAACAGCCCCCTGCTG | |
| | TCCATTCCTTATTCCATAGAAAAGCCTTGACTTGAGGTTAGATTT | |
| | TTTTTATATTTTGTTTTGTGTTATTTTTTTCTTTAACATCCCTAAAA | |
| | TTTTCCTTACATGTTTTACTAGCCAGATTTTTCCTCCTCCTGAC | |
| | TACTCCAGTCATAGCTGTCCCTCTTGTTCTTATGGAGATCCCTCG | |
| | ACCTGCAGCCCAAGCTTGGCGTAATCATGGTCATAGCTGTTTCCT | |
| | GTGTGAAATTGTTATCCGCTCACAATTCCACACAACATACGAGC | |
| | CGGAAGCATAAAGTGTAAAGCCTGGGGTGCCTAATGAGTGAGCT | |
| | AACTCACATTAATTGCGTTGCGCTCACTGCCCGCTTTCCAGTCGG | |
| | GAAACCTGTCGTGCCAGCTGCATTAATGAATCGGCCAACGCGCA | |
| | CCATAGTCCCGCCCCTAACTCCGCCCATCCGCCCCCTAACTCCGC | |
| | CCAGTTCCGCCCATTCTCCGCCCCATGGCTGACTAATTTTTTTTAT | |
| | TTATGCAGAGGCCGAGGCCGCCTCGGCCTCTGAGCTATTCCAGA | |
| | AGTAGTGAGGAGGCTTTTTTGGAGGCCTAGGCTTTTGCAAAAAG | |

TABLE 1-continued

Exemplary Sequences

| SEQ ID NO: | Sequence* Nucleic Acid | Description |
|---|---|---|

CTAACTTGTTTATTGCAGCTTATATATGGTTACAAATAAAGCAATA
GCATCACAAATTCACAAATAAAGCATTTTTTCACTGCATTCTA
GTTGTGGTTTGTCCAAACTCATCAATGTATCTTATCATGTCTGGA
TCCGCTGCATTAATGAATCGGCCAACGCGCGGGAGAGGCGGTT
TGCGCTATTGGGCGCGCTCTTCCGCTTCCTCACTGACTCGCTGC
GCTCGGTCGTTCGGCTGCGGCGAGCGGGTATCAGCTCACTCAAAG
GCGGTAATACGGTTATCCACAGAATCAGGGGGATAACGCAGGAA
AGAACATGTGAGCAAAAGGCCAGCAAAAGGCCAGGAACCGTAA
AAAGGCCGCGTTGCTGGCGTTTTTCCATAGGCTCCGCCCCCCTGA
CGAGCATCACAAAAATCGACGCTCAAGTCAGAGGTGGCGAAAC
CCGACAGGACTATAAAGATACCAGGCGTTTCCCCCTGGAAGCTC
CCTCGTGCGCTCTCCTGTTCCGACCCTGCCGCTTACCGGATACCT
GTCCGCCTTTCTCCCTTCGGGAAGCGTGGCGCTTTCTCATAGCTC
ACGCTGTAGGTATCTCAGTTCGGTGTAGGTCGTTCGCTCCAAGCT
GGGCTGTGTGCACGAACCCCCCGTTCAGCCCGACCCGCTGCGCCT
TATCCGGTAACTATCGTCTTGAGTCCAACCCGGTAAGACACGAC
TTATCGCCACTGGCAGCAGCCACTGGTAACAGGATTAGCAGAGC
GAGGTATGTAGGCGGTGCTACAGAGTTCTTGAAGTGGTGGCCTA
ACTACGGCTACACTAGAAGAACAGTATTTGGTATCTGCGCTCTG
CTGAAGCCAGTTACCTTCGGAAAAAGAGTTGGTAGCTCTTGATC
CGGCAAACAAACCACCGCTGGTAGCGGTGGTTTTTTTGTTTGCAA
GCAGCAGATTACGCGCAGAAAAAAGGATCTCAAGAAGATCCTT
TGATCTTTTCTACGGGGTCTGACGCTCAGTGGAACGAAAACTCA
CGTTAAGGGATTTTGGTCATGAGATTATCAAAAAGGATCTTCAC
CTAGATCCTTTTAAATTAAAAATGAAGTTTTAAATCAATCTAAAG
TATATATGAGTAAACTTGGTCTGACAGTTACCAATGCTTAATCAG
TGAGGCACCTATCTCAGCGATCTGTCTATTTCGTTCATCCATAGT
TGCCTGACTCCCCGTCGTGTAGATAACTACGATACGGGAGGGCT
TACCATCTGGCCCCAGTGCTGCAATGATACCGCGAGACCCACGC
TCACCGGCTCCAGATTTATCAGCAATAAACCAGCCAGCCGGAAG
GGCCGAGCGCAGAAGTGGTCCTGCAACTTTATCCGCCTCCATCC
AGTCTATTAATTGTTGCCGGGAAGCTAGAGTAAGTAGTTCGCCA
GTTAATAGTTTGCGCAACGTTGTTGCCATTGCTACAGGCATCGTG
GTGTCACGCTCGTCGTTTGGTATGGCTTCATTCAGCTCCGGTTCC
CAACGATCAAGGCGAGTTACATGATCCCCCATGTTGTGCAAAAA
AGCGGTTAGCTCCTTCGGTCCTCCGATCGTTGTCAGAAGTAAGTT
GGCCGCAGTGTTATCACTCATGGTTATGGCAGCACTGCATAATTC
TCTTACTGTCATGCCATCCGTAAGATGCTTTTCTGTGACTGGTGA
GTATCAACCAAGTCATTCTGAGAATAGTGTATGCGGCGACCGA
GTTGCTCTTGCCCGGCGTCAATACGGGATAATACCGCGCCACAT
AGCAGAACTTTAAAAGTGCTCATCATTGGAAAACGTTCTTCGGG
GCGAAAACTCTCAAGGATCTTACCGCTGTTGAGATCCAGTTCGA
TGTAACCCACTCGTGCACCCAACTGATCTTCAGCATCTTTTACTT
TCACCAGCGTTTCTGGGTGAGCAAAAACAGGAAGGCAAAATGCC
GCAAAAAAGGGAATAAGGGCGACACGGAAATGTTGAATACTCA
TACTCTTCCTTTTTCAATATTATTGAAGCATTTATCAGGGTTATTG
TCTCATGAGCGGATACATATTTGAATGTATTTAGAAAAATAAAC
AAATAGGGGTTCCGCGCACATTTCCCCGAAAAGTGCCACCTGG

TABLE 1-continued

Exemplary Sequences

| SEQ ID NO: | Sequence* Nucleic Acid | Description |
|---|---|---|
| 6 | GCCACGGGCGGAACTCATCGCCGCCTGCCTTGCCCGCTGCTGGAC AGGGGCTCGGCTGTTGGGCACTGACAATTCCGTGGT | Woodchuck Hepatitis Virus Posttranscriptional Regulatory Element Alpha Component |
| 7 | AATCAACCTCTGGATTACAAAATTTGTGAAAGATTGACTGGTATT CTTAACTATGTTGCTCCTTTTACGCTATGTGGATACGCTGCTTTA ATGCCTTTGTATCATGCTATTGCTTCCCGTATGGCTTTCATTTTCT CCTCCTTGTATAAATCCTGGTTGCTGTCTCTTTATGAGGAGTTGT GGCCCGGTTGTCAGGCAACGTGGCGTGGTGTGCACTGTGTTTGCTG ACGCAACCCCACTGGTTGGGGCATTGCCACCACCTGTCAGCTC CTTTCCGGGACTTTCGCTTTCCCCCTCCCTATTGCCACGGCGGAA CTCATCGCCGCCTGCCTTGCCCGCTGCTGGACAGGGGCTCGGCTG TTGGGCACTGACAATTCCGTGGTGTTGTCGGGGAAGCTGACGTC CTTTCCATGGCTGCTCGCCTGTGTTGCCACCTGGATTCTGCGCGG GACGTCCTTCTGCTACGTCCCTTCGGCCCTCAATCAGCGGACCT TCCTTCCCGCGGCTGCTGCCGGCTCTGCGGCCTCTTCCGCGTCT TCGCCTTCGCCCTCAGACGAGTCGGATCTCCCTTTGGGCCGCCTC CCCGCCTG | Woodchuck Hepatitis Virus Posttranscriptional Regulatory Element |
| 8 | EGRGSLLTCGDVEENPGP | T2A |
| 9 | ATNFSLLKQAGDVEENPGP | P2A |
| 10 | QCTNYALLKLAGDVESNPGP | E2A |
| 11 | VKQTLNFDLLKLAGDVESNPGP | F2A |
| 12 | GSGEGRGSLLTCGDVEENPGP | T2A |
| 13 | GSGATNFSLLKQAGDVEENPGP | P2A |
| 14 | GSGQCTNYALLKLAGDVESNPGP | E2A |
| 15 | GSGVKQTLNFDLLKLAGDVESNPGP | F2A |
| 16 | ctgtttaaaagaaaaggggggattggggggtacagtgcaggggaaagaaataagaatagcaaca gacatacaaaactaaagaattacaaaaacaaattcaaaaatttatcaacaagcttgatcgatggct ccggtgccctgcagtgggcagaggcagcatcgcccacagtccccgagaagttggggggaggtcggc aattgaaccggtgcctagagaaggtggccgggtaaactgggaaagtgatgtcgtgtactggctccgct ttttcccgaggtgggggagaaacctatataagtgcagtagtcgccgtgaacgttcttttcgcaacgggtttg ccgccagaacacagtgtcgtgacgcgatccacgccgtcggcccgaccctgtgaacccgtgtcgcagagg cttgggcagccgagcgagcggctggccaaggactccgagctcgagtccgatggagccgcgcggc caaggcgcgcaagagagcgggctccgccgccgccaccatggctctgccccgtctggccgcctcacccgaccctggtcctctggctgctgc ccggaggcggctcgccgccgccaccatgctctgcccctctgggcctctggctgctgctg | 64-AAV-CAR-T- Regs sequence |

TABLE 1-continued

Exemplary Sequences

| SEQ ID NO: | Sequence* Nucleic Acid | Description |
|---|---|---|
| | acgcgcaagaccagacattgtgacacagtctcctgtcttcctttagtgtatcctcgggcagagggcca<br>ccatctcatgcaggccagccaaagtgtcagttcatctactataatttatacactggatcaacagaaatca<br>ggacagccaccaaactcctcatcaagtatgcatccaacctagaatctgggtccctgtcagttcagtggc<br>agtgggtctgggacagacttctccctcaacatccatcctgtgaggagggaggactgcaacatattactgtc<br>agcacagttgggagattccatacacgttcggaggggggaccaagctggagatcaaaaggcgtactagcgg<br>tggttgctccggggtccgccggggccgcagtcggtggcctgcacggagtcaggacctg<br>gctggtggcaccctttcacagagcctgtccatcacatgcaccgtctcaggattcttcattaagcggctatggcat<br>aagtgggtcgccagcctccagggaaagcctggagtggctgggttgatcatgggtgatggaaccaca<br>gactataattcagtctccaaatccagactgagcatcagcaaggacaaccaaggagcagttttcttaaaaa<br>tgaacagtcgcaaactgatgacacaggcactcctgtaccagaggccctccggccttctataagtacct<br>ctactttgactactggggccaaggcaccactctcacagtctcctcactcgacccccaaactctctgacaaaact<br>cacacatgcccaccgtgcccagcacctgaggcaggaccgtcagtcttcctcttccccccaaaacccaa<br>ggacaccctcatgatctcccggacccctgaggtcacatgcgtggtggtggacgtgagccacgaagaccct<br>gaggtcaagttcaactggtacgtggacggcgtggaggtgcataatgccaagacaaagccgcgggaggag<br>cagtaccagagcacgtaccgtgtggtcagcgtcctcaccgtcctgcaccaggactggctgaatggcaagg<br>agtacaagtgcaaggtctccaacaaagccctcccagcccccatcgagaaaaccatctccaaagccaaagg<br>gcagccccgagaaccacaggtgtacaccctgcccccatcccgggatgagctgaccaagaaccaggtcag<br>cctgacctgcctggtcaaaggcttctatcccagcgacatcgccgtggagtgggagagcaatgggcagccg<br>gagaacaactacaagaccacgcctcccgtgctggactccgacggctccttcttcctctacagcaagctcacc<br>gtggacaagagcaggtggcagcaggggaacgtcttctcatgctccgtgatgcatgaggctctgcacaacc<br>actacacgcagaagagcctctccctgtctccgggtaaatga<br>ctgagagtgaagttcagcaaggtacgtggagtgccagccgatcagagctcctgccatggcctctctgaac<br>gagcaaattaggatacccagagagaagagcagacgctggccgcggaccctgagatgg<br>gggaaagccgagaaggaaaacccaggaaaggccgacgtggagggcacgatggcccaagaaagtaagatggcg<br>gaggcctacagtgctgacaggcaaagggccaaccacgacacctcacatgcaggcccctgccccctgccagtgt<br>actaatttatctcctgaaattggctcggaaatgtgagagcaacccgggccggaattcatgcccaacccta<br>ggccagccaagctcatggcctccttccttgcccatccccagggtccttggcccatttgccaagctggaagactg<br>cacccaagggctcagaacttctagggacccaggggctctgccacccatcccagctgcagtgcgccctagt<br>catgtgtgcaccgctggggccgtctcccaccacccaccctcggggagtcctctcccaggacgacca<br>cacttcatgcatcagctctgatctcccaccactctgctgccgactggggttgctctccccctcaaggccggccactggac<br>aaccagccagtgatcagctccaccaccttggctgctgcagaagtcggcctcacctgcgcaccttccca<br>cgtcgacccggatcaatggcctggcggtgtgagacatgtgagggagcagagagttctcaagcactgccaa<br>atggagtctgcagctccggtgtggaggctccggggaggctgcagtgcagccggtgttgcagtgcggcacct<br>gcagatcatctcctgatgagaaggcaaggccagtgctcctccagagagaagtgtgcagtctctgg<br>agcagcaggtggactggagctggaaaggagaagggagctgctatgcagcccacctgctggaagatggcg<br>ctggccaaggtccatctgtggctccaatggacaagaggctcttgctcatcgtgctagccacagtactcagggc<br>agtgtgtccccggctggtgctgtcggaggctccagagcggcgccttgcagtgcggaggcacct<br>ctgggaagcccatgcaatagcaataagtctccttcccagagttctccacaacatggacttcttcaagtaccacaatatg<br>cgacccctttcacctactgcgcaccccttatccgatggcgcatcctggaacgccccggagaggcagaggacact<br>caatgaaatctaccatggttactcgcatgttcgcctacttccagaaaaccaccccgcaccctgaagaaatgcc<br>atccgccacaacctagcctgcacaagtgcttgtgcgagtgacctggagagcagaggaggagagtgtggacc | Description |

TABLE 1-continued

Exemplary Sequences

| SEQ ID NO: | Sequence*-Nucleic Acid | Description |
|---|---|---|
| | gtagatgaattgagtttcgcaagaagagagagccaacgcccaacaagtgctccaatcctgccccagtg | |
| | tactaattatgctcctgaaattggctggagatgttgagagcaaccccggccgatgccacctctcgcctc | |
| | ctcttctcctcctttcctcacccccatggaagtcagccgcggaaccctcagtggtgaagtggaagag | |
| | ggagtaacgctgtgctgcagtgctgcctcaaggggacctcagatgccccactcagcagctgacctggtctc | |
| | gggagtccccgcttaaaccctcttaaaacctcagcctgggctgccaggcctggaatccacatgaggccc | |
| | ctggccatccggctttcacctctcaacagtgggggcttctcacctgtgccagccggggcccc | |
| | cctctgagaaggcctggcagcctggcctggctgttggctgacagtcaatggagggcagcgggagcgttccgttgga | |
| | atgttcgacctcagtgctggccagcctggctgtggtgccgaaggcctcaagaccgccctgagatctggaggagccct | |
| | ccgttgtgtcccaccgaggacagcagcctcagccagacgcccagaccccctcctgacccatgtgcac | |
| | acacctggcctgctctgtgggtacccccgactctgtccagggcccctcctgaccatatgtgggtaa | |
| | tgggacgggtcctgttgtcccggccacagctcaagacgctgaaagtattattgtcaccggcggcaacc | |
| | tgaccatccaacctgagacactgctcggcccagtactatggcactggcgaggactgtggggct | |
| | ggaagtctcagctgactggctattgactctctgcctgtccctgtgggcattcttcatcctcaaaga | |
| | gcctggtctgagagaggaaaagatgattagataaattgaataaaacaaaatggtgggcaacatttacattttaggggatat | |
| | tgtttttcctgattgggtatacattaaatgttaataaacaacatgttaagaaacttcccgttattacgctctgttcctgt | |
| | gtaattactagttcaggtgtgccacaagacaaacatgttaagaaacttcccgttattacgctctgttcctgt | |
| | taatcaaccctgattacaaaattgtgaaagatgactgatatctctaactatgtgtcctttacgctgtgtgg | |
| | atatgctgcttttatagcctctgtatctagctattgttcccgtacggctttttcctcctctgtataatcctgg | |
| | ttgtgtctctttagaggagttggccccgttgccgtcgtcggctgtggtgtctgtttgctgacgca | |
| | accccactggctgggcattgccaccactgtcaactcctttctgggatttcgcttcccccctccgatcgc | |
| | cacggagaactcatcgcgtcgccgctgccgcgactaggtgctggcactgataatt | |
| | ccgtggtgttgtcgggaagctgacgtcgtccttcctcgaggggggcccgtaaccttaagaccaatgactta | |
| | caagcagctgtagatctggcttttgctactggtctctctgttagaccagatctgagctcggggagctctggcta | |
| | aagacaagatctgtttttgcttgactggtctctctgttagaccagatctgagctcggggagctctggcta | |
| | actaggaaccccacgctaagcctcaagctgcctggctgtggtgtgccgctgttgt | |
| | gtgactctggtaactagagatccccccagaccctttagtcagtggaaaatcctagcagtagtagttcatgtc | |
| | atcttattattcagatcgattctaaactgcaagaaatgaatatcagagagtgagaggaacttgttattgcagcttat | |
| | aatgttacaaataataagcaatagcatcacaaaattcacaaataaagcattttttcactgcatctcagttgtgtttt | |
| | gtccaaaacctgtctatcttctatatgctcggtgctagctatccgcccagtccgcccat | |
| | tctccgcccatggctgactaattatttttattatgcagaggccgcaggcccgcctcggcctcgagctattccag | |
| | aagagtgaggagctgctttttggaggcctgaggtcttgcgtcgagacgtcaccaattcgcccctatagtgagtc | |
| | gtattacgcgcgctcactggccgtcgttttacaacgtcggtttttacaacctggaaaacctggctaccaacttaat | |
| | cgccttgcagcacatccccctttcgccagctggcgtaatagcgaagaggcccgcaccgatcgcccttccca | |
| | acagttgcgcagcctgaatggcgaatgggacgcgccctgtagcggcgcattaagcgcggcgggtgt | |
| | ggtggttacgcgcagcgtgaccgctacacttgccagcgccctagcgcccgctcctttcgctttcttccctt | |
| | ttccgccacgttcgccggctttccccgtcaagctctaaatcggggcatccctttagggttccgatttagtgctt | |
| | tacggcacctcgaccccaaaaaacttgattagggtgatggttcacgtagtgggccatcgccctgatagacg | |
| | gtttttcgccctttgacgttggagtccacgttctttaatagtggactcttgttccaaactggaacaacactcaacc | |
| | ctatctcggtctattcttttgatttataagggatttgccgatttcggcctattggttaaaaaatgagctgatttaac | |
| | aaaaatttaacgcgaattttaacaaaatattaacgtttacaatttccggtggcacttttcgggaaatgtgcg | |
| | cggaacccctatttgtttatttttctaaatacattcaaatatgtatccgctcatgagacaataaccctgataaatgc | |
| | ttcaataatattgaaaaaggaagagtatgagtattcaacatttccgtgtcgcccttattcccttttttgcggcattt | |
| | gccttcctgtttttgctcacccagaaacgctggtgaaagtaaaagatgctgaagatcagttgggtgcacgagt | |
| | gggttacatcgaactggatctcaacagcggtaagatccttgagagttttcgccccgaagaacgttttccaatg | |
| | atgagcacttttaaagttctgctatgtggcgcggtattatcccgtattgacgccgggcaagagcaactcggtc | |
| | gccgcatacactattctcagaatgacttggttgagtactcaccagtcacagaaaagcatcttacggatggcat | |

TABLE 1-continued

Exemplary Sequences

| SEQ ID NO: | Sequence*Nucleic Acid | Description |
|---|---|---|
| | gacagtaagagaattatgcagtgctgccataaccatgagtgatgataacactcgcggccaacttacttctgacaac | |
| | gatcggaggaccgaggagctaaccgctttttgcacaacatggggatcatgtcatgtaactcgccttgatcgttg | |
| | ggaaccggagctgaatgaagccataccaaacgacgagcgtgacaccacgatgcctgtagcaatgcaac | |
| | aacgttgccaaactattaactggcgaactacttactctagcctcccgcaacaattaatagactggatggag | |
| | gcggataaagttgcaggaccacttctgcgctcggccctccggctggcttgtggtttattgctgataaatctggag | |
| | ccggtgagcgtgggtctgcgcggtatcattgcagcactggggccagtgagtcaagcctccgtatcgtagtta | |
| | tctacacgacggggagtcaggcaactatggatgaacgaaatagacagatcgctgagataggtgcctcactg | |
| | attaagcattggtaactggtcagaccaagttactcatatacttagattgatttaaaacttcattttaatttaaaa | |
| | ggatctaggtgaagatcctttttgataatctcatgaccaaaatcccttaacgtgagttttcgttccacttgagcgtc | |
| | agaccccgtagaaaagatcaaaggatcttcttgagatcctttttttctgcgcgtaatctgctgcttgcaaacaa | |
| | aaaaaccaccgctaccagcggtggtttgtttgccggatcaagagctaccaactctttttccgaaggtaactggc | |
| | ttcagcagagcgcagataccaaatactgtccttctagtgtagccgtagttaggccaccacttcaagaactctgt | |
| | agcaccgcctacatacctcgctctgctaatcctgttaccagtggctgctgccagtggcgataagtcgtgtctta | |
| | ccgggttggactcaagacgatagttaccggataaggcgcagcggtcgggctgaacggggggttcgtgca | |
| | cacagcccagcttggagcgaacgacctacaccgaactgagatacctacacgctgagctgagaaagcg | |
| | ccacgcttcccgaagggagaaaggcggacaggtatccggtaagcggcagggtcggaacaggagagcg | |
| | cacgagggagcttccagggggaaacgcctggtatctttatagtcctgtcgggtttcgccacctctgacttgag | |
| | cgtcgatttttgtgatgctcgtcaggggggcggagcctatggaaaaacgccagcaacgcggcctttttacgg | |
| | ttcctggccttttgctggccttttgctcacatgttctttcctgcgttatcccctgattctgtggataaccgtattacc | |
| | gcctttgagtgagctgataccgctcgccgcagccgaacgaccgagcgcagcgagtcagtgagcgcacg | |
| | gcgagaagcgcccaatacgcaaaccgcctctccccgcgcgttggccgattcattaatgcagctggcacg | |
| | acaggtttcccgactggaaagcgggcagtgagcgcaacgcaattaatgtgagttagctcactcattaggca | |
| | ccccaggctttacactttatgcttccggctcgtatgttgtgtggaattgtgagcggataacaatttcacacagga | |
| | aacagctatgaccatgattacgccaagcgcgcaattaaccctcactaaagggaacaaaagctgggagctgca | |
| | agcttaatgagtctttatgcaatactctgtagtcttgcaacatgtaacaatgttagcaatgatagctgcctacaa | |
| | ggagagaaaaagcacccgtgcatgccgattggtggaagtaaggtggtacgatcgtgccttattaggaaggc | |
| | aacagacgggttgacatgctgacgaccactgaatgccaatcagtatattgtattaagtgcct | |
| | agtcgatacataaacgggtctctctggttagaccagatctgagcctgggagctctcggctaactagggaa | |
| | cccactgcttaagcctcaataaagcttgccttgagtgcttcaagtagtgtgtgcccgtctgttgtgtgactctgg | |
| | taactagagatccctcagacccttttagtcagtgtggaaaatctctagcagtggcgcccgaacagggacttg | |
| | aaagcgaaagggaaaccagaggagctctctcgacgcaggactcggcttgctgaagcgcgcacggcaag | |
| | aggcgaggggcggcgactggtgagtacgccaaaaattttgactagcggaggctagaaggagagatg | |
| | ggtgcgagagcgtcagtattaagcggggggagaattagatcgcgatgggaaaaaattcggttaaggccagg | |
| | gggaaagaaaaaatataaattaaaacatatagtatgggcaagcagggagctagaacgattcgcagttaatc | |
| | ctggcctgttagaaacatcagaaggctgtagacaaatccggctacaaccatcccttcagacaggat | |
| | cagagaacttagatcattatataatacagtagcaaccctctattgtgtgcatcaaaggatagagataaaaga | |
| | caccaaggaagctttagacaagatagaggaagagcaaaacaaaagtaagaccaccgcacagcaagcgg | |
| | ccgctgatcttcagacctggaggaggagatatgagggacaattggagaagtgaattatataaatataaagta | |
| | gtaaaaattgaaccattaggagtagcacccaccaaggcaaagagaagagtggtgcagagagaaaaaaga | |
| | gcagtgggaataggagctttgttccttgggttcttgggagcagcaggaagcactatgggcgcagcctcaat | |
| | gacgctgacggtacaggccagacaattattgtctggtatagtgcagcagcagaacaatttgctgagggctat | |
| | tgaggcgcaacagcatctgttgcaactcacagtctggggcatcaagcagctccaggcaagaatcctggctg | |
| | tggaaagatacctaaaggatcaacagctcctggggatttggggttgctctggaaaactcatttgcaccactgc | |
| | tgtgccttggaatgctagttggagtaataaatctctggaacagatttggaatcacacgacctggatggagtgg | |
| | gacagagaaattaacaattacacaagcttaatacactccttaattgaagaatcgcaaaaccagcaagaaaag | |
| | aatgaacaagaattattggaattagataaatgggcaagtttgtggaattggtttaacataacaaattggctgtgg | |
| | tatataaaattattcataatgatagtaggaggcttggtaggtttaagaatagtttttgctgtactttctatagtgaat | |
| | agagttaggcagggatattcaccattatcgtttcagacccacctcccaaccccgaggggacccgacaggcc | |

TABLE 1-continued

Exemplary Sequences

| SEQ ID NO: | Sequence* Nucleic Acid | Description |
|---|---|---|
| 17 | cgaaggaatagaagaagaaggtggagagagagacagagacagagatccatccgattagtgaacggatctcg acggtatcggtt | 65-AAV-CAR-T-Cells sequence | ctgtttaaaagaaaaggggggattgggggtacagtgcagggggaaagaatgatagtagacataatagcaaca
gacatacaaactaaagaattacaaaaacaaattcaaaaattttatccaacaagcttgatcgatggct
ccggtgccctgcagtgggcaggagcgcacatcgcccggggtaaactggaaagtgatgtcgtgatcggtctccgcct
aattgaaccggtgctcagagaaggtggcgcggggagaaccgtatataagtgcagtagtcgccgtgaacgtgtacggggtttg
tttccccggaggtggggggagaacacagtgtcgtgacgcggatcccacgcgtcggccgcacgcgtaagctttagcgcagagg
cctgggcgcagccggcaggacgcccggccccggccggttccagaaggaggaggagcccgcgc
caagcgcgcgaagagagcgggctgcctccgagtccgagccggaggaggacggcgcgcgcggc
ccggacggcggcctcgcccgccaccatgtcgttgcccgtcaccgcactgctgctgctgcctgctgctgtgc
acgccgcaagaccggacatgtgtgacacagtcctctgtccttggatatcctcgggcagagggcca
ccattcattcaggccgcagccagtgtcgctcatctacctatattttatcacactggtatcaacagaaatca
ggacagccacccaaactcctcatcaagtatgcatccaacctagaatctgggtccctgcagttcagtggc
agtggtcttgggacagacttctccctcacactcctcaacatccatctgtgaggaggcagtactcaacatattactgtc
agcacagttgggagattccataccagcttcggagggggggcgcagccaggtgaatctgagataaaagcagtactagcgg
tggtgctccgggggggtttccgggacggcccggcagcgcagccaggctgcagccagtgccagtcaggagccttcaggagctcaggacctg
gcctgtgcgacccccacagagctccgtcatcacactgcacgtccaggattctcattaagcggctatgcat
aagctggtctgcgcagctccaggaaagcgtcggaatgctcggattgataggggtgatgaaccaca
gactataattcagtctcaaatccagactgagcatcagcaaggacaaccccaggcccaggtttcttaaaaa
tgaacagtctgcaaactgatgacacagccaggtacttcgttaccagagggccctccggccttcgtataagtacct
ctactttgactactgggcaaggcaccactcacagtctcctcacagttctcgaccccaaatcttctgacaaaact
cacacatgccacccgtgcccagcacctctctgtggccaggcccgtcagtcttcctcttcccccccaaaacccaa
ggacacccctcatgatctcccggacccctgaggtcacatgcgtggtggtggacgtgagccacgaggaccct
gaggtcaagttcaactggtacgtggacggcgtggaggtgcataatgccaagacaaagccgcgggaggag
cagtacaacagcacgtaccgtgtggtcagcgtcctcaccgtcctgcaccaggactggctgaatggcaagg
agtacaagtgcaaggtctccaacaaagccctcccagcccccatcgagaaaaccatctccaaagccaaagg
gcagccccgagaaccacaggtgtacaccctgcccccatcccgggatgagctgaccaagaaccaggtcag
cctgacctgcctggtcaaaggcttctatcccagcgacatcgccgtggagtgggagagcaatgggcagccg
gagaacaactacaagaccacgcctcccgtgctggactccgacggctccttcttcctctacagcaagctcacc
gtggacaagagcaggtggcagcaggggaacgtcttctcatgctccgtgatgcatgaggctctgcacaacc
actacacgcagaagagcctctccctgtctccgggtaaatgagggtggtggtgtggtgagctttgctgctgctat
agcttgctagtaacagtggcctttattattttctggtgtgaggagtcaagaggagggagtcccaccagtgact
acatgaacatgacctcccgcctgagtgtcttaccagctatgccccaccaccgcg
acttcgcagcctatcgctccaaacgggcagaagaaactcctgtatattccagaaagaagaagaaccattatgagacc
agtacaaactactcaagaggaagatggccagtagcaagtgctgccgattccaagacagggccagaacacagctcgatac
ctgagagtgaagtctcagctacggcacgatctcaaaagagctgccggggccagcagggccagaaccagctctataac
gagctcaatctactctcaggacgaagagttttgacacaaggcaacctggttgcgggacccctgagatgg
gggaaagccgagaggaaggaagaaaccctcagaaggcctgtcaatgaactcagaaagataaagatggcg
gagccttacagtgagattggatgaaagcgagagcgactacgacggcccttcacatgcgccccctgcccgcagtgt
actaattatgtctcttgaaattgctggaagtgttgagagcaacccgccggaattcatgccacctcctc
gcctcctcttcctcctcctccacccatggaagctcagaccatctagtggtgaaggtgga
agaggagaataacgctgtgctgtcagtgcctccaggggacctcagagctgggctgccaggcctgggaatccacatgagg
tctcgggactctctccccgtttaaacctctccaggacgtccttcacagctccttccacagctgacctcggggctttctacctggcttctcacctgctggggactacagcatatgagg
ccccctgg ccatcctggctcctgctttcatcttcaacgtctccaacgtcctccaacagatggcagtctcctgcagcagcggggggc
cccctgcggagaagctgctcgagaagcgcggcagtggcagctgggcagcagctggggcggcgggagctgttccggt TABLE 1-continued Exemplary Sequences

| SEQ ID NO: | Sequence* Nucleic Acid | Description |
|---|---|---|

```
ggaatgtttcggacctagtggcctggcgtggcctgagaacaggtcctcagagggccccagctccct
tccggaagtcatagagcccaagtgtagtgtggccaagaccgccctgagatctgggaggggag
cctccgtgtgccaccgaggacagcgctgaaccagagcctcagccaggacctcaccatggccctggct
ccacactctggctgtcctgggggtaccccctgactctgtgtccagggacccctcctctggaccatgtgc
acccaagggccctaagtcattgctgagcctagagctgaaggacgatcgccgccagagatatgtggt
aatggagacgggtcgtgtgccccggccacagctcaagctgaaagtattattgtcaccggtggcaa
cctgaccatgtcattccacctggagatcactgctcggccagtacctatggcactggctgctgaggactggtgg
ctggaagctcagctgactttggcttctgatctctgctcctgctgtcctgtgtggcatcttcatcttcaaa
gagccctggctcctgaggaggaaaagatgatctagataaattcgagcatcttaccgccatttatttcccatattgt
tctgttttctgattggggtatacattacaaatgtgggcaatcacatttttaggggat
atgtaattactagttcaggtgtattgccacaagacaaacatgttaagaaacttcccgttattacgcctgttcct
gttaatcaacctctggatacaaaatttgtgaagattgactgatattcttaactatgttgctcctttacgctgtgt
ggtatatgctgcttatagcctcgatctagctaattgttcccgcacgctttcgttctcctccttctgtataaatcct
ggttcgtgtctttagaggagtgtgccgtgtcctcaacgtggcgtggctgtttgctgacg
caaccccacggctggggaattgccaccaccgtcaaccccttctgggacttcgcttccccctcccgatc
gccacggcagaactcatcgccgctgcctgcccgctgccgctggacaggggctagttgtgggactgata
attccgtggtgttgtcgggaaggccgctcctttcctcgaggggggccggtaccttaagaccaatgac
ttacaaggcgctgagatcttagccacttttaaaagaaaggggacctgaaggggctaattcactcccca
acgagacaagatcgctttgtcgtactgggctctctggttagaccagatctgagcctggagctctg
gctaactaggaaccactgcttaagctccaataaagttgcttgagtgcttcaagtagtgtgccgtctg
ttgtgatctggctaactagagatccctcagacccttttagtcagtgtggaaaatctctagcagtagtggt
gtcatcttattattcagtattataacttcaagagaaatgaatatcagagagtgagaggaacttctattggcagct
tatatggttacacaataaagcaatacaacttttcacaataaaagcattttttcactgcattctagttgtggtttgg
ttgtccaaactcatcaatgtatcttatcatgtctggctctagctatccgccctcactccgccccagttccgcc
attctccgccccatggctgactaattatttattatgcagaggccgaggccgcctcggcctctgagctattcc
agaagtagtgaggaggctttttggaggcctaggctttgcgtgagacgtaaccaaatctgccctatagtgag
tcgtattacgcgcgctcacttggccgtcttacaacgtcgtgactgggaaaacctggcgttacccaactta
atcgccttgcagcacatccccctttcgccagctggcgtaatagcgaagaggcccgcaccgatcgccctttc
caacagttgcgcagcctgaatggcgaatggcgcctgatgcggtattttctccttacgcatctgtgcggtatt
gtggggtggggtacgcgcgagcgtgacccgtcacacttgccagcgccctagcgcccgctcctttcgctttcttcccttc
cttctcgccacgttcgccggctttccccgtcaagctctaaatcgggggctccctttagggttccgatttagtgc
tttacggcacctcgaccccaaaaacttgattagggtgatggttcacgtagtgggccatcgccctgatagac
ggtttttcgccctttgacgttggagtccacgttctttaatagtggactcttgttccaaactgaacaacactcaac
cctatctcggtctattcttttgatttataaggggattttgccgatttcggcctattggttaaaaaatgagctgattaa
caaaaatttaacgcgaattttaacaaaatattaacgtttacaatttcccaggtggcactttttcggggaaatgtgc
gcggaacccctatttgtttatttttctaaatacattcaaatatgtatccgctcatgagacaataaaccctgataaatg
cttcaataatattgaaaaaggaagagtatgagtattcaacatttccgtgtcgcccttattccccttttttgcggcatt
ttgccttcctgtttttgctcacccagaaacgctggtgaaagtaaaagatgctgaagatcagttgggtgcacgag
tgggttacatcgaactggatctcaacagcggtaagatccttgagagttttcgccccgaagaacgttttccaatg
atgagcacttttaaagttctgctatgtggcgcggtattatcccgtattgacgccgggcaagagcaactcggtc
gccgcatacactattctcagaatgacttggttgagtactcaccagtcacagaaaagcatcttacggatggcat
gacagtaagagaattatgcagtgctgccataaccatgagtgataacactgcggccaacttacttctgacaac
gatcggaggaccgaaggagctaaccgcttttttgcacaacatgggggatcatgtaactcgccttgatcgttg
ggaaccggagctgaatgaagccataccaaacgacgagcgtgacaccacgatgcctgtagcaatggcaac
aacgttgcgcaaactattaactggcgaactacttactctagcttcccggcaacaattaatagactggatggag
gcggataaagttgcaggaccacttctgcgctcggcccttccggctggctggtttattgctgataaatctggag
ccggtgagcgtgggtctcgcggtatcattgcagcactggggccagatggtaagccctcccgtatcgtagtta
tctacacgacggggagtcaggcaactatggatgaacgaaatagacagatcgctgagataggtgcctcactg
```

*

TABLE 1-continued

Exemplary Sequences

| SEQ ID NO: | Sequence* Nucleic Acid | Description |
|---|---|---|
| | attaagcattggtaactgtcagaccagccaagttactcatcatatacttagattgattaaaacttcattttaatttaaaa<br>ggattaggtgaagatcctttgataatctcatgaccaaaatccctaacgtgagtttcgtccacctgagcgtc<br>agaccccgtagaaaagatcaaaggatcttcctgagatccttttttctgcgcgtaatctgctgcttgcaaacaaa<br>aaaaccaccgctaccagcggtggtttgtttgccggatcaagagctaccaactctttttccgaaggtaactggc<br>ttcagcagagcgcagataccaaatactgtccttctagtgtagccgtagttaggccaccacttcaagaactctgt<br>agcaccgcctacatacctcgctctgctaatcctgttaccagtggctgctgccagtggcgataagtcgtgtctta<br>ccgggttggactcaagacgatagttaccggataaggcgcagcggtcgggctgaacggggggttcgtgca<br>cacagcccagcttggagcgaacgacctacaccgaactgagatacctacagcgtgagctatgagaaagcg<br>ccacgcttcccgaagggagaaaggcggacaggtatccggtaagcggcagggtcggaacaggagagcg<br>cacgagggagcttccagggggaaacgcctggtatctttatagtcctgtcgggtttcgccacctctgacttgag<br>cgtcgatttttgtgatgctcgtcaggggggcggagcctatggaaaaacgccagcaacgcggcctttttacgg<br>ttcctggccttttgctggccttttgctcacatgttctttcctgcgttatcccctgattctgtggataaccgtattacc<br>gcctttgagtgagctgataccgctcgccgcagccgaacgaccgagcgcagcgagtcagtgagcgagga<br>agcggaagagcgcccaatacgcaaaccgcctctccccgcgcgttggccgattcattaatgcagctggcacg<br>acaggtttcccgactggaaagcgggcagtgagcgcaacgcaattaatgtgagttagctcactcattagga<br>cccaggcttacactttatgcttccggctcgtatgttgtgtggaattgtgagcggataacaatttcacacagga<br>aacagctatgaccatgattacgccaagcgcgcaattaaccctcactaaagggaacaaaagctggagctgca<br>agcttaatgtagtctta gtttgcaatactttgtagtcttgcaacatggtaacgatgagttagcaacatgccttacaa<br>ggagagaaaaagcaccgtgcatgccgattggtggaagtaaggtggtacgatcgtgccttattaggaaggc<br>aacagacgggtctgacatggatcggcttacgtctcctgtggaagcctgatctgagcctgggagtgggagaa<br>agctcgataca taaacgggtctctctggttagaccagatctgagcctgggagctctggctaactaggaa<br>cccactgcttaagcctcaataaagcttgccttgagtgcttcaagtagtgtgtgcccgtctgttgtgtgactctgg<br>taactagagatccctcagacccttttagtcagtgtggaaaatctctagcagtggcgcccgaacagggacttg<br>aaagcgaaagggaaaccagaggagctctctcgacgcaggactcggcttgctgaagcgcgcacggcaag<br>aggcgaggggcggcgactggtgagtacgccaaaaattttgactagcggaggctagaaggagagagatg<br>ggtgcgagagcgtcagtattaagcggggggagaattagatcgcgatgggaaaaaattcggttaaggccagg<br>gggaaagaaaaatataaattaaaacatatagtatgggcaagcagggagctagaacgattcgcagttaatc<br>ctggcctgttagaaacatcagaaggctgtagacaaatactgggacagctacaaccatcccttcagacaggat<br>cagaagaacttagatcattatataatacagtagcaaccctctattgtgtgcatcaaaggatagagataaaaga<br>caccaaggaagctttagacaagatagaggaagagcaaaacaaaagtaagaccaccgcacagcaagcgg<br>cagcagctgacacaggacacaagcaaccaggtcagccaaaattaccctatagtgcagaacatccagggg<br>caaatggtacatcaggccatatcacctagaactttaaatgcatgggtaaaagtagtagaagagaaggctttc<br>agcccagaagtgatacccatgttttcagcattatcagaaggagccaccccacaagatttaaacaccatgctg<br>aatacagtggggggacatcaagcagccatgcaaatgttaaaagagaccatcaatgaggaagctgcagaat<br>gggatagagtgcatccagtgcatgcagggcctattgcaccaggccagatgagagaaccaaggggaagtg<br>acatagcaggaactactagtacccttcaggaacaaataggatggatgacaaataatccacctatcccagtag<br>gagagatctataaaagatggataatcctgggattaaataaaatagtaagaatgtatagccctaccagcattctg<br>gacataagacaaggaccaaaggaaccctttagagactatgtagaccggttctataaaactctaagagccgag<br>caagcttcacaggaggtaaaaaattggatgacagaaaccttgttggtccaaaatgcgaacccagattgtaag<br>actattttaaaagcattgggaccagcggctacactagaagaaatgatgacagcatgtcagggagtgggggg<br>acccggccataaagcaagagttttggctgaagcaatgagccaagtaacaaattcagctaccataatgatgca<br>gagaggcaattttaggaaccaaagaaagattgttaagtgtttcaactggcttctatgttctatagtgatgaat<br>agagttacaggctctgtacattttgagagccacctagccgatggtggccataattatggaaacctatagtgaat<br>cgaggatagaagaaggtggagagagagacaggacagatccattcgattagtgaacggatccgtctggctctg<br>acggtatcggtt | |
| 18 | aacaagcttgatcgatggctccggtgcccgtcagtggcagagcgcacatcgcccacagtccccgagaa<br>gttggggggaggggtcggcaattgaaccggtgcctagagaaggtggcgcgggggtaaactgggaaagtg<br>atgtcgtgtactggctccgcctttttcccgagggtgggggagaaccgtatataagtgcagtagtcgccgtga<br>acgtctcttttcgcaacgggtttgccgccagaacacaggtcgcgcggatccacgcgtgcggccgcgca | EF1-alpha |

TABLE 1-continued

Exemplary Sequences

| SEQ ID NO: | Sequence*·Nucleic Acid | Description |
|---|---|---|
| | cgcgtaagctt | |
| 19 | GGCATTGATTATTGACTAGTTATTAATAGTAATCAATTACGGGGT<br>CATTAGTTCATAGCCCATATATATGGAGTTCCGCGTTACATAACTTA<br>CGGTAAATGGCCCGCCTGGCTGACCGCCCAACGACCCCCGCCCA<br>TTGACGTCAATAATGACGTATGTTCCCATAGTAACGCCAATAGG<br>GACTTTCCATTGACGTCAATGGGTGGAGTATTTACGGTAAACTGC<br>CCACTTGGCAGTACATCAAGTGTATCATATGCCAAGTCCGCCCCC<br>TATTGACGTCAATGACGGTAAATGGCCCGCCTGGCATTATGCCC<br>AGTACATGACCTTACGGGACTTTCCTACTTGGCAGTACATCTACG<br>TATTAGTCATCGCTATTACCATGGTGATGCGGTTTTGGCAGTACA<br>CCAATGGGCGTGGATAGCGGTTTGACTCACGGGGATTTCCAAGT<br>CTCCACCCCATTGACGTCAATGGGAGTTTGTTTTGGCACCAAAAT<br>CAACGGGACTTTCCAAAATGTCGTAATAACCCCGCCCGGTTGAC<br>GCAAATGGGCGGTAGGCGTGTACGGTGGGAGGTCTATATAAGCA<br>GAgGT | CMV |
| 20 | ggcgcccagtgtgatgggatatctgcagaattcgcccttatgggatccgaacagagagacagcagaatatg<br>ggccaaacaggatatctgtggtaagcagtcctgccccgctcagggccaagaacagttggaacagcaga<br>atatgggccaaacaggatatctggtaagcagttcctgccccgctcagggccaagaacagatggtcccc<br>agatgcggtcccgccctcagcagttctcagagaaccatcagatgtttccaggtgcccaaggacctgaaat<br>gaccctgtgccttatttgaactaaccaatcagttcgcttctgtttcgctttcgctttctgtctccgagctct<br>atataagcagagctgtttgttagtgaacgtcagatcgcctggagacgccatccacgctgttttgacctccatag<br>aagacaccgactctaga | MND2 |
| 21 | GTAACGGCCATTTTGCAAGGCatggaaaaataccaagaatagagaagttcagatc<br>aaggcgggtacatgaaaatagctaacggtggccaaacaggatctctgcggtggcagttccggcccccg<br>gcccggggccaagaacagatggtcaccgcagttcggccccgagttcttcggcagccgagacctgaaat<br>cagatatgggccaaccccaacctcagcagttcttaagaccccatcagatgtttccaggtctcggcggcttctctgttctccgagctct<br>ataaagagctcacaacccctcacccggcgccagtccccGACGACTGAGTCGCCCG<br>GG | SFFV |
| 22 | Gacattgtgacacagtctcctgcttcttcctactggtatctctgggcagagggccaccatctcatgcagg<br>gccagcccaaagtggtcagttcatctcatccaacctagaatctgggtccctcagttcagtggcagtgggtctgggac<br>aactcctcatcaagtatgcatccaacctctgtggaggaggatactgcaacatattactgtcagcacagtggga<br>agactctcctcacacggttcggaggggggaccaagtggaaataaaggcagtactagccggtggtctccggg<br>ggcggttccggtggggggggcggcagtcgtcagcagggtcaaggagtcaggacctggctggcacc<br>ctcagaggcctgtccatcacatgaccgcctcaggattctcattaagcggctatggctcaagcgggtcgc<br>cagcctccaggaaagctggaatggctcagaggttgataggggtgatggaaccacagactataattcagct<br>ctcaatccagactgagcctcaggatgaccaggaacaatccaagagccaggttttcttaaaatgaacagtctgcaa<br>actgatgacacagccagtgtacttctgtaccacagaggggcctcttcatagtacccttacttttgactactg<br>gggccaaggcaccactctcacagtctccta | AAV-ScFv<br>sequence (from<br>D3 antibody) |
| 23 | gacaaaactcacacatgcccaccgtgcccagcacctcctgtggcaggaccgtcagtcttcctcttccccca<br>aaaccaaggacaccctcatgatctcccggacccctgaggtcacatgcgtggtggtggacgtgagccacg<br>aagaccctgaggtcaagttcaactggtacgtggacggcgtggaggtgcataatgccaagacaaagccgcg | Long hinge (IgG1<br>hinge-IgG2 hinge,<br>IgG1 CH2CH3) |

TABLE 1-continued

Exemplary Sequences

| SEQ ID NO: | Sequence* Nucleic Acid | Description |
|---|---|---|
| | ggaggagcagtaccagagcacgtaccgtggtcagcgtcctccacgtcctgcaccaggactgctgaat ggcaaggagtacaagtgcaaggtctccaacaaagcctccagcatcgagaaaaccatctccaaag ccaaagggcagccccgagaaccacagtgtacacctgcccccatccaggatgagctgaccaagaacc aggtcagcctgacctgcctggtcaaagggttctatcccagcgacatcgccgtggagtgggagcaatgg gcagccggagaacaactacaagaccacgcctcccgtgctggactccgacggctccttcttcctctacagca gctcaccgtggacaagagcaggtggcagcaggggaacgtcttctcatgctccgtgatgcatgaggctctg cacaaccactacacgcagaagagcctctccctgtctccc | |
| 24 | ATTGAAGTTATGTATCCTCCTCCTTACCTAGACAATGAGAGAGAGC AATGGAACCATTATCCATGTGAAAGGAAACACCTTTGTCCAAG TCCCCTATTTCCCGACCTTCTAAGCCC | Short Hinge (CD28 extracellular domain) |
| 25 | TTTTGGGTGCTGGTGGTGGTTGGTGGAGTCCTGGCTTGCTATAGC TTGCTAGTAACAGTGGCCTTTATTATTTTCTGGGTG | Transmembrane (CD28 transmembrane domain) |
| 26 | Aggagtaagagaggagcaggggaggtcacagtgactacatgaacatgactcccgcgcccgggcccac ccgcaagcattaccagccctatgcccaccacgcgacttcgcagcctatcgctcc | Human CD28 signaling domain |
| 27 | AACAGCAGAGAAACAGAGAGGCGGCCAGAGCGACTACACTGAACA TGACCCCCAGAAGGCCAGGCCTGACCAGAAAGCCCTACCAGCCC TACGCCCCTGCCAGAGACTTCGCCGCCTACAGACCC | Murine CD28 signaling domain |
| 28 | Aaacgggggcagaagaaaactcctgtatatattcaaacaaccatttatgagaccagtacaaactactcaaga ggaagatggctgagtcgccgattccagaagacgaagaggaggatgtgaactg | Human 4-1BB signaling domain |
| 29 | TCTGTGCTCAAATGGATCAGGAAAAAATTCCCCACATATTCAA GCAACCATTTAAGAGAGACCACTGGAGCAGCTCAAGGAAGAT GCTTGTAGCTGCCGATGTCCACAGAAGAAGAAGAGGAGGAG GAGGCTATGAGCTG | Murine 4-1BB signaling domain |
| 30 | Agagtgaagttcagcaggagcgacaggagccgccccccgctaccagcagggccagaaccagctctataacga gctcaatctaggacgaagaagagaggtacgatgtttggacaagaagactggccgcgggacccctgagcatggg gggaaagcccagaagggaagaaccccaggaaggcctgtacaatgaactgcagaaagataagatgatggcgg aggcctacagtgagattgggatgaaaggcgagcgccggaggggcacgggggacgggcctttaccag ggtctcagtacagcacccaaggacacctacgacgcccttcacactgcagccctgcccctcgc | Human CD3z |
| 31 | AGAGCCAAGTTCAGCAGGTTCAGCAGATCCGCCGAGATCGCCGCCAACCTGCA GGATCCCAACCAGCTGTACAACGAGCTGAACCTGGGCAGACGGG AGGAATACCGACGTGCTGGAAAAGAGAGAGAGCCAGGGACCCCGA GATGGGCGCAAGCCAACGAGCAGCAGAGAAAACCCTCAGGAGGGC GTCTACAACCCCTGCAGAAGACAAGATGGCCGAGGCCTACAG CGAGATCGGCACCAAGGGCGAGCAGAAGAAGAGGGGCAAGGGCCAC GATGGCCCTGTACCAGGGCCTGTCCACCGCCAAGGACACCTA CGACGCCCTGCACATGCAGACCCCTGCCCCCAGATGA | Murine CD3z |

TABLE 1-continued

Exemplary Sequences

| SEQ ID NO: | Sequence* Nucleic Acid | Description |
|---|---|---|
| 32 | Atgccacctcctcgcctcctcttcttcctcctcttcctcaccccatggaagtcaggccgaggaacctctag tggtcaaggggaagaggagataacggctgctgctcagtcgagtgcctcaagggaccctcagatggcccactca gcagctgacctggctcggagtccccggccatctggctttcatcttcaacgtctctcaacagatggggggcttttcacctg gaatccacatgagcccgccatctggccatctgggtcttctggagaaggtggccccccctctgggagactggaaggctgcagcgg ggagctgttccggtggaatgttccgaccagaggtttcccgtgagaaacaggtcctcagagg gcccagctccccttccggagagagccttcatgagacccaagcgtgtatgtgtggccaaagacgccctgagat ctggaggagagagcctccgtgtccaacctgctgctcctgggtgtcctgtcctcagggggccccctctc ctggaccccagtgccaagggccccagaggctgaagcggcatcggccggcc agagatatgggtaatggagacggtctgttgttcccgggccacagctcaagacgctggaagtattat tgtaccggcgacctggcaacctgaccatcaatccactggagatcactggctggccagtaatatgcactggctg ctgggactggtggctggagagtccctgagctgtgtgtcaggtgtgtcttctgctctgcctgtgtccctgtgggc attcttcattcttcaaagagccctggtcctgaggaggaaaga | CD19 extracellular domain |
| 33 | Atgttctctggtgtgacaagcctttctgcttctgtgagttaccacaccccagcattctctctgatcccacgcaagt gtgtaacggaataggtatggtgaattctaaagatcactctccataaatgctacgaatattaaacacttcaaaaa ctgcacctccatcagtggcgatctccacactcgccgtggtggcattt1aggggtgactcctcacacatactcctc ctctggatccacaggaactggatattctgaaaccgtaaggaaatcacagggtattgctgattcaggctg gcctgaaaacaggagacggactccatgcttgagaacctagaacatcatcctgggattacgctccctcaaggagataagtga tggagatgtgataattcaggaaacaccaaaattgctatgcaaatacaataaactgaaaaaactgtttggga cctccggtcagaaaccaaaatataagcaacaggtgaaaacgcctgaagctctgcccaagcatgcagcccaggtctca ccatgcctgctgccccccgaggcgtgctgggcgtcgggggccggccaaggtgcaaccttctggaggtgagcaaggacgcgggacc ctggtgcatacaagtgccaccagtgctgccactcatgtgccccactgcaagacgcgccggcgaggagtca tgggagaaacaacacaccccggtcttggaagtacgcagacgccgccatgtgtgcccatgggcctaagaccccgtcccatcg ctgcacctacggatgcactggcaggtcttgaaggctgtccaacgaagtgccaagatcccgtccatcg ccactggatcctagat | EGFR extracellular domain |
| 34 | Cagtgtactaattatgctctcagaaattggctgagatgagagagcaaccccgggccg | E2A |
| 35 | Gaagtcgtgtgatcactacttacgtcggtcagtgcggtgatgtagaagagaatccggtccg | T2A |
| 36 | Gccacaaacactcctctgctaaagcaagcaggtcgatgagagagaaaacccccgggcct | P2A |
| 37 | atggctgccgatggttatcaccaggatggctcgaggacaacctctctgagggcattcgcgagtggtgggcg ctgaaacctggcgcccaggccaaagccaacctggacaacgcctagaggtcctcgatcggtgct tcctgctacaagtacctcggacccacacaagcgactcgacaagggggagcccgtcaacgcgcggacgc agcggccctcgagcacgacgaaggctacgaccagctcgaggcgggtgacaatccgtacctgcggta taacacgccgcacgccgagcccgagatcaggagcctctgcaagagagatacgtcattggggcaacctcgggcga gcagtcacggccggccgagtcagagagcgctgaacctctggctcggagaggaagggctaagacggctcc tggaaagaagaggaccggtagagccttctggagcttcctctacggctgggaaggagggggcatcggcaagaaa ggccaacagccgccgcagaaaaaagactcaattagtcagcccttggtggacactcagagctggccagatacaatgggtggcgtggcggca acctctggacaaataacgaaggccgcgacggggtgggttgcaattccggttcca catggctgggcgacagagtctcaccaccgccacccccgacaacctgggcgccctgccacctcacaaccacacacct | AAV8-capsid sequence |

TABLE 1-continued

Exemplary Sequences

| SEQ ID NO: | Sequence*-Nucleic Acid | Description |
|---|---|---|
| | ctacaagcaaatctccaacggacatcgggaggagcacaagcacaacaccacttcggctacagcacc<br>cctcggggtgattagacataacagattccactgcccactaccacgtgactggcagcgactcatcaacca<br>caactgggggattccggccaagagactcagcttcaagcttcacaacatccagtcaaggagtcacgcaga<br>atgaaggcaccaagaccatcgccaataacctcaccagcaccatccaggtgatacggactcggagtaccag<br>ctgcgtacgactcggctctgcccaccaggctgcctgctccgacccgcggacgtgacatgatcccc<br>agtacgactcacctaacactcaacaacggtagcaggctcagcgcgggacgctcctcactactgcctggaatactt<br>tccacgcagatgctgagaaccggcaacaacaccagatacttacacacaggacgctgcatccacagc<br>agtcacgcccacagccagcacaggaggcacggcaaaatacgcagactctgggcttcagccaaggtgggcctaatacaat<br>ggccaatcagcgaagaactggtgctgcaggacccgaacccgtctcaacgacaaccgg<br>gcaaaacaacaaatagcaactagcctggactgctgtggaccaaataccatctgaatggaagaaatcattggc<br>taatcctggccatcctatggcaacacacaaagacgcagaggacgcgattatcccagtaacggggatcctgatt<br>taggcaaacaacaaaacctgctacagaggaatacggtatcgtgctgcagataacctgcagcgacaaaacacg<br>caaacaccaaccctgtgctacagaggaataccggtatcgtgctgcagcgacaaaaacacg<br>gctcctcaaattggaactgtcaacagccaggggcttaccggtatggtctggagaaccggacgtgta<br>cctgcagggtcccatctgggccaagattcctcacacggacggcaacacaccacgtctccgtgatgggcg<br>gctaggctgaaacatctcccgcctcagatccctgatccaagaacacgcctgtacctgcggatcctccgacca<br>ccttcaaccagtcaagctgaactcatcacgcaatacagcacaggtcaggctgaattgaat<br>gggagctgcagaaggaaaacaacaagcaagcgctggaacccgagatccagtcagctcaactactacaaat<br>ctacaagtgtggactagctgaaatacagaaggcgtgtactctgaacccgcccccattggcaccgttacct<br>caccgtatcctg | |
| 38 | atggctgccgatggttatcaccagattggctcgagacaacctttagtgaaggaattcgcgagtggtgggctt<br>tgaaacctggagcccctcaactccaaggcaaatcaacaacaacaagacaacgctcgagtcagtgcaccg<br>ggttacaaataccaggacccggcacgacctcgacaaggggagccggcacacagacagacgcggc<br>ggcctcgagcacgacaagcctcgaccagcagcctcaaggccggagacaaccgtacctcaagtaca<br>accagcgacgcgcagaccgagatcagtcaaagaagatacgtcattggggcaacctcgggcgag<br>cagtcaccaggccaaaagaggcacttgaacctcaagtctggaggaggacggctaagacggctcctg<br>gaaagaagaggcctgtagagcagtctgagcagtctcctgaaccggactcctccgcgggtattggcaaatcgggtgc<br>acagccgcgtaaaagagacctcaatacggtcaagtggtggacactcggggacggctcagtccagaccctcaacca<br>atcggagaacctccgcagccccggaccggtgggatctatacaatgatcaggcggtggcgccaccagt<br>ggcagacaataacgaaggtgccgatggagtgggtgaacctcggcggaaattggcattggcattggcgatcccatggc<br>tggggacagagtcatcaccaccagcaccctggaggatcttcaaatgacaaacgcctacttcggtacagcaccccctggg<br>ggtattttgacttcaacagattccaacagttcaacagctgcagcgaactcatcaacaacaactg<br>gggattccggcctaagcgactcaacttcaagctcttcaacattcagtcaagaggttacggacaacaatgg<br>agtcaagaccatccgccaataacttaccagcacggtcaggttcacggactcagatatcagctccgta<br>ctgctcgggtcggctcacgagggctgctccccgccgtggtgcttctgtcatgattcccagtacgg<br>gtatctgacgttaatgatgagacgaggccggcgcgcgtggtcctttactgcctgaatattccgtcgc<br>aaatgctaagaacgggtaacaacttccagttcagttcagctgttgagaacgtaccttccatagcacgtacgc<br>tcacagcccaaagctggaccgactaatgatccactcactgactgactacctctctcaaagactatta<br>acggtctgacagaatcaacaaacgctaaaatcagtggccggaacccagcaacatggctgtccaggg<br>aagaaactacatacctgaccaggctaccgacaacacaactgtctcaacactgtgactcaaaaacaacaca<br>gcgaattgcttgctggctggcttcttcttgggcctcaatgagctaatagcttgatgaatcctggacctgcta<br>tggccagccaaagaagaaggaggaccgttctttcctttgtctggatcttaatttggcaaacaaggaact<br>ggaagagacaacgtggatcggacacaaagtcatgataaccaacgaagaagaaataaaactactaacccgg<br>tagcaacggagtcctatggaacggttccgggtatggtttggacgagagatgttggcaggacaccggc<br>gggttcaaaccaagagaatacttccgggtatgcttggcaggacgagagatgttggcaggaccccattt | AAV9-capsid sequence |

TABLE 1-continued

Exemplary Sequences

| SEQ ID NO: | Sequence*-Nucleic Acid | Description |
|---|---|---|
| | gggccaaaattcctcacacggacggcaactttcacccttctccgctgatggagggtttggaatgaagcacc cgcctcctcagatcctcatcaaaaacacacctgtacctgcggatcctccacggcctccaacaaggacaag ctgaactctttcatcaccaccagtattctactggccaagtcagcgtggagatcgagtgggagctgcagaaggaa aacagcaagc | |
| 39 | DIVLTQSPASLAVSLGQRATISCRASQSVSSTYNFIHWYQQKSGQP PKLLIKYASNLESGVPVRFSGSGSGTDFSLNIHPVEEDTATYYCQH SWEIPYTFGGGAKLEIKGSTSGGGSGGGSGGGSQVQLKESGPGL VAPSQSLSITCTVSGFSLSGYGISWVRQPPGKRLEWLGLIWGDGTTD YNSALKSRLSISKDNSKSQVFLKMNSLQTDDTARYFCTRGPPAFYK YLYFDYWGQGTTLTVSS | Translated AAV-ScFv sequence (from D3 antibody) |

*Unless otherwise specified, nucleic acid sequences are described 5' to 3' and amino acid sequences are described N-terminus to C-terminus

EQUIVALENTS AND SCOPE

It is to be understood that this disclosure is not limited to any or all of the particular embodiments described expressly herein, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents (i.e., any lexicographical definition in the publications and patents cited that is not also expressly repeated in the disclosure should not be treated as such and should not be read as defining any terms appearing in the accompanying claims). If there is a conflict between any of the incorporated references and this disclosure, this disclosure shall control. In addition, any particular embodiment of this disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

In the claims articles such as "a," "an," and "the" may mean one or more than one unless indicated to the contrary or otherwise evident from the context. Wherever used herein, a pronoun in a gender (e.g., masculine, feminine, neuter, other, etc. . . . ) the pronoun shall be construed as gender neutral (i.e., construed to refer to all genders equally)

regardless of the implied gender unless the context clearly indicates or requires otherwise. Wherever used herein, words used in the singular include the plural, and words used in the plural includes the singular, unless the context clearly indicates or requires otherwise. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists (e.g., in Markush group format), each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included in such ranges unless otherwise specified. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Each element disclosed in the disclosure may be replaced by an alternative feature serving the same, equivalent, or similar purpose. Thus, unless expressly stated otherwise, each feature disclosed is only an example of a generic series of equivalent or similar features.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the disclosure, as defined in the following claims.

What is claimed is:

1. An isolated nucleic acid comprising an expression construct encoding a chimeric antigen receptor (CAR), wherein the CAR comprises:
   (i) an antigen binding domain comprising the amino acid sequence set forth in SEQ ID NO: 39;
   (ii) a transmembrane domain; and
   (iii) a cytoplasmic signaling domain.

2. The isolated nucleic acid of claim 1, wherein the transmembrane domain is a CD28 transmembrane domain or wherein the cytoplasmic signaling domain comprises one or more of a CD28 signaling domain, a 4-1BB signaling domain, and a CD3 signaling domain.

3. The isolated nucleic acid of claim 1, wherein:
   the expression construct further comprises a promoter operably linked to a nucleic acid sequence encoding the CAR; or
   the expression construct further comprises a Woodchuck Hepatitis Virus Posttranscriptional Regulatory Element (WPRE).

4. The isolated nucleic acid of claim 1, wherein the expression construct further comprises a FoxP3 encoding nucleic acid sequence.

5. The isolated nucleic acid of claim 1, wherein the expression construct is flanked by viral long terminal repeats (LTRs).

6. A host cell comprising the isolated nucleic acid of claim 1.

7. The host cell of claim 6, wherein the host cell is an immune cell.

8. A composition comprising a plurality of the host cell of claim 6.

9. The composition of claim 8, further comprising a pharmaceutically acceptable excipient.

10. A vector comprising a nucleic acid encoding a CAR having the sequence as set forth in SEQ ID NO: 1.

11. The isolated nucleic acid of claim 1, wherein the antigen binding domain is encoded by the nucleotide sequence set forth in SEQ ID NO: 22.

12. The isolated nucleic acid of claim 3, wherein the promoter is an EF1alpha (EF1α) promoter.

13. The isolated nucleic acid of claim 4, wherein the sequences the nucleic acid sequence encoding the CAR and the FoxP3 encoding nucleic acid sequence are linked by a nucleic acid sequence encoding a 2A self-cleaving peptide.

14. The isolated nucleic acid of claim 5, wherein the LTRs are HIV LTRs.

15. The host cell of claim 6, wherein the host cell is a human cell.

16. The host cell of claim 7, wherein the immune cell is a T-cell or a regulatory T-cell (T-reg).

* * * * *